(12) United States Patent
Giese et al.

(10) Patent No.: US 10,487,092 B2
(45) Date of Patent: Nov. 26, 2019

(54) PYRAZOLOPYRIDINAMINES AS MKNK1 AND MKNK2 INHIBITORS

(71) Applicant: BAYER PHARMA AKTIENGESELLSCHAFT, Berlin (DE)

(72) Inventors: Anja Giese, Berlin (DE); Ulrich Klar, Berlin (DE); Keith Graham, Berlin (DE); Georg Kettschau, Berlin (DE); Detlev Sülzle, Berlin (DE); Philip Lienau, Berlin (DE); Kirstin Petersen, Berlin (DE); Julien LeFranc, Berlin (DE); Nicole Schmidt, San Francisco, CA (US)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/537,694

(22) PCT Filed: Dec. 14, 2015

(86) PCT No.: PCT/EP2015/079587
§ 371 (c)(1),
(2) Date: Jun. 19, 2017

(87) PCT Pub. No.: WO2016/096721
PCT Pub. Date: Jun. 23, 2016

(65) Prior Publication Data
US 2018/0162877 A1 Jun. 14, 2018

(30) Foreign Application Priority Data

Dec. 19, 2014 (EP) ..................................... 14199096
Sep. 29, 2015 (EP) ..................................... 15187501

(51) Int. Cl.
| | | |
|---|---|---|
| A61K 31/519 | (2006.01) | |
| C07D 495/04 | (2006.01) | |
| C07D 519/00 | (2006.01) | |
| A61P 37/00 | (2006.01) | |
| A61P 29/00 | (2006.01) | |
| A61P 35/00 | (2006.01) | |

(52) U.S. Cl.
CPC ............ *C07D 519/00* (2013.01); *A61P 29/00* (2018.01); *A61P 35/00* (2018.01); *A61P 37/00* (2018.01); *C07D 495/04* (2013.01)

(58) Field of Classification Search
CPC ........................... A61K 31/519; C07D 495/04
USPC .......................................... 514/267; 544/250
See application file for complete search history.

(56) References Cited

U.S. PATENT DOCUMENTS

| | | | |
|---|---|---|---|
| 5,011,472 A | 4/1991 | Aebischer et al. | |
| 5,023,252 A | 6/1991 | Hseih | |

FOREIGN PATENT DOCUMENTS

| | | |
|---|---|---|
| WO | 2005/010008 | 2/2005 |
| WO | 2006/023843 | 3/2006 |
| WO | 2012/097013 | 7/2012 |
| WO | 2013/174735 | 11/2013 |
| WO | 2013/174744 | 11/2013 |
| WO | 2014/118229 | 8/2014 |

OTHER PUBLICATIONS

International Search Report for PCT/EP2015/079587, six pages, dated Feb. 12, 2016.
Written Opinion of the ISA for PCT/EP2015/079587, seven pages, dated Feb. 12, 2016.
Azab "Utility of the enaminonitrile moiety in the synthesis of some biologically active thienopyrimidine derivatives" *Phosphorus, Sulfur and Silicon and the Related Elements*, vol. 183, No. 7, pp. 1766-1782 (Jun. 2008).
Mertens et al. "Regioselective sulfonylation and N- to 0-sulfonyl migration of quinazolin-4(3H)-ones and analogous thienopyrimidin-4(3H)-ones" *Journal of Organic Chemistry*, vol. 78, No. 18, pp. 8966-8979 (Aug. 2013).
Miyashita et al. "Aroylation of fused pyrimidines: Synthesis of 4-aroylfuro[2,3-d]-, 4-aroylthieno[2,3-d]-, and 4-aroylisoxazolo[5,4-d]pyrimidines" *Heterocycles*, vol. 45, No. 11, pp. 2159-2173 (1997).
Patil et al. "Synthesis of 7-methyl-4-substituted-5,6,7,8-tetrahydrobenzo[b]thieno[2,3-d] pyrimidines as antimicrobial agents" *Journal of the Indian Chemical Society*, vol. 68, No. 3, pp. 169-171 (Mar. 1991).
Shestopalov et al. "Microwave-assisted synthesis of substituted fluoroazines using KF•2H$_2$O" *Tetrahedron Letters*, vol. 50, No. 37, pp. 5727-5259 (Sep. 2009).
Ahn et al. "Pathophysiology and immune dysfunction in endometriosis" BioMed Res. Int. 2015:795976 (2015).

(Continued)

*Primary Examiner* — Brenda L Coleman
(74) *Attorney, Agent, or Firm* — Morrison & Foerster LLP

(57) ABSTRACT

The present invention relates to substituted pyrazolopyridinamine compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative and/or angiogenesis disorder, inflammatory disease and disease associated with inflammatory pain, as a sole agent or in combination with other active ingredients.

22 Claims, 1 Drawing Sheet
Specification includes a Sequence Listing.

(56) References Cited

OTHER PUBLICATIONS

Anand et al. "Clinical trial of the p38 MAP kinase inhibitor dilmapimod in neuropathic pain following nerve injury" Eur. J. Pain 15:1040-1048 (2011).
Berge et al. "Pharmaceutical Salts" J. Pharmaceut. Sci. 66:1-19 (1977).
Blagden et al. "The biological and therapeutic relevance of mRNA translation in cancer" Nature 8:280-291 (2011).
Boesch et al. "An expedient method for resolution of 3-amino-3-(3'-pyridyl)propionic acid and related compounds" Org. Process Res. Dev. 5:23-27 (2001).
Brown et al. "p38 MAP kinase inhibitors as potential therapeutics for the treatment of joint degeneration and pain associated with osteoarthritis" J. Inflamm. 5:1-8 (2008).
Buxade et al. "The MNKs: MAP kinase-interacting kinases (MAP kinase signal-integrating kinases)" Front. Biosci. 13:5359-5374 (2008).
Cendrowski et al. "MNK1 is a novel acinar cell-specific kinase required for exocrine pancreatic secretion and response to pancreatitis in mice" Gut 64:937-947 (2014).
Chaplan et al. "Quantitative assessment of tactile allodynia in the rat paw" J. Neurosci. Meth. 53:55-63 (1994).
Cheng et al. "p38 mediates mechanical allodynia in a mouse model of type 2 diabetes" Mol. Pain 6:1-14 (2010).
Chrestensen et al. "Loss of MNK function sensitizes fibroblasts to serum-withdrawal induced apoptosis" Genes Cells 12:1133-1140 (2007).
Chrestensen et al. "MNK1 and MNK2 regulation in HER2-overexpressing breast cancer lines" J. Biol. Chem. 282:4243-4252 (2007).
Christmann et al. *Asymmetric Synthesis: The Essentials* $2^{nd}$ Ed., Wiley, (2007).
Crouch et al. "The use of ATP bioluminescence as a measure of cell proliferation and cytotoxicity" J. Immunol. Meth. 160:81-88 (1993).
Cunningham "A growing issue: Cell proliferation assays" The Scientist 15:26 (2001).
Fehr et al. "Syntheses of the enantiomers of γ-cyclogeranic acid, γ-cyclocitral, and γ-damascone: Enantioselective protonation of enolates" Helv. Chim. Acta 78:539-552 (1995).
Fortin et al. "Translational control of human neutrophil responses by MNK1" J. Leukoc. Biol. 94:693-703 (2013).
Gerlach et al. "[Effects of reaction conditions on the enantioseiective protonation of lactone enolates]" Chem. Berch. 127:1981-1988 with English abstract (1994).
Gewald et al. "[2-Aminothiophenes from methylene active nitriles, carbonyl compounds and sulfur]" Chem. Berch. 99:94-100 (1966).
Greene et al. *Protective Groups in Organic Synthesis* $3^{rd}$ Ed., Wiley (1999).
Hill et al. "Pamapimod, a novel p38 mitogen-activated protein kinase inhibitor: Preclinical analysis of efficacy and selectivity" J. Pharmacol. Exp. Ther. 327:610-619 (2008).
International Union of Pure and Applied Chemistry "Rules for the nomenclature of organic chemistry section E: Stereochemistry" Pure Appl. Chem. 45:11-30 (1976).
Jauch et al. "Crystal structures of the MNK2 kinase domain reveal an inhibitory conformation and a zinc binding site" Structure 13:1559-1568 (2005).
Jauch et al. "Mitogen-activated protein kinases interacting kinases are autoinhibited by a reprogrammed activation segment" EMBO J. 25:4020-4032 (2006).
Ji et al. "MAP kinase and pain" Brain Res. Rev. 60:135-148 (2009).
Joshi et al. "MNK kinases in cytokine signaling and regulation of cytokine responses" Biomol. Concepts. 3:127-139 (2012).
Joshi et al. "MNK kinase pathway: Cellular functions and biological outcomes" World J. Biol. Chem. 5:321-333 (2014).
Kendall "Synthesis and reactions of pyrazolo[1,5-a]pyridines and related heterocycles" Curr. Org. Chem. 15:2481-2518 (2011).
Kendall et al. "Discovery of pyrazolo[1,5-a]pyridines as p110α-selective PI3 kinase inhibitors" Bioorg. Med. Chem. 20:69-85 (2012).
Kivitz et al. "A randomized, placebo-controlled phase 2 study of ARRY-797 in patients osteoarthritis pain refractory to NSAID treatment showed statistically significant improvements in WOMAC pain and in biomarkers of bone and cartilage degradation" ACR/ARHP Annual Meeting, abstract L1, three pages (2012).
Kjellerup et al. "Pro-inflammatory cytokine release in keratinocytes is mediated through the MAPK signal-integrating kinases" Exp. Dermatol. 17:498-504 (2008).
Konicek et al. "Therapeutic inhibition of MAP kinase interacting kinase blocks eukaryotic initiation factor 4E phosphorylation and suppresses outgrowth of experimental lung metastases" Cancer Res. 71:1849-1857 (2011).
Konicek et al. "Targeting the eIF4F translation initiation complex for cancer therapy" Cell Cycle 7:2466-2471 (2008).
Lin et al. "p38 MAPK: A potential target of chronic pain" Curr. Med. Chem. 21:4405-4418 (2014).
Malutan et al. "Pro-inflammatory cytokines for evaluation of inflammatory status in endometriosis" Centr. Eur. J. Immunol. 40:96-102 (2015).
Melemedjian et al. "IL-6- and NGF-induced rapid control of protein synthesis and noci-ceptive plasticity via convergent signaling to the eIF4F complex" J. Neurosci. 30:15113-15123 (2010).
Miyazawa "Enzymatic resolution of amino acids via ester hydrolysis" Amino Acids 16:191-213 (1999).
Nema et al. "Excipients and their use in injectable products" PDA J. Pharm. Sci. Technol. 51:166-171 (1997).
Park et al. "Efficient palladium-catalyzed amination of aryl chlorides using dicyclohexyl-amino[(2,6-dimethyl)morpholino]phenylphosphine as a PN2 ligand" Synthesis 5:0815-0823 (2009).
Powell et al. "Compendium of excipients for parenteral formulations" PDA J. Pharm. Sci. Technol. 5:238-239 (1998).
Rowlett et al. "MNK kinases regulate multiple TLR pathways and innate proinflammatory cytokines in macrophages" Am. J. Physiol. Gastrointest. Liver Physiol. 294:G452-G459 (2008).
Roy et al. "A novel method for large-scale synthesis of lamivudine through cocrystal formation of racemic lamivudine with (S)-(−)-1,1'-bi(2-naphthol) [(S)-(BINOL)]" Org. Process Res. Dev. 13:450-455 (2009).
Shiina et al. "Non-enzymatic dynamic kinetic resolution of racemic α-arylalkanoic acids: An advanced asymmetric synthesis of chiral nonsteroidal anti-inflammatory drugs (NSAIDs)" Catal. Sci. Technol. 2:2200-2205 (2012).
Shiina et al. "Kinetic resolution of racemic carboxylic acids using achiral alcohols by the promotion of benzoic anhydrides and tetramisole derivatives: Production of chiral non-steroidal anti-inflammatory drugs and their esters" Eur. J. Org. Chem. 35:5887-5890 (2008).
Sikora et al. "Imbalance in cytokines from interleukin-1 family— Role in pathogenesis of endometriosis" Am. J. Reprod. Immunol. 68:138-145 (2012).
Storz et al. "Process research of (R)-cyclohexyl lactic acid and related building blocks: A comparative study" Org. Process Res. Dev. 7:559-570 (2003).
Strickley "Parental formulations of small molecules therapeutics marketed in the United States" J. Pharm. Sci. Technol. 6:324-349 (1999).
Tosti et al. "Pathogenetic mechanisms of deep infiltrating endometriosis" Reprod. Sci. 22:1053-1059 (2015).
Ueda et al. "MNK2 and MNK1 are essential for constitutive and inducible phosphorylation of eukaryotic initiation factor 4E but not for cell growth or development" Mol. Cell. Biol. 24:6539-6549 (2004).
Wendel et al. "Dissecting eIF4E action in tumorigenesis" Genes Dev. 21:3232-3237 (2007).
Yoshino et al. "Possible pathophysiological roles of mitogen-activated protein kinases (MAPKs) in endometriosis" Am. J. Reprod. Immunol. 52:306-311 (2004).
Yoshizawa et al. "Overexpression of phospho-eIF4E is associated with survival through AKT pathway in non-small cell lung cancer" Clin. Cancer Res. 16:240-248 (2010).

SEQUENCE LISTING

```
<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: biotin-Ahx-IKKRKLTRRKSLKG peptide

<400> SEQUENCE: 1

Ile Lys Lys Arg Lys Leu Thr Arg Arg Lys Ser Leu Lys Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: biotin-Ahx-AEEEEYFELVAKKK peptide

<400> SEQUENCE: 2
```

```
Ala Glu Glu Glu Glu Tyr Phe Glu Leu Val Ala Lys Lys Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: biotin-Ttds-YISPLKSPYKISEG peptide

<400> SEQUENCE: 3

Tyr Ile Ser Pro Leu Lys Ser Pro Tyr Lys Ile Ser Glu Gly
1               5                   10

<210> SEQ ID NO 4
<211> LENGTH: 13
<212> TYPE: PRT
<213> ORGANISM: Artificial Sequence
<220> FEATURE:
<223> OTHER INFORMATION: biotin-KVEKIGEGTYGVV peptide

<400> SEQUENCE: 4

Lys Val Glu Lys Ile Gly Glu Gly Thr Tyr Gly Val Val
1               5                   10

<210> SEQ ID NO 5
<211> LENGTH: 15
<212> TYPE: PRT
<213> ORGANISM: Artificial Sequence
<220> FEATURE:
<223> OTHER INFORMATION: biotin-Ahx-GGEEEEYFELVKKKK peptide

<400> SEQUENCE: 5

Gly Gly Glu Glu Glu Glu Tyr Phe Glu Leu Val Lys Lys Lys Lys
1               5                   10                  15
```

PYRAZOLOPYRIDINAMINES AS MKNK1 AND MKNK2 INHIBITORS

This application is the U.S. national phase of International Application No. PCT/EP2015/079587, filed 14 Dec. 2015, which designated the U.S. and claims priority to Application Nos. EP 14199096.0, filed 19 Dec. 2014, and EP 15187501.0, filed 29 Sep. 2015; the entire contents of each of which are hereby incorporated by reference.

The present invention relates to substituted pyrazolopyridinamine compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative, angiogenesis disorders, inflammatory diseases or diseases associated with inflammatory pain, as a sole agent or in combination with other active ingredients.

BACKGROUND OF THE INVENTION

The present invention relates to chemical compounds that inhibit MKNK1 kinase (also known as MAP Kinase interacting Kinase, Mnk1) and/or MKNK2 kinase (also known as MAP Kinase interacting Kinase, Mnk2). Human MKNKs comprise a group of four proteins encoded by two genes (Gene symbols: MKNK1 and MKNK2) by alternative splicing. The b-forms lack a MAP kinase-binding domain situated at the C-terminus. The catalytic domains of the MKNK1 and MKNK2 are very similar and contain a unique DFD (Asp-Phe-Asp) motif in subdomain VII, which usually is DFG (Asp-Phe-Gly) in other protein kinases and suggested to alter ATP binding [Jauch et al., Structure 13, 1559-1568, 2005 and Jauch et al., EMBO J25, 4020-4032, 2006].MKNK1a binds to and is activated by ERK and p38MAP Kinases, but not by JNK1.MKNK2a binds to and is activated only by ERK. MKNK1 b has low activity under all conditions and MKNK2b has a basal activity independent of ERK or p38MAP Kinase. [Buxade M et al., Frontiers in Bioscience 5359-5374,May 1, 2008]

MKNKs have been shown to phosphorylate eukaryotic initiation factor 4E (elF4E), heterogeneous nuclear RNA-binding protein A1 (hnRNP A1), polypyrimidine-tract binding protein-associated splicing factor (PSF), cytoplasmic phospholipase A2 (cPLA2) and Sprouty 2 (hSPRY2) [Buxade M et al., Frontiers in Bioscience 5359-5374,May 1, 2008]. elF4E is an oncogene that is amplified in many cancers and is phosphorylated exclusively by MKNKs proteins as shown by KO-mouse studies [Konicek et al., Cell Cycle 7:16, 2466-2471, 2008; Ueda et al., Mol Cell Biol 24, 6539-6549, 2004]. elF4E has a pivotal role in enabling the translation of cellular mRNAs. elF4E binds the 7-methylguanosine cap at the 5' end of cellular mRNAs and delivers them to the ribosome as part of the elF4F complex, also containing elF4G and elF4A. Though all capped mRNAs require elF4E for translation, a pool of mRNAs is exceptionally dependent on elevated elF4E activity for translation. These so-called "weak mRNAs" are usually less efficiently translated due to their long and complex 5'UTR region and they encode proteins that play significant roles in all aspects of malignancy including VEGF, FGF-2, c-Myc, cyclin D1, survivin, BCL-2, MCL-1, MMP-9, heparanase, etc. Expression and function of elF4E is elevated in multiple human cancers and directly related to disease progression [Konicek et al., Cell Cycle 7:16, 2466-2471, 2008].

MKNK1 and MKNK2 are the only kinases known to phosphorylate elF4E at Ser209. Overall translation rates are not affected by elF4E phosphorylation, but it has been suggested that elF4E phosphorylation contributes to polysome formation (i.e. multiple ribosome on a single mRNA) that ultimately enables more efficient translation of "weak mRNAs" [Buxade M et al., Frontiers in Bioscience 5359-5374, May 1, 2008]. Alternatively, phosphorylation of elF4E by MKNK proteins might facilitate elF4E release from the 5' cap so that the 48S complex can move along the "weak mRNA" in order to locate the start codon [Blagden S P and Willis A E, Nat Rev Clin Oncol. 8(5):280-91, 2011]. Accordingly, increased elF4E phosphorylation predicts poor prognosis in non-small cell lung cancer patients [Yoshizawa et al., Clin Cancer Res. 16(1):240-8, 2010]. Further data point to a functional role of MKNK1 in carcinogenesis, as overexpression of constitutively active MKNK1, but not of kinase-dead MKNK1, in mouse embryo fibroblasts accelerates tumor formation [Chrestensen C. A. et al., Genes Cells 12, 1133-1140, 2007]. Moreover, increased phosphorylation and activity of MKNK proteins correlate with overexpression of HER2 in breast cancer [Chrestensen, C. A. et al., J. Biol. Chem. 282, 4243-4252, 2007]. Constitutively active, but not kinase-dead, MKNK1 also accelerated tumor growth in a model using Ep-Myc transgenic hematopoietic stem cells to produce tumors in mice. Comparable results were achieved when an elF4E carrying a S209D mutation was analyzed. The S209D mutation mimicks a phosphorylation at the MKNK1 phosphorylation site. In contrast, a non-phosphorylatable form of elF4E attenuated tumor growth [Wendel H G, et al., Genes Dev. 21(24):3232-7, 2007]. A selective MKNK inhibitor that blocks elF4E phosphorylation induces apoptosis and suppresses proliferation and soft agar growth of cancer cells in vitro. This inhibitor also suppresses outgrowth of experimental B16 melanoma pulmonary metastases and growth of subcutaneous HCT116 colon carcinoma xenograft tumors without affecting body weight [Konicek et al., Cancer Res. 71(5):1849-57, 2011]. In summary, elF4E phosphorylation through MKNK protein activity can promote cellular proliferation and survival and is critical for malignant transformation. Inhibition of MKNK activity may provide a tractable cancer therapeutic approach. Furthermore it has been found that MKNK1 is an acinar cell-specific kinase required for exocrine pancreatic secretion [Cendrowski J, Sanchez-Arévalo Lobo V J, Sendler M, et al. Gut Published Online First: Jul. 18, 2014; doi:10.1136/gutjnl-2013-306068].

The kinases MKNK1 and MKNK2 are important downstream targets of the Erk and p38 mitogen-activated protein kinase (MAPK) pathways and their activity can also be modulated by MAPK independent signals. The MKNKs are directly involved in regulating mRNA translation and, therefore, are key mediators of oncogenic progression and cytokine signaling. In particular, MAPK pathways such as Erk and p38 have been shown to play important roles in modulating immune responses by mediating the production of cytokines that control the initiation of innate immunity; the activation of adaptive immunity; and by regulating cellular responses to cytokines involved in immune responses. In addition, Erk and p38 contribute to pain sensitivity and p38 kinase inhibitors have shown pre-clinical and clinical efficacy regarding pain [Brown, Heitmeyer, et al., J Inflamm (Lond), 2008; Hill, Dabbagh, et al., J Pharmacol Exp TherJi, 2008; Gereau, et al., Brain Res Rev, 2009; Cheng, Dauch, et al., Mol Pain, 2010; Anand, Shenoy, et al., European Journal of Pain, 2011; Daves, Aitchison, et al., American College of Rheumatology Annual Meeting, 2012; Lin, Wang, et al., Curr Med Chem, 2014]. As MKNK kinases are effectors of MAPK pathways, these observations suggest that they may play important roles in mediating cytokine production and inflammatory pain. Recent studies support the involvement of MKNK kinases in different inflammatory processes [Rowlett, Chrestensen, et al., Am J Physiol Gastrointest Liver Physiol, 2008; Kjellerup, Kragballe, et al., Experimental Dermatology, 2008; Melemedjian, Asiedu, et al., J Neurosci, 2010; Fortin, Mayer, et al., Journal of Leukocyte Biolog, 2013]. Due to the induction of MKNK kinases by different inflammatory stimuli (sterile inflammation and pathogens) and their ability to regulate the expression of different cytokines which mediate the pathogenesis of multiple disorders such as auto-immune diseases, allergies, neurological disorders, sepsis, cardiovascular diseases, metabolic diseases, obesity and cancer. MKNKs represent a central node in regulating inflammation. [Joshi et al.; *World J Biol Chem* 2014 Aug. 26; 5(3): 321-333; Joschi et al., *Biomol Concepts.* 2012 April; 3(2): 127-139]

Imbalance in cytokines from Interleukin-1 family and their role in the pathogenesis of Endometriosis has been reported in the literature [*American Journal of Reproductive Immunology* 68 (2012) 138-145] as well as the possible pathophysiological roles of Mitogen-Activated Protein Kinases (MAPKs) in Endometriosis [Yoshino et al.; *AJRI* 2004; 52: 306-311]. More recently, the role of pro-inflammatory cytokines for evaluation of inflammatory status and their pathogenetic mechanisms in endometriosis has been illustrated [Tosti et al.; *Reproductive Sciences* 2015, 1-7; Malutan et al., *Centr Eur J Immunol* 2015; 40 (1): 96-102; Soo Hyun Ahn et al., *BioMed Research International, Vol.* 2015, Article ID 795976, 12 pages]. Women with endometriosis have elevated levels of key pro-inflammatory cytokines, i.e. IL-1β, IL-6, and TNF-α. At the same time, IL-1β and IL-6 could be used as predictors for endometriosis.

Substituted pyrazolopyridinamine compounds of general formula (I) have not been disclosed in prior art for the treatment or prophylaxis of different diseases.

So, the state of the art described above does not describe the specific substituted pyrazolopyridinamine compounds of general formula (I) of the present invention as defined herein or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have been found to effectively inhibit MKNK1 kinase.

Furthermore, the compounds according to the present invention have been found to effectively inhibit MKNK2 kinase.

In contrast to other MKNK1 and/or MKNK2 kinase inhibitors, the pyrazolopyridinamines according to the invention are mainly active on sterile and pathogenic inflammatory responses and do not interfere directly with cell viability.

The pyrazolopyridinamines according to the present invention may be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1 and/or MKNK2 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The pyrazolopyridinamines according to the present invention may be used for the treatment or prophylaxis of inflammatory and/or immunological diseases as described in the summary of the invention.

Furthermore, the compounds according to the invention may be used for the treatment or prophylaxis of a gynecological disease, preferably dysmenorrhea, dyspareunia or endometriosis, adenomyosis, endometriosis-associated pain, or other endometriosis-associated symptoms, wherein said symptoms are in particular endometriosis-associated proliferation, dysmenorrhea, dyspareunia, dysuria, or dyschezia.

SUMMARY OF THE INVENTION

The present invention covers compounds of general formula (I):

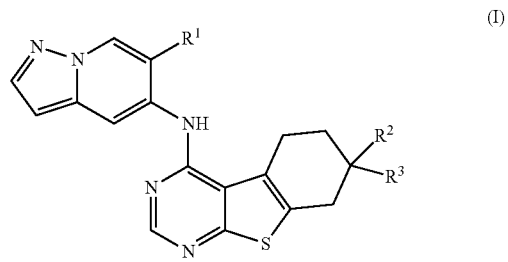

(I)

in which:
R$^1$ represents a hydrogen atom or a halogen atom or a group selected from: hydroxy-, cyano-, C$_1$-C$_6$-alkyl-, C$_2$-C$_6$-alkenyl-, C$_2$-C$_6$-alkynyl-, C$_1$-C$_6$-alkoxy-, halo-C$_1$-C$_6$-alkoxy-, C$_3$-C$_6$-cycloalkyl-, C$_4$-C$_8$-cycloalkenyl-, C$_3$-C$_6$-cycloalkyloxy-, (3- to 10-membered heterocycloalkyl)-, (3- to 10-membered heterocycloalkyl)-O—, C$_5$-C$_8$-cycloalkenyloxy-, (5- to 10-membered heterocycloalkenyl)-, (5- to 10-membered heterocycloalkenyl)-O—, —N(R$^{5a}$)R$^{5b}$, —SR$^{5a}$, and —SF$_5$;
wherein said C$_1$-C$_6$-alkyl-, C$_2$-C$_6$-alkenyl-, C$_2$-C$_6$-alkynyl-, C$_1$-C$_6$-alkoxy-, C$_3$-C$_6$-cycloalkyl-, C$_4$-C$_8$-cycloalkenyl-, C$_3$-C$_6$-cycloalkyloxy-, (3- to 10-membered heterocycloalkyl)-, (3- to 10-membered heterocycloalkyl)-O—, C$_5$-C$_8$-cycloalkenyloxy-, (5- to 10-membered heterocycloalkenyl)-, and (5- to 10-membered heterocycloalkenyl)-O— group is optionally substituted, identically or differently, with 1, 2, 3, 4 or 5 R$^4$ groups;
R$^2$ represents a hydrogen atom or a group selected from: C$_1$-C$_6$-alkyl-, C$_2$-C$_6$-alkenyl-, C$_1$-C$_6$-alkoxy-, halo-C$_1$-C$_6$-alkyl-, and halo-C$_1$-C$_6$-alkoxy-;

wherein said $C_1$-$C_6$-alkyl-, $C_2$-$C_6$-alkenyl-, and $C_1$-$C_6$-alkoxy-group is optionally substituted, identically or differently, with 1, 2, or 3 $R^7$ groups;

$R^3$ represents a hydrogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, and —$(CH_2)_q$—X—$(CH_2)_p$—$R^5$;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- and heteroaryl-group is optionally substituted, identically or differently, with 1, 2, 3, 4 or 5 $R^4$ groups;

X represents a bond or a bivalent group selected from: —O—, —S—, —S(=O)—, —S(=O)$_2$—, —S(=O)—N($R^{5a}$)—, —N($R^{5a}$)—S(=O)—, —S(=O)$_2$—N($R^{5a}$)—, —N($R^{5a}$)—S(=O)$_2$—, —S(=O)(=N$R^{5a}$)—, —C(=O)—, —N($R^{5a}$)—, —C(=O)—O—, —O—C(=O)—, —C(=S)—O—, —O—C(=S)—, —C(=O)—N($R^{5a}$)—, —N($R^{5a}$)—C(=O)—, —N($R^{5a}$)—C(=O)—N($R^{5b}$)—, —O—C(=O)—N($R^{5a}$)—, —N($R^{5a}$)—C(=O)—O—;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^6$—O—, —C(=O)—$R^6$, —C(=O)—O—$R^6$, —O—C(=O)—$R^6$, —N($R^{6a}$)—C(=O)—$R^{6b}$, —N($R^{6a}$)—C(=O)—O—$R^{6b}$, —N($R^{6a}$)—C(=O)—N($R^{6b}$)$R^{6c}$, —N($R^{6a}$)$R^{6b}$, —N($R^{6a}$)$R^{6d}$, —C(=O)—N($R^{6a}$)$R^{6b}$, $R^6$—S—, $R^6$—S(=O)—, $R^6$—S(=O)$_2$—, —N($R^{6a}$)—S(=O)—$R^{6b}$, —S(=O)—N($R^{6a}$)$R^{6b}$, —N($R^{6a}$)—S(=O)$_2$—$R^{6b}$, —S(=O)$_2$—N($R^{6a}$)$R^{6b}$, —S(=O)=N($R^{6a}$)$R^{6b}$, —N=S(=O)($R^{6a}$)$R^{6b}$ or —($C_1$-$C_6$-alkyl)-N($R^{6a}$)$R^{6b}$;

$R^{5a}$, $R^{5b}$ are the same or different and are independently selected from $R^5$;

$R^5$ represents a hydrogen atom or a group selected from: $C_1$-$C_6$-alkyl-, $C_3$-$C_6$-cycloalkyl-, 3- to 10-membered heterocycloalkyl-, aryl-, and heteroaryl-;

wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 $R^4$ groups;

or

N($R^{5a}$)$R^5$ together represent a 3- to 10-membered heterocycloalkyl-group, said group being optionally substituted, identically or differently, with 1, 2, 3, 4 or 5 $R^4$ groups;

$R^{6a}$, $R^{6b}$, $R^{6c}$ are the same or different and are independently selected from $R^6$;

$R^6$ represents a hydrogen atom, a $C_1$-$C_6$-alkyl- or a $C_3$-$C_6$-cycloalkyl-group;

or $R^{6a}$ and $R^{6b}$, or $R^{6a}$ and $R^{6c}$, or $R^{6b}$ and $R^{6c}$ together may form a $C_2$-$C_6$-alkylene group, in which optionally one methylene can be replaced by —O—, —C(=O)—, —NH—, or —N($C_1$-$C_4$-alkyl)-;

$R^{5d}$ represents —($C_1$-$C_6$-alkyl)-N($R^{6a}$)$R^{6b}$;

$R^7$ represents halo-, hydroxy-, oxo-(O=), cyano-, nitro-, p represents an integer of 0, 1, 2 or 3;

q represents an integer of 0, 1, 2 or 3;

or a tautomer, an N-oxide, a hydrate, a solvate, or a salt thereof, or a mixture of same.

The present invention further relates to methods of preparing compounds of general formula (I), to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

Figure 1A:
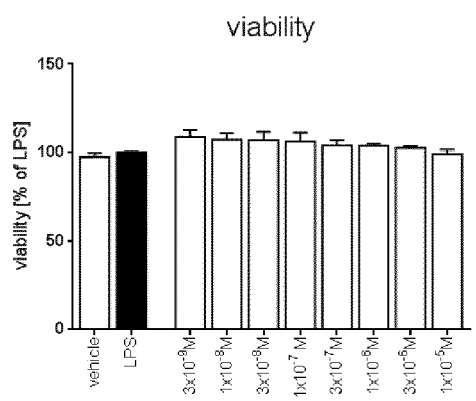
FIG. 1a depicts effect of the compound of example 41 on cell viability in human peripheral blood mononuclear cells in vitro.

The terms as mentioned in the present text have preferably the following meanings:

The term "halogen atom", "halo-" or "Hal-" is to be understood as meaning a fluorine, chlorine, bromine or iodine atom, preferably a fluorine, chlorine or bromine atom.

The term "$C_1$-$C_{10}$-alkyl" is to be understood as preferably meaning a linear or branched, saturated, monovalent hydrocarbon group having 1, 2, 3, 4, 5, 6, 7, 8, 9 or 10 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3, 4, 5 or 6 carbon atoms ("$C_1$-$C_6$-alkyl"), more particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group; even more particularly 1, 2 or 3 carbon atoms ("$C_1$-$C_3$-alkyl"), e.g. a methyl, ethyl, n-propyl- or iso-propyl group.

The term "$C_1$-$C_{10}$-alkylene" is to be understood as preferably meaning a linear or branched, saturated, bivalent hydrocarbon group having 1, 2, 3, 4, 5, 6, 7, 8, 9 or 10 carbon atoms, e.g. a methylene, ethylene, n-propylene, n-butylene, n-pentylene, 2-methylbutylene, n-hexylene, 3-methylpentylene group, or an isomer thereof. Particularly, said group is linear and has 2, 3, 4 or 5 carbon atoms ("$C_2$-$C_5$-alkylene"), e.g. an ethylene, n-propylene, n-butylene, n-pentylene group, more particularly 3 or 4 carbon atoms ("$C_3$-$C_4$-alkylene"), e.g. an n-propylene or n-butylene group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —$CF_3$, —$CHF_2$, —$CH_2F$, —$CF_2CF_3$ or —$CH_2CF_3$.

The term "$C_1$-$C_6$-alkoxy" is to be understood as preferably meaning a linear or branched, saturated, monovalent, hydrocarbon group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$ or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$ or —$CH_2CH_2OCH_2CF_3$.

The term "$C_2$-$C_{10}$-alkenyl" is to be understood as preferably meaning a linear or branched, monovalent hydrocarbon group, which contains one or more double bonds, and which has 2, 3, 4, 5, 6, 7, 8, 9 or 10 carbon atoms, particularly 2, 3, 4, 5 or 6 carbon atoms ("$C_2$-$C_6$-alkenyl"), more particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropyl prop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_{10}$-alkynyl" is to be understood as preferably meaning a linear or branched, monovalent hydrocarbon group which contains one or more triple bonds, and which contains 2, 3, 4, 5, 6, 7, 8, 9 or 10 carbon atoms, particularly 2, 3, 4, 5 or 6 carbon atoms ("$C_2$-$C_6$-alkynyl"), more particularly 2 or 3 carbon atoms ("$C_2$-$C_3$-alkynyl"). Said $C_2$-$C_{10}$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylbut-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl.

The term "$C_3$-$C_{10}$-cycloalkyl" is to be understood as meaning a saturated, monovalent, mono-, or bicyclic hydrocarbon ring which contains 3, 4, 5, 6, 7, 8, 9 or 10 carbon atoms ("$C_3$-$C_{10}$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl, or a bicyclic hydrocarbon ring, e.g. a perhydropentalenylene or decalin ring. Particularly, said ring contains 3, 4, 5 or 6 carbon atoms ("$C_3$-$C_6$-cycloalkyl").

The term "$C_3$-$C_6$-cycloalkyloxy" refers to a ($C_3$-$C_6$-cycloalkyl)-O— group in which "$C_3$-$C_6$-cycloalkyl" is as defined herein. Examples include, but are not limited to, cyclopropanoxy and cyclobutanoxy.

The term "$C_4$-$C_{10}$-cycloalkenyl" is to be understood as preferably meaning a non-aromatic, monovalent, mono- or bicyclic hydrocarbon ring which contains 4, 5, 6, 7, 8, 9 or 10 carbon atoms and one, two, three or four double bonds, in conjugation or not, as the size of said cycloalkenyl ring allows. Said $C_4$-$C_{10}$-cycloalkenyl group is for example, a monocyclic hydrocarbon ring, e.g. a cyclobutenyl, cyclopentenyl, or cyclohexenyl or a bicyclic hydrocarbon, e.g.:

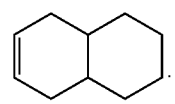

The term "$C_5$-$C_8$-cycloalkenyloxy" refers to a ($C_5$-$C_8$-cycloalkenyl)-O— group in which "$C_5$-$C_8$-cycloalkenyl" is as defined herein.

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from —C(=O)—, —O—, —S—, —S(=O)—, —S(=O)$_2$—, —N(R$^a$)—, in which R$^a$ represents a hydrogen atom or a $C_1$-$C_6$-alkyl group; it being possible for said heterocycloalkyl group to be attached to the rest of the molecule via any one of the carbon atoms or, if present, the nitrogen atom. Heterospirocycloalkyl, heterobicycloalkyl and bridged heterocycloalkyl, as defined infra, are also included within the scope of this definition.

The term "heterospirocycloalkyl" is to be understood as meaning a saturated, monovalent bicyclic hydrocarbon radical in which the two rings share one common ring carbon atom, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom or a $C_1$-$C_6$-alkyl- or $C_3$-$C_7$-cycloalkyl-group; it being possible for said heterospirocycloalkyl-group to be attached to the rest of the molecule via any one of the carbon atoms or, if present, the nitrogen atom. Said heterospirocycloalkyl-group is, for example, azaspiro[2.3]hexyl-, azaspiro[3.3]heptyl-, oxaazaspiro[3.3]heptyl-, thiaazaspiro[3.3]heptyl-, oxaspiro[3.3]heptyl-, oxazaspiro[5.3]nonyl-, oxazaspiro[4.3]octyl-, oxazaspiro[5.5]undecyl-, diazaspiro[3.3]heptyl-, thiazaspiro[3.3]heptyl-, thiazaspiro[4.3]octyl-, or azaspiro[5.5]decyl-.

The term "heterobicycloalkyl" is to be understood as meaning a saturated, monovalent bicyclic hydrocarbon radical in which the two rings share two immediately adjacent ring atoms, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom or a $C_1$-$C_6$-alkyl- or $C_3$-$C_7$-cycloalkyl-group; it being possible for said heterobicycloalkyl-group to be attached to the rest of the molecule via any one of the carbon atoms or, if present, the nitrogen atom. Said heterobicyoalkyl-group is, for example, azabicyclo[3.3.0]octyl-, azabicyclo[4.3.0]nonyl-, diazabicyclo[4.3.0]nonyl-, oxazabicyclo[4.3.0]nonyl-, thiazabicyclo[4.3.0]nonyl-, or azabicyclo[4.4.0]decyl-.

The term "bridged heterocycloalkyl" is to be understood as meaning a saturated, monovalent bicyclic hydrocarbon radical in which the two rings share two common ring atoms which are not immediately adjacent, and wherein said bicyclic hydrocarbon radical contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- or $C_3$-$C_7$-cycloalkyl-group; it being possible for said bridged heterocycloalkyl-group to be attached to the rest of the molecule via any one of the carbon atoms or, if present, the nitrogen atom. Said bridged heterocycloalkyl-group is, for example, azabicyclo[2.2.1]heptyl-, oxazabicyclo[2.2.1]heptyl-, thiazabicyclo[2.2.1]heptyl-, diazabicyclo[2.2.1]heptyl-, azabicyclo[2.2.2]octyl-, diazabicyclo[2.2.2]octyl-, oxazabicyclo[2.2.2]octyl-, thiazabicyclo[2.2.2]octyl-, azabicyclo[3.2.1]octyl-, diazabicyclo[3.2.1]octyl-, oxazabicyclo[3.2.1]octyl-, thiazabicyclo[3.2.1]octyl-, azabicyclo[3.3.1]nonyl-, diazabicyclo[3.3.1]nonyl-, oxazabicyclo[3.3.1]nonyl-, thiazabicyclo[3.3.1]nonyl-, azabicyclo[4.2.1]nonyl-, diazabicyclo[4.2.1]nonyl-, oxazabicyclo[4.2.1]nonyl, thiazabicyclo[4.2.1]nonyl-, azabicyclo[3.3.2]decyl-, diazabicyclo[3.3.2] decyl-, oxazabicyclo[3.3.2]decyl-, thiazabicyclo[3.3.2]decyl-, or azabicyclo[4.2.2]decyl-.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said 3- to 10-membered heterocycloalkyl can contain 4 or 5 carbon atoms, and one or more of the above-mentioned heteroatom-containing groups (a "5- to 6-membered heterocycloalkyl").

Particularly, without being limited thereto, said 3- to 10-membered heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

Said 3- to 10-membered heterocycloalkyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

The term "4- to 10-membered heterocycloalkenyl", is to be understood as meaning an non-aromatic, unsaturated, monovalent, mono- or bicyclic hydrocarbon ring which contains 3, 4, 5, 6, 7, 8 or 9 carbon atoms, and one or more heteroatom-containing groups selected from —C(=O)—, —O—, —S—, —S(=O)—, —S(=O)$_2$—, —N(R$^a$)—, in which R$^a$ represents a hydrogen atom or a $C_1$-$C_6$-alkyl group; it being possible for said heterocycloalkenyl group to be attached to the rest of the molecule via any one of the carbon atoms or, if present, the nitrogen atom. Examples of said heterocycloalkenyl are e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic or partially aromatic, mono-, bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group. Preferably, the aryl group is a phenyl group.

The term "heteroaryl" is understood as preferably meaning a monovalent, monocyclic, bicyclic or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.;

or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, particularly $C_1$-$C_2$, $C_1$-$C_3$, $C_1$-$C_4$, $C_1$-$C_5$, $C_1$-$C_6$, more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$, particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_6$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "protective group" is a protective group attached to a nitrogen in intermediates used for the preparation of compounds of the general formula (I). Such groups are introduced e.g. by chemical modification of the respective amino group in order to obtain chemoselectivity in a subsequent chemical reaction. Protective groups for amino groups are described for example in T. W. Greene and P. G. M. Wuts in *Protective Groups in Organic Synthesis*, $3^{rd}$ edition, Wiley 1999; more specifically, said groups can be selected from substituted sulfonyl groups, such as mesyl-, tosyl- or phenylsulfonyl-, acyl groups such as benzoyl, acetyl or tetrahydropyranoyl-, or carbamate based groups, such as tert.-butoxycarbonyl (Boc), or can include silicon, as in e.g. 2-(trimethylsilyl)ethoxymethyl (SEM).

The invention includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^{2}$H (deuterium), $^{3}$H (tritium), $^{11}$C, $^{13}$C, $^{14}$C, $^{15}$C, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^{3}$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

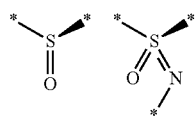

for example, in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

Pure stereoisomers can be obtained by resolution of racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel O D and Chiracel O J among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R) or (S) isomers, or (E) or (Z) isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

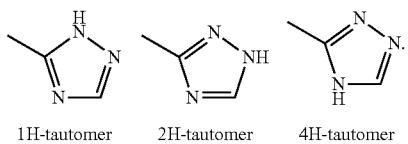

1H-tautomer   2H-tautomer   4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol, or with a quaternary ammonium salt, such as tetramethylammonium, tetraethylammonium, tetra(n-propyl)ammonium, tetra (n-butyl)ammonium, or N-benzyl-N,N,N-trimethylammonium.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula (I):

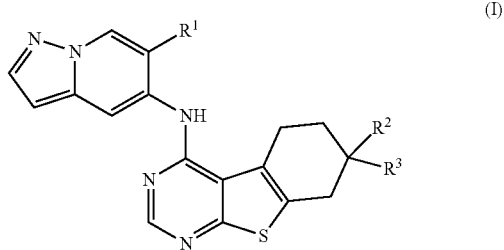

(I)

in which:

$R^1$ represents a hydrogen atom or a halogen atom or a group selected from: hydroxy-, cyano-, $C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —N($R^{5a}$)$R^{5b}$, —S$R^{5a}$, and —SF$_5$; wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, and (5- to 10-membered heterocycloalkenyl)-O— group is optionally substituted, identically or differently, with 1, 2, 3, 4 or 5 $R^4$ groups;

$R^2$ represents a hydrogen atom or a group selected from: $C_1$-$C_6$-alkyl-, $C_2$-$C_6$-alkenyl-, $C_1$-$C_6$-alkoxy-, halo-$C_1$-$C_6$-alkyl-, and halo-$C_1$-$C_6$-alkoxy-; wherein said $C_1$-$C_6$-alkyl-, $C_2$-$C_6$-alkenyl-, and $C_1$-$C_6$-alkoxy-group is optionally substituted, identically or differently, with 1, 2, or 3 $R^7$ groups;

$R^3$ represents a hydrogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, and —(CH$_2$)$_q$—X—(CH$_2$)$_p$—$R^5$; wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- and heteroaryl-group is optionally substituted, identically or differently, with 1, 2, 3, 4 or 5 $R^4$ groups;

X represents a bond or a bivalent group selected from: —O—, —S—, —S(═O)—, —S(═O)$_2$—, —S(═O)—N($R^{5a}$)—, —N($R^{5a}$)—S(═O)—, —S(═O)$_2$—N($R^{5a}$)—, —N($R^{5a}$)—S(═O)$_2$—, —S(═O)(═N$R^{5a}$)—, —C(═O)—, —N($R^{5a}$)—, —C(═O)—O—, —O—C(═O)—, —C(═S)—O—, —O—C(═S)—, —C(═O)—N($R^{5a}$)—, —N($R^{5a}$)—C(═O)—, —N($R^{5a}$)—C(═O)—N($R^{5b}$)—, —O—C(═O)—N($R^{5a}$)—, —N($R^{5a}$)—C(═O)—O—;

$R^4$ represents halo-, hydroxy-, oxo-(O═), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^6$—O—, —C(═O)—$R^6$, —C(═O)—O—$R^6$, —O—C(═O)—$R^6$, —N($R^{6a}$)—C(═O)—$R^{6b}$, —N($R^{6a}$)—C(═O)—O—$R^{6b}$, —N($R^{6a}$)—C(═O)—N($R^{6b}$)$R^{6c}$, —N($R^{6a}$)$R^{6b}$, —N($R^{6a}$)$R^{6d}$, —C(═O)—N($R^{6a}$)$R^{6b}$, $R^6$—S—, $R^6$—S(═O)—, $R^6$—S(═O)$_2$—, —N($R^{6a}$)—S(═O)—$R^{6b}$, —S(═O)—N($R^{6a}$)$R^{6b}$, —N($R^{6a}$)—S(═O)$_2$—$R^{6b}$, —S(═O)$_2$—N($R^{6a}$)$R^{6b}$, —S(═O)═N($R^{6a}$)$R^{6b}$, —N═S(═O)($R^{6a}$)$R^{6b}$ or —($C_1$-$C_6$-alkyl)-N($R^{6a}$)$R^{6b}$;

$R^{5a}$, $R^{5b}$ are the same or different and are independently selected from $R^5$;

$R^5$ represents a hydrogen atom or a group selected from: $C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 $R^4$ groups;

or

N($R^{5a}$)$R^5$ together represent a 3- to 10-membered heterocycloalkyl-group, said group being optionally substituted, identically or differently, with 1, 2, 3, 4 or 5 $R^4$ groups;

$R^{6a}$, $R^{6b}$, $R^{6c}$ are the same or different and are independently selected from $R^6$;

$R^6$ represents a hydrogen atom, a $C_1$-$C_6$-alkyl- or a $C_3$-$C_6$-cycloalkyl-group;

or $R^{6a}$ and $R^{6b}$, or $R^{6a}$ and $R^{6c}$, or $R^{6b}$ and $R^{6c}$ together may form a $C_2$-$C_6$-alkylene group, in which optionally one methylene can be replaced by —O—, —C(═O)—, —NH—, or —N($C_1$-$C_4$-alkyl)-;

$R^{6d}$ represents —($C_1$-$C_6$-alkyl)-N($R^{6a}$)$R^{6b}$;

$R^7$ represents halo-, hydroxy-, oxo-(O═), cyano-, nitro-, p represents an integer of 0, 1, 2 or 3;

q represents an integer of 0, 1, 2 or 3;

or a tautomer, an N-oxide, a hydrate, a solvate, or a salt thereof, or a mixture of same.

In a preferred embodiment, the invention relates to compounds of formula (I), supra, in which $R^1$ represents a hydrogen atom or a halogen atom or a group selected from: hydroxy-, cyano-, $C_2$-$C_6$-alkenyl-, $C_2$-$C_6$-alkynyl-, $C_1$-$C_6$- alkoxy-, halo-$C_1$-$C_6$-alkyl-, halo-$C_1$-$C_6$-alkoxy-, hydroxy-$C_1$-$C_6$-alkyl-, $C_1$-$C_3$-alkoxy-$C_1$-$C_3$-alkyl-, —$N(R^{5a})R^{5b}$, —$SR^{5a}$, —$SCF_3$, and —$SF_5$.

In another preferred embodiment, the invention relates to compounds of formula (I), supra, wherein $R^1$ represents a hydrogen atom or a halogen atom or a group selected from: cyano-, $C_1$-$C_6$-alkoxy-, halo-$C_1$-$C_6$-alkoxy-, hydroxy-$C_1$-$C_6$-alkyl-, $C_1$-$C_3$-alkoxy-$C_1$-$C_3$-alkyl-, and —S—$C_1$-$C_6$-alkyl).

In another preferred embodiment, the invention relates to compounds of formula (I), supra, wherein $R^1$ represents a hydrogen atom or a group selected from: cyano-, $C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_3$-alkoxy-$C_1$-$C_3$-alkyl-, and —S—($C_1$-$C_6$-alkyl).

In another preferred embodiment, the invention relates to compounds of formula (I), supra, wherein $R^1$ represents a hydrogen atom or a group selected from: $C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, and —S—($C_1$-$C_3$-alkyl).

In another preferred embodiment, the invention relates to compounds of formula (I), supra, wherein $R^1$ represents a hydrogen atom or a group selected from: $C_1$-$C_3$-alkyl-, $C_1$-$C_3$-alkoxy-, halo-$C_1$-$C_3$-alkyl-, and —S—($C_1$-$C_3$-alkyl).

In another preferred embodiment, the invention relates to compounds of formula (I), supra, wherein $R^1$ represents a hydrogen atom or a group selected from: —O—$CH_3$, —S—$CH_3$.

In another preferred embodiment, the invention relates to compounds of formula (I), supra, wherein $R^1$ represents a hydrogen atom or a chlorine atom or a group selected from: —O—$CH_3$, —$N(CH_3)_2$.

In another preferred embodiment, the invention relates to compounds of formula (I), supra, wherein $R^1$ represents a hydrogen atom a —O—$CH_3$ group.

In another preferred embodiment, the invention relates to compounds of formula (I), supra, wherein $R^1$ represents a hydrogen atom.

In another preferred embodiment, the invention relates to compounds of formula (I), supra, wherein $R^1$ represents a —O—$CH_3$ group.

In another preferred embodiment, the invention relates to compounds of formula (I), supra, wherein $R^2$ represents a hydrogen atom.

In another preferred embodiment, the invention relates to compounds of formula (I), supra, wherein $R^2$ represents a chlorine atom.

In another preferred embodiment, the invention relates to compounds of formula (I), supra, wherein $R^2$ represents a —$N(CH_3)_2$ group.

In another preferred embodiment, the invention relates to compounds of formula (I), supra, wherein $R^1$ represents a hydrogen atom and $R^2$ represents a hydrogen atom.

In another preferred embodiment, the invention relates to compounds of formula (Ia):

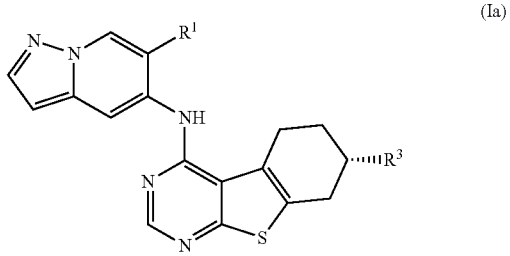

(Ia)

in which $R^1$ and $R^3$ are as defined for compounds of formula (I).

In another preferred embodiment, the invention relates to compounds of formula (Ia), supra, in which $R^1$ represents a hydrogen atom or a —O—$CH_3$ group, and in which and $R^3$ is as defined for compounds of formula (I).

In another preferred embodiment, the invention relates to compounds of formula (Ia), supra, in which $R^1$ represents a hydrogen atom, and in which and $R^3$ is as defined for compounds of formula (I).

In another preferred embodiment, the invention relates to compounds of formula (I), supra, wherein $R^3$ represents a hydrogen atom or a group selected from: $C_1$-$C_6$-alkyl-, $C_3$-$C_6$-cycloalkyl-, 3- to 10-membered heterocycloalkyl-, cyano-, and —$(CH_2)_q$—X—$(CH_2)_p$—$R^5$; wherein said $C_1$-$C_6$-alkyl-, $C_3$-$C_6$-cycloalkyl-, and 3- to 10-membered heterocycloalkyl-group is optionally substituted, identically or differently, with 1, 2, 3, 4 or 5 $R^4$ groups.

In another preferred embodiment, the invention relates to compounds of formula (I), supra, wherein $R^3$ represents a hydrogen atom or a group selected from: $C_1$-$C_6$-alkyl- and —$(CH_2)_q$—X—$(CH_2)_p$—$R^5$; wherein said $C_1$-$C_6$-alkyl-group is optionally substituted, identically or differently, with 1, 2, 3, 4 or 5 $R^4$ groups.

In another preferred embodiment, the invention relates to compounds of formula (I), supra, wherein $R^3$ represents a hydrogen atom.

In another preferred embodiment, the invention relates to compounds of formula (I), supra, wherein $R^3$ represents —$(CH_2)_q$—X—$(CH_2)_p$—$R^5$.

In another preferred embodiment, the invention relates to compounds of formula (I), supra, wherein $R^3$ represents —X—$R^5$.

In another preferred embodiment, the invention relates to compounds of formula (I), supra, wherein $R^3$ represents —C(=O)—O—$R^5$.

In another preferred embodiment, the invention relates to compounds of formula (I), supra, wherein $R^3$ represents —C(=O)—$R^5$.

In another preferred embodiment, the invention relates to compounds of formula (I), supra, wherein $R^3$ represents —C(=O)—$N(R^{5a})R^5$.

In another preferred embodiment, the invention relates to compounds of formula (I), supra, wherein $R^3$ represents —$S(=O)_2$—$R^5$.

In another preferred embodiment, the invention relates to compounds of formula (I), supra, wherein $R^3$ represents —C(=O)—$N(R^{5a})R^5$; and wherein $R^1$ represents a hydrogen atom.

In another preferred embodiment, the invention relates to compounds of formula (I), supra, wherein $R^3$ represents —C(=O)—$N(R^{5a})R^5$; and wherein $R^1$ represents a hydrogen atom or a —O—$CH_3$ group.

In another preferred embodiment, the invention relates to compounds of formula (I), supra, wherein $R^3$ represents —C(=O)—$N(R^{5a})R^5$; and wherein $R^1$ represents a —O—$CH_3$ group.

In another preferred embodiment, the invention relates to compounds of formula (I), supra, wherein $R^3$ represents —C(=O)—$N(R^{5a})R^5$; and wherein $R^2$ represents a hydrogen atom.

In another preferred embodiment, the invention relates to compounds of formula (I), supra, wherein $R^3$ represents —C(=O)—$N(R^{5a})R^5$; wherein $R^1$ represents a hydrogen atom, and wherein $R^2$ represents a hydrogen atom.

In another preferred embodiment, the invention relates to compounds of formula (I), supra, wherein $R^3$ represents —C(=O)—N($R^{5a}$)$R^5$; wherein $R^1$ represents a hydrogen atom or a —O—$CH_3$ group, and wherein $R^2$ represents a hydrogen atom.

In another preferred embodiment, the invention relates to compounds of formula (I), supra, wherein $R^3$ represents —C(=O)—N($R^{5a}$)$R^5$; wherein $R^1$ represents a —O—$CH_3$ group, and wherein $R^2$ represents a hydrogen atom.

In another preferred embodiment, the invention relates to compounds of formula (I), supra, wherein X represents a bond or a bivalent group selected from: —O—, —S—, —S(=O)—, —S(=O)$_2$—, —S(=O)—N($R^{5a}$)—, —N($R^{5a}$)—S(=O)—, —S(=O)$_2$—N($R^{5a}$)—, —N($R^{5a}$)—S(=O)$_2$—, —S(=O)(=N$R^{5a}$)—, —C(=O)—, —N($R^{5a}$)—, —C(=O)—O—, —O—C(=O)—, —C(=S)—O—, —O—C(=S)—, —C(=O)—N($R^{5a}$)—, and —N($R^{5a}$)—C(=O)—.

In another preferred embodiment, the invention relates to compounds of formula (I), supra, wherein X represents a bond or a bivalent group selected from: —S(=O)$_2$—, —C(=O)—, —N($R^{5a}$)—, —C(=O)—O—, and —C(=O)—N($R^{5a}$)—.

In another preferred embodiment, the invention relates to compounds of formula (I), supra, wherein X represents a bivalent group selected from: —S(=O)$_2$—, —C(=O)—, —N($R^{5a}$)—, —C(=O)—O—, and —C(=O)—N($R^{5a}$)—.

In another preferred embodiment, the invention relates to compounds of formula (I), supra, wherein X represents —S(=O)$_2$—.

In another preferred embodiment, the invention relates to compounds of formula (I), supra, wherein X represents —C(=O)—.

In another preferred embodiment, the invention relates to compounds of formula (I), supra, wherein X represents —N($R^{5a}$)—.

In another preferred embodiment, the invention relates to compounds of formula (I), supra, wherein X represents —C(=O)—O—.

In another preferred embodiment, the invention relates to compounds of formula (I), supra, wherein X represents —C(=O)—N($R^{5a}$)—.

In another preferred embodiment, the invention relates to compounds of formula (I), supra, wherein X represents —C(=O)— or —C(=O)—N($R^{5a}$)—.

In another preferred embodiment, the invention relates to compounds of formula (I), supra, wherein X represents —C(=O)—N($R^{5a}$)—; and wherein $R^1$ represents a hydrogen atom.

In another preferred embodiment, the invention relates to compounds of formula (I), supra, wherein X represents —C(=O)—N($R^{5a}$)—; and wherein $R^1$ represents a hydrogen atom or a —O—$CH_3$ group.

In another preferred embodiment, the invention relates to compounds of formula (I), supra, wherein X represents —C(=O)—N($R^{5a}$)—; and wherein $R^1$ represents a —O—$CH_3$ group.

In another preferred embodiment, the invention relates to compounds of formula (I), supra, wherein X represents —C(=O)—N($R^{5a}$)—; and wherein $R^2$ represents a hydrogen atom.

In another preferred embodiment, the invention relates to compounds of formula (I), supra, wherein X represents —C(=O)—N($R^{5a}$)—; wherein $R^1$ represents a hydrogen atom, and wherein $R^2$ represents a hydrogen atom.

In another preferred embodiment, the invention relates to compounds of formula (I), supra, wherein X represents —C(=O)—N($R^{5a}$)—; wherein $R^1$ represents a hydrogen atom or a —O—$CH_3$ group, and wherein $R^2$ represents a hydrogen atom.

In another preferred embodiment, the invention relates to compounds of formula (I), supra, wherein X represents —C(=O)—N($R^{5a}$)—; wherein $R^1$ represents a —O—$CH_3$ group, and wherein $R^2$ represents a hydrogen atom.

In another preferred embodiment, the invention relates to compounds of formula (Ib):

(Ib)

in which $R^1$, $R^{5a}$ and $R^5$ are as defined for compounds of formula (I).

In another preferred embodiment, the invention relates to compounds of formula (Ib), supra, in which $R^1$ represents a hydrogen atom or a —O—$CH_3$ group, and in which $R^{5a}$ and $R^5$ are as defined for compounds of formula (I).

In another preferred embodiment, the invention relates to compounds of formula (Ib), supra, in which $R^1$ represents a hydrogen atom, and in which $R^{5a}$ and $R^5$ are as defined for compounds of formula (I).

In another preferred embodiment, the invention relates to compounds of formula (I), supra, wherein $R^4$ represents halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^6$—O—, —C(=O)—$R^6$, —C(=O)—O—$R^6$, —O—C(=O)—$R^6$, —N($R^{6a}$)—C(=O)—$R^{6b}$, —N($R^{6a}$)—C(=O)—N($R^{6b}$)$R^{6c}$, —N($R^{6a}$)$R^{6b}$, —C(=O)—N($R^{6a}$)$R^{6b}$, $R^6$—S—, $R^6$-S(=O)—, $R^6$—S(=O)$_2$—, —N($R^{6a}$)—S(=O)—$R^{6b}$, —S(=O)—N($R^{6a}$)$R^{6b}$, —N($R^{6a}$)—S(=O)$_2$—$R^{6b}$, —S(=O)$_2$—N($R^{6a}$)$R^{6b}$, —S(=O)=N($R^{6a}$)$R^{6b}$ or —N=S(=O)($R^{6a}$)$R^{6b}$.

In another preferred embodiment, the invention relates to compounds of formula (I), supra, wherein $R^4$ represents halo-, hydroxy-, cyano-, nitro-, $C_1$-$C_3$-alkyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, halo-$C_1$-$C_3$-alkoxy-$C_1$-$C_3$-alkyl-, $R^6$—O—, —C(=O)—$R^6$, —C(=O)—O—$R^6$, —O—C(=O)—$R^6$, —N($R^{6a}$)$R^{6b}$, —C(=O)—N($R^{6a}$)$R^{6b}$, $R^6$—S—, $R^6$—S(=O)—, $R^6$—S(=O)$_2$—, —N($R^{6a}$)—S(=O)—$R^{6b}$, —S(=O)—N($R^{6a}$)$R^{6b}$, —N($R^{6a}$)—S(=O)$_2$—$R^{6b}$, or —S(=O)$_2$—N($R^{6a}$)$R^{6b}$.

In another preferred embodiment, the invention relates to compounds of formula (I), supra, wherein $R^4$ represents halo-, hydroxy-, cyano-, $C_1$-$C_3$-alkyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, or —N($R^{6a}$)$R^{6b}$.

In another preferred embodiment, the invention relates to compounds of formula (I), supra, wherein $R^4$ represents halo-, hydroxy-, cyano-, $C_1$-$C_6$-alkyl-, $C_1$-$C_6$-alkoxy-, —N($R^{6a}$)—C(=O)—O—$R^{6b}$, —N($R^{6a}$)$R^{6b}$, —N($R^{6a}$)$R^{6d}$, —C(=O)—N($R^{6a}$)$R^{6b}$ or —($C_1$-$C_6$-alkyl)-N($R^{6a}$)$R^{6b}$.

In another preferred embodiment, the invention relates to compounds of formula (I), supra, wherein $R^4$ represents halo-, hydroxy-, cyano-, $C_1$-$C_3$-alkyl-, $C_1$-$C_3$-alkoxy-, —N($R^{6a}$)—C(=O)—O—$R^{6b}$, —N($R^{6a}$)$R^{6b}$, —N($R^{6a}$)$R^{6d}$, —C(=O)—N($R^{6a}$)$R^{6b}$ or —($C_1$-$C_3$-alkyl)-N($R^{6a}$)$R^{6b}$.

In another preferred embodiment, the invention relates to compounds of formula (I), supra, wherein $R^4$ represents hydroxy-, $C_1$-$C_3$-alkyl-, —N($R^{6a}$)$R^{6b}$ or —N($R^{6a}$)$R^{6d}$.

In another preferred embodiment, the invention relates to compounds of formula (I), supra, wherein $R^4$ represents hydroxy-, $C_1$-$C_3$-alkyl-, —N($R^{6a}$)$R^{6b}$ or —N($R^{6a}$)$R^{6d}$, and in which $R^1$ represents a hydrogen atom.

In another preferred embodiment, the invention relates to compounds of formula (I), supra, wherein $R^4$ represents hydroxy-, $C_1$-$C_3$-alkyl-, —N($R^{6a}$)$R^{6b}$ or —N($R^{6a}$)$R^{6d}$, and in which $R^2$ represents a hydrogen atom.

In another preferred embodiment, the invention relates to compounds of formula (I), supra, wherein $R^4$ represents hydroxy-, $C_1$-$C_3$-alkyl-, —N($R^{6a}$)$R^{6b}$ or —N($R^{6a}$)$R^{6d}$, and in which $R^1$ represents a hydrogen atom and $R^2$ represents a hydrogen atom.

In another preferred embodiment, the invention relates to compounds of formula (I), supra, wherein $R^4$ represents fluoro-, hydroxy-, cyano-, methyl-, methoxy-, —N(CH$_3$)$_2$, —NH$_2$, —($C_1$-$C_3$-alkyl)-N(CH$_3$)$_2$, —C(=O)—N(CH$_3$)$_2$, —N(CH$_3$)—($C_1$-$C_3$-alkyl)-N(CH$_3$)$_2$ or —N(H)—C(=O)—O—($C_1$-$C_4$-alkyl).

In another preferred embodiment, the invention relates to compounds of formula (I), supra, wherein $R^4$ represents fluoro-, hydroxy-, cyano-, methyl-, methoxy-, —N(CH$_3$)$_2$, —NH$_2$, —($C_1$-$C_3$-alkyl)-N(CH$_3$)$_2$, —C(=O)—N(CH$_3$)$_2$, —N(CH$_3$)—($C_1$-$C_3$-alkyl)-N(CH$_3$)$_2$ or —N(H)—C(=O)—O—($C_1$-$C_4$-alkyl), and in which $R^1$ represents a hydrogen atom.

In another preferred embodiment, the invention relates to compounds of formula (I), supra, wherein $R^4$ represents fluoro-, hydroxy-, cyano-, methyl-, methoxy-, —N(CH$_3$)$_2$, —NH$_2$, —($C_1$-$C_3$-alkyl)-N(CH$_3$)$_2$, —C(=O)—N(CH$_3$)$_2$, —N(CH$_3$)—($C_1$-$C_3$-alkyl)-N(CH$_3$)$_2$ or —N(H)—C(=O)—O—($C_1$-$C_4$-alkyl), and in which $R^2$ represents a hydrogen atom.

In another preferred embodiment, the invention relates to compounds of formula (I), supra, wherein $R^4$ represents fluoro-, hydroxy-, cyano-, methyl-, methoxy-, —N(CH$_3$)$_2$, —NH$_2$, —($C_1$-$C_3$-alkyl)-N(CH$_3$)$_2$, —C(=O)—N(CH$_3$)$_2$, —N(CH$_3$)—($C_1$-$C_3$-alkyl)-N(CH$_3$)$_2$ or —N(H)—C(=O)—O—($C_1$-$C_4$-alkyl), and in which $R^1$ represents a hydrogen atom and $R^2$ represents a hydrogen atom.

In another preferred embodiment, the invention relates to compounds of formula (I), supra, wherein $R^4$ represents hydroxy-, methyl-, —N(CH$_3$)$_2$, —NH$_2$ or —N(CH$_3$)—($C_1$-$C_3$-alkyl)-N(CH$_3$)$_2$.

In another preferred embodiment, the invention relates to compounds of formula (I), supra, wherein $R^4$ represents hydroxy-, methyl-, —N(CH$_3$)$_2$, —NH$_2$ or —N(CH$_3$)—(CH$_2$)$_2$—N(CH$_3$)$_2$.

In another preferred embodiment, the invention relates to compounds of formula (I), supra, wherein $R^4$ represents halo-, hydroxy-, cyano-, $C_1$-$C_3$-alkyl-, $C_1$-$C_3$-alkoxy-, —N($R^{6a}$)—C(=O)—O—, —N($R^{6a}$)$R^{6b}$ or —C(=O)—N($R^{6a}$)$R^{6b}$.

In another preferred embodiment, the invention relates to compounds of formula (I), supra, wherein $R^4$ represents fluoro-, hydroxy-, cyano-, $C_1$-$C_3$-alkyl-, $C_1$-$C_3$-alkoxy-, —N($R^{6a}$)—C(=O)—O—, —N($R^{6a}$)$R^{6b}$ or —C(=O)—N($R^{6a}$)$R^{6b}$.

In another preferred embodiment, the invention relates to compounds of formula (I), supra, wherein $R^4$ represents halo-, hydroxy-, cyano-, $C_1$-$C_3$-alkyl-, $C_1$-$C_3$-alkoxy-, or —N($R^{6a}$)$R^{6b}$.

In another preferred embodiment, the invention relates to compounds of formula (I), supra, wherein $R^4$ represents fluoro-, hydroxy-, cyano-, $C_1$-$C_3$-alkyl-, $C_1$-$C_3$-alkoxy-, or —N($R^{6a}$)$R^{6b}$.

In another preferred embodiment, the invention relates to compounds of formula (I), supra, wherein $R^{5a}$ represents a hydrogen atom or a $C_1$-$C_3$-alkyl-group.

In another preferred embodiment, the invention relates to compounds of formula (I), supra, wherein $R^{5a}$ represents a hydrogen atom.

In another preferred embodiment, the invention relates to compounds of formula (I), supra, wherein $R^{5a}$ represents a $C_1$-$C_6$-alkyl-group; wherein said $C_1$-$C_6$-alkyl-group is optionally substituted, identically or differently, with 1, 2, 3, 4 or 5 $R^4$ groups.

In another preferred embodiment, the invention relates to compounds of formula (I), supra, wherein $R^{5a}$ represents a $C_1$-$C_3$-alkyl-group; wherein said $C_1$-$C_3$-alkyl-group is optionally substituted, identically or differently, with 1, 2, 3, 4 or 5 $R^4$ groups.

In another preferred embodiment, the invention relates to compounds of formula (I), supra, wherein $R^{5a}$ represents a $C_1$-$C_3$-alkyl-group.

In another preferred embodiment, the invention relates to compounds of formula (I), supra, wherein $R^{5a}$ represents a methyl-group.

In another preferred embodiment, the invention relates to compounds of formula (I), supra, wherein $R^{5b}$ represents a hydrogen atom or a $C_1$-$C_3$-alkyl-group.

In another preferred embodiment, the invention relates to compounds of formula (I), supra, wherein $R^{5b}$ represents a hydrogen atom.

In another preferred embodiment, the invention relates to compounds of formula (I), supra, wherein $R^{5b}$ represents a $C_1$-$C_6$-alkyl-group; wherein said $C_1$-$C_6$-alkyl-group is optionally substituted, identically or differently, with 1, 2, 3, 4 or 5 $R^4$ groups.

In another preferred embodiment, the invention relates to compounds of formula (I), supra, wherein $R^{5b}$ represents a $C_1$-$C_3$-alkyl-group; wherein said $C_1$-$C_3$-alkyl-group is optionally substituted, identically or differently, with 1, 2, 3, 4 or 5 $R^4$ groups.

In another preferred embodiment, the invention relates to compounds of formula (I), supra, wherein $R^{5b}$ represents a $C_1$-$C_3$-alkyl-group.

In another preferred embodiment, the invention relates to compounds of formula (I), supra, wherein $R^{5b}$ represents a methyl-group.

In another preferred embodiment, the invention relates to compounds of formula (I), supra, wherein $R^{5b}$ represents a 3- to 10-membered heterocycloalkyl-group, wherein said 3- to 10-membered heterocycloalkyl-group is optionally substituted, identically or differently, with 1, 2, 3, 4 or 5 $R^4$ groups.

In another preferred embodiment, the invention relates to compounds of formula (I), supra, wherein $R^{5b}$ represents a 4- to 7-membered heterocycloalkyl-group, wherein said 4- to 7-membered heterocycloalkyl-group is optionally substituted, identically or differently, with 1, 2 or 3 $R^4$ groups.

In another preferred embodiment, the invention relates to compounds of formula (I), supra, wherein $R^5$ represents a hydrogen atom.

In another preferred embodiment, the invention relates to compounds of formula (I), supra, wherein $R^5$ represents a $C_1$-$C_6$-alkyl-group; wherein said $C_1$-$C_6$-alkyl-group is optionally substituted, identically or differently, with 1, 2, 3, 4 or 5 $R^4$ groups.

In another preferred embodiment, the invention relates to compounds of formula (I), supra, wherein $R^5$ represents a $C_1$-$C_3$-alkyl-group; wherein said $C_1$-$C_3$-alkyl-group is optionally substituted, identically or differently, with 1, 2, 3, 4 or 5 $R^4$ groups.

In another preferred embodiment, the invention relates to compounds of formula (I), supra, wherein $R^5$ represents a $C_1$-$C_3$-alkyl-group; wherein said $C_1$-$C_3$-alkyl-group is optionally substituted, identically or differently, with 1 or 2 $R^4$ groups.

In another preferred embodiment, the invention relates to compounds of formula (I), supra, wherein $R^5$ represents a $C_1$-$C_3$-alkyl-group, wherein said $C_1$-$C_3$-alkyl-group is substituted with a —N($R^{6a}$)$R^{6b}$ group.

In another preferred embodiment, the invention relates to compounds of formula (I), supra, wherein $R^5$ represents a $C_2$-$C_3$-alkyl-group, wherein said $C_2$-$C_3$-alkyl-group is substituted with a —N(CH$_3$)$_2$ or —NH$_2$ group.

In another preferred embodiment, the invention relates to compounds of formula (I), supra, wherein $R^5$ represents a —(CH$_2$)$_2$—NH$_2$ group or a —(CH$_2$)$_3$—N(CH$_3$)$_2$ group.

In another preferred embodiment, the invention relates to compounds of formula (I), supra, wherein $R^5$ represents a $C_1$-$C_3$-alkyl-group.

In another preferred embodiment, the invention relates to compounds of formula (I), supra, wherein $R^5$ represents a 3- to 10-membered heterocycloalkyl-group, wherein said 3- to 10-membered heterocycloalkyl-group is optionally substituted, identically or differently, with 1, 2, 3, 4 or 5 $R^4$ groups.

In another preferred embodiment, the invention relates to compounds of formula (I), supra, wherein $R^5$ represents a group selected from: $C_1$-$C_4$-alkyl-, 4- to 7-membered heterocycloalkyl-; wherein said $C_1$-$C_4$-alkyl-group and 4- to 7-membered heterocycloalkyl-group are optionally substituted, identically or differently, with 1 or 2 $R^4$ groups.

In another preferred embodiment, the invention relates to compounds of formula (I), supra, wherein $R^5$ represents a group selected from: $C_1$-$C_4$-alkyl-, 4- to 7-membered heterocycloalkyl-; wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said $C_1$-$C_4$-alkyl-group and 4- to 7-membered heterocycloalkyl-group are optionally substituted, identically or differently, with 1 or 2 $R^4$ groups.

In another preferred embodiment, the invention relates to compounds of formula (I), supra, wherein $R^5$ represents a group selected from: $C_1$-$C_4$-alkyl-, 4- to 7-membered heterocycloalkyl-; wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said $C_1$-$C_4$-alkyl-group and 4- to 7-membered heterocycloalkyl-group are optionally substituted, identically or differently, with 1 or 2 $R^4$ groups, and in which compounds $R^1$ represents a hydrogen atom.

In another preferred embodiment, the invention relates to compounds of formula (I), supra, wherein $R^5$ represents a group selected from: $C_1$-$C_4$-alkyl-, 4- to 7-membered heterocycloalkyl-; wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said $C_1$-$C_4$-alkyl-group and 4- to 7-membered heterocycloalkyl-group are optionally substituted, identically or differently, with 1 or 2 $R^4$ groups, and in which compounds $R^2$ represents a hydrogen atom.

In another preferred embodiment, the invention relates to compounds of formula (I), supra, wherein $R^5$ represents a group selected from: $C_1$-$C_4$-alkyl-, 4- to 7-membered heterocycloalkyl-; wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said $C_1$-$C_4$-alkyl-group and 4- to 7-membered heterocycloalkyl-group are optionally substituted, identically or differently, with 1 or 2 $R^4$ groups, and in which compounds $R^1$ represents a hydrogen atom, and $R^2$ represents a hydrogen atom.

In another preferred embodiment, the invention relates to compounds of formula (I), supra, wherein $R^5$ represents a group selected from: $C_2$-$C_3$-alkyl-, 4- to 7-membered heterocycloalkyl-; wherein said 4- to 7-membered heterocycloalkyl-group is selected from: diazabicyclo[2.2.1]heptyl, pyrrolidinyl, piperidinyl, azetidinyl; wherein said $C_2$-$C_3$-alkyl-group and 4- to 7-membered heterocycloalkyl-group are optionally substituted, identically or differently, with 1 or 2 $R^4$ groups.

In another preferred embodiment, the invention relates to compounds of formula (I), supra, wherein N($R^{5a}$)$R^5$ together represent a 3- to 10-membered heterocycloalkyl-group, said group being optionally substituted, identically or differently, with 1, 2, 3, 4 or 5 $R^4$ groups.

In another preferred embodiment, the invention relates to compounds of formula (I), supra, wherein N($R^{5a}$)$R^5$ together represent a 4- to 7-membered heterocycloalkyl-group, said group being optionally substituted, identically or differently, with 1, 2, 3, 4 or 5 $R^4$ groups.

In another preferred embodiment, the invention relates to compounds of formula (I), supra, wherein N($R^{5a}$)$R^5$ together represent a 4- to 7-membered heterocycloalkyl-group, wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said 4- to 7-membered heterocycloalkyl-group is optionally substituted, identically or differently, with 1 or 2 $R^4$ groups.

In another preferred embodiment, the invention relates to compounds of formula (I), supra, wherein N($R^{5a}$)$R^5$ together represent a 4- to 7-membered heterocycloalkyl-group, wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said 4- to 7-membered heterocycloalkyl-group is optionally substituted, identically or differently, with 1 or 2 $R^4$ groups, and in which compounds $R^1$ represents a hydrogen atom.

In another preferred embodiment, the invention relates to compounds of formula (I), supra, wherein N($R^{5a}$)$R^5$ together represent a 4- to 7-membered heterocycloalkyl-group, wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said 4- to 7-membered heterocycloalkyl-group is optionally substituted, identically or differently, with 1 or 2 $R^4$ groups, and in which compounds $R^2$ represents a hydrogen atom.

In another preferred embodiment, the invention relates to compounds of formula (I), supra, wherein $N(R^{5a})R^5$ together represent a 4- to 7-membered heterocycloalkyl-group, wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said 4- to 7-membered heterocycloalkyl-group is optionally substituted, identically or differently, with 1 or 2 $R^4$ groups, and in which compounds $R^1$ represents a hydrogen atom, and $R^2$ represents a hydrogen atom.

In another preferred embodiment, the invention relates to compounds of formula (I), supra, wherein $N(R^{5a})R^5$ together represent a 4- to 7-membered heterocycloalkyl-group, wherein said 4- to 7-membered heterocycloalkyl-group is selected from: diazabicyclo[2.2.1]heptyl, pyrrolidinyl, piperidinyl, azetidinyl; wherein said 4- to 7-membered heterocycloalkyl-group is optionally substituted, identically or differently, with 1 or 2 $R^4$ groups.

In another preferred embodiment, the invention relates to compounds of formula (I), supra, wherein $N(R^{5a})R^5$ together represent a group selected from:

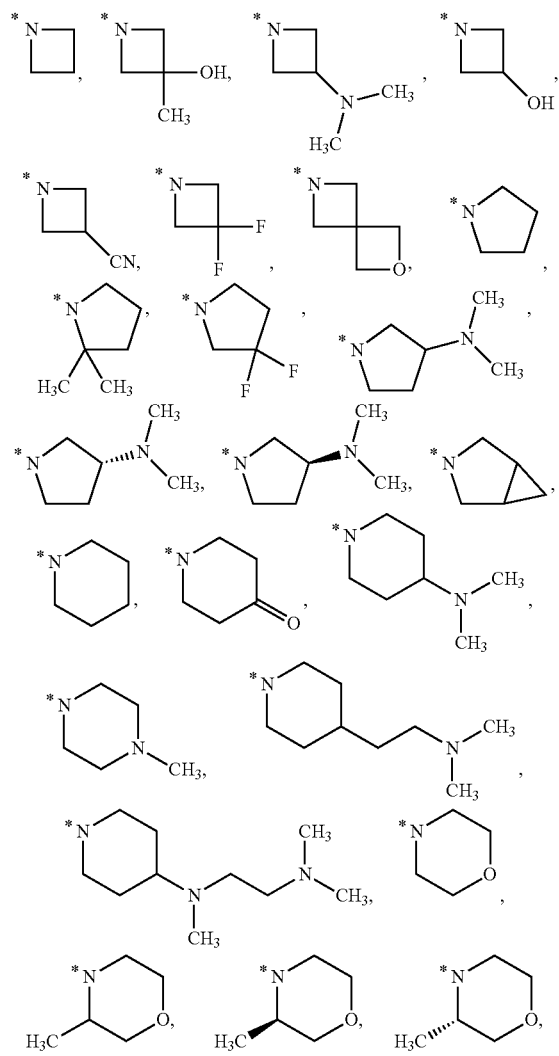

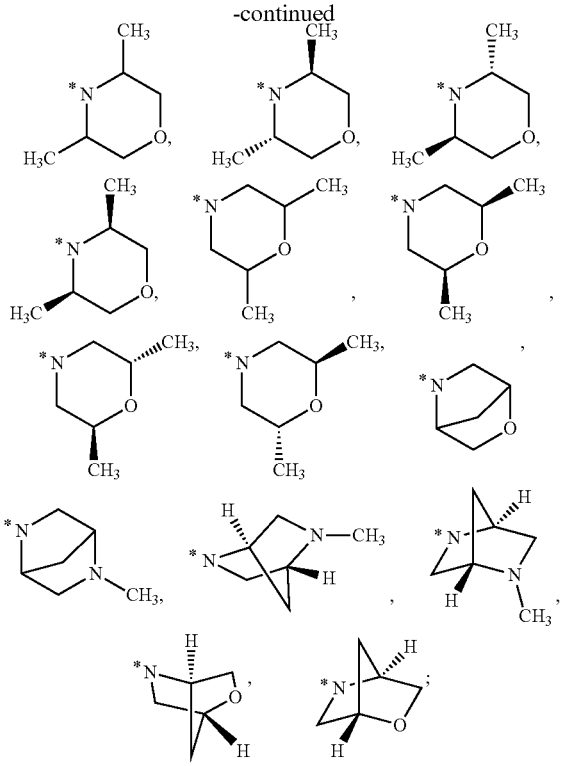

wherein * indicates the point of attachment of said groups with the rest of the molecule.

In another preferred embodiment, the invention relates to compounds of formula (I), supra, wherein $N(R^{5a})R^5$ together represent a group selected from:

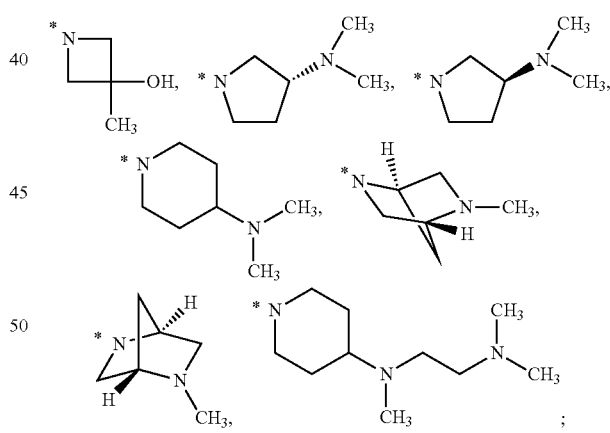

wherein * indicates the point of attachment of said groups with the rest of the molecule.

In another preferred embodiment, the invention relates to compounds of formula (I), supra, wherein $R^{6a}$ represents a hydrogen atom or a $C_1$-$C_6$-alkyl-group.

In another preferred embodiment, the invention relates to compounds of formula (I), supra, wherein $R^{6a}$ represents a hydrogen atom or a $C_1$-$C_3$-alkyl-group.

In another preferred embodiment, the invention relates to compounds of formula (I), supra, wherein $R^{6a}$ represents a $C_1$-$C_3$-alkyl-group.

In another preferred embodiment, the invention relates to compounds of formula (I), supra, wherein $R^{6a}$ represents a methyl-group.

In another preferred embodiment, the invention relates to compounds of formula (I), supra, wherein $R^{6a}$ represents a methyl-group and wherein $R^{6b}$ represents a methyl-group.

In another preferred embodiment, the invention relates to compounds of formula (I), supra, wherein $R^{6a}$ represents a methyl-group, wherein $R^{6b}$ represents a methyl-group, and wherein $R^2$ represents a hydrogen atom.

In another preferred embodiment, the invention relates to compounds of formula (I), supra, wherein $R^{6a}$ represents a methyl-group, wherein $R^{6b}$ represents a methyl-group, and wherein $R^1$ represents a hydrogen atom.

In another preferred embodiment, the invention relates to compounds of formula (I), supra, wherein $R^{6a}$ represents a methyl-group, wherein $R^{6b}$ represents a methyl-group, and wherein $R^1$ represents a hydrogen atom or a —O—CH$_3$ group.

In another preferred embodiment, the invention relates to compounds of formula (I), supra, wherein $R^{6a}$ represents a methyl-group, wherein $R^{6b}$ represents a methyl-group, wherein $R^2$ represents a hydrogen atom, and wherein $R^1$ represents a hydrogen atom or a —O—CH$_3$ group.

In another preferred embodiment, the invention relates to compounds of formula (I), supra, wherein $R^{6b}$ represents a hydrogen atom or a $C_1$-$C_6$-alkyl-group.

In another preferred embodiment, the invention relates to compounds of formula (I), supra, wherein $R^{6b}$ represents a hydrogen atom or a $C_1$-$C_3$-alkyl-group.

In another preferred embodiment, the invention relates to compounds of formula (I), supra, wherein $R^{6b}$ represents a $C_1$-$C_3$-alkyl-group.

In another preferred embodiment, the invention relates to compounds of formula (I), supra, wherein $R^{6b}$ represents a methyl-group.

In another preferred embodiment, the invention relates to compounds of formula (I), supra, wherein $R^{6c}$ represents a hydrogen atom or a $C_1$-$C_6$-alkyl-group.

In another preferred embodiment, the invention relates to compounds of formula (I), supra, wherein $R^{6c}$ represents a hydrogen atom or a $C_1$-$C_3$-alkyl-group.

In another preferred embodiment, the invention relates to compounds of formula (I), supra, wherein $R^{6c}$ represents a $C_1$-$C_3$-alkyl-group.

In another preferred embodiment, the invention relates to compounds of formula (I), supra, wherein $R^{6c}$ represents a methyl-group.

In another preferred embodiment, the invention relates to compounds of formula (I), supra, wherein $R^{6d}$ represents a —$C_1$-$C_3$-alkyl)-N($R^{6a}$)$R^{6b}$ group.

In another preferred embodiment, the invention relates to compounds of formula (I), supra, wherein $R^{6d}$ represents a —($C_1$-$C_3$-alkyl)-N(CH$_3$)$_2$ group.

In another preferred embodiment, the invention relates to compounds of formula (I), supra, wherein $R^6$ represents a hydrogen atom or a $C_1$-$C_6$-alkyl-group.

In another preferred embodiment, the invention relates to compounds of formula (I), supra, wherein $R^6$ represents a hydrogen atom or a $C_1$-$C_3$-alkyl-group.

In another preferred embodiment, the invention relates to compounds of formula (I), supra, wherein $R^6$ represents a $C_1$-$C_3$-alkyl-group.

In another preferred embodiment, the invention relates to compounds of formula (I), supra, wherein $R^6$ represents a methyl-group.

In another preferred embodiment, the invention relates to compounds of formula (I), supra, wherein $R^7$ represents a halogen atom.

In another preferred embodiment, the invention relates to compounds of formula (I), supra, wherein p represents 0 or 1.

In another preferred embodiment, the invention relates to compounds of formula (I), supra, wherein q represents 0 or 1.

In another preferred embodiment, the invention relates to compounds of formula (I), supra, wherein p represents 0.

In another preferred embodiment, the invention relates to compounds of formula (I), supra, wherein q represents 0.

In another preferred embodiment, the invention relates to compounds of formula (I), supra, wherein p represents 0 and q represents 0.

It is to be understood that the present invention relates also to any combination of the preferred embodiments described above. Some examples of combinations are given hereinafter. However, the invention is not limited to these combinations.

In a preferred embodiment, the invention relates to compounds of formula (I), supra, in which:

$R^1$ represents a hydrogen atom or a halogen atom or a group selected from: hydroxy-, cyano-, $C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —N($R^{5a}$)$R^{5b}$, —S$R^{5a}$, and —SF$_5$; wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, and (5- to 10-membered heterocycloalkenyl)-O— group is optionally substituted, identically or differently, with 1, 2, 3, 4 or 5 $R^4$ groups;

$R^2$ represents a hydrogen atom or a group selected from: $C_1$-$C_6$-alkyl-, $C_2$-$C_6$-alkenyl-, $C_1$-$C_6$-alkoxy-, halo-$C_1$-$C_6$-alkyl-, and halo-$C_1$-$C_6$-alkoxy-; wherein said $C_1$-$C_6$-alkyl-, $C_2$-$C_6$-alkenyl-, and $C_1$-$C_6$-alkoxy-group is optionally substituted, identically or differently, with 1, 2, or 3 $R^7$ groups;

$R^3$ represents a hydrogen atom or a group selected from: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, and —(CH$_2$)$_q$—X—(CH$_2$)$_p$—$R^5$; wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl- and heteroaryl-group is optionally substituted, identically or differently, with 1, 2, 3, 4 or 5 $R^4$ groups;

X represents a bond or a bivalent group selected from: —O—, —S—, —S(=O)—, —S(=O)$_2$—, —S(=O)—N($R^{5a}$)—, —N($R^{5a}$)—S(=O)—, —S(=O)$_2$—N($R^{5a}$)—, —N($R^{5a}$)—S(=O)$_2$—, —S(=O)(=N$R^{5a}$)—, —C(=O)—, —N($R^{5a}$)—, —C(=O)—O—, —O—C(=O)—, —C(=S)—O—, —O—C(=S)—, —C(=O)—N($R^{5a}$)—, —N($R^{5a}$)—C(=O)—, —N($R^{5a}$)—C(=O)—N($R^{5b}$)—, —O—C(=O)—N($R^{5a}$)—, —N($R^{5a}$)—C(=O)—O—;

$R^4$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^6$—O—, —C(=O)—$R^6$, —C(=O)—O—$R^6$, —O—C(=O)—$R^6$, —N($R^{6a}$)—C(=O)—$R^{6b}$, —N($R^{6a}$)—C(=O)—N($R^{6b}$)$R^{6c}$, —N($R^{6a}$)$R^{6b}$, —C(=O)—N($R^{6a}$)$R^{6b}$, $R^6$—S—, $R^6$—S(=O)—, $R^6$—S(=O)$_2$—, —N($R^{6a}$)—S(=O)—$R^{6b}$, —S(=O)—N($R^{6a}$)$R^{6b}$, —N($R^{6a}$)—S(=O)$_2$—$R^{6b}$, —S(=O)$_2$—N($R^{6a}$)$R^{6b}$, —S(=O)=N($R^{6a}$)$R^{6b}$ or —N=S(=O)($R^{6a}$)$R^{6b}$;

$R^{5a}$, $R^{5b}$ are the same or different and are independently selected from $R^5$;

$R^5$ represents a hydrogen atom or a group selected from: $C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 $R^4$ groups;

or

N($R^{5a}$)$R^5$ together represent a 3- to 10-membered heterocycloalkyl-group, said group being optionally substituted, identically or differently, with 1, 2, 3, 4 or 5 $R^4$ groups;

$R^{6a}$, $R^{6b}$, $R^{6c}$ are the same or different and are independently selected from $R^6$;

$R^6$ represents a hydrogen atom, a $C_1$-$C_6$-alkyl- or a $C_3$-$C_6$-cycloalkyl-group;

or $R^{6a}$ and $R^{6b}$, or $R^{6a}$ and $R^{6c}$, or $R^{6b}$ and $R^{6c}$ together may form a $C_2$-$C_6$-alkylene group, in which optionally one methylene can be replaced by —O—, —C(=O)—, —NH—, or —N($C_1$-$C_4$-alkyl)-;

$R^7$ represents halo-, hydroxy-, oxo-(O=), cyano-, nitro-, p represents an integer of 0, 1, 2 or 3;

q represents an integer of 0, 1, 2 or 3;

or a tautomer, an N-oxide, a hydrate, a solvate, or a salt thereof, or a mixture of same.

In another preferred embodiment, the invention relates to compounds of formula (I), supra, in which:

$R^1$ represents a hydrogen atom or a group selected from: $C_1$-$C_3$-alkyl-, $C_1$-$C_3$-alkoxy-, halo-$C_1$-$C_3$-alkyl-, and —S—$C_1$-$C_3$-alkyl);

$R^2$ represents a hydrogen atom;

$R^3$ represents a group selected from: $C_1$-$C_6$-alkyl-, $C_3$-$C_6$-cycloalkyl-, 3- to 10-membered heterocycloalkyl-, cyano-, and —(CH$_2$)$_q$—X—(CH$_2$)$_p$—$R^5$; wherein said $C_1$-$C_6$-alkyl-, $C_3$-$C_6$-cycloalkyl-, and 3- to 10-membered heterocycloalkyl-group is optionally substituted, identically or differently, with 1, 2, 3, 4 or 5 $R^4$ groups;

X represents a bond or a bivalent group selected from: —O—, —S—, —S(=O)—, —S(=O)$_2$—, —S(=O)—N($R^{5a}$)—, —N($R^{5a}$)—S(=O)—, —S(=O)$_2$—N($R^{5a}$)—, —N($R^{5a}$)—S(=O)$_2$—, —S(=O)(=N$R^{5a}$)—, —C(=O)—, —N($R^{5a}$)—, —C(=O)—O—, —O—C(=O)—, —C(=S)—O—, —O—C(=S)—, —C(=O)—N($R^{5a}$)—, and —N($R^{5a}$)—C(=O)—;

$R^4$ represents halo-, hydroxy-, cyano-, nitro-, $C_1$-$C_3$-alkyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, halo-$C_1$-$C_3$-alkoxy-$C_1$-$C_3$-alkyl-, $R^6$—O—, —C(=O)—$R^6$, —C(=O)—O—$R^6$, —O—C(=O)—$R^6$, —N($R^{6a}$)$R^{6b}$, —C(=O)—N($R^{6a}$)$R^{6b}$, $R^6$—S—, $R^6$—S(=O)—, $R^6$—S(=O)$_2$—, —N($R^{6a}$)—S(=O)—$R^{6b}$, —S(=O)—N($R^{6a}$)$R^{6b}$, —N($R^{6a}$)—S(=O)$_2$—$R^{6b}$, or —S(=O)$_2$—N($R^{6a}$)$R^{6b}$;

$R^{5a}$, $R^{5b}$ are the same or different and are independently selected from $R^5$;

$R^5$ represents a hydrogen atom or a group selected from: $C_1$-$C_6$-alkyl-, $C_3$-$C_6$-cycloalkyl-, 3- to 10-membered heterocycloalkyl-, aryl-, and heteroaryl-; wherein said $C_1$-$C_6$-alkyl-, $C_3$-$C_6$-cycloalkyl-, 3- to 10-membered heterocycloalkyl-, aryl- and heteroaryl-group is optionally substituted, identically or differently, with 1, 2, 3, 4 or 5 $R^4$ groups;

or

N($R^{5a}$)$R^5$ together represent a 3- to 10-membered heterocycloalkyl-group, said group being optionally substituted, identically or differently, with 1, 2, 3, 4 or 5 $R^4$ groups;

$R^{6a}$, $R^{6b}$, $R^{6c}$ are the same or different and are independently selected from $R^6$;

$R^6$ represents a hydrogen atom or a $C_1$-$C_6$-alkyl-group;

p represents an integer of 0 or 1;

q represents an integer of 0 or 1;

or a tautomer, an N-oxide, a hydrate, a solvate, or a salt thereof, or a mixture of same.

In another preferred embodiment, the invention relates to compounds of formula (I), supra, in which:

$R^1$ represents a hydrogen atom or a group selected from: $C_1$-$C_3$-alkyl-, $C_1$-$C_3$-alkoxy-, halo-$C_1$-$C_3$-alkyl-, and —S—$C_1$-$C_3$-alkyl);

$R^2$ represents a hydrogen atom;

$R^3$ represents a group selected from: $C_1$-$C_6$-alkyl-, $C_3$-$C_6$-cycloalkyl-, 3- to 10-membered heterocycloalkyl-, cyano-, and —(CH$_2$)$_q$—X—(CH$_2$)$_p$—$R^5$; wherein said $C_1$-$C_6$-alkyl-, $C_3$-$C_6$-cycloalkyl-, and 3- to 10-membered heterocycloalkyl-group is optionally substituted, identically or differently, with 1, 2, 3, 4 or 5 $R^4$ groups;

X represents a bivalent group selected from: —C(=O)—, —C(=O)—O—, and —C(=O)—N($R^{5a}$)—;

$R^4$ represents halo-, hydroxy-, cyano-, $C_1$-$C_3$-alkyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, —NR$^{6a}$R$^{6b}$, —($C_1$-$C_6$-alkyl)-N($R^{6a}$)$R^{6b}$ or —N($R^{6a}$)$R^{6d}$;

$R^{5a}$, $R^{5b}$ are the same or different and are independently selected from $R^5$;

$R^5$ represents a hydrogen atom or a $C_1$-$C_3$-alkyl-group; wherein said $C_1$-$C_3$-alkyl-group is optionally substituted, identically or differently, with 1, 2, 3, 4 or 5 $R^4$ groups;

or

N($R^{5a}$)$R^5$ together represent a 3- to 10-membered heterocycloalkyl-group, said group being optionally substituted, identically or differently, with 1 or 2 $R^4$ groups;

$R^{6a}$, $R^{6b}$, $R^{6c}$ are the same or different and are independently selected from $R^6$;

$R^6$ represents a hydrogen atom or a $C_1$-$C_6$-alkyl-group;

$R^{6d}$ represents a —($C_1$-$C_3$-alkyl)-NR$^{6a}$R$^{6b}$ group;

p represents an integer of 0 or 1;

q represents an integer of 0 or 1;

or a tautomer, an N-oxide, a hydrate, a solvate, or a salt thereof, or a mixture of same.

In another preferred embodiment, the invention relates to compounds of formula (I), supra, in which:

$R^1$ represents a hydrogen atom or a group selected from: $C_1$-$C_3$-alkyl-, $C_1$-$C_3$-alkoxy-, halo-$C_1$-$C_3$-alkyl-, and —S—$C_1$-$C_3$-alkyl);

$R^2$ represents a hydrogen atom;

$R^3$ represents a group selected from: $C_1$-$C_6$-alkyl-, $C_3$-$C_6$-cycloalkyl-, 3- to 10-membered heterocycloalkyl-, cyano-, and —(CH$_2$)$_q$—X—(CH$_2$)$_p$—R$^5$; wherein said C$_1$-C$_6$-alkyl-, C$_3$-C$_6$-cycloalkyl-, and 3- to 10-membered heterocycloalkyl-group is optionally substituted, identically or differently, with 1, 2, 3, 4 or 5 R$^4$ groups;

X represents a bivalent group selected from: —C(=O)—, —C(=O)—O—, and —C(=O)—N(R$^{5a}$)—;

R$^4$ represents halo-, hydroxy-, cyano-, C$_1$-C$_3$-alkyl-, halo-C$_1$-C$_3$-alkyl-, C$_1$-C$_3$-alkoxy-, halo-C$_1$-C$_3$-alkoxy-, hydroxy-C$_1$-C$_3$-alkyl-, C$_1$-C$_3$-alkoxy-C$_1$-C$_3$-alkyl-, or —N(R$^{6a}$)R$^{6b}$;

R$^{5a}$, R$^{5b}$ are the same or different and are independently selected from R$^5$;

R$^5$ represents a hydrogen atom or a C$_1$-C$_3$-alkyl-group; wherein said C$_1$-C$_3$-alkyl-group is optionally substituted, identically or differently, with 1, 2, 3, 4 or 5 R$^4$ groups;

or

N(R$^{5a}$)R$^5$ together represent a 3- to 10-membered heterocycloalkyl-group, said group being optionally substituted, identically or differently, with 1 or 2 R$^4$ groups;

R$^{6a}$, R$^{6b}$, R$^{6c}$ are the same or different and are independently selected from R$^6$;

R$^6$ represents a hydrogen atom or a C$_1$-C$_6$-alkyl-group;

P represents an integer of 0 or 1;

q represents an integer of 0 or 1;

or a tautomer, an N-oxide, a hydrate, a solvate, or a salt thereof, or a mixture of same.

In another preferred embodiment, the invention relates to compounds of formula (I), supra, in which:

R$^1$ represents a hydrogen atom or a group selected from: —O—CH$_3$, —S—CH$_3$;

R$^2$ represents a hydrogen atom;

R$^3$ represents —(CH$_2$)$_q$—X—(CH$_2$)$_p$—R$^5$;

X represents a bivalent group selected from: —C(=O)—, —C(=O)—O—, and —C(=O)—N(R$^{5a}$)—;

R$^4$ represents halo-, hydroxy-, cyano-, C$_1$-C$_3$-alkyl-, halo-C$_1$-C$_3$-alkyl-, C$_1$-C$_3$-alkoxy-, halo-C$_1$-C$_3$-alkoxy-, hydroxy-C$_1$-C$_3$-alkyl-, C$_1$-C$_3$-alkoxy-C$_1$-C$_3$-alkyl-, or —N(R$^{6a}$)R$^{6b}$;

R$^{5a}$, R$^{5b}$ are the same or different and are independently selected from R$^5$;

R$^5$ represents a hydrogen atom or a C$_1$-C$_3$-alkyl-group; wherein said C$_1$-C$_3$-alkyl-group is optionally substituted, identically or differently, with 1 or 2 R$^4$ groups;

or

N(R$^{5a}$)R$^5$ together represent a 3- to 10-membered heterocycloalkyl-group, said group being optionally substituted, identically or differently, with 1 or 2 R$^4$ groups;

R$^{6a}$, R$^{6b}$, R$^{6c}$ are the same or different and are independently selected from R$^6$;

R$^6$ represents a hydrogen atom or a C$_1$-C$_3$-alkyl-group;

p represents 0;

q represents 0;

or a tautomer, an N-oxide, a hydrate, a solvate, or a salt thereof, or a mixture of same.

In another preferred embodiment, the invention relates to compounds of formula (I), supra, in which:

R$^1$ represents a hydrogen atom;

R$^2$ represents a hydrogen atom;

R$^3$ represents a —(CH$_2$)$_q$—X—(CH$_2$)$_p$—R$^5$ group;

X represents a bivalent group selected from: —C(=O)—, —C(=O)—N(R$^{5a}$)—;

R$^4$ represents halo-, hydroxy-, cyano-, C$_1$-C$_3$-alkyl-, C$_1$-C$_3$-alkoxy-, —N(R$^{6a}$)—C(=O)—O—R$^{6b}$, —N(R$^{6a}$)R$^{6b}$, —N(R$^{6a}$)R$^{6d}$, —C(=O)—N(R$^{6a}$)R$^{6b}$ or —(C$_1$-C$_3$-alkyl)-N(R$^{6a}$)R$^{6b}$;

R$^{5a}$ represents a C$_1$-C$_3$-alkyl-group;

R$^5$ represents a group selected from: C$_1$-C$_4$-alkyl-, 4- to 7-membered heterocycloalkyl-; wherein said C$_1$-C$_4$-alkyl-group and 4- to 7-membered heterocycloalkyl-group are optionally substituted, identically or differently, with 1 or 2 R$^4$ groups;

or

N(R$^{5a}$)R$^5$ together represent a 4- to 7-membered heterocycloalkyl-group, said group being optionally substituted, identically or differently, with 1 or 2 R$^4$ groups;

R$^{6a}$, R$^{6b}$ are the same or different and are independently selected from R$^6$;

R$^6$ represents a hydrogen atom or a C$_1$-C$_3$-alkyl-group;

R$^{6d}$ represents a —C$_1$-C$_3$-alkyl)-N(R$^{6a}$)R$^{6b}$ group;

p represents 0;

q represents 0;

or a tautomer, an N-oxide, a hydrate, a solvate, or a salt thereof, or a mixture of same.

In another preferred embodiment, the invention relates to compounds of formula (I) or (Ib), supra, in which:

R$^1$ represents a hydrogen atom;

R$^2$ represents a hydrogen atom;

R$^3$ represents a —(CH$_2$)$_q$—X—(CH$_2$)$_p$—R$^5$ group;

X represents a bivalent —C(=O)—N(R$^{5a}$)— group;

R$^4$ represents halo-, hydroxy-, cyano-, C$_1$-C$_3$-alkyl-, C$_1$-C$_3$-alkoxy-, —N(R$^{6a}$)—C(=O)—O—R$^{6b}$, —N(R$^{6a}$)R$^{6b}$, —N(R$^{6a}$)R$^{6d}$, —C(=O)—N(R$^{6a}$)R$^{6b}$ or —(C$_1$-C$_3$-alkyl)-N(R$^{6a}$)R$^{6b}$;

R$^{5a}$ represents a C$_1$-C$_3$-alkyl-group;

R$^5$ represents a group selected from: C$_1$-C$_4$-alkyl-; wherein said C$_1$-C$_4$-alkyl-group is optionally substituted, identically or differently, with 1 or 2 R$^4$ groups;

or

N(R$^{5a}$)R$^5$ together represent a 4- to 7-membered heterocycloalkyl-group; wherein said 4- to 7-membered heterocycloalkyl-group is selected from: oxaazaspiro[3.3]heptyl, azabicyclo[3.1.0]hexyl, oxazabicyclo[2.2.1]heptyl-, diazabicyclo[2.2.1]heptyl, pyrrolidinyl, piperidinyl, piperazinyl, azetidinyl, morpholinyl; wherein said 4- to 7-membered heterocycloalkyl-group is optionally substituted, identically or differently, with 1 or 2 R$^4$ groups;

R$^{6a}$, R$^{6b}$ are the same or different and are independently selected from R$^6$;

R$^6$ represents a hydrogen atom or a C$_1$-C$_3$-alkyl-group;

R$^{6d}$ represents a —(C$_1$-C$_3$-alkyl)-N(R$^{6a}$)R$^{6b}$ group;

p represents 0;

q represents 0;

or a tautomer, an N-oxide, a hydrate, a solvate, or a salt thereof, or a mixture of same.

In another preferred embodiment, the invention relates to compounds of formula (I) or (Ib), supra, in which:

R$^1$ represents a hydrogen atom;

R$^2$ represents a hydrogen atom;

R$^3$ represents a —(CH$_2$)$_q$—X—(CH$_2$)$_p$—R$^5$ group;

X represents a bivalent —C(=O)—N(R$^{5a}$)— group;

R$^4$ represents hydroxy-, C$_1$-C$_3$-alkyl-, —N(R$^{6a}$)R$^{6b}$ or —N(R$^{6a}$)R$^{6d}$;

R$^{5a}$ represents a methyl-group;

R$^5$ represents a group selected from: C$_1$-C$_3$-alkyl-; wherein said C$_1$-C$_3$-alkyl-group is substituted with a —N(R$^{6a}$)R$^{6b}$ group;

or

N(R$^{5a}$)R$^5$ together represent a 4- to 7-membered heterocycloalkyl-group; wherein said 4- to 7-membered heterocycloalkyl-group is selected from: diazabicyclo[2.2.1]heptyl, pyrrolidinyl, piperidinyl, azetidinyl; wherein said 4- to 7-membered heterocycloalkyl-group is optionally substituted, identically or differently, with 1 or 2 $R^4$ groups;

$R^{6a}$, $R^{6b}$ are the same or different and are independently selected from $R^6$;

$R^6$ represents a hydrogen atom or a methyl-group;

$R^{6d}$ represents a —($C_1$-$C_3$-alkyl)-N($CH_3$)$_2$ group;

p presents 0;

q represents 0;

or a tautomer, an N-oxide, a hydrate, a solvate, or a salt thereof, or a mixture of same.

In another preferred embodiment, the invention relates to compounds of formula (Ia):

(Ia)

in which:

$R^1$ represents a hydrogen atom or a chlorine atom or a group selected from:
  methoxy-, —N($CH_3$)$_2$;

$R^3$ represents —X—$R^5$;

X represents —C(═O)—O— or —C(═O)—N($R^{5a}$)—;

$R^4$ represents fluoro-, hydroxy-, cyano-, methyl-, methoxy-, —N($R^{5a}$)—C(═O)—O—$R^{6b}$, —N($R^{6a}$)$R^{6b}$ or —C(═O)—N($R^{6a}$)$R^{6b}$;

$R^{5a}$ represents a hydrogen atom or a methyl group;

$R^5$ represents a $C_1$-$C_6$-alkyl-group; wherein said $C_1$-$C_6$-alkyl-group is optionally substituted, identically or differently, with 1, 2 or 3 $R^4$ groups;

or

N($R^{5a}$)$R^5$ together represent a 4- to 7-membered heterocycloalkyl-group, said group being optionally substituted, identically or differently, with 1 or 2 $R^4$ groups;

$R^{6a}$ represents a hydrogen atom or a methyl-group;

$R^{6b}$ represents a hydrogen atom or a methyl-group;

or a tautomer, an N-oxide, a hydrate, a solvate, or a salt thereof, or a mixture of same.

It is to be understood that the present invention relates to any sub-combination within any embodiment or aspect of the present invention of compounds of general formula (I), supra.

More particularly still, the present invention covers compounds of general formula (I) which are disclosed in the Examples section of this text, infra.

In accordance with another aspect, the present invention covers methods of preparing compounds of the present invention, said methods comprising the steps as described in the Experimental Section herein.

In a preferred embodiment, the present invention relates to a method of preparing compounds of general formula (I), supra, in which method an intermediate compound of general formula (II):

(II)

in which $R^2$ and $R^3$ are as defined for general formula (I), supra, and LG represents a leaving group, preferably a chlorine atom;

is allowed to react with an intermediate compound of general formula (III):

(III)

in which $R^1$ is as defined for general formula (I), supra.

In accordance with a further aspect, the present invention covers intermediate compounds which are useful in the preparation of compounds of the present invention of general formula (I), particularly in the method described herein. In particular, the present invention covers compounds of general formula (II):

(II)

in which $R^2$ and $R^3$ are as defined for the compounds of general formula (I), supra, and LG represents a leaving group, preferably a chlorine atom.

Synthesis of Compounds of General Formula (I) of the Present Invention

Compounds of general formula (I) can be synthesized according to the general procedure depicted in Scheme 1, wherein LG stands for a leaving group.

Scheme 1

(II) +

(III)

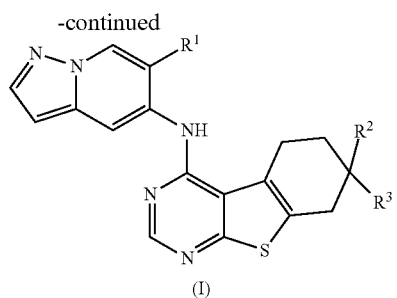

(I)

Scheme 1 exemplifies the main route that allows variations in $R^1$, $R^2$ and $R^3$. The coupling of compounds of formula (II) with pyrazolo[1,5-a]pyridin-5-amines such as (III) can be accomplished by reacting the two reactants in a suitable solvent, such as ethanol or a related lower aliphatic alcohol of the formula $C_1$-$C_4$-alkyl-OH or a cyclic ether, such as tetrahydrofuran or 1,4-dioxane, optionally in the presence of an acid such as hydrochloric acid. The compounds of formula (III) can be used either as free base or as corresponding salt with organic or inorganic acids. Alternatively, such amination reactions can be performed using catalysis by metals, such as palladium (see e.g. J. Y. Yoon et al., *Synthesis* 2009, (5), 815, and literature cited therein), to give compounds of formulae (I) or (III).

Modification of any of the substituents, $R^1$, $R^2$ and $R^3$ can be achieved before and/or after the exemplified transformation. However, also other routes may be used to synthesise the target compounds, in accordance with common general knowledge of a person skilled in the art of organic synthesis.

Said modifications can be such as the introduction of protecting groups, cleavage of protecting groups, reduction or oxidation of functional groups, formation or cleavage of esters or carboxamides, halogenation, metallation, substitution or other reactions known to a person skilled in the art. These transformations include those which introduce a functionality which allows for further interconversion of substituents. Appropriate protecting groups and their introduction and cleavage are well-known to a person skilled in the art (see for example T. W. Greene and P. G. M. Wuts in Protective Groups in Organic Synthesis, 3$^{rd}$ edition, Wiley 1999). Further, it is possible that two or more successive steps may be performed without work-up being performed between said steps, e.g. a "one-pot" reaction, as it is well-known to a person skilled in the art.

Compounds of the general formula (II), wherein $R^2$ and $R^3$ have the meanings as given for general formula (I), and wherein LG stands for a leaving group, can be readily prepared as shown in Scheme 2 by a so-called Gewald thiophene synthesis (for a seminal publication see e.g. K. Gewald et al., *Chem. Ber.* 1966, 94, 99), starting from ketones of the general formula (IV), to give the intermediate thiophene derivatives (V). Said intermediates are then cyclised to the thienopyrimidones (VI) employing a suitable $C_1$ synthon such as formamide. The resulting pyrimidones (VI) are then transferred into compounds of the general formula (II) by suitable procedures known to the person skilled in the art, such as treatment with a chlorinating agent. An instructive exemplary protocol for the sequence outlined in Scheme 2 can be found in WO 2005/010008, example 14, steps 1 to 3.

If $R^3$ in compounds of the formula (II) comprises a carboxylic ester, e.g. an ethyl ester, it is well possible to convert said ester into a carboxamide in the presence of LG e.g. representing a chloride, by mild ester hydrolysis using e.g. lithium hydroxide, followed by carboxamide coupling by procedures well known to the person skilled in the art.

Scheme 2

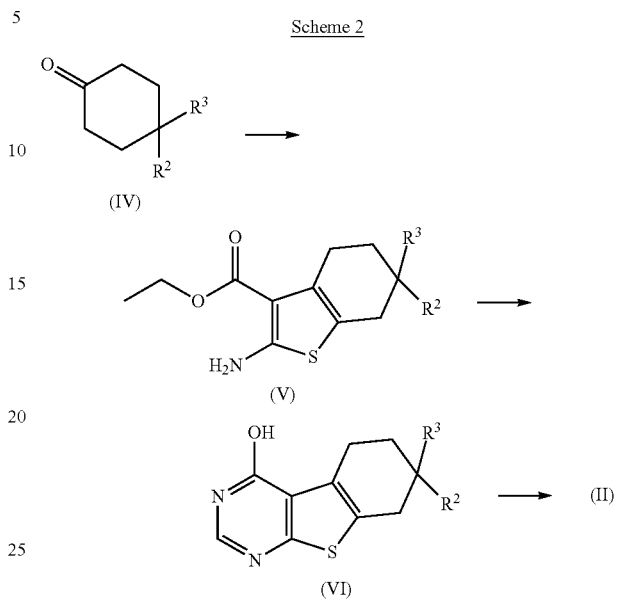

Multiple methods of isolating pure enantiomers from isomeric mixtures, e.g. racemic mixtures of chiral compounds are known to the person skilled in the art. Said methods encompass preparative HPLC on chiral stationary phase, kinetic resolution of racemic mixtures (for some examples see e.g. I. Shiina et al., Catal. Sci Technol. 2012, 2, 2200-2205; I. Shiina et al., Eur. J. Org. Chem. 2008, 5887-5890; D. G. Walker et al., Organic Process Research & Development 2001, 5, 23-27; B. N. Roy et al., Organic Process Research & Development 2009, 13, 450; T. Storz and P. Dittmar, Organic Process Research & Development 2003, 7, 559), enantioselective protonation (for some examples see e.g. C. Fehr and G. Galindo, Helv. Chim. Acta 1995, 78, 539-552, S. Hünig et al., Chem. Ber. 1994, 127, 1981-1988; S. Hünig et al., Chem. Ber. 1994, 127, 1969), enzymatic resolution (for some examples see e.g. T. Miyazawa, Amino Acids 1999, 16, 191-213), or, preferably and outlined in more detail below, temporary derivatisation with an enantiopure chiral synthon, separation of the resulting diastereomers, and removal of said chiral synthon, resulting in the isolation of the pure enantiomers of the parent compound (for some examples see e.g. Asymmetric Synthesis—The Essentials. Edited by Mathias Christmann and Stefan Bräse WILEY-VCH Verlag GmbH & Co. KGaA, Weinheim).

Scheme 3

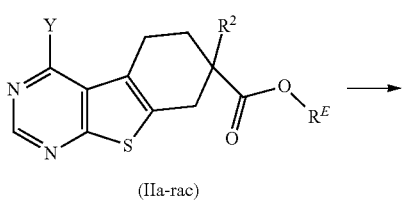

(IIa-rac)

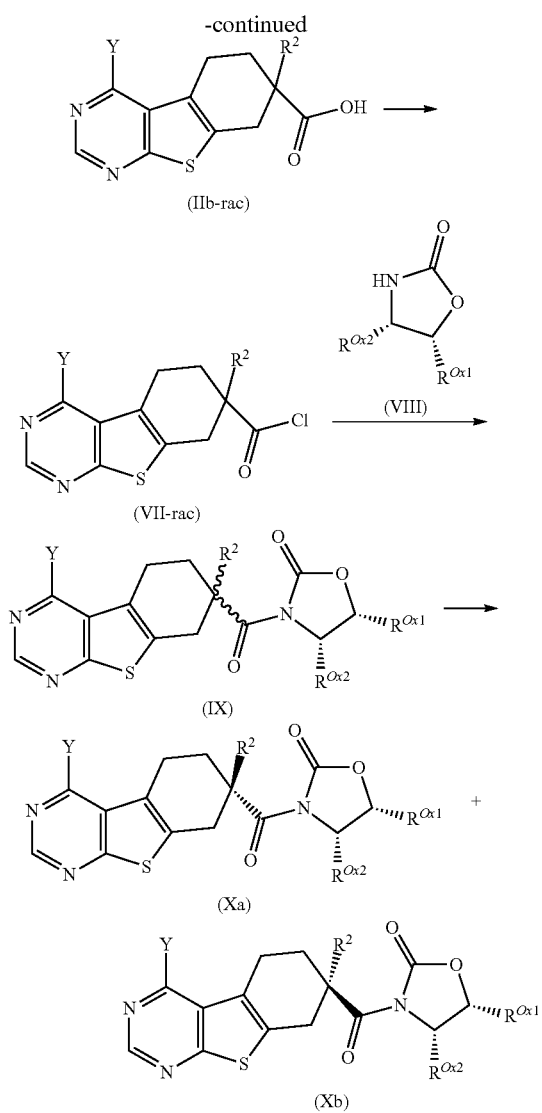

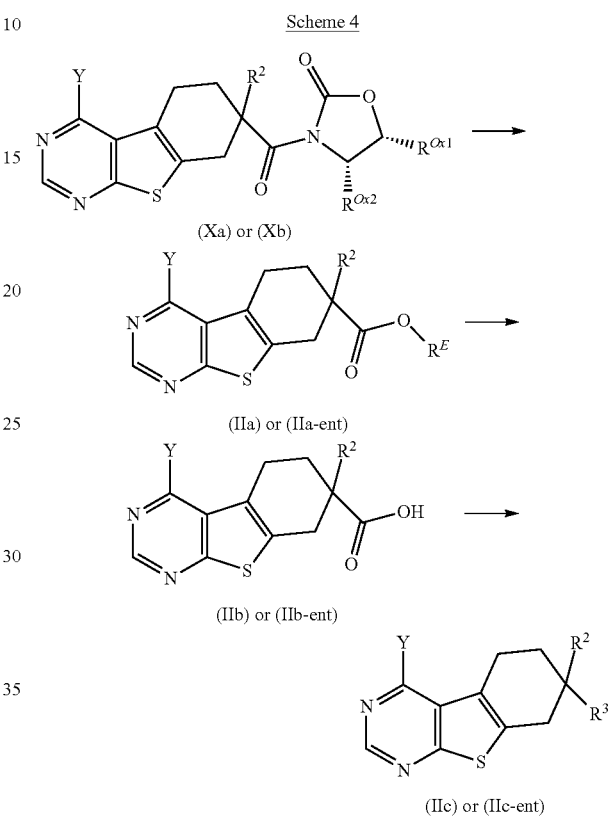

Scheme 3 illustrates the transformation of racemic pyrimidine synthons of the formula (IIa-rac), in which $R^E$ represents a $C_1$-$C_6$-alkyl group, and in which Y stands for a leaving group LG or a hydroxyl group, into an activated form such as an acid chloride of the formula (VII-rac). It is well possible to hydrolyse the ester group present in said synthons (IIa-rac) in the presence of Y e.g. representing a group LG e.g. representing a chloride, by mild ester hydrolysis using e.g. lithium hydroxide, as known by the person skilled in the art, to give carboxylic acids of formula (IIb-rac). These can be readily converted into acid chlorides of the formula (VII-rac) by methods well known to the person skilled in the art, such as the reaction with an inorganic acid chloride such as thionyl chloride.

Said acid chlorides (VII-rac) are subsequently reacted with a chiral, enantiomerically pure synthon such as an oxazolidinone of the formula (VIII), in which $R^{Ox1}$ represents a hydrogen atom or a $C_1$-$C_4$-alkyl group, preferably methyl, and in which $R^{Ox2}$ represents an aryl, aryl-$(CH_2)_n$— or a $C_1$-$C_4$-alkyl-group, wherein n is an integer selected from 1, 2 and 3, and wherein $R^{Ox2}$ preferably represents phenyl, after deprotonation of said oxazolidinone using a suitable deprotonation agent such as n-butyllithium or sodium hydride, at temperatures ranging from −78° C. to 0° C., preferably below −40° C., to give the amide coupling product of formula (IX) as mixture of two diastereoisomers. Said mixture can then be separated into the pure stereoisomers of formulae (Xa) and (Xb) using methods known to the person skilled in the art, such as fractionised crystallisation or column chromatography on silica gel.

Scheme 4 illustrates the transformation of the enatiomerically pure stereoisomer (Xa) or (Xb) to compounds of formula (IIa) or (IIa-ent), in which $R^E$ represents a $C_1$-$C_6$-alkyl group, and in which Y stands for a leaving group LG or a hydroxyl group, and whereby (IIa) and (ent-IIa) refer to the two enantiomers of the structure shown. The enatiomerically pure stereoisomer (IIa) or (IIa-ent) can subsequently be further transformed into the compounds of the present invention as outlined in Scheme 1. Said transformation can be accomplished by various ways known to the person skilled in the art; preferably, intermediates of the formula (Xa) or (Xb) are subjected to a transesterification reaction using, for example, titanium(IV)tetraethanolate in ethanol preferentially at elevated temperature. The resulting pyrimidine based ester synthons as pure stereoisomers of formula (IIa) or (IIa-ent) can subsequently be subjected to mild hydrolysis, as discussed supra, to give enantiopure carboxylic acids of formula (IIb) or (IIb-ent).

For example, further elaboration of compounds of formulae (IIb) or (IIb-ent), e.g. into compounds of the formulae (IIc) or (IIc-ent), in which $R^3$ stands for —C(=O)NR$^5$R$^4$, can be accomplished by coupling with amines of formula HN(R$^5$)R$^4$, in which R$^4$ and R$^5$ have the meaning as given for general formula (I) and which are widely commercially available, with a suitable coupling agent, such as HATU, TBTU, or 2,4,6-tripropyl-1,3,5,2,4,6-trioxatriphosphinane 2,4,6-trioxide (also known as T3P), as outlined in Scheme 4, to eventually give enantiopure amides of the general formula (I).

If needed, compounds of formulae (IIa), (IIa-ent), (IIa-rac), (IIb), (IIb-ent), (IIb-rac), (IIc), (IIc-ent), (VII-rac), (IX), (Xa) and (Xb), in which Y represents a hydroxy group can be converted into the respective compounds in which Y stands for a leaving group LG, i.e. into compounds of formulae (II) referred to in Schemes 1 and 2, by the methods described supra.

Scheme 5

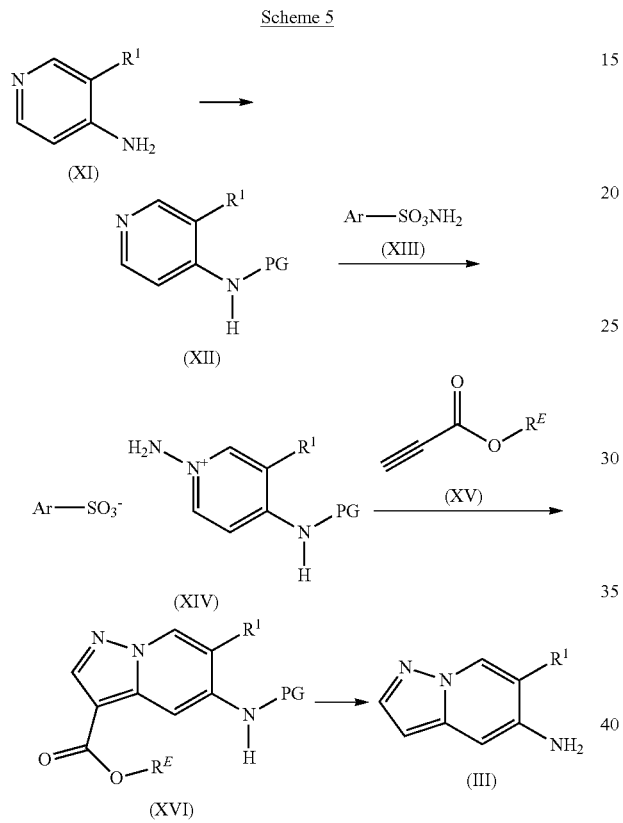

Compounds of the formula (III) are commercially available or can be synthesised by adapting procedures known to the person skilled in the art (see e.g. J. D. Kendall et al., *Bioorganic & Medicinal Chemistry* Vol. 20 (2012) 69-85; J. D. Kendall *Current Organic Chemistry*, 2011, 15, 2481-2518).

Scheme 5 exemplifies one route that allows variations and modifications in $R^1$ starting from commercially available 4-amino-pyridines of the formula (XI). The amino group in (XI) may be optionally protected by a suitable protective group (PG) like, for example, a tert-butyloxycarbonyl- or a allyloxycarbonyl-group, to give compounds of the formula (XII). N-Amination to compounds of the formula (XIV) is achieved by reacting compounds of the formula (XII) with commercially available aminooxy-sulfonyl compounds of the formula (XIII) in which Ar represents a optionally substituted aryl group, like, for example, 2-[(aminooxy)sulfonyl]-1,3,5-trimethylbenzene. This transformation can also be achieved by reacting compounds of the formula (XII) with O-(2,4-dinitrophenyl)hydroxylamine. Compounds of the formula (XIV) react with propiolate compounds of formula (XV) in which $R^E$ represents a hydrogen or a $C_1$-$C_6$-alkyl group optionally in the presence of an organic or inorganic base to compounds of formula (XVI). Cleavage of the ester ($R^E$=hydrogen), decarboxylation and removal of the protective group (PG) give compounds of formula (III).

However, also other routes may be used to synthesise the target compounds (III), in accordance with common general knowledge of a person skilled in the art of organic synthesis. The order of transformations exemplified in Scheme 5 is therefore not intended to be limiting. In addition, interconversion of any of the substituents as defined herein for $R^1$, PG and $R^E$ can be achieved before and/or after the exemplified transformations as described supra.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "xHCl", "xCF$_3$COOH", "xNa$^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The IUPAC names of the examples and intermediates were generated using the program 'ACD/Name batch version 12.01' from ACD LABS, and were adapted if needed.

Example 1

(RS) N,N-Dimethyl-4-(pyrazolo[1,5-a]pyridin-5-ylamino)-5,6,7,8-tetrahydro[1]benzothieno[2,3-d]pyrimidine-7-carboxamide

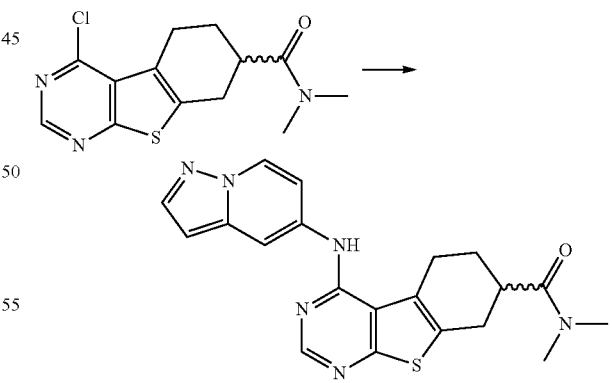

A mixture comprising 100 mg (338 µmol) (RS)-4-chloro-N,N-dimethyl-5,6,7,8-tetrahydro[1]benzothieno[2,3-d]pyrimidine-7-carboxamide (prepared according to intermediate example 1a), 45 mg pyrazolo[1,5-a]pyridin-5-amine, 2 mL dimethyl sulfoxide and 177 µL N-ethyl-N-isopropylpropan-2-amine was heated at 100° C. for 16 hours. The crude product was purified by chromatography to give 48.8 mg (37%) of the title compound.

$^1$H NMR (DMSO-d6): δ=1.77 (1H), 2.07 (1H), 2.87 (3H), 2.89-2.99 (2H), 3.09 (3H), 3.12-3.33 (3H), 6.49 (1H), 7.13 (1H), 7.91 (1H), 8.10 (1H), 8.37 (1H), 8.50 (1H), 8.60 (1H) ppm.

Example 1a (RS)-4-Chloro-N,N-dimethyl-5,6,7,8-tetrahydro[1]benzothieno[2,3-d]pyrimidine-7-carboxamide

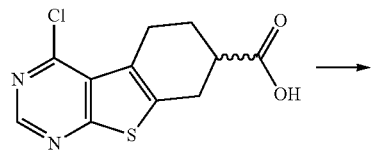

A mixture comprising 4.54 g (16.90 mmol) (RS)-4-chloro-5,6,7,8-tetrahydro[1]benzothieno[2,3-d]pyrimidine-7-carboxylic acid (prepared according to WO2013174744), 182 mL N,N-dimethylformamide, 8.83 mL N-ethyl-N-isopropylpropan-2-amine, 42.2 mL N-methylmethanamine solution (2M in tetrahydrofuran) and 40.2 mL 2,4,6-tripropyl-1,3,5,2,4,6-trioxatriphosphinane 2,4,6-trioxide solution (50% in N,N-dimethylformamide) was stirred at 23° C. for 1 hour. The mixture was poured into water, ice was added, the precipitate washed with water and diethyl ether and dried to give 3.44 g (65%) of the title compound.

Example 2

(7S)-4-(Pyrazolo[1,5-a]pyridin-5-ylamino)-5,6,7,8-tetrahydro[1]benzothieno[2,3-d]pyrimidine-7-carboxylic acid

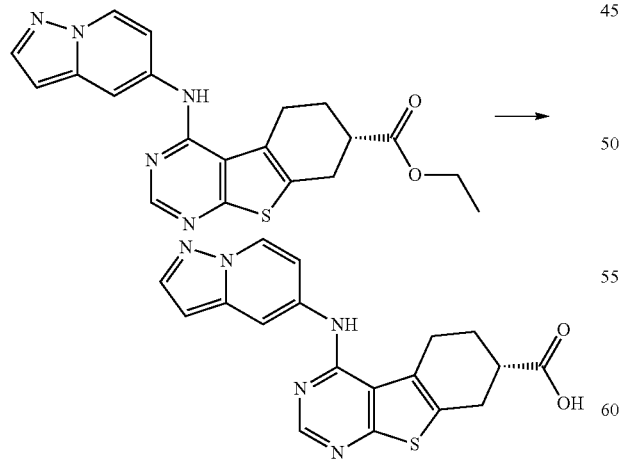

A mixture comprising 1.17 g (2.97 mmol) ethyl (7S)-4-(pyrazolo[1,5-a]pyridin-5-ylamino)-5,6,7,8-tetrahydro[1]benzothieno[2,3-d]pyrimidine-7-carboxylate (prepared according to intermediate example 2a), 51 mL tetrahydrofuran and 17.8 mL lithium hydroxide solution (1M in water) was stirred at 23° C. for 16 hours. The mixture was acidified with hydrochloric acid, the precipitate was filtered off, washed with water and dried to give 895 mg (54%) of the title compound.

$^1$H NMR (DMSO-d6): δ=1.94 (1H), 2.21 (1H), 2.86 (1H), 3.01 (1H), 3.10 (1H), 3.14-3.30 (2H), 6.51 (1H), 7.15 (1H), 7.93 (1H), 8.11 (1H), 8.41 (1H), 8.52 (1H), 8.62 (1H), 12.52 (1H) ppm.

Example 2a

Ethyl (7S)-4-(pyrazolo[1,5-a]pyridin-5-ylamino)-5,6,7,8-tetrahydro[1]benzothieno[2,3-d]pyrimidine-7-carboxylate

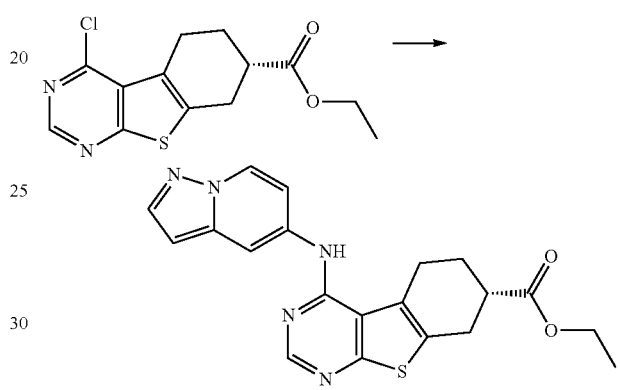

750 mg (2.53 mmol) ethyl (7S)-4-chloro-5,6,7,8-tetrahydro[1]benzothieno[2,3-d]pyrimidine-7-carboxylate (prepared according to intermediate example 2b) were transformed in analogy to example 1 to give after working up and purification 1.17 g (59%) of the title compound.

Example 2b

Ethyl (7S)-4-chloro-5,6,7,8-tetrahydro[1]benzothieno[2,3-d]pyrimidine-7-carboxylate

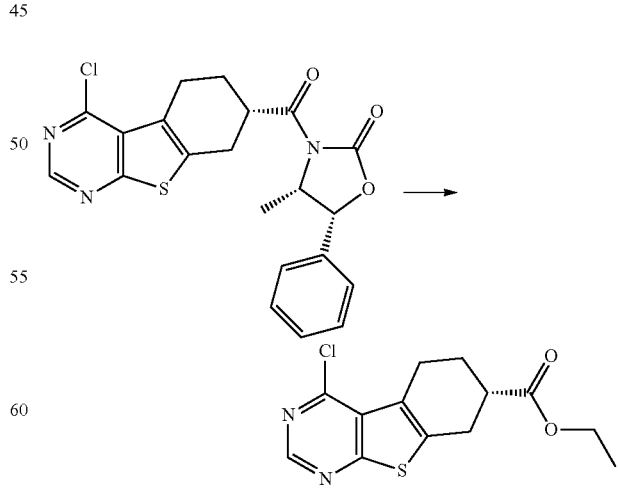

A mixture comprising 27.6 g (64.6 mmol) (4S,5R)-3-{[(7S)-4-chloro-5,6,7,8-tetrahydro[1]benzothieno[2,3-d]pyrimidin-7-yl]carbonyl}-4-methyl-5-phenyl-1,3-oxazolidin- 2-one (prepared according to intermediate example 2c), 830 mL ethanol and 24.4 mL titanium (4+) tetraethanolate was refluxed for 20 hours. 1.4 L ethyl acetate and 18 mL water were added and the mixture was stirred for 30 minutes. Silica gel was added and stirring was continued for 10 minutes. The mixture was filtered through celite, the solvents were removed and the residue was purified by chromatography to give 18.8 g (93%) of the title compound.

Example 2c (4S,5R)-3-{[(7S)-4-Chloro-5,6,7,8-tetrahydro[1]benzothieno[2,3-d]pyrimidin-7-yl]carbonyl}-4-methyl-5-phenyl-1,3-oxazolidin-2-one (A) and (4S,5R)-3-{[(7R)-4-chloro-5,6,7,8-tetrahydro[1]benzothieno[2,3-d]pyrimidin-7-yl]carbonyl}-4-methyl-5-phenyl-1,3-oxazolidin-2-one (B)

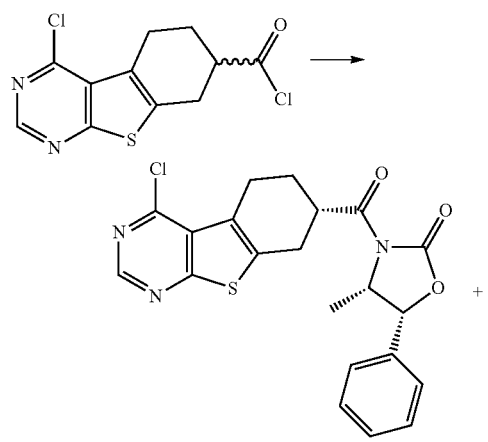

To a solution of 26.8 g (4S,5R)-4-methyl-5-phenyl-1,3-oxazolidin-2-one in 428 mL tetrahydrofurane were added 70 mL n-buthyllithium (2.5M in hexane) at 78° C. and the mixture was stirred at −60° C. for 1 hour. A solution of 45.8 g (159 mmol) 4-chloro-5,6,7,8-tetrahydro[1]benzothieno[2,3-d]pyrimidine-7(RS)-carbonyl chloride (prepared according to intermediate example 2d) in 428 mL tetrahydrofurane was added and stirring was continued at −70° C. for 1 hour. The mixture was poured into water, tetrahydrofurane was removed, the precipitate was filtered off, washed with water and resolved in dichloromethane. The organic layer was dried over sodium sulphate followed by addition of acetonitrile. The dichloromethane was removed, the precipitate filtered, washed with acetonitrile and diethylether to give 27.6 g (38%) of the title compound A. From the mother liquor a second precipitate was obtained on standing overnight to give 25.5 g (35%) of the title compound B.

Example 2d

4-Chloro-5,6,7,8-tetrahydro[1]benzothieno[2,3-d]pyrimidine-7(RS)-carbonyl chloride

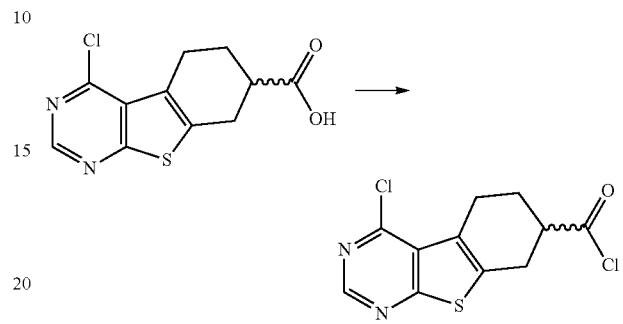

A mixture comprising 42.87 g (159 mmol) (RS)-4-chloro-5,6,7,8-tetrahydro[1]benzothieno[2,3-d]pyrimidine-7-carboxylic acid (prepared according to WO2013174744) and 349 mL thionyl chloride was heated at 100° C. for 3 hours. The reagent was removed to give the title compound that was used without further purification.

Example 3

[(3R)-3-Methylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone

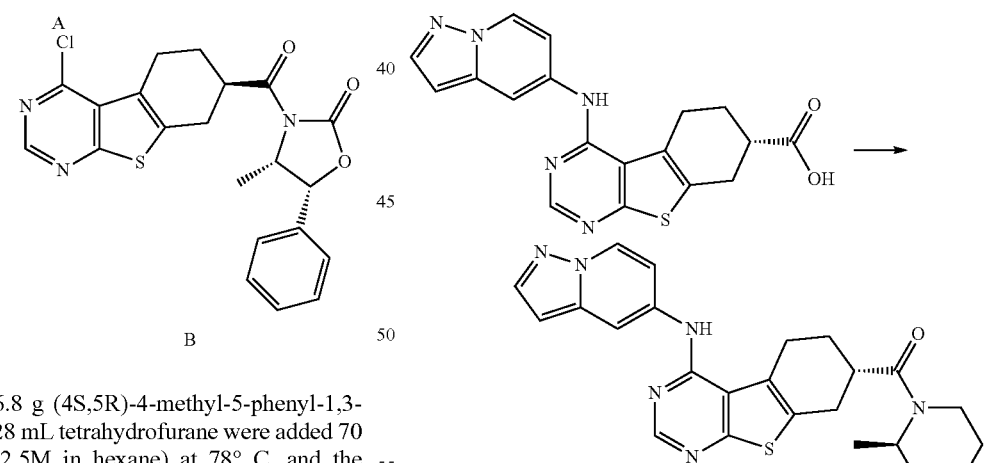

A mixture comprising 150 mg (410 µmol) (7S)-4-(pyrazolo[1,5-a]pyridin-5-ylamino)-5,6,7,8-tetrahydro[1]benzothieno[2,3-d]pyrimidine-7-carboxylic acid (prepared according to example 2), 6.13 mL dimethyl sulfoxide, 215 µL N-ethyl-N-isopropylpropan-2-amine, 280 µL (3R)-3-methylmorpholine and 716 µL 2,4,6-tripropyl-1,3,5,2,4,6-trioxatriphosphinane 2,4,6-trioxide solution (50% in N,N-dimethylformamide) was stirred at 23° C. for 16 hours. The crude mixture was purified by chromatography to give 55.4 mg (30%) of the title compound.

¹H NMR (DMSO-d6): δ=1.17+1.31 (3H), 1.78 (1H), 2.02+2.11 (1H), 2.86-3.91 (11H), 4.10+4.44 (1H), 6.51 (1H), 7.14 (1H), 7.93 (1H), 8.11 (1H), 8.41 (1H), 8.52 (1H), 8.61+8.63 (1H) ppm.

Example 4

(7S)—N-[2-(Dimethylamino)ethyl]-N-methyl-4-(pyrazolo[1,5-a]pyridin-5-ylamino)-5,6,7,8-tetrahydro[1]benzothieno[2,3-d]pyrimidine-7-carboxamide

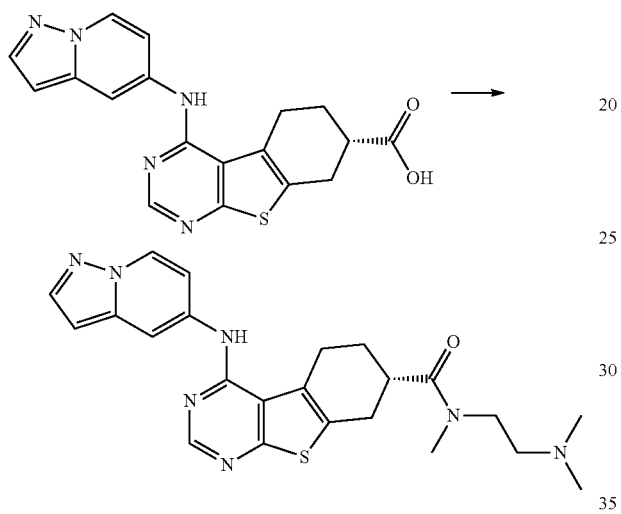

150 mg (410 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using N,N,N'-trimethylethane-1,2-diamine to give after working up and purification 46.4 mg (25%) of the title compound.

¹H NMR (DMSO-d6): δ=1.71-1.88 (1H), 2.07 (1H), 2.17+2.19 (6H), 2.36 (1H), 2.43 (1H), 2.89+3.11 (3H), 2.91-3.56 (7H), 6.51 (1H), 7.14 (1H), 7.93 (1H), 8.11 (1H), 8.40 (1H), 8.52 (1H), 8.61+8.63 (1H) ppm.

Example 5

[(2R,6S)-2,6-Dimethylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone

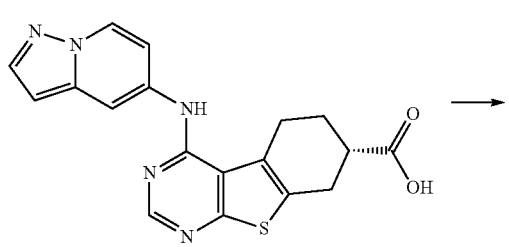

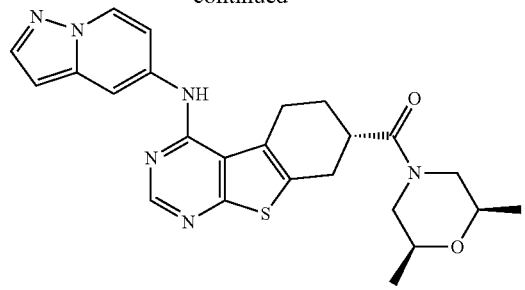

150 mg (410 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using (2R,6S)-2,6-dimethylmorpholine to give after working up and purification 7.1 mg (4%) of the title compound.

¹H NMR (DMSO-d6): δ=1.12 (6H), 1.81 (1H), 2.06 (1H), 2.29 (1H), 2.79 (1H), 2.89-3.07 (2H), 3.15-3.60 (5H), 3.95 (1H), 4.33 (1H), 6.51 (1H), 7.15 (1H), 7.93 (1H), 8.12 (1H), 8.40 (1H), 8.52 (1H), 8.63 (1H) ppm.

Example 6

[(3R)-3-(Dimethylamino)pyrrolidin-1-yl][(7S)-4-(pyrazolo[1,5-a]pyridin-5-ylamino)-5,6,7,8-tetrahydro[1]benzothieno[2,3-d]pyrimidin-7-yl]methanone

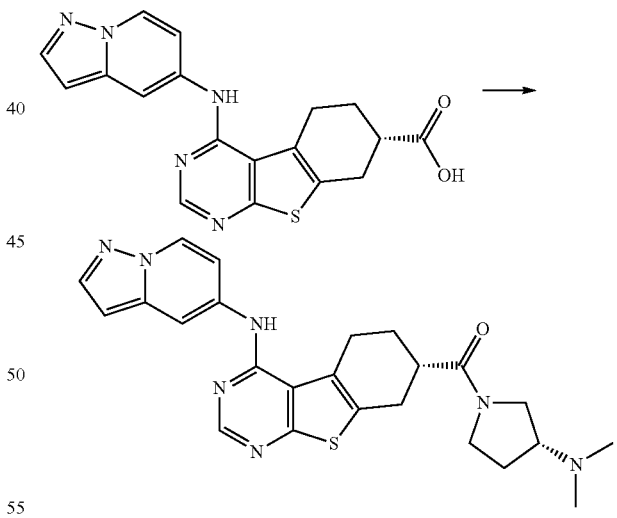

150 mg (410 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using (3R)—N,N-dimethylpyrrolidin-3-amine to give after working up and purification 35.2 mg (19%) of the title compound.

¹H NMR (DMSO-d6): δ=1.60-1.84 (2H), 1.98-2.15 (2H), 2.17 (6H), 2.58-2.77 (2H), 2.92-3.94 (8H), 6.51 (1H), 7.15 (1H), 7.93 (1H), 8.11 (1H), 8.40 (1H), 8.52 (1H), 8.61+8.63 (1H) ppm.

Example 7

[(3S)-3-Methylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone

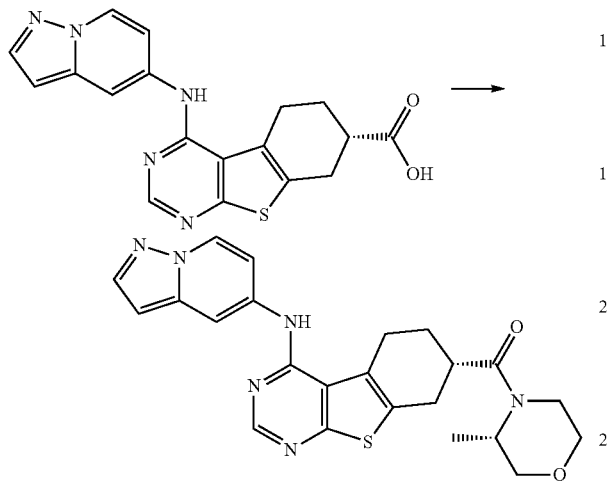

100 mg (274 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using (3S)-3-methylmorpholine to give after working up and purification 24.7 mg (19%) of the title compound.

$^1$H NMR (DMSO-d6): δ=1.17+1.31 (3H), 1.79 (1H), 1.95-2.14 (1H), 2.87-3.91 (11H), 4.09+4.44 (1H), 6.51 (1H), 7.14 (1H), 7.93 (1H), 8.11 (1H), 8.41 (1H), 8.52 (1H), 8.62+8.63 (1H) ppm.

Example 8

(7S)—N-(2-Methoxyethyl)-N-methyl-4-(pyrazolo[1,5-a]pyridin-5-ylamino)-5,6,7,8-tetrahydro[1]benzothieno[2,3-d]pyrimidine-7-carboxamide

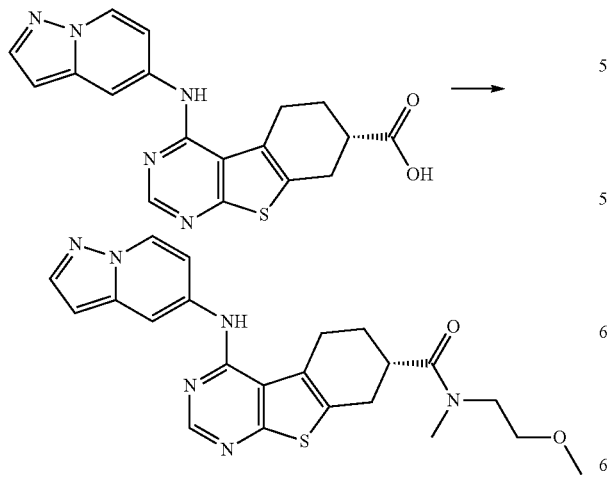

100 mg (274 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using 2-methoxy-N-methylethanamine to give after working up and purification 32.7 mg (27%) of the title compound.

$^1$H NMR (DMSO-d6): δ=1.80 (1H), 2.08 (1H), 2.89+3.13 (3H), 2.91-3.03 (2H), 3.10-3.30 (3H), 3.27+3.29 (3H), 3.43-3.53 (3H), 3.60 (1H), 6.51 (1H), 7.15 (1H), 7.93 (1H), 8.11 (1H), 8.40 (1H), 8.52 (1H), 8.63 (1H) ppm.

Example 9

[(2S,6S)-2,6-Dimethylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone

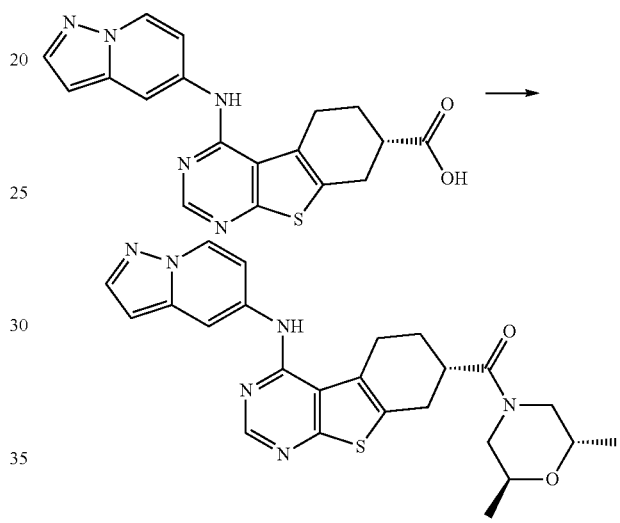

100 mg (274 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using (2S,6S)-2,6-dimethylmorpholine to give after working up and purification 30.3 mg (24%) of the title compound.

$^1$H NMR (DMSO-d6): δ=1.10+1.13 (6H), 1.84 (1H), 2.06 (1H), 2.98 (2H), 3.16-3.42 (5H), 3.47 (1H), 3.72 (1H), 3.95 (2H), 6.51 (1H), 7.16 (1H), 7.93 (1H), 8.12 (1H), 8.39 (1H), 8.52 (1H), 8.62 (1H) ppm.

Example 10

[(2R,6R)-2,6-Dimethylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone

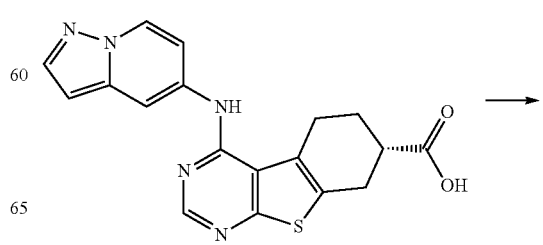

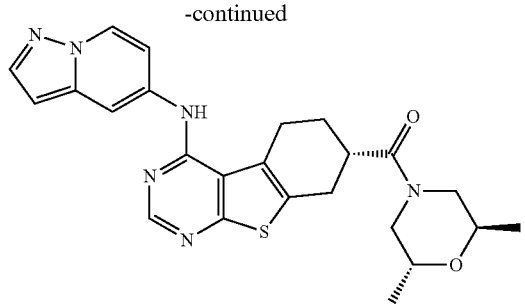

100 mg (274 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using (2R,6R)-2,6-dimethylmorpholine to give after working up and purification 25.2 mg (19%) of the title compound.

$^1$H NMR (DMSO-d6): δ=1.10+1.14 (6H), 1.83 (1H), 2.08 (1H), 2.91 (1H), 3.05 (1H), 3.17-3.31 (4H), 3.55 (2H), 3.69 (1H), 3.95 (2H), 6.51 (1H), 7.14 (1H), 7.93 (1H), 8.11 (1H), 8.40 (1H), 8.52 (1H), 8.63 (1H) ppm.

Example 11

Morpholin-4-yl[(7S)-4-(pyrazolo[1,5-a]pyridin-5-ylamino)-5,6,7,8-tetrahydro[1]benzothieno[2,3-d]pyrimidin-7-yl]methanone

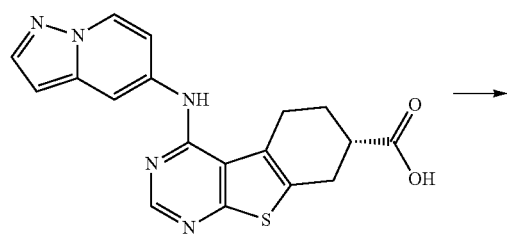

100 mg (274 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using morpholine to give after working up and purification 24.0 mg (18%) of the title compound.

$^1$H NMR (DMSO-d6): δ=1.82 (1H), 2.07 (1H), 2.90-3.06 (2H), 3.15-3.66 (11H), 6.51 (1H), 7.14 (1H), 7.93 (1H), 8.11 (1H), 8.41 (1H), 8.52 (1H), 8.62 (1H) ppm.

Example 12

3-Azabicyclo[3.1.0]hex-3-yl[(7S)-4-(pyrazolo[1,5-a]pyridin-5-ylamino)-5,6,7,8-tetrahydro[1]benzothieno[2,3-d]pyrimidin-7-yl]methanone

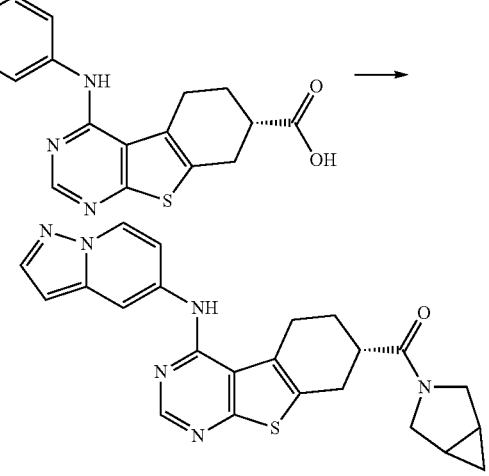

100 mg (274 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using 3-azabicyclo[3.1.0]hexane to give after working up and purification 5.0 mg (4%) of the title compound.

$^1$H NMR (DMSO-d6): δ=0.13 (1H), 0.72 (1H), 1.56 (1H), 1.64 (1H), 1.76 (1H), 2.08 (1H), 2.83-3.80 (8H), 6.51 (1H), 7.14 (1H), 7.93 (1H), 8.11 (1H), 8.19 (1H), 8.39 (1H), 8.52 (1H), 8.62 (1H) ppm.

Example 13

[(3R,5S)-3,5-Dimethylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone

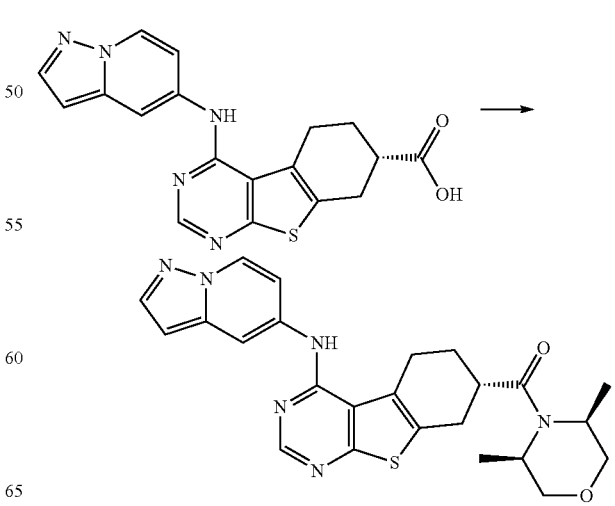

80 mg (219 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using (3R,5S)-3,5-dimethylmorpholine to give after working up and purification 11.2 mg (11%) of the title compound.

¹H NMR (DMSO-d6): δ=1.23 (3H), 1.35 (3H), 1.72-2.14 (2H), 2.92 (1H), 2.98-3.30 (4H), 3.49 (1H), 3.57 (1H), 3.67-3.76 (2H), 3.98+4.10 (1H), 4.29 (1H), 6.51 (1H), 7.14 (1H), 7.93 (1H), 8.11 (1H), 8.40 (1H), 8.52 (1H), 8.62 (1H) ppm.

Example 14

[(3R,5R)-3,5-Dimethylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone

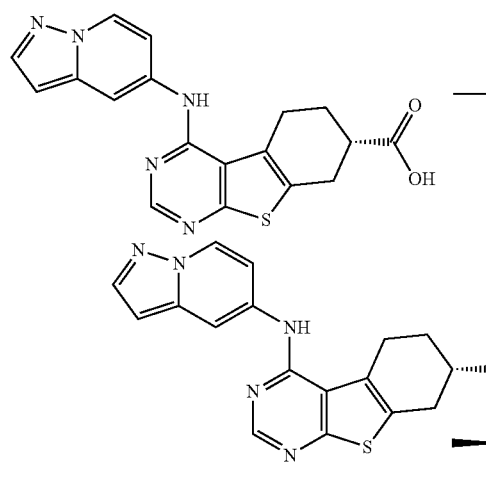

80 mg (219 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 3 using (3R,5R)-3,5-dimethylmorpholine to give after working up and purification 15.4 mg (14%) of the title compound.

¹H NMR (DMSO-d6): δ=1.32 (6H), 1.92 (1H), 2.06 (1H), 2.86 (1H), 2.98-3.40 (4H), 3.58 (2H), 3.95-4.13 (4H), 6.51 (1H), 7.16 (1H), 7.93 (1H), 8.13 (1H), 8.39 (1H), 8.53 (1H), 8.63 (1H) ppm.

Example 15

(7S)-4-[(6-Methoxypyrazolo[1,5-a]pyridin-5-yl)amino]-N,N-dimethyl-5,6,7,8-tetrahydro[1]benzothieno[2,3-d]pyrimidine-7-carboxamide

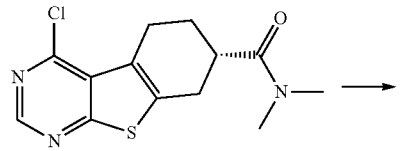

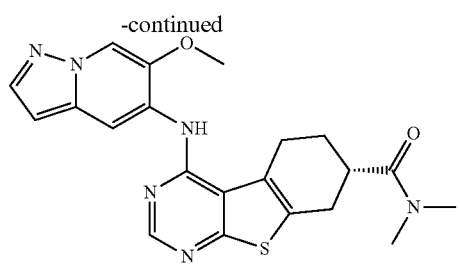

A mixture comprising 52.2 mg (176 µmol) (7S)-4-chloro-N,N-dimethyl-5,6,7,8-tetrahydro[1]benzothieno[2,3-d]pyrimidine-7-carboxamide (prepared according to intermediate example 15a), 28.8 mg 6-methoxypyrazolo[1,5-a]pyridin-5-amine (prepared according to intermediate example 15c), 1 mL ethanol was heated at 120° C. for 16 hours. 300 µL N,N-diethylethanamine were added, the precipitate was filtered off and dried to give 3.8 mg (5%) of the title compound.

¹H NMR (DMSO-d6): δ=1.84 (1H), 2.18 (1H), 2.89 (3H), 2.97 (2H), 3.12 (3H), 3.15-3.29 (3H), 4.02 (3H), 6.52 (1H), 7.84 (1H), 8.36 (1H), 8.54 (1H), 8.63 (1H), 8.85 (1H) ppm.

Example 15a (7S)-4-Chloro-N,N-dimethyl-5,6,7,8-tetrahydro[1]benzothieno[2,3-d]pyrimidine-7-carboxamide

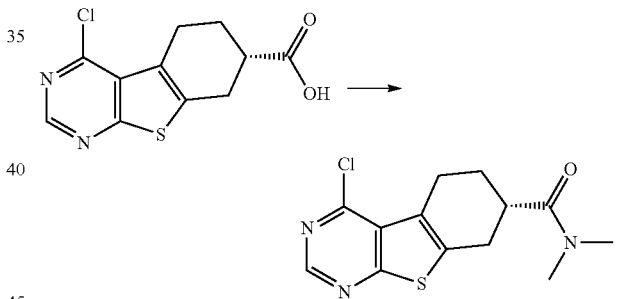

372 mg (1.38 mmol) (7S)-4-chloro-5,6,7,8-tetrahydro[1]benzothieno[2,3-d]pyrimidine-7-carboxylic acid (prepared according to intermediate example 15b) were transformed in analogy to intermediate example 1a to give after working up and purification 308 mg (75%) of the title compound.

Example 15b (7S)-4-Chloro-5,6,7,8-tetrahydro[1]benzothieno[2,3-d]pyrimidine-7-carboxylic acid

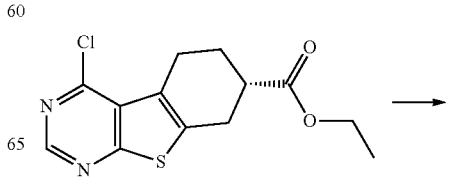

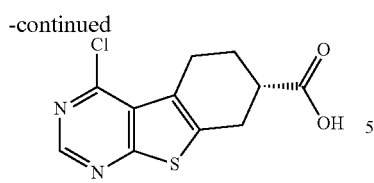

4.38 g (14.76 mmol) ethyl (7S)-4-chloro-5,6,7,8-tetrahydro[1]benzothieno[2,3-d]pyrimidine-7-carboxylate (prepared according to intermediate example 2b) were transformed in analogy to example 2 to give after working up and purification 3.87 g (93%) of the title compound.

Example 15c

6-Methoxypyrazolo[1,5-a]pyridin-5-amine

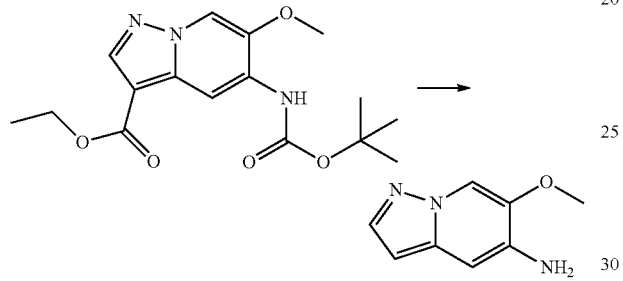

A mixture comprising 120 mg (358 μmol) ethyl 5-[(tert-butoxycarbonyl)amino]-6-methoxypyrazolo[1,5-a]pyridine-3-carboxylate (prepared according to intermediate example 15d) and 3.0 mL sulfuric acid (40%) was heated under reflux for 16 hours. Under cooling, the mixture was neutralized by addition of sodium hydroxide solution and extracted with dichloromethane. After removal of the solvent 29.5 mg (51%) of the title compound was isolated.

Example 15d

Ethyl 5-[(tert-butoxycarbonyl)amino]-6-methoxy-pyrazolo[1,5-a]pyridine-3-carboxylate

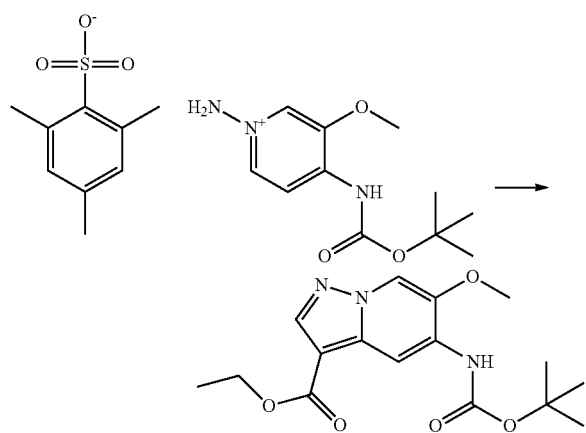

A mixture comprising 3.75 g (8.52 mmol) 1-amino-4-[(tert-butoxycarbonyl)amino]-3-methoxypyridinium 2,4,6-trimethylbenzenesulfonate (prepared according to intermediate example 15e), 12 mL N,N-dimethylformamide, 1.25 g potassium carbonate and 459 μL ethyl propiolate was stirred at 23° C. for 16 hours.

Example 15e

1-Amino-4-[(tert-butoxycarbonyl)amino]-3-methoxypyridinium 2,4,6-trimethylbenzenesulfonate

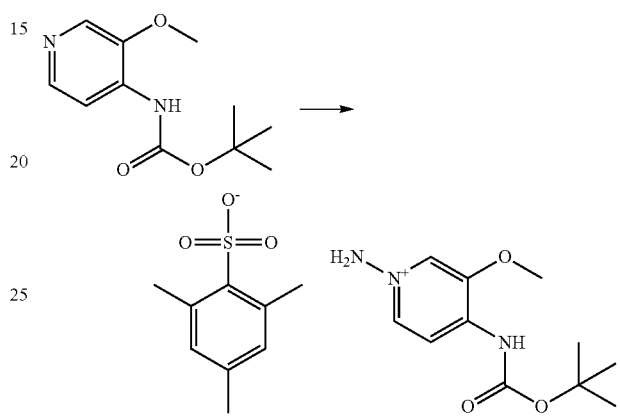

A solution of 2.33 g 2-[(aminooxy)sulfonyl]-1,3,5-trimethylbenzene (CAS-No: 36015-40-7) in 100 mL dichloromethane was cooled to 3° C. A solution of 1.99 g (8.87 mmol) tert-butyl (3-methoxypyridin-4-yl)carbamate (prepared according to intermediate example 15f) in 30 mL dichloromethane was added dropwise and the mixture was stirred at 23° C. for 16 hours. The solvent was removed to give 3.74 g (96%) of the title compound that was used without further purification.

Example 15f tert-Butyl (3-methoxypyridin-4-yl)carbamate

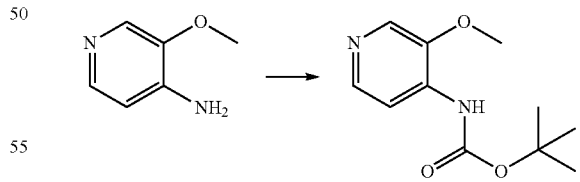

A mixture comprising 1.00 g (8.06 mmol) 3-methoxy-pyridin-4-amine (CAS-No: 52334-90-4), 10 mL tetrahydrofuran, 1.54 mL N-ethyl-N-isopropylpropan-2-amine and 2.04 mL di-tert-butyl dicarbonate was stirred at 23° C. for 16 hours. Saturated aqueous ammonium chloride was added and the mixture extracted with ethyl acetate. The organic layer was washed with water, brine and dried. After removal of the solvents 1.99 g of the crude title compound were obtained that was used without further purification.

Example 16

(7S)—N-Isopropyl-N-methyl-4-(pyrazolo[1,5-a]pyridin-5-ylamino)-5,6,7,8-tetrahydro[1]benzothieno[2,3-d]pyrimidine-7-carboxamide

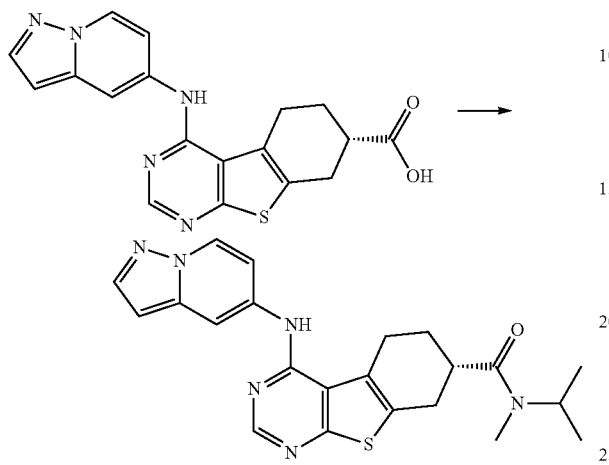

A mixture comprising 100 mg (274 µmol) (7S)-4-(pyrazolo[1,5-a]pyridin-5-ylamino)-5,6,7,8-tetrahydro[1]benzothieno[2,3-d]pyrimidine-7-carboxylic acid (prepared according to example 2), 5.0 mL N,N-dimethylacetamide, 286 µL N-ethyl-N-isopropylpropan-2-amine, 143 µL N-methylpropan-2-amine and 489 µL 2,4,6-tripropyl-1,3,5,2,4,6-trioxatriphosphinane 2,4,6-trioxide solution (50% in ethyl acetate) was stirred at 50° C. for 16 hours. The crude mixture was purified by chromatography to give 68.5 mg (57%) of the title compound.

$^1$H NMR (DMSO-d6): δ=1.05+1.18 (6H), 1.79 (1H), 2.03 (1H), 2.71+2.90 (3H), 2.86-3.30 (5H), 4.25+4.72 (1H), 6.48 (1H), 7.13 (1H), 7.91 (1H), 8.10 (1H), 8.37 (1H), 8.49 (1H), 8.60 (1H) ppm.

Example 17

(7S)—N,N-Dimethyl-4-(pyrazolo[1,5-a]pyridin-5-ylamino)-5,6,7,8-tetrahydro[1]benzothieno[2,3-d]pyrimidine-7-carboxamide

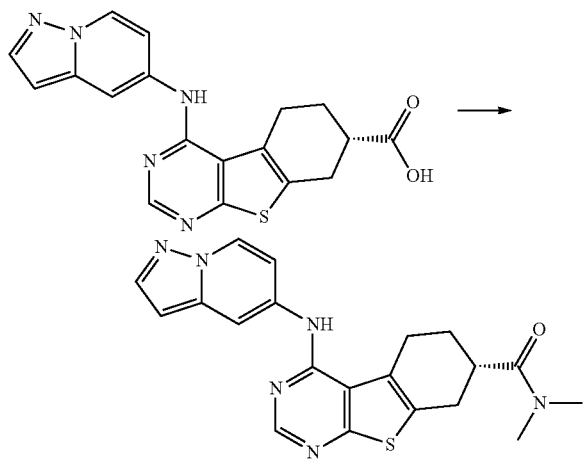

70 mg (192 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using N-methylmethanamine to give after working up and purification 47.9 mg (61%) of the title compound.

$^1$H NMR (DMSO-d6): δ=1.77 (1H), 2.08 (1H), 2.87 (3H), 2.94 (2H), 3.09 (3H), 3.12-3.29 (3H), 6.49 (1H), 7.13 (1H), 7.91 (1H), 8.10 (1H), 8.37 (1H), 8.50 (1H), 8.60 (1H) ppm.

Example 18

(7S)—N-(2,2-Difluoroethyl)-N-methyl-4-(pyrazolo[1,5-a]pyridin-5-ylamino)-5,6,7,8-tetrahydro[1]benzothieno[2,3-d]pyrimidine-7-carboxamide

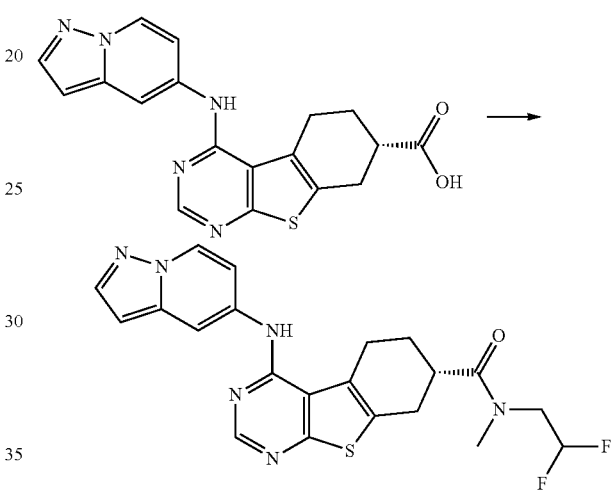

70 mg (192 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using 2,2-difluoro-N-methylethanamine to give after working up and purification 51.5 mg (58%) of the title compound.

$^1$H NMR (DMSO-d6): δ=1.80 (1H), 2.01-2.14 (1H), 2.93+3.19 (3H), 2.92-3.00 (2H), 3.14-3.36 (3H), 3.76+3.95 (2H), 6.12+6.15 (1H), 6.49 (1H), 7.12+7.14 (1H), 7.91 (1H), 8.09 (1H), 8.38 (1H), 8.50 (1H), 8.60 (1H) ppm.

Example 19

(7S)—N-(2-Hydroxy-2-methylpropyl)-N-methyl-4-(pyrazolo[1,5-a]pyridin-5-ylamino)-5,6,7,8-tetrahydro[1]benzothieno[2,3-d]pyrimidine-7-carboxamide

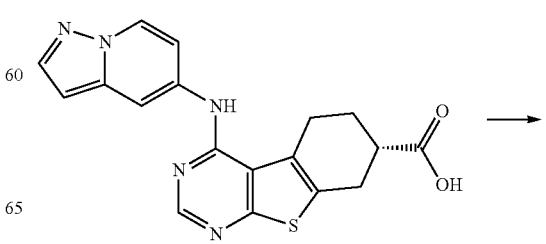

-continued

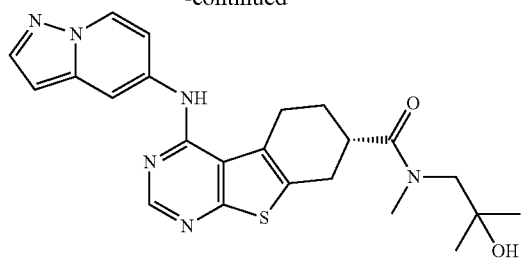

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using 2-methyl-1-(methylamino)propan-2-ol to give after working up and purification 64.3 mg (66%) of the title compound.

$^1$H NMR (DMSO-d6): δ=1.07+1.14 (6H), 1.79 (1H), 2.05+2.13 (1H), 2.86-3.01 (2H), 2.97+3.22 (3H), 3.16-3.42 (5H), 4.52+4.61 (1H), 6.51 (1H), 7.14 (1H), 7.93 (1H), 8.11 (1H), 8.40 (1H), 8.52 (1H), 8.63 (1H) ppm.

Example 20

Azetidin-1-yl[(7S)-4-(pyrazolo[1,5-a]pyridin-5-ylamino)-5,6,7,8-tetrahydro[1]benzothieno[2,3-d]pyrimidin-7-yl]methanone

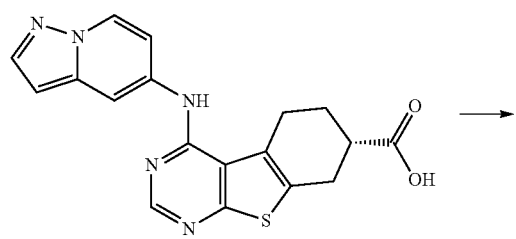

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using azetidine to give after working up and purification 42.6 mg (49%) of the title compound.

$^1$H NMR (DMSO-d6): δ=1.76 (1H), 2.07 (1H), 2.23 (2H), 2.75 (1H), 2.93 (2H), 3.14-3.31 (2H), 3.90 (2H), 4.25 (2H), 6.50 (1H), 7.14 (1H), 7.93 (1H), 8.11 (1H), 8.40 (1H), 8.52 (1H), 8.62 (1H) ppm.

Example 21

(7S)—N-Ethyl-N-(2-hydroxyethyl)-4-(pyrazolo[1,5-a]pyridin-5-ylamino)-5,6,7,8-tetrahydro[1]benzothieno[2,3-d]pyrimidine-7-carboxamide

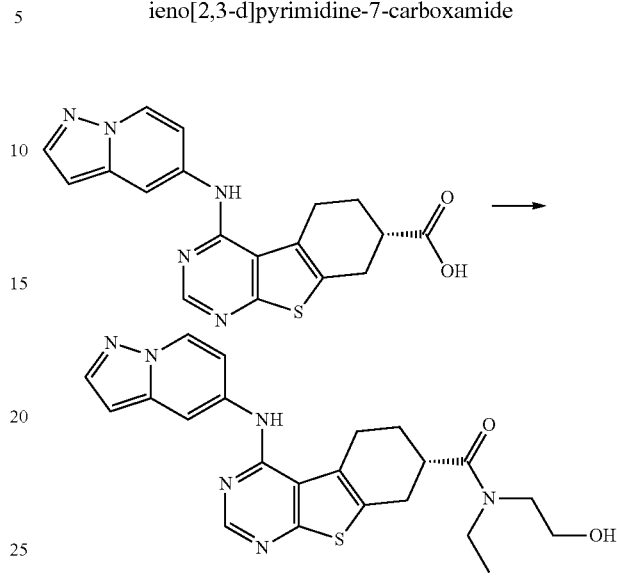

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using 2-(ethylamino)ethanol to give after working up and purification 23.2 mg (25%) of the title compound.

$^1$H NMR (DMSO-d6): δ=1.05+1.16 (3H), 1.81 (1H), 2.07 (1H), 2.88-3.60 (11H), 4.69+4.88 (1H), 6.51 (1H), 7.15 (1H), 7.93 (1H), 8.11 (1H), 8.40 (1H), 8.52 (1H), 8.62 (1H) ppm.

Example 22

1-{[(7S)-4-(Pyrazolo[1,5-a]pyridin-5-ylamino)-5,6,7,8-tetrahydro[1]benzothieno[2,3-d]pyrimidin-7-yl]carbonyl}azetidine-3-carbonitrile

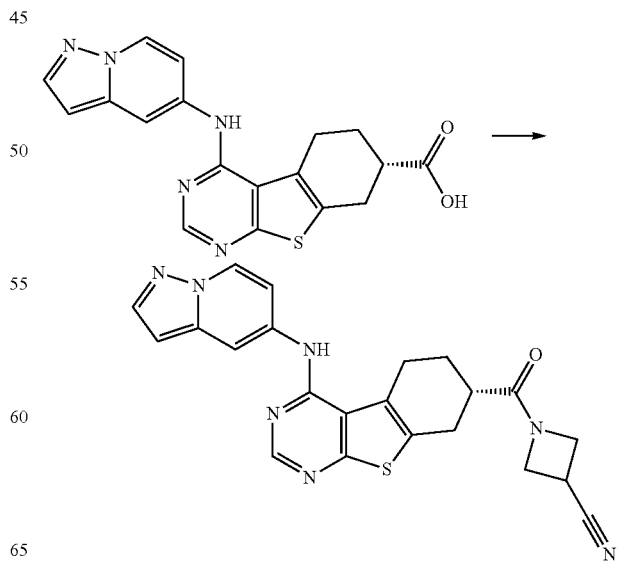

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using azetidine-3-carbonitrile to give after working up and purification 67.2 mg (69%) of the title compound.

¹H NMR (DMSO-d6): δ=1.76 (1H), 2.07 (1H), 2.75 (1H), 2.84-3.03 (2H), 3.12-3.29 (2H), 3.81 (1H), 4.04 (1H), 4.17 (1H), 4.42-4.60 (2H), 6.49 (1H), 7.12 (1H), 7.91 (1H), 8.09 (1H), 8.38 (1H), 8.50 (1H), 8.60 (1H) ppm.

Example 23

(3,3-Difluoroazetidin-1-yl)[(7S)-4-(pyrazolo[1,5-a]pyridin-5-ylamino)-5,6,7,8-tetrahydro[1]benzothieno[2,3-d]pyrimidin-7-yl]methanone

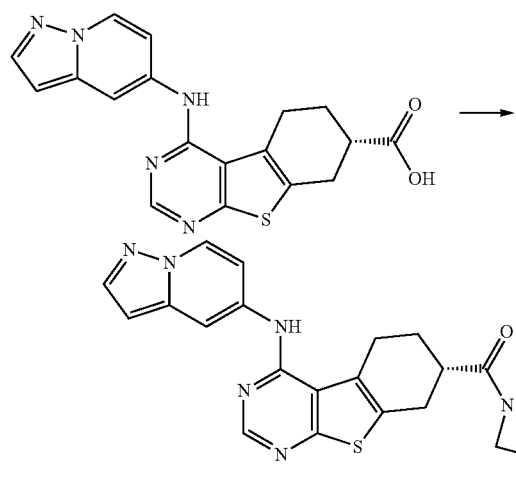

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using 3,3-difluoroazetidine to give after working up and purification 59.7 mg (63%) of the title compound.

¹H NMR (DMSO-d6): δ=1.79 (1H), 2.12 (1H), 2.84 (1H), 2.93 (1H), 3.02 (1H), 3.17 (1H), 3.27 (1H), 4.32 (2H), 4.75 (2H), 6.49 (1H), 7.12 (1H), 7.91 (1H), 8.08 (1H), 8.40 (1H), 8.50 (1H), 8.60 (1H) ppm.

Example 24

(3-Hydroxyazetidin-1-yl)[(7S)-4-(pyrazolo[1,5-a]pyridin-5-ylamino)-5,6,7,8-tetrahydro[1]benzothieno[2,3-d]pyrimidin-7-yl]methanone

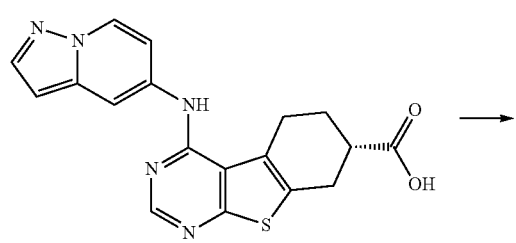

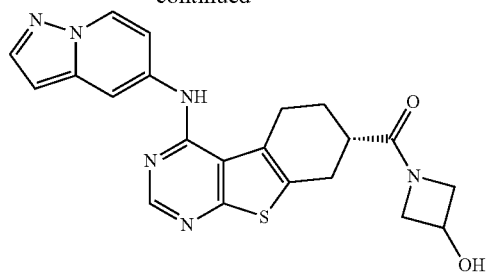

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using azetidin-3-ol to give after working up and purification 45.1 mg (50%) of the title compound.

¹H NMR (DMSO-d6): δ=1.76 (1H), 2.07 (1H), 2.78 (1H), 2.93 (2H), 3.20 (1H), 3.29 (1H), 3.63 (1H), 3.93-4.12 (2H), 4.37-4.53 (2H), 5.76 (1H), 6.50 (1H), 7.14 (1H), 7.93 (1H), 8.11 (1H), 8.40 (1H), 8.52 (1H), 8.62 (1H) ppm.

Example 25 tert-Butyl [2-(methyl{[(7S)-4-(pyrazolo[1,5-a]pyridin-5-ylamino)-5,6,7,8-tetrahydro[1]benzothieno[2,3-d]pyrimidin-7-yl]carbonyl}amino)ethyl]carbamate

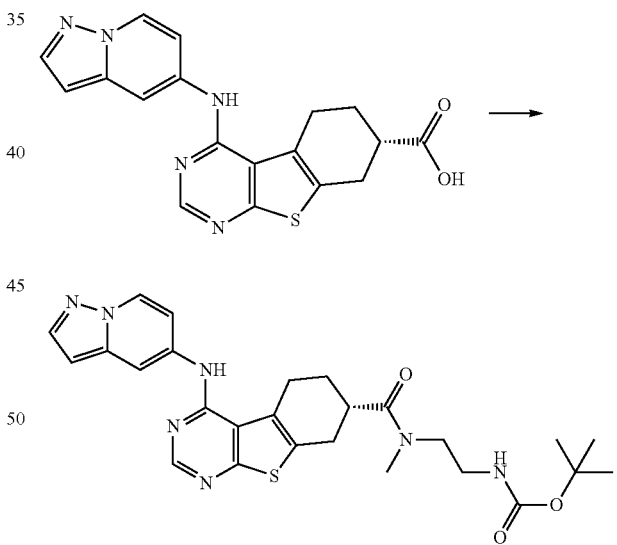

200 mg (547 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using tert-butyl [2-(methylamino)ethyl] carbamate to give after working up and purification 134 mg (45%) of the title compound.

¹H NMR (DMSO-d6): δ=1.31+1.39 (9H), 1.79 (1H), 2.09 (1H), 2.86+3.11 (3H), 2.87-3.61 (9H), 6.51 (1H), 6.85+7.04 (1H), 7.14 (1H), 7.93 (1H), 8.11 (1H), 8.41 (1H), 8.52 (1H), 8.62 (1H) ppm.

Example 26

(7S)—N-[2-(Dimethylamino)-2-oxoethyl]-N-methyl-4-(pyrazolo[1,5-a]pyridin-5-ylamino)-5,6,7,8-tetrahydro[1]benzothieno[2,3-d]pyrimidine-7-carboxamide

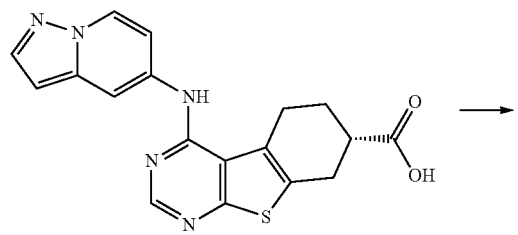

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using N,N,N²-trimethylglycinamide to give after working up and purification 55.4 mg (55%) of the title compound.

$^1$H NMR (DMSO-d6): δ=1.78 (1H), 2.04+2.15 (1H), 2.82+2.84 (3H), 2.86+3.10 (3H), 2.90 (1H), 2.94-2.99 (4H), 3.14-3.35 (3H), 4.12+4.33 (1H), 4.26+4.48 (1H), 6.51 (1H), 7.15 (1H), 7.93 (1H), 8.11 (1H), 8.39 (1H), 8.51 (1H), 8.62 (1H) ppm.

Example 27

(7S)—N-[3-(Dimethylamino)propyl]-N-methyl-4-(pyrazolo[1,5-a]pyridin-5-ylamino)-5,6,7,8-tetrahydro[1]benzothieno[2,3-d]pyrimidine-7-carboxamide

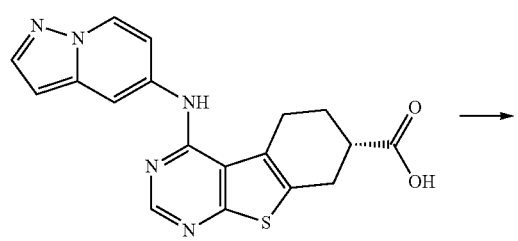

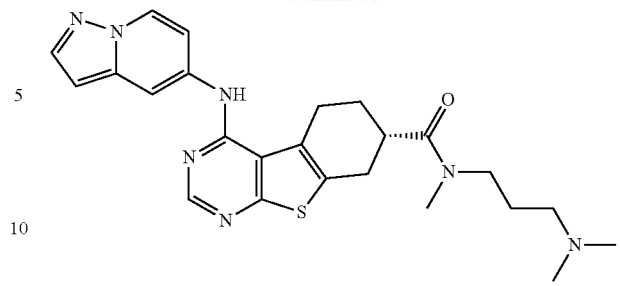

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using N,N,N'-trimethylpropane-1,3-diamine to give after working up and purification 55.1 mg (55%) of the title compound.

$^1$H NMR (DMSO-d6): δ=1.61 (1H), 1.69 (1H), 1.80 (1H), 2.06 (1H), 2.12 (3H), 2.13 (3H), 2.19 (2H), 2.86+3.09 (3H), 2.96 (2H), 3.11-3.39 (4H), 3.43 (1H), 6.51 (1H), 7.14 (1H), 7.93 (1H), 8.11 (1H), 8.40 (1H), 8.52 (1H), 8.62 (1H) ppm.

Example 28

[3-(Dimethylamino)azetidin-1-yl][(7S)-4-(pyrazolo[1,5-a]pyridin-5-ylamino)-5,6,7,8-tetrahydro[1]benzothieno[2,3-d]pyrimidin-7-yl]methanone

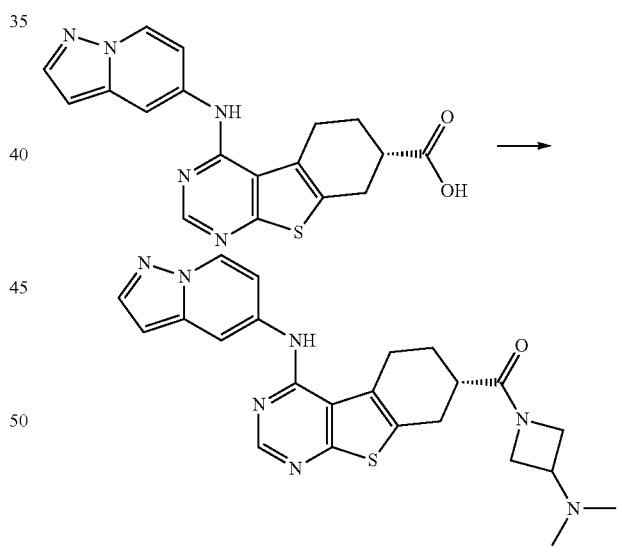

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using N,N-dimethylazetidin-3-amine to give after working up and purification 68.6 mg (71%) of the title compound.

$^1$H NMR (DMSO-d6): δ=1.76 (1H), 2.05 (1H), 2.08 (6H), 2.77 (1H), 2.92 (2H), 3.05 (1H), 3.17 (1H), 3.28 (1H), 3.66 (1H), 3.88 (1H), 4.03 (1H), 4.23 (1H), 6.48 (1H), 7.12 (1H), 7.91 (1H), 8.09 (1H), 8.38 (1H), 8.50 (1H), 8.60 (1H) ppm.

Example 29

(4-Methylpiperazin-1-yl)[(7S)-4-(pyrazolo[1,5-a]pyridin-5-ylamino)-5,6,7,8-tetrahydro[1]benzothieno[2,3-d]pyrimidin-7-yl]methanone

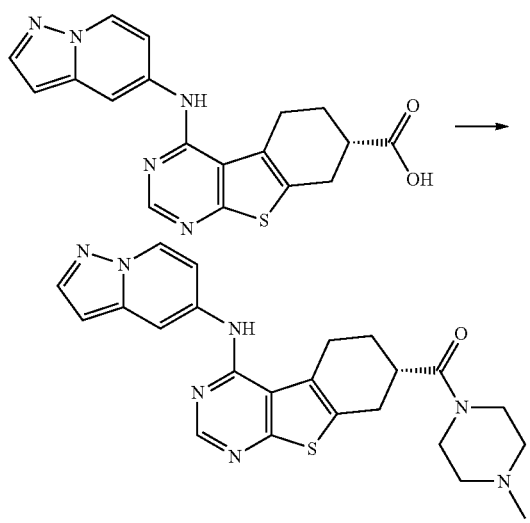

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using 1-methylpiperazine to give after working up and purification 63.5 mg (66%) of the title compound.

$^1$H NMR (DMSO-d6): δ=1.79 (1H), 2.04 (1H), 2.19 (3H), 2.27 (2H), 2.34 (2H), 2.91 (1H), 2.99 (1H), 3.13-3.29 (3H), 3.50 (2H), 3.55 (2H), 6.48 (1H), 7.13 (1H), 7.91 (1H), 8.10 (1H), 8.37 (1H), 8.50 (1H), 8.60 (1H) ppm.

Example 30

(3-Hydroxy-3-methylazetidin-1-yl)[(7S)-4-(pyrazolo[1,5-a]pyridin-5-ylamino)-5,6,7,8-tetrahydro[1]benzothieno[2,3-d]pyrimidin-7-yl]methanone

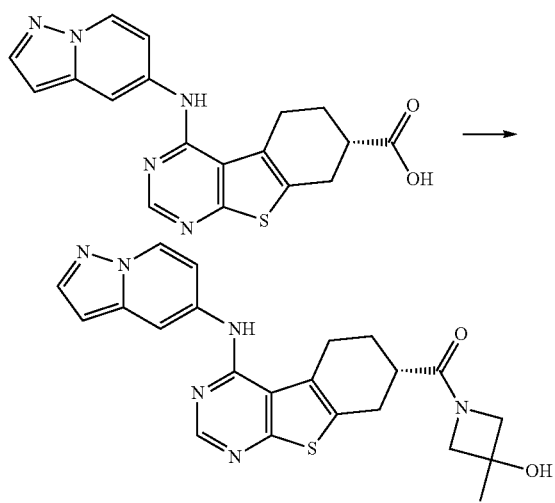

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using 3-methylazetidin-3-ol to give after working up and purification 49.5 mg (53%) of the title compound.

$^1$H NMR (DMSO-d6): δ=1.41 (3H), 1.78 (1H), 2.07 (1H), 2.78 (1H), 2.94 (2H), 3.20 (1H), 3.30 (1H), 3.70-3.78 (2H), 4.01-4.15 (2H), 5.68 (1H), 6.51 (1H), 7.14 (1H), 7.93 (1H), 8.11 (1H), 8.40 (1H), 8.52 (1H), 8.62 (1H) ppm.

Example 31

{4-[2-(Dimethylamino)ethyl]piperazin-1-yl}[(7S)-4-(pyrazolo[1,5-a]pyridin-5-ylamino)-5,6,7,8-tetrahydro[1]benzothieno[2,3-d]pyrimidin-7-yl]methanone

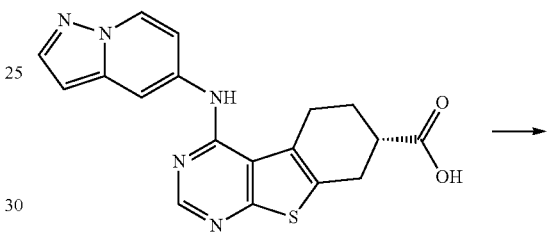

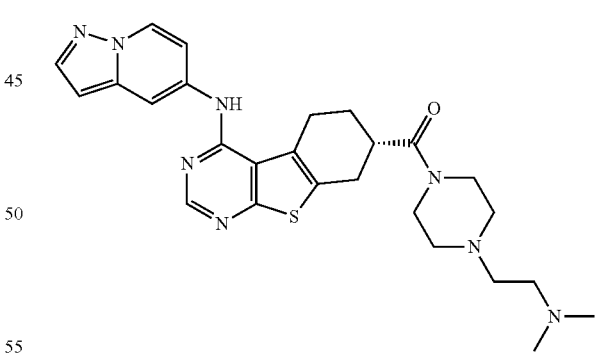

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using N,N-dimethyl-2-(piperazin-1-yl)ethanamine to give after working up and purification 59.3 mg (54%) of the title compound.

$^1$H NMR (DMSO-d6): δ=1.81 (1H), 2.06 (1H), 2.14 (6H), 2.31-2.49 (8H), 2.92 (1H), 3.01 (1H), 3.14-3.29 (3H), 3.50 (2H), 3.56 (2H), 6.51 (1H), 7.15 (1H), 7.93 (1H), 8.12 (1H), 8.39 (1H), 8.52 (1H), 8.62 (1H) ppm.

Example 32

[4-(Dimethylamino)piperidin-1-yl][(7S)-4-(pyrazolo[1,5-a]pyridin-5-ylamino)-5,6,7,8-tetrahydro[1]benzothieno[2,3-d]pyrimidin-7-yl]methanone

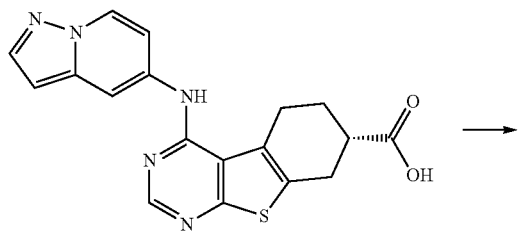

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using N,N-dimethylpiperidin-4-amine to give after working up and purification 54.9 mg (53%) of the title compound.

$^1$H NMR (DMSO-d6): δ=1.20 (1H), 1.34 (1H), 1.71-1.87 (2H), 2.04 (1H), 2.17 (6H), 2.31 (1H), 2.61 (1H), 2.85-3.36 (7H), 4.01 (1H), 4.40 (1H), 6.49 (1H), 7.14 (1H), 7.91 (1H), 8.10 (1H), 8.36 (1H), 8.50 (1H), 8.60 (1H) ppm.

Example 33

1-{[(7S)-4-(Pyrazolo[1,5-a]pyridin-5-ylamino)-5,6,7,8-tetrahydro[1]benzothieno[2,3-d]pyrimidin-7-yl]carbonyl}piperidin-4-one

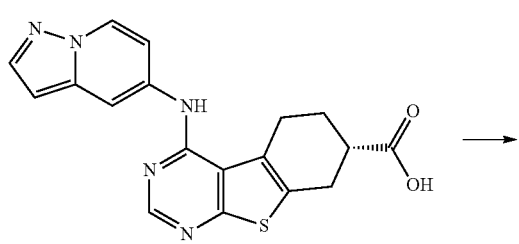

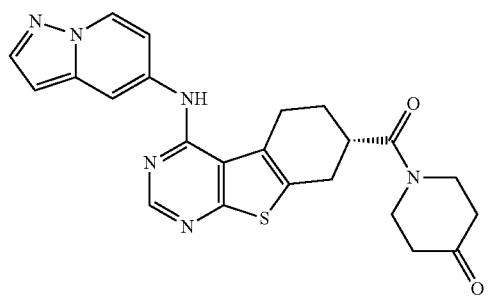

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using piperidin-4-one to give after working up and purification 46.5 mg (48%) of the title compound.

$^1$H NMR (DMSO-d6): δ=1.86 (1H), 2.14 (1H), 2.40 (2H), 2.44-2.57 (2H) 2.98-3.07 (2H), 3.20-3.39 (3H), 3.71-3.95 (4H), 6.51 (1H), 7.15 (1H), 7.93 (1H), 8.12 (1H), 8.41 (1H), 8.52 (1H), 8.62 (1H) ppm.

Example 34

(3,3-Difluoropyrrolidin-1-yl)[(7S)-4-(pyrazolo[1,5-a]pyridin-5-ylamino)-5,6,7,8-tetrahydro[1]benzothieno[2,3-d]pyrimidin-7-yl]methanone

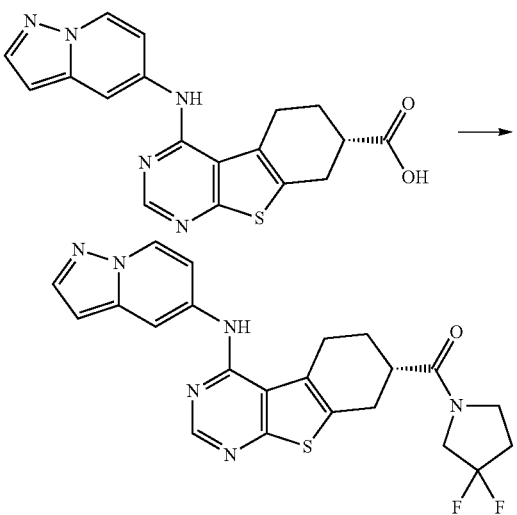

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using 3,3-difluoropyrrolidine to give after working up and purification 61.0 mg (62%) of the title compound.

$^1$H NMR (DMSO-d6): δ=1.79 (1H), 2.11 (1H), 2.35-2.57 (3H), 2.90-3.07 (3H), 3.21 (1H), 3.56 (1H), 3.70-3.93 (2H), 4.03+4.14 (1H), 6.49 (1H), 7.12 (1H), 7.91 (1H), 8.09 (1H), 8.39 (1H), 8.50 (1H), 8.60 (1H) ppm.

Example 35

2-Oxa-6-azaspiro[3.3]hept-6-yl[(7S)-4-(pyrazolo[1,5-a]pyridin-5-ylamino)-5,6,7,8-tetrahydro[1]benzothieno[2,3-d]pyrimidin-7-yl]methanone

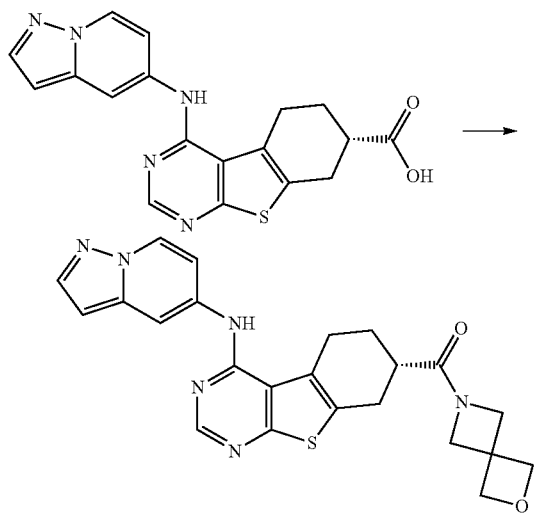

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using 2-oxa-6-azaspiro[3.3]heptane to give after working up and purification 37.2 mg (39%) of the title compound.

¹H NMR (DMSO-d6): δ=1.74 (1H), 2.05 (1H), 2.72 (1H), 2.84-2.95 (2H), 3.17 (1H), 3.27 (1H), 4.05 (2H), 4.38 (1H), 4.44 (1H), 4.64-4.72 (4H), 6.49 (1H), 7.12 (1H), 7.91 (1H), 8.09 (1H), 8.38 (1H), 8.50 (1H), 8.60 (1H) ppm.

Example 36

(1S,4S)-2-Oxa-5-azabicyclo[2.2.1]hept-5-yl[(7S)-4-(pyrazolo[1,5-a]pyridin-5-ylamino)-5,6,7,8-tetrahydro[1]benzothieno[2,3-d]pyrimidin-7-yl]methanone

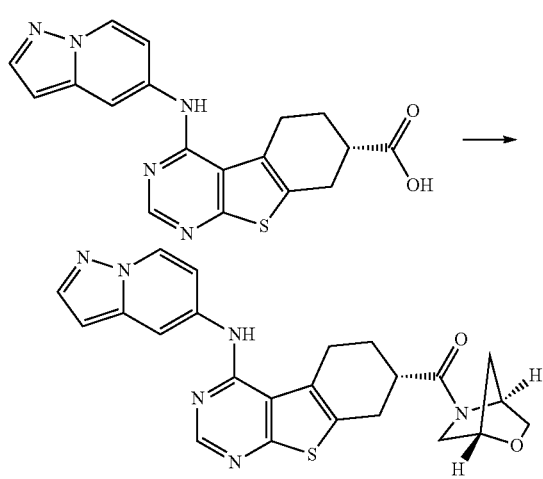

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using (1S,4S)-2-oxa-5-azabicyclo[2.2.1]heptane to give after working up and purification 71.9 mg (75%) of the title compound.

¹H NMR (DMSO-d6): δ=1.75-1.90 (3H), 2.08 (1H), 2.79-3.37 (6H), 3.54-3.79 (3H), 4.63+4.67 (1H), 4.77+4.88 (1H), 6.51 (1H), 7.14 (1H), 7.93 (1H), 8.11 (1H), 8.40 (1H), 8.52 (1H), 8.62 (1H) ppm.

Example 37

(1R,4R)-2-Oxa-5-azabicyclo[2.2.1]hept-5-yl[(7S)-4-(pyrazolo[1,5-a]pyridin-5-ylamino)-5,6,7,8-tetrahydro[1]benzothieno[2,3-d]pyrimidin-7-yl]methanone

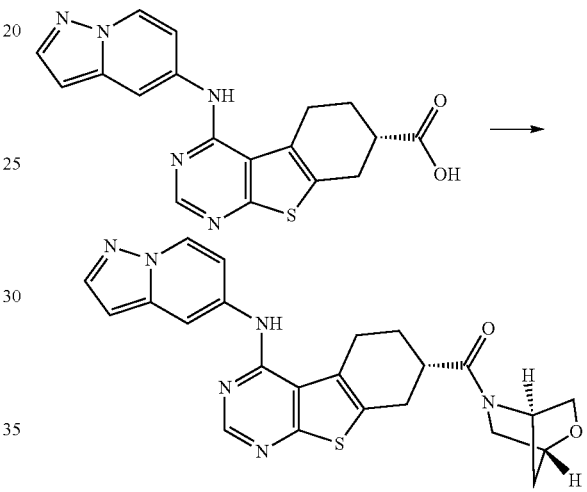

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using (1R,4R)-2-oxa-5-azabicyclo[2.2.1]heptane to give after working up and purification 59.7 mg (62%) of the title compound.

¹H NMR (DMSO-d6): δ=1.76-1.92 (3H), 2.11 (1H), 2.76-3.38 (6H), 3.45-3.79 (3H), 4.62+4.68 (1H), 4.80 (1H), 6.51 (1H), 7.14 (1H), 7.93 (1H), 8.11 (1H), 8.41 (1H), 8.52 (1H), 8.63 (1H) ppm.

Example 38

[(1S,4S)-5-Methyl-2,5-diazabicyclo[2.2.1]hept-2-yl][(7S)-4-(pyrazolo[1,5-a]pyridin-5-ylamino)-5,6,7,8-tetrahydro[1]benzothieno[2,3-d]pyrimidin-7-yl]methanone

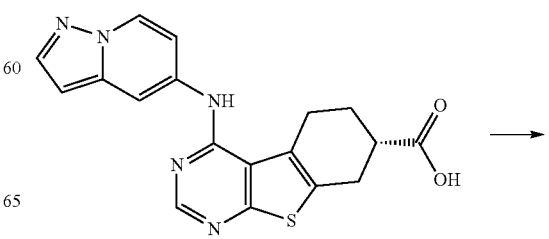

-continued

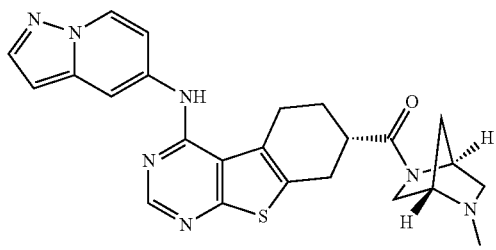

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using (1S,4S)-2-methyl-2,5-diazabicyclo[2.2.1]heptane to give after working up and purification 22.0 mg (22%) of the title compound.

¹H NMR (DMSO-d6): δ=1.64 (1H), 1.73-1.86 (2H), 2.04 (1H), 2.31 (3H), 2.43 (1H), 2.72-3.70 (9H), 4.52+4.58 (1H), 6.48 (1H), 7.12 (1H), 7.91 (1H), 8.09 (1H), 8.38 (1H), 8.50 (1H), 8.60 (1H) ppm.

Example 39

(7S)—N-(2-Aminoethyl)-N-methyl-4-(pyrazolo[1,5-a]pyridin-5-ylamino)-5,6,7,8-tetrahydro[1]benzothieno[2,3-d]pyrimidine-7-carboxamide

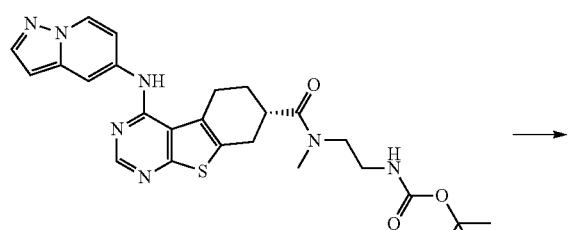

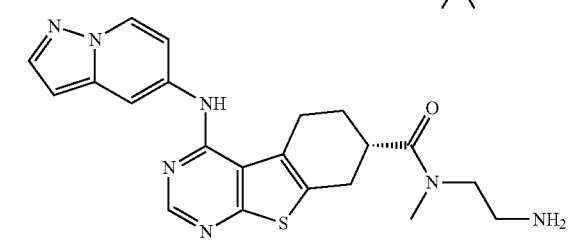

A mixture comprising 50 mg (96 μmol) tert-butyl [2-(methyl{[(7S)-4-(pyrazolo[1,5-a]pyridin-5-ylamino)-5,6,7,8-tetrahydro[1]benzothieno[2,3-d]pyrimidin-7-yl]carbonyl}amino)ethyl] carbamate (prepared according to example 25), 2.0 mL dichloromethane and 221 μL trifluoroacetic acid was stirred at 23° C. for 3 hours. 0.5 mL N,N-diethylethanamine were added and the solvent removed. The residue was purified by chromatography to give 26.1 mg (61%) of the title compound.

¹H NMR (DMSO-d6): δ=1.81 (1H), 2.09 (1H), 2.67 (1H), 2.72 (1H), 2.82 (1H), 2.87+3.11 (3H), 2.96 (2H), 3.13-3.43 (3H), 6.51 (1H), 7.15 (1H), 7.93 (1H), 8.11 (1H), 8.40 (1H), 8.52 (1H), 8.62 (1H) ppm.

Example 40

(4-{[2-(Dimethylamino)ethyl](methyl)amino}piperidin-1-yl)[(7S)-4-(pyrazolo[1,5-a]pyridin-5-ylamino)-5,6,7,8-tetrahydro[1]benzothieno[2,3-d]pyrimidin-7-yl]methanone

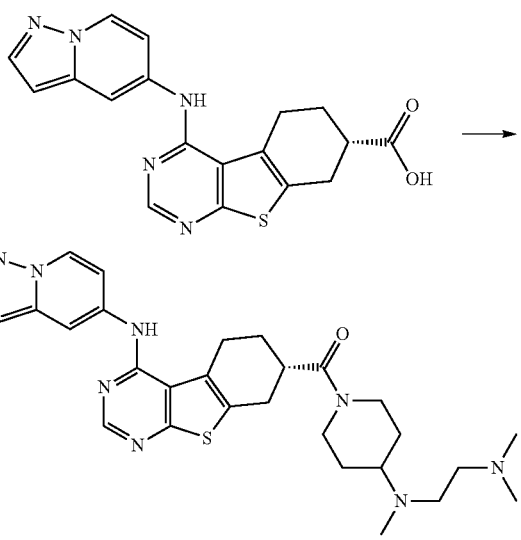

75 mg (205 μmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using N,N,N'-trimethyl-N'-(piperidin-4-yl)ethane-1,2-diamine to give after working up and purification 52.0 mg (45%) of the title compound.

¹H NMR (DMSO-d6): δ=1.24 (1H), 1.38 (1H), 1.67-1.86 (3H), 2.05 (1H), 2.12 (6H), 2.17 (3H), 2.27 (2H), 2.43-2.62 (4H), 2.86-3.10 (3H), 3.13-3.29 (3H), 4.03 (1H), 4.46 (1H), 6.49 (1H), 7.14 (1H), 7.91 (1H), 8.10 (1H), 8.36 (1H), 8.50 (1H), 8.60 (1H) ppm.

Example 41

[(3S)-3-(Dimethylamino)pyrrolidin-1-yl][(7S)-4-(pyrazolo[1,5-a]pyridin-5-ylamino)-5,6,7,8-tetrahydro[1]benzothieno[2,3-d]pyrimidin-7-yl]methanone

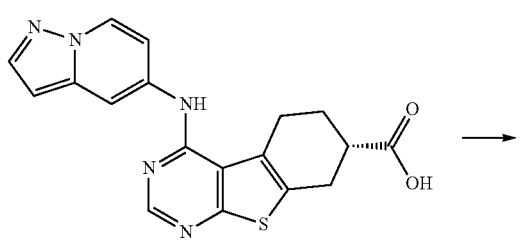

-continued

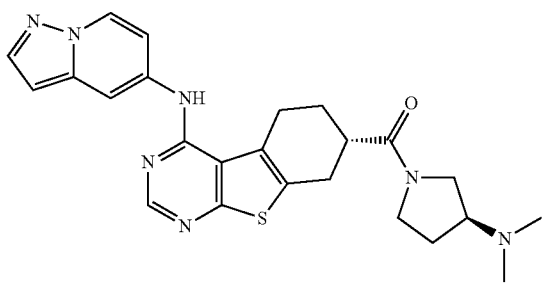

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using (3S)—N,N-dimethylpyrrolidin-3-amine to give after working up and purification 51.3 mg (51%) of the title compound.

$^1$H NMR (DMSO-d6): δ=1.57-1.74 (2H), 1.98-2.14 (2H), 2.16 (6H), 2.61+2.73 (1H), 2.88-3.80 (9H), 6.49 (1H), 7.12+7.14 (1H), 7.91 (1H), 8.09 (1H), 8.37 (1H), 8.50 (1H), 8.60 (1H) ppm.

Example 42

[(1R,4R)-5-Methyl-2,5-diazabicyclo[2.2.1]hept-2-yl][(7S)-4-(pyrazolo[1,5-a]pyridin-5-ylamino)-5,6,7,8-tetrahydro[1]benzothieno[2,3-d]pyrimidin-7-yl]methanone

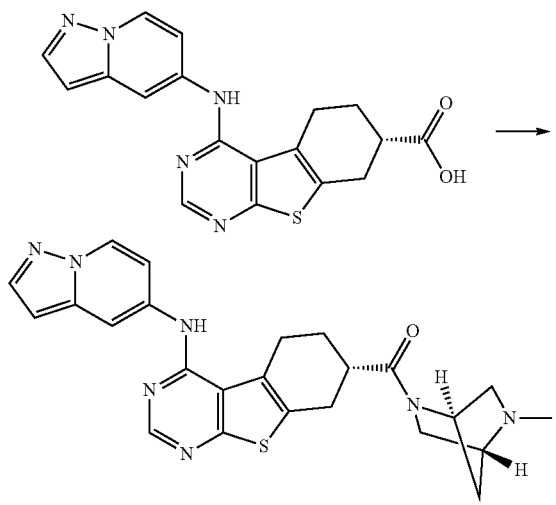

75 mg (205 µmol) (7S)-4-(Pyrazolo[1,5-a]pyridin-5-ylamino)-5,6,7,8-tetrahydro[1]benzothieno[2,3-d]pyrimidine-7-carboxylic acid (prepared according to example 2) were transformed in analogy to example 16 using (1R,4R)-2-methyl-2,5-diazabicyclo[2.2.1]heptane to give after working up and purification 74.8 mg (71%) of the title compound.

$^1$H NMR (DMSO-d6): δ=1.61+1.70 (1H), 1.75-1.90 (2H), 2.08 (1H), 2.31+2.34 (3H), 2.42+2.55 (1H), 2.76-3.05 (4H), 3.11-3.62 (5H), 4.55 (1H), 6.51 (1H), 7.14 (1H), 7.93 (1H), 8.12 (1H), 8.41 (1H), 8.52 (1H), 8.63 (1H) ppm.

Example 43

(7S)-4-[(6-Chloropyrazolo[1,5-a]pyridin-5-yl)amino]-N-(3,3,3-trifluoropropyl)-5,6,7,8-tetrahydro[1]benzothieno[2,3-d]pyrimidine-7-carboxamide

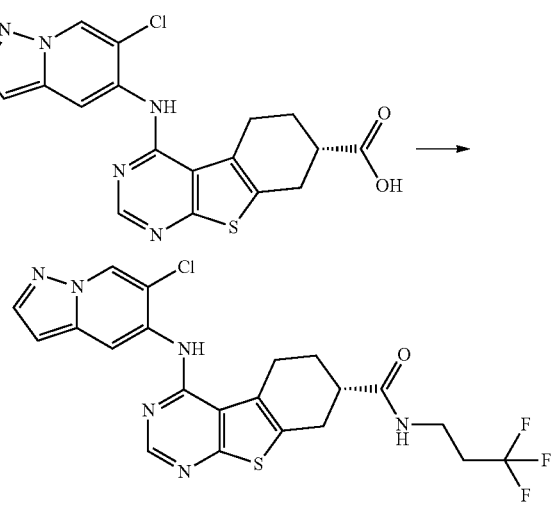

A mixture comprising 75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a), 3.65 mL N,N-dimethylacetamide, 294 µL N-ethyl-N-isopropylpropan-2-amine, 140 mg 3,3,3-trifluoropropan-1-aminium chloride and 335 µL 2,4,6-tripropyl-1,3,5,2,4,6-trioxatriphosphinane 2,4,6-trioxide solution (50% in N,N-dimethylformamide) was stirred at 23° C. for 5 hours. The crude mixture was concentrated and the residue crystallized from diethyl ether and ethanol to give 46.9 mg (48%) of the title compound.

$^1$H NMR (DMSO-d6): δ=1.87 (1H), 2.16 (1H), 2.40-2.53 (2H), 2.69 (1H), 2.97 (2H), 3.16 (1H), 3.26-3.43 (3H), 6.66 (1H), 8.03 (1H), 8.28 (1H), 8.33 (1H), 8.50 (1H), 8.52 (1H), 9.15 (1H) ppm.

Example 43a (7S)-4-[(6-Chloropyrazolo[1,5-a]pyridin-5-yl)amino]-5,6,7,8-tetrahydro[1]benzothieno[2,3-d]pyrimidine-7-carboxylic acid

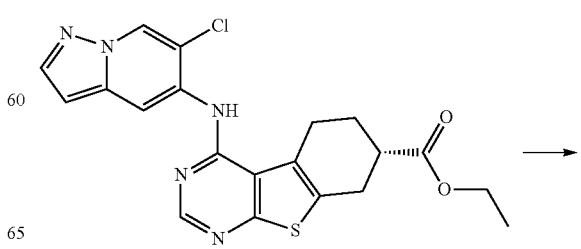

-continued

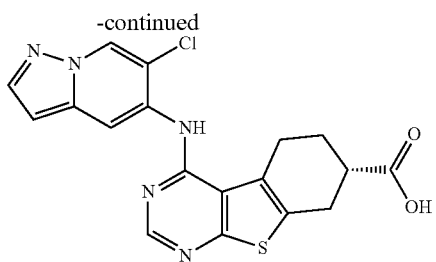

965 mg (2.26 mmol) ethyl (7S)-4-[(6-chloropyrazolo[1,5-a]pyridin-5-yl)amino]-4b,5,6,7,8,8a-hexahydro[1]benzothieno[2,3-d]pyrimidine-7-carboxylate (prepared according to intermediate example 43b) were transformed in analogy to example 2 to give after working up 857 mg (95%) of the title compound.

Example 43b

Ethyl (7S)-4-[(6-chloropyrazolo[1,5-a]pyridin-5-yl)amino]-4b,5,6,7,8,8a-hexahydro[1]benzothieno[2,3-d]pyrimidine-7-carboxylate

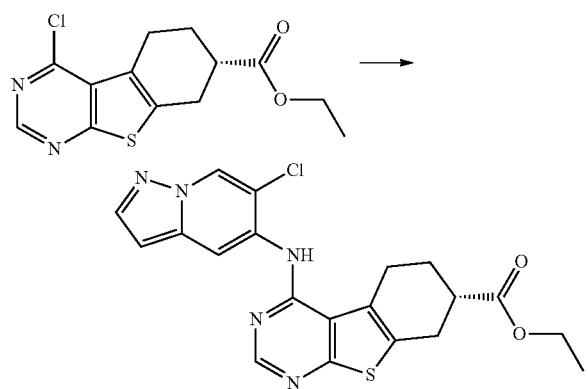

To a solution of 2.00 g (6.7 mmol) ethyl (7S)-4-chloro-5,6,7,8-tetrahydro[1]benzothieno[2,3-d]pyrimidine-7-carboxylate (prepared according to intermediate example 2b) were added 76 mg palladium(II) acetate, 315 mg 1,1'-binaphthalene-2,2'-diylbis(diphenylphosphane), 1.10 g 6-chloropyrazolo[1,5-a]pyridin-5-amine (prepared according to intermediate example 43c) and 3.29 g cesium carbonate. The mixture was stirred at 80° C. for 15 h. Water was added, the mixture extracted with DCM, the organic layer washed with hydrochloric acid (2M), water, brine and dried over sodium sulfate. After filtration and concentration the residue was crystallized from ethanol to give 1.73 mg (57%) of the title compound.

Example 43c

6-Chloropyrazolo[1,5-a]pyridin-5-amine

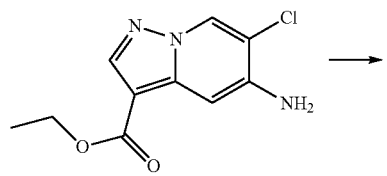

-continued

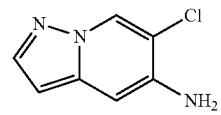

A suspension of 2.60 g (10.9 mmol) ethyl 5-amino-6-chloro-pyrazolo[1,5-a]pyridine-3-carboxylate (prepared according to intermediate example 43d) in 40 mL $H_2SO_4$ (40%) was stirred at 100° C. for 4 h. The solution was allowed to cool to 15° C. and then added to 150 mL aqueous saturated potassium carbonate. The mixture was extracted with dichloromethane, the combined organic layer was dried over sodium sulfate, filtered, concentrated under reduced pressure. The residue was diluted with concentrated hydrochloric acid, the solvent was removed at reduced pressure to afford the crude product which was purified by chromatography to give 1.52 g (84%) of the title compound Example 43d Ethyl 5-amino-6-chloro-pyrazolo[1,5-a]pyridine-3-carboxylate

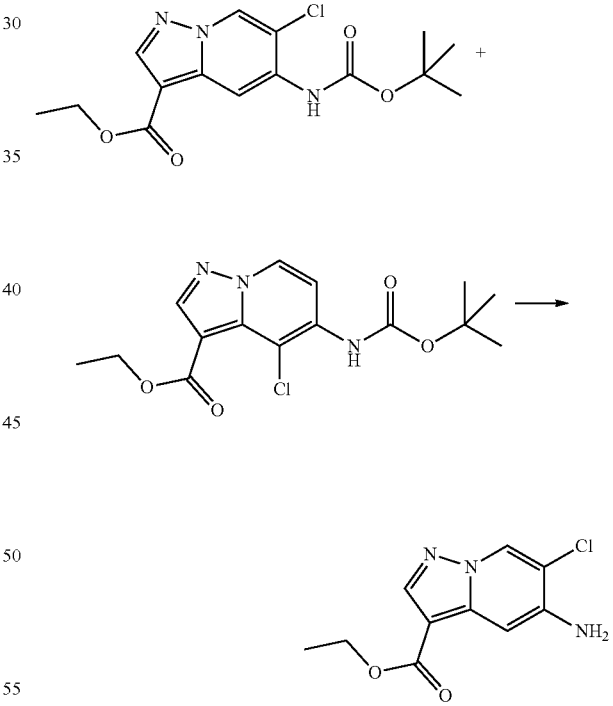

A mixture of 16 g (44 mmol) ethyl 5-(tert-butoxycarbonylamino)-6-chloro-pyrazolo[1,5-a]pyridine-3-carboxylate and ethyl 5-(tert-butoxycarbonylamino)-4-chloro-pyrazolo[1,5-a]pyridine-3-carboxylate (prepared according to intermediate example 43e) in 50 mL dichloromethane and 50 mL trifluoroacetic acid was stirred at 10° C. for 2 h. The residue was diluted with aqueous saturated potassium carbonate, extracted with dichloromethane and concentrated. The crude product was purified by column chromatography to give 2.6 g (24%) of the title compound.

Example 43e

Ethyl 5-(tert-butoxycarbonylamino)-6-chloro-pyrazolo[1,5-a]pyridine-3-carboxylate and ethyl 5-(tert-butoxycarbonylamino)-4-chloro-pyrazolo[1,5-a]pyridine-3-carboxylate

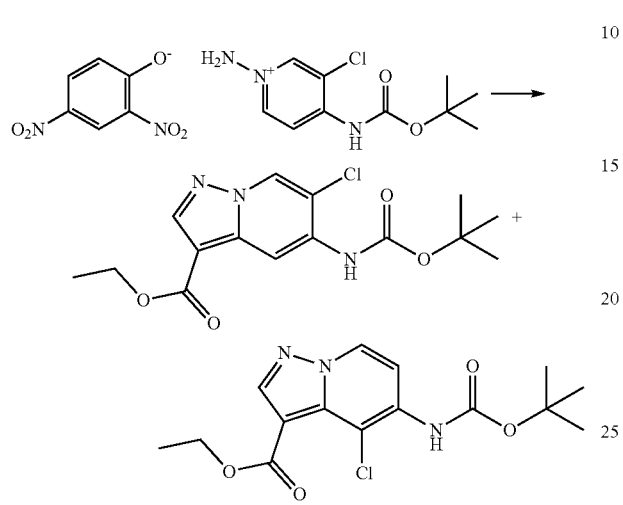

To a solution of 25 g crude 1-amino-4-((tert-butoxycarbonyl)amino)-3-chloropyridin-1-ium 2,4-dinitrophenolate (prepared according to intermediate example 43f) in 100 mL DMF was added 24.2 g potassium carbonate. The mixture was stirred at 20° C. for 1 h, 5.73 g ethyl propiolate was added and the mixture was stirred at 20° C. for 18 h. The mixture was diluted with water, extracted with ethyl acetate and concentrated. The residue was purified by chromatography to give 8.0 g (60%) of a mixture of the title compounds.

Example 43f

1-Amino-4-((tert-butoxycarbonyl)amino)-3-chloropyridin-1-ium 2,4-dinitrophenolate

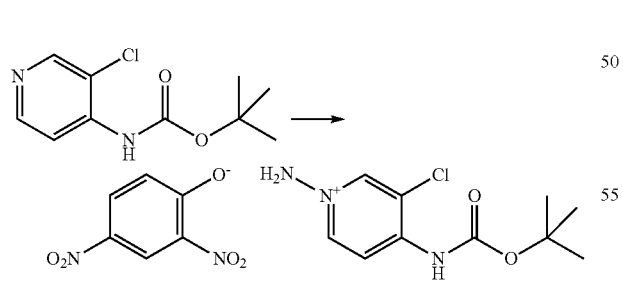

A solution of 9.0 g (39.4 mmol) tert-butyl N-(3-chloro-4-pyridyl)carbamate (prepared according to WO2008130021) and 15.7 g O-(2,4-dinitrophenyl)hydroxylamine in 120 mL acetonitrile was stirred at 50° C. for 40 h. The mixture was evaporated under reduced pressure to afford 25 g of the crude product which was used without further purification.

Example 44

(7S)-4-[(6-Chloropyrazolo[1,5-a]pyridin-5-yl)amino]-N-(propan-2-yl)-5,6,7,8-tetrahydro[1]benzothieno[2,3-d]pyrimidine-7-carboxamide

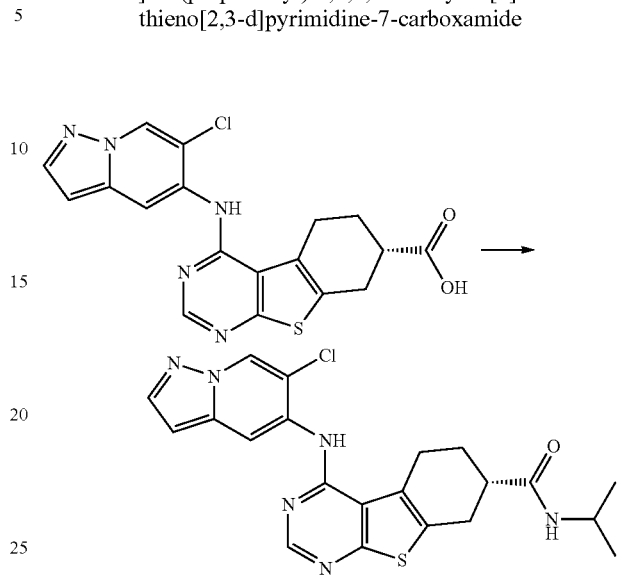

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using propan-2-amine to give after working up and purification 56.5 mg (65%) of the title compound.

$^1$H NMR (DMSO-d6): δ=1.09 (6H), 1.84 (1H), 2.14 (1H), 2.63 (1H), 2.96 (2H), 3.14 (1H), 3.31 (1H), 3.88 (1H), 6.66 (1H), 7.87 (1H), 8.03 (1H), 8.33 (1H), 8.50 (1H), 8.53 (1H), 9.15 (1H) ppm.

Example 45

(7S)-4-[(6-Chloropyrazolo[1,5-a]pyridin-5-yl)amino]-N,N-dimethyl-5,6,7,8-tetrahydro[1]benzothieno[2,3-d]pyrimidine-7-carboxamide

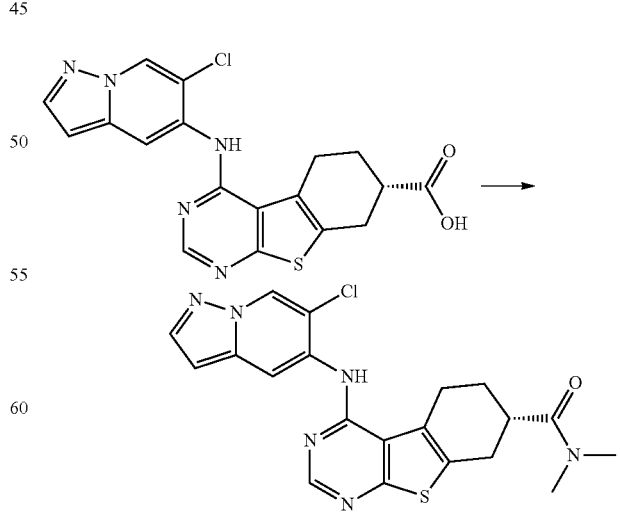

75 mg (188 µmol) (7S)-4-[(6-chloropyrazolo[1,5-a]pyridin-5-yl)amino]-5,6,7,8-tetrahydro[1]benzothieno[2,3-d]

pyrimidine-7-carboxylic acid (prepared according to example 43a) were transformed in analogy to example 43 using N-methylmethanamine to give after working up and purification 42.6 mg (51%) of the title compound.

¹H NMR (DMSO-d6): δ=1.81 (1H), 2.13 (1H), 2.89 (3H), 2.91-3.03 (2H), 3.11 (3H), 3.16-3.27 (2H), 3.32 (1H), 6.66 (1H), 8.03 (1H), 8.33 (1H), 8.49 (2H), 9.15 (1H) ppm.

Example 46

(7S)-4-[(6-Chloropyrazolo[1,5-a]pyridin-5-yl)amino]-N-ethyl-N-methyl-5,6,7,8-tetrahydro[1]benzothieno[2,3-d]pyrimidine-7-carboxamide

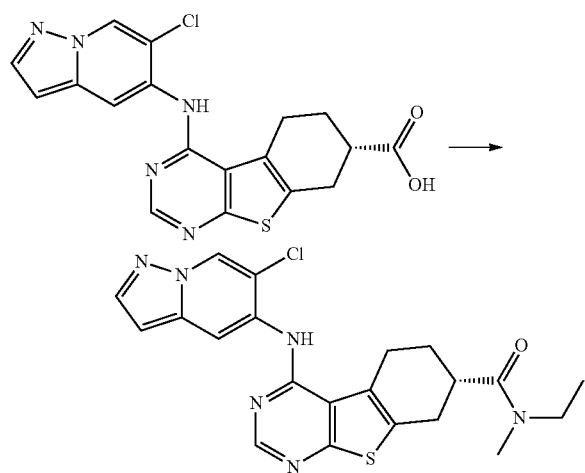

75 mg (188 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N-methylethanamine to give after working up and purification 66.1 mg (83%) of the title compound.

¹H NMR (DMSO-d6): δ=1.04+1.16 (3H), 1.75-1.90 (1H), 2.10 (1H), 2.86+3.08 (3H), 2.89-3.04 (2H), 3.11-3.52 (5H), 6.66 (1H), 8.03 (1H), 8.34 (1H), 8.46-8.53 (2H), 9.15 (1H) ppm.

Example 47

(7S)-4-[(6-Chloropyrazolo[1,5-a]pyridin-5-yl)amino]-N-(2,2-difluoroethyl)-N-methyl-5,6,7,8-tetrahydro[1]benzothieno[2,3-d]pyrimidine-7-carboxamide

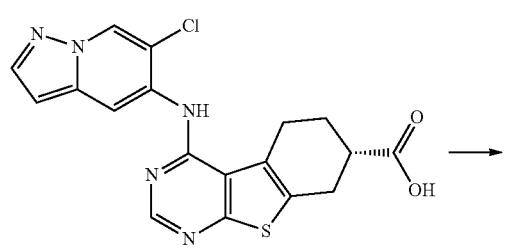

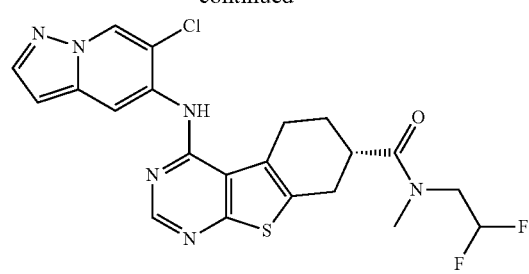

75 mg (188 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 2,2-difluoro-N-methylethanamine to give after working up and purification 67.1 mg (71%) of the title compound.

¹H NMR (DMSO-d6): δ=1.83 (1H), 2.10+2.16 (1H), 2.92-3.04 (2H), 2.96+3.21 (3H), 3.17-3.36 (3H), 3.67-4.04 (2H), 6.14+6.30 (1H), 6.66 (1H), 8.03 (1H), 8.35 (1H), 8.46-8.51 (2H), 9.15 (1H) ppm.

Example 48

(7S)-4-[(6-Chloropyrazolo[1,5-a]pyridin-5-yl)amino]-N-methyl-N-(3,3,3-trifluoropropyl)-5,6,7,8-tetrahydro[1]benzothieno[2,3-d]pyrimidine-7-carboxamide

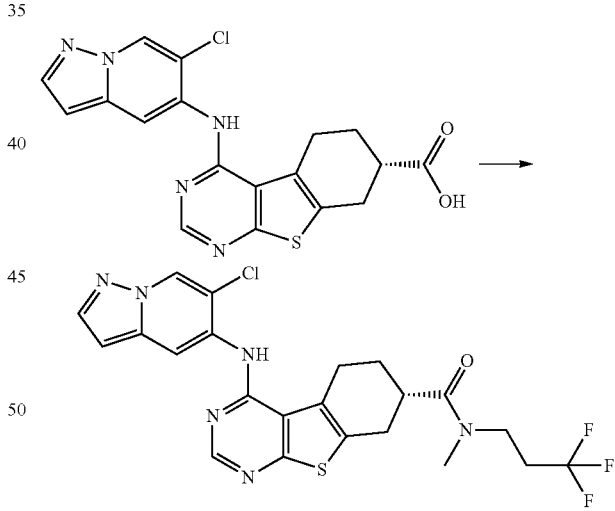

75 mg (188 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 3,3,3-trifluoro-N-methylpropan-1-aminium chloride to give after working up and purification 68.9 mg (69%) of the title compound.

¹H NMR (DMSO-d6): δ=1.81 (1H), 2.12 (1H), 2.47-2.76 (2H), 2.89+3.14 (3H), 2.92-3.02 (2H), 3.09-3.26 (2H), 3.31 (1H), 3.47-3.72 (2H), 6.66 (1H), 8.03 (1H), 8.33 (1H), 8.47-8.52 (2H), 9.15 (1H) ppm.

Example 49

(7S)—N-Butyl-4-[(6-chloropyrazolo[1,5-a]pyridin-5-yl)amino]-N-methyl-5,6,7,8-tetrahydro[1]benzothieno[2,3-d]pyrimidine-7-carboxamide

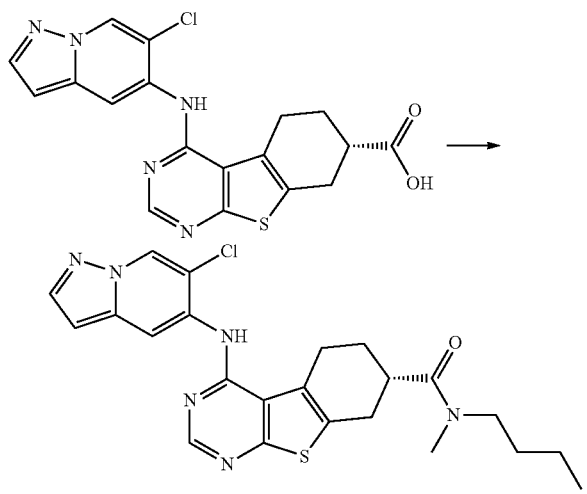

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N-methylbutan-1-amine to give after working up and purification 75.3 mg (81%) of the title compound.

$^1$H NMR (DMSO-d6): δ=0.88-0.94 (3H), 1.21-1.35 (2H), 1.42-1.58 (2H), 1.83 (1H), 2.10 (1H), 2.86+3.08 (3H), 2.90-3.01 (2H), 3.12-3.43 (5H), 6.66 (1H), 8.03 (1H), 8.33 (1H), 8.46-8.54 (2H), 9.15 (1H) ppm.

Example 50

1-((7S)-4-[(6-Chloropyrazolo[1,5-a]pyridin-5-yl)amino]-5,6,7,8-tetrahydro[1]benzothieno[2,3-d]pyrimidin-7-ylcarbonyl)azetidine-3-carbonitrile

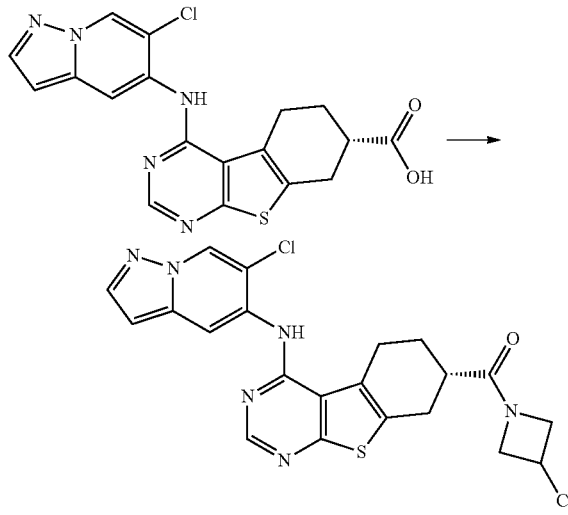

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 3-cyanoazetidinium chloride to give after working up and purification 34.2 mg (46%) of the title compound.

$^1$H NMR (DMSO-d6): δ=1.79 (1H), 2.14 (1H), 2.78 (1H), 2.86-3.03 (2H), 3.17 (1H), 3.31 (1H), 3.82 (1H), 4.06 (1H), 4.19 (1H), 4.47-4.60 (2H), 6.66 (1H), 8.03 (1H), 8.34 (1H), 8.49 (2H), 9.14 (1H) ppm.

Example 51

(7S)-4-[(6-Chloropyrazolo[1,5-a]pyridin-5-yl)amino]-N-[3-(dimethylamino)propyl]-N-methyl-5,6,7,8-tetrahydro[1]benzothieno[2,3-d]pyrimidine-7-carboxamide

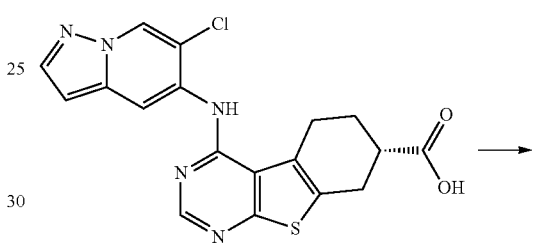

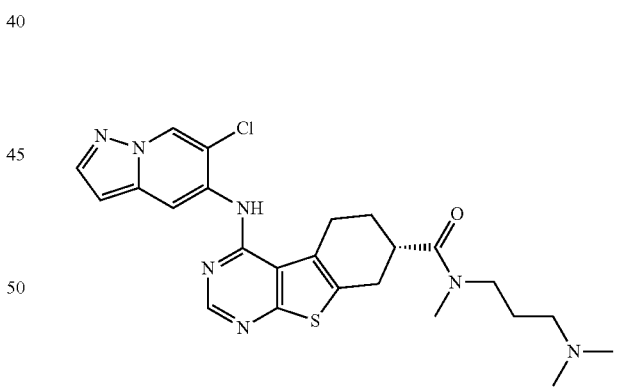

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N,N,N'-trimethylpropane-1,3-diamine to give after working up and purification 72.3 mg (74%) of the title compound.

$^1$H NMR (DMSO-d6): δ=1.61+1.69 (2H), 1.83 (1H), 2.08 (1H), 2.12 (3H), 2.13 (3H), 2.20 (2H), 2.86+3.10 (3H), 2.91-3.03 (2H), 3.13-3.48 (5H), 6.66 (1H), 8.03 (1H), 8.34 (1H), 8.45-8.55 (2H), 9.15 (1H) ppm.

Example 52

(7S)-4-[(6-Chloropyrazolo[1,5-a]pyridin-5-yl)amino]-5,6,7,8-tetrahydro[1]benzothieno[2,3-d]pyrimidin-7-yl(3-hydroxy-3-methylazetidin-1-yl)methanone

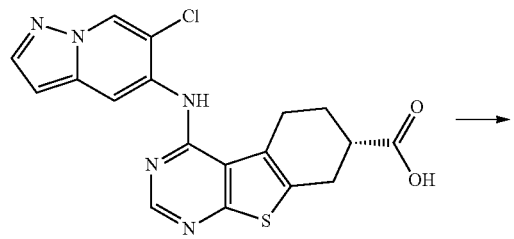

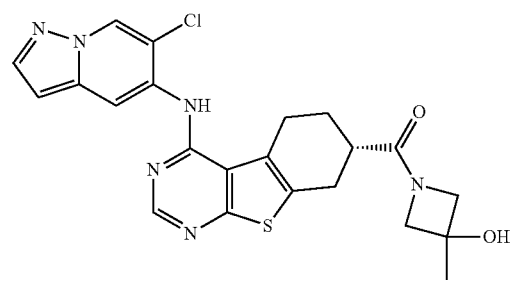

40 mg (100 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 3-hydroxy-3-methylazetidinium chloride to give after working up and purification 40.6 mg (82%) of the title compound.

$^1$H NMR (DMSO-d6): δ=1.41 (3H), 1.80 (1H), 2.12 (1H), 2.79 (1H), 2.94 (2H), 3.18 (1H), 3.31 (1H), 3.74 (2H), 4.03-4.15 (2H), 5.68 (1H), 6.66 (1H), 8.03 (1H), 8.33 (1H), 8.43-8.54 (2H), 9.14 (1H) ppm.

Example 53

(7S)-4-[(6-Chloropyrazolo[1,5-a]pyridin-5-yl)amino]-N-[2-(dimethylamino)ethyl]-N-methyl-5,6,7,8-tetrahydro[1]benzothieno[2,3-d]pyrimidine-7-carboxamide

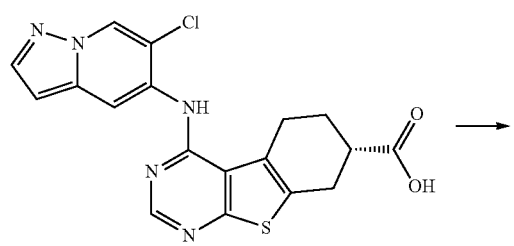

-continued

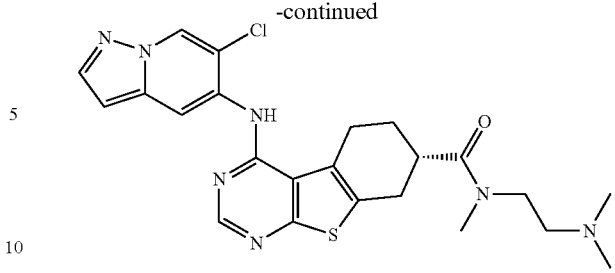

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N,N,N'-trimethylethane-1,2-diamine to give after working up and purification 71.1 mg (74%) of the title compound.

$^1$H NMR (DMSO-d6): δ=1.82 (1H), 2.11 (1H), 2.17 (3H), 2.19 (3H), 2.36 (1H), 2.43 (1H), 2.89+3.11 (3H), 2.91-3.04 (2H), 3.13-3.27 (2H), 3.28-3.52 (3H), 6.66 (1H), 8.03 (1H), 8.33 (1H), 8.46-8.54 (2H), 9.15 (1H) ppm.

Example 54

(7S)-4-[(6-Chloropyrazolo[1,5-a]pyridin-5-yl)amino]-5,6,7,8-tetrahydro[1]benzothieno[2,3-d]pyrimidin-7-yl[3-(dimethylamino)azetidin-1-yl]methanone

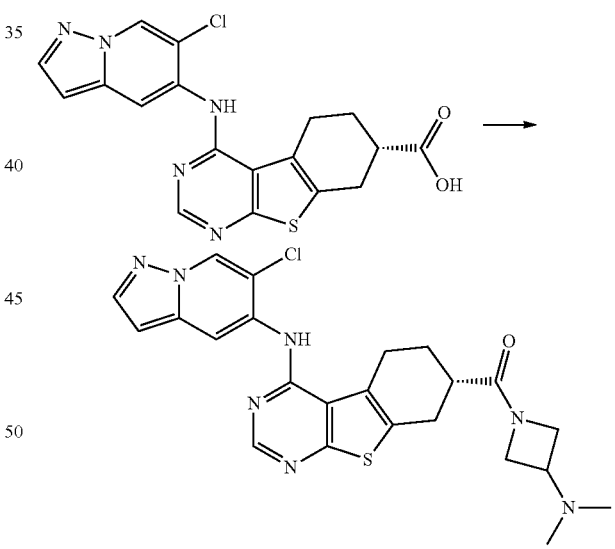

40 mg (100 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 3-(dimethylammonio)azetidinium dichloride to give after working up and purification 35.5 mg (70%) of the title compound.

$^1$H NMR (DMSO-d6): δ=1.80 (1H), 2.10 (6H), 2.13 (1H), 2.80 (1H), 2.87-2.98 (2H), 3.06 (1H), 3.18 (1H), 3.30 (1H), 3.67 (1H), 3.89 (1H), 4.05 (1H), 4.26 (1H), 6.66 (1H), 8.03 (1H), 8.34 (1H), 8.50 (2H), 9.15 (1H) ppm.

Example 55

(7S)-4-[(6-Chloropyrazolo[1,5-a]pyridin-5-yl)amino]-N-(2-hydroxyethyl)-N-methyl-5,6,7,8-tetrahydro[1]benzothieno[2,3-d]pyrimidine-7-carboxamide

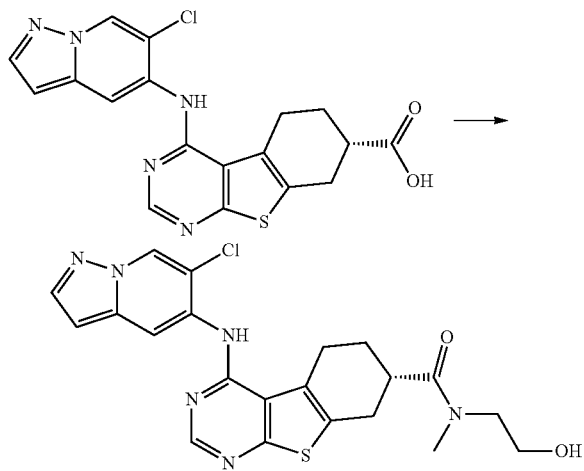

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 2-(methylamino)ethanol to give after working up and purification 30.3 mg (34%) of the title compound.

$^1$H NMR (DMSO-d6): δ=1.82 (1H), 2.14 (1H), 2.89+3.15 (3H), 2.91-3.04 (2H), 3.16-3.59 (7H), 4.70+4.88 (1H), 6.66 (1H), 8.03 (1H), 8.34 (1H), 8.45-8.52 (2H), 9.15 (1H) ppm.

Example 56

(7S)-4-[(6-Chloropyrazolo[1,5-a]pyridin-5-yl)amino]-N-(2-methoxyethyl)-N-methyl-5,6,7,8-tetrahydro[1]benzothieno[2,3-d]pyrimidine-7-carboxamide

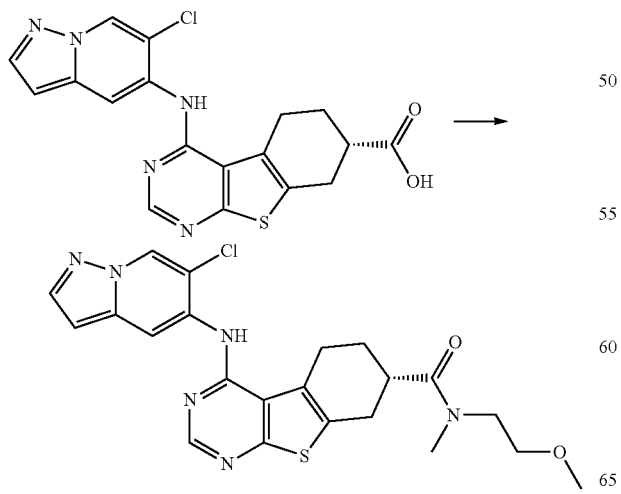

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 2-methoxy-N-methylethanamine to give after working up and purification 78.1 mg (84%) of the title compound.

$^1$H NMR (DMSO-d6): δ=1.82 (1H), 2.11 (1H), 2.89+3.14 (3H), 2.92-3.02 (2H), 3.16-3.31 (3H), 3.27+3.29 (3H), 3.42-3.69 (4H), 6.66 (1H), 8.03 (1H), 8.34 (1H), 8.49 (2H), 9.15 (1H) ppm.

Example 57

(7S)-4-[(6-Chloropyrazolo[1,5-a]pyridin-5-yl)amino]-N-methyl-N-(propan-2-yl)-5,6,7,8-tetrahydro[1]benzothieno[2,3-d]pyrimidine-7-carboxamide

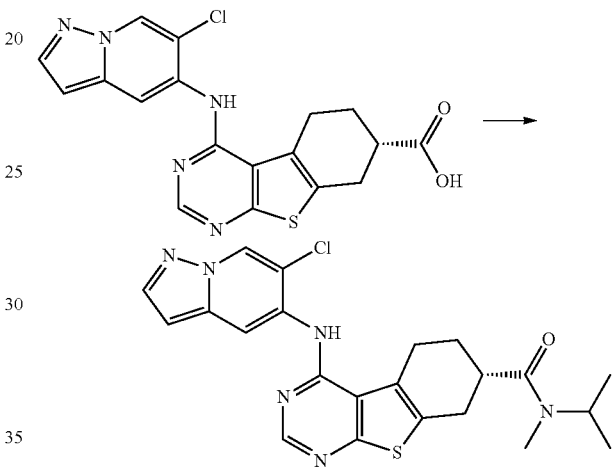

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N-methylpropan-2-amine to give after working up and purification 65.5 mg (73%) of the title compound.

$^1$H NMR (DMSO-d6): δ=1.06-1.19 (6H), 1.82 (1H), 2.10 (1H), 2.72+2.92 (3H), 2.88-3.27 (4H), 3.30 (1H), 4.29+4.73 (1H), 6.66 (1H), 8.03 (1H), 8.34 (1H), 8.47-8.53 (2H), 9.15 (1H) ppm.

Example 58

(7S)-4-[(6-Chloropyrazolo[1,5-a]pyridin-5-yl)amino]-5,6,7,8-tetrahydro[1]benzothieno[2,3-d]pyrimidin-7-yl[(3R)-3-(dimethylamino)pyrrolidin-1-yl]methanone

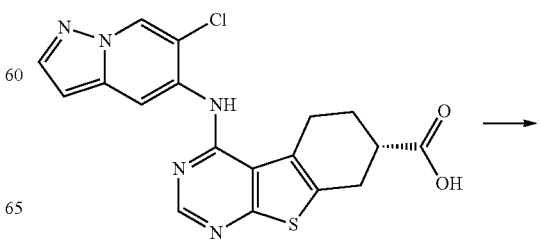

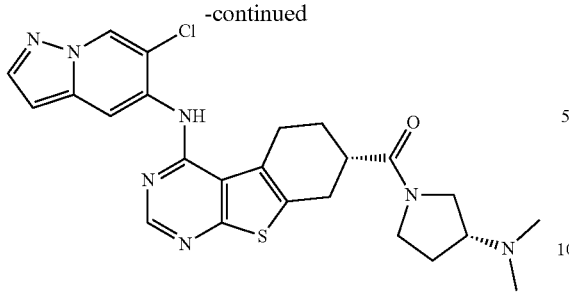

40 mg (100 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (3R)—N,N-dimethylpyrrolidin-3-amine to give after working up and purification 41.3 mg (79%) of the title compound.

$^1$H NMR (DMSO-d6): δ=1.59-1.87 (2H), 2.00-2.15 (2H), 2.17 (6H), 2.60-2.75 (1H), 2.92-3.08 (3H), 3.15-3.68 (5H), 3.79+3.90 (1H), 6.66 (1H), 8.03 (1H), 8.35 (1H), 8.42-8.53 (2H), 9.15 (1H) ppm.

Example 59

(7S)-4-[(6-Chloropyrazolo[1,5-a]pyridin-5-yl)amino]-5,6,7,8-tetrahydro[1]benzothieno[2,3-d]pyrimidin-7-yl[(3S)-3-(dimethylamino)pyrrolidin-1-yl]methanone

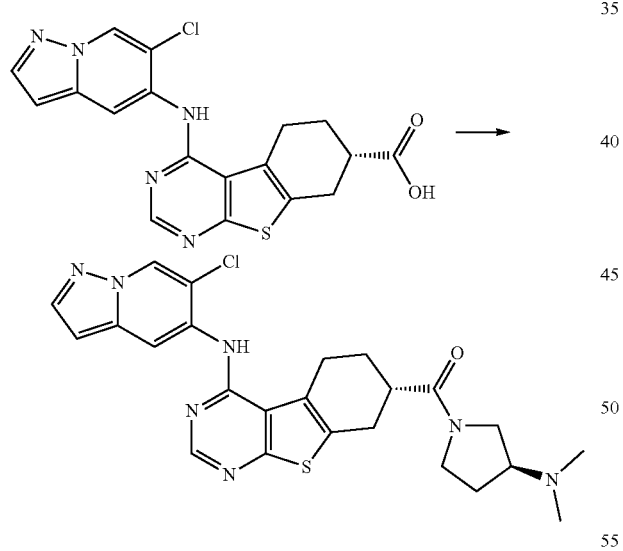

40 mg (100 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (3S)—N,N-dimethylpyrrolidin-3-amine to give after working up and purification 39.4 mg (75%) of the title compound.

$^1$H NMR (DMSO-d6): δ=1.59-1.86 (2H), 1.99-2.15 (2H), 2.17 (6H), 2.62+2.73 (1H), 2.92-3.06 (3H), 3.14-3.68 (5H), 3.75+3.83 (1H), 6.66 (1H), 8.03 (1H), 8.34 (1H), 8.41-8.55 (2H), 9.15 (1H) ppm.

Example 60

(7S)-4-[(6-Chloropyrazolo[1,5-a]pyridin-5-yl)amino]-5,6,7,8-tetrahydro[1]benzothieno[2,3-d]pyrimidin-7-yl[(3S,4S)-3,4-dihydroxypyrrolidin-1-yl]methanone

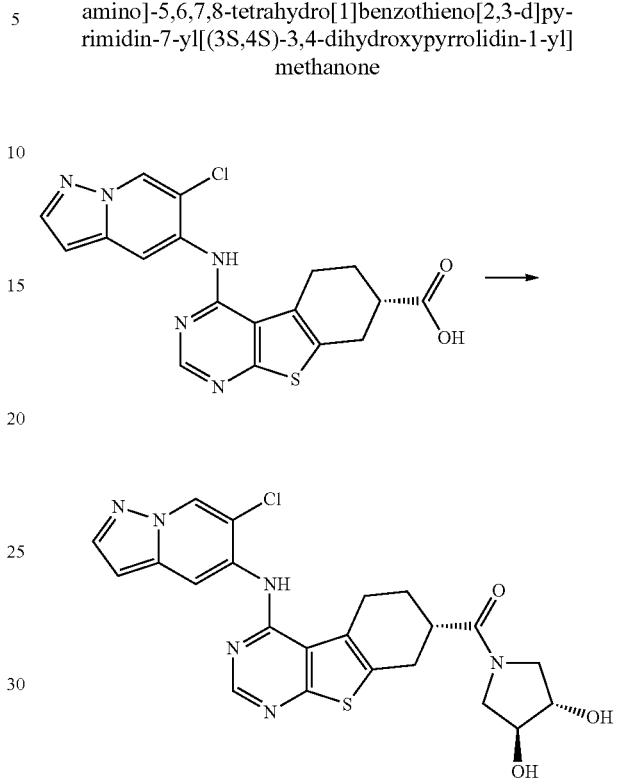

40 mg (100 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (3S,4S)-pyrrolidine-3,4-diol to give after working up and purification 74.8 mg (51%) of the title compound.

$^1$H NMR (DMSO-d6): δ=1.81 (1H), 2.15 (1H), 2.91-3.07 (3H), 3.22 (1H), 3.29-3.48 (4H), 3.75 (1H), 3.94 (1H), 4.01 (1H), 5.15 (1H), 5.23 (1H), 6.66 (1H), 8.03 (1H), 8.33 (1H), 8.50 (1H), 8.51 (1H), 9.15 (1H) ppm.

Example 61

(7S)-4-[(6-Chloropyrazolo[1,5-a]pyridin-5-yl)amino]-5,6,7,8-tetrahydro[1]benzothieno[2,3-d]pyrimidin-7-yl[4-(dimethylamino)piperidin-1-yl]methanone

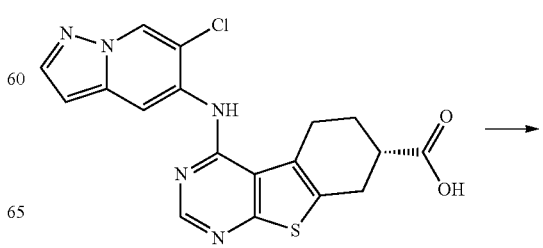

-continued

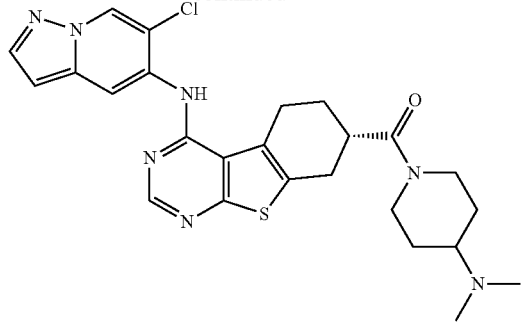

40 mg (100 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N,N-dimethylpiperidin-4-amine to give after working up and purification 40.1 mg (75%) of the title compound.

¹H NMR (DMSO-d6): δ=1.21 (1H), 1.35 (1H), 1.74-1.89 (3H), 2.10 (1H), 2.19 (6H), 2.33 (1H), 2.62 (1H), 2.88-3.14 (3H), 3.18-3.32 (3H), 4.06 (1H), 4.42 (1H), 6.66 (1H), 8.03 (1H), 8.34 (1H), 8.49 (2H), 9.15 (1H) ppm.

Example 62

(7S)-4-[(6-Chloropyrazolo[1,5-a]pyridin-5-yl)amino]-5,6,7,8-tetrahydro[1]benzothieno[2,3-d]pyrimidin-7-yl(4-[2-dimethylamino)ethyl](methyl)aminopiperidin-1-yl)methanone

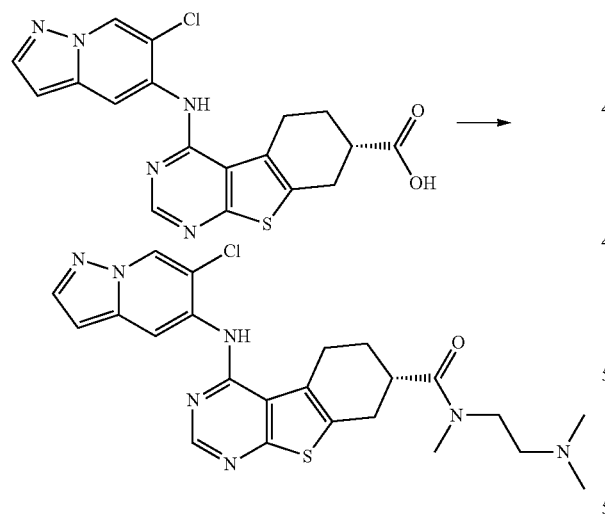

40 mg (100 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 4-{[2-(dimethylammonio)ethyl](methyl)ammonio}piperidinium trichloride to give after working up and purification 32.7 mg (55%) of the title compound.

¹H NMR (DMSO-d6): δ=1.24 (1H), 1.39 (1H), 1.67-1.91 (3H), 2.09 (1H), 2.13 (6H), 2.18 (3H), 2.29 (2H), 2.43-2.63 (4H), 2.87-3.12 (3H), 3.18-3.31 (3H), 4.08 (1H), 4.48 (1H), 6.66 (1H), 8.02 (1H), 8.34 (1H), 8.48 (2H), 9.14 (1H) ppm.

Example 63

(7S)4-[(6-Chloropyrazolo[1,5-a]pyridin-5-yl)amino]-N-[3-(dimethylamino)propyl]-N-(2-hydroxyethyl)-5,6,7,8-tetrahydro[1]benzothieno[2,3-d]pyrimidine-7-carboxamide

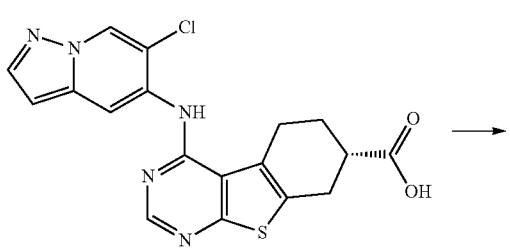

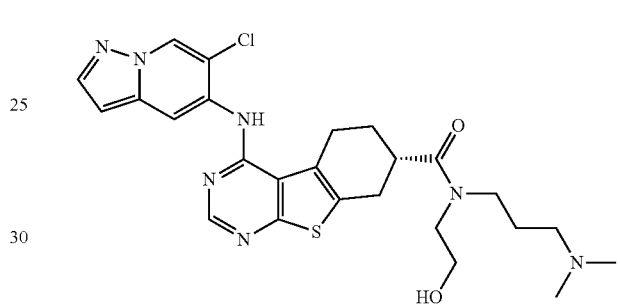

40 mg (100 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 2-{[3-(dimethylamino)propyl]amino}ethanol to give after working up and purification 74.8 mg (71%) of the title compound.

¹H NMR (DMSO-d6): δ=1.56-1.73 (2H), 1.84 (1H), 2.09 (1H), 2.11 (3H), 2.13 (3H), 2.20 (2H), 2.88-3.05 (2H), 3.13-3.57 (9H), 4.70+4.89 (1H), 6.66 (1H), 8.03 (1H), 8.34 (1H), 8.49 (2H), 9.15 (1H) ppm.

Example 64

(7S)-4-[(6-Chloropyrazolo[1,5-a]pyridin-5-yl)amino]-5,6,7,8-tetrahydro[1]benzothieno[2,3-d]pyrimidin-7-yl[(2R,6S)-2,6-dimethylmorpholin-4-yl]methanone

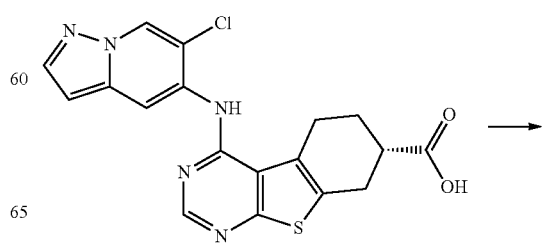

-continued

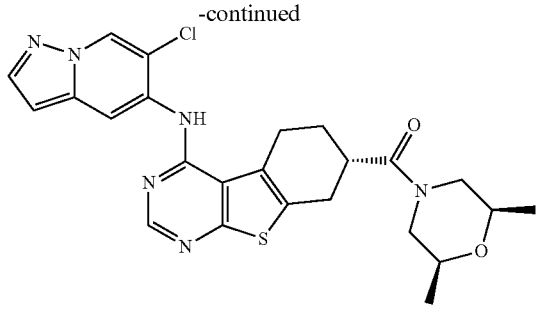

75 mg (188 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (2R,6S)-2,6-dimethylmorpholine to give after working up and purification 44.0 mg (45%) of the title compound.

$^1$H NMR (DMSO-d6): δ=1.08-1.16 (6H), 1.84 (1H), 2.10 (1H), 2.28 (1H), 2.77 (1H), 2.89-3.07 (2H), 3.17-3.33 (3H), 3.45 (1H), 3.54 (1H), 3.99 (1H), 4.32 (1H), 6.66 (1H), 8.03 (1H), 8.36 (1H), 8.42-8.51 (2H), 9.15 (1H) ppm.

Example 65

(7S)-4-[(6-Chloropyrazolo[1,5-a]pyridin-5-yl)amino]-5,6,7,8-tetrahydro[1]benzothieno[2,3-d]pyrimidin-7-yl(4-methylpiperazin-1-yl)methanone

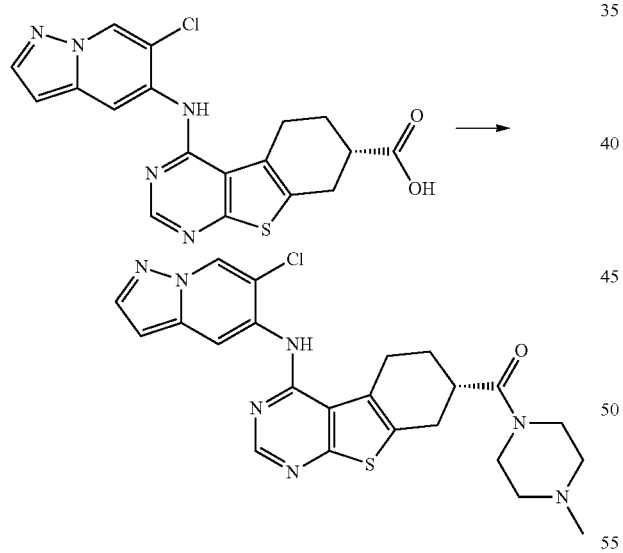

40 mg (100 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 1-methylpiperazine to give after working up and purification 37.6 mg (74%) of the title compound.

$^1$H NMR (DMSO-d6): δ=1.83 (1H), 2.10 (1H), 2.21 (3H), 2.28 (2H), 2.35 (2H), 2.88-3.06 (2H), 3.23 (2H), 3.30 (1H), 3.51 (2H), 3.59 (2H), 6.66 (1H), 8.03 (1H), 8.33 (1H), 8.49 (2H), 9.15 (1H) ppm.

Example 66

(7S)-4-[(6-Chloropyrazolo[1,5-a]pyridin-5-yl)amino]-5,6,7,8-tetrahydro[1]benzothieno[2,3-d]pyrimidin-7-yl4-[2-(dimethylamino)ethyl]piperazin-1-ylmethanone

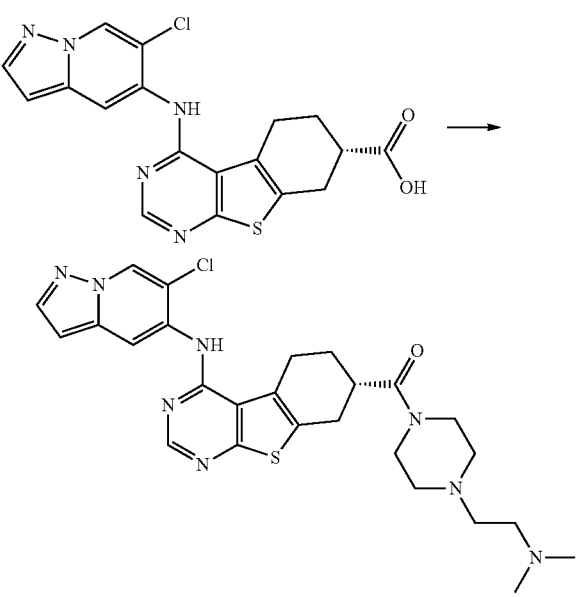

40 mg (100 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N,N-dimethyl-2-(piperazin-1-yl)ethanamine to give after working up and purification 38.9 mg (69%) of the title compound.

$^1$H NMR (DMSO-d6): δ=1.83 (1H), 2.10 (1H), 2.15 (6H), 2.31-2.47 (8H), 2.88-3.06 (2H), 3.22 (2H), 3.30 (1H), 3.50 (2H), 3.57 (2H), 6.66 (1H), 8.03 (1H), 8.34 (1H), 8.49 (2H), 9.15 (1H) ppm.

Example 67

(7S)-4-[(6-Chloropyrazolo[1,5-a]pyridin-5-yl)amino]-N-[2-(dimethylamino)ethyl]-N-ethyl-3,5,6,7,8-tetrahydro[1]benzothieno[2,3-d]pyrimidine-7-carboxamide

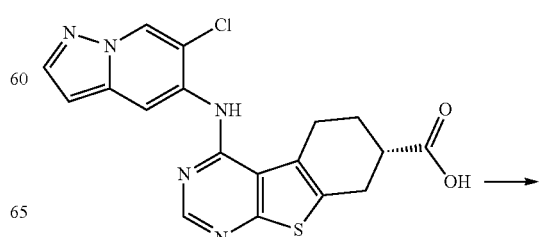

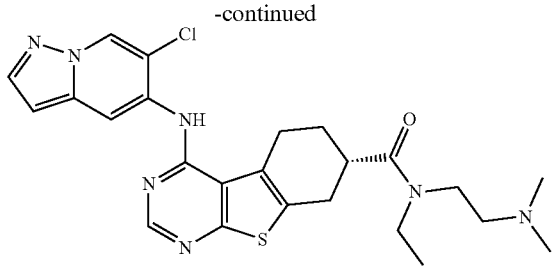

75 mg (188 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N'-ethyl-N,N-dimethylethane-1,2-diamine to give after working up and purification 61.7 mg (63%) of the title compound.

$^1$H NMR (DMSO-d6): δ=1.05+1.16 (3H), 1.84 (1H), 2.08 (1H), 2.17 (3H), 2.19 (3H), 2.35+2.43 (2H), 2.88-3.13 (3H), 3.17-3.51 (6H), 6.66 (1H), 8.02 (1H), 8.32 (1H), 8.47-8.54 (2H), 9.14 (1H) ppm.

Example 68

(7S)-4-[(6-Chloropyrazolo[1,5-a]pyridin-5-yl)amino]-5,6,7,8-tetrahydro[1]benzothieno[2,3-d]pyrimidin-7-yl(morpholin-4-yl)methanone

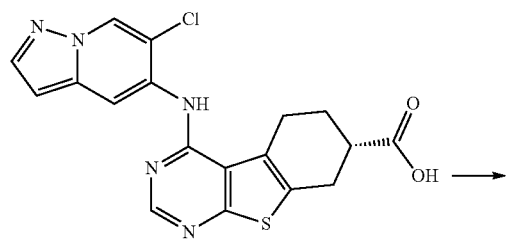

75 mg (188 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using morpholine to give after working up and purification 61.7 mg (63%) of the title compound.

$^1$H NMR (DMSO-d6): δ=1.83 (1H), 2.12 (1H), 2.91-3.06 (2H), 3.21 (2H), 3.31 (1H), 3.46-3.65 (8H), 6.66 (1H), 8.03 (1H), 8.33 (1H), 8.49 (2H), 9.15 (1H) ppm.

Example 69

(7S)-4-[(6-Chloropyrazolo[1,5-a]pyridin-5-yl)amino]-N-ethyl-N-(2-hydroxyethyl)-5,6,7,8-tetrahydro[1]benzothieno[2,3-d]pyrimidine-7-carboxamide

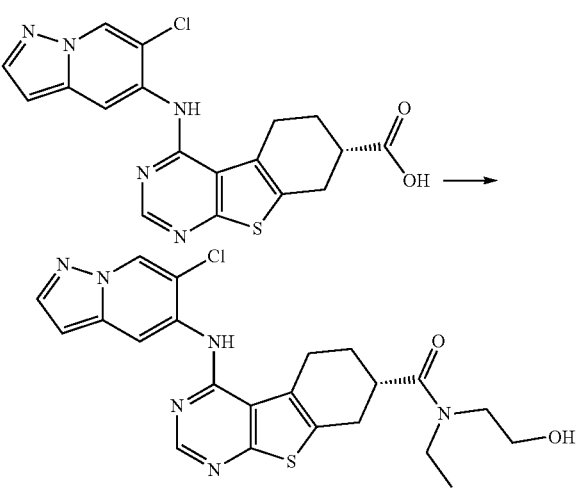

75 mg (188 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 2-(ethylamino)ethanol to give after working up and purification 67.4 mg (72%) of the title compound.

$^1$H NMR (DMSO-d6): δ=1.05+1.16 (3H), 1.84 (1H), 2.10 (1H), 2.88-3.58 (11H), 4.70+4.87 (1H), 6.66 (1H), 8.03 (1H), 8.34 (1H), 8.49 (2H), 9.15 (1H) ppm.

Example 70

(7S)-4-[(6-Chloropyrazolo[1,5-a]pyridin-5-yl)amino]-N-ethyl-N-(2-methoxyethyl)-5,6,7,8-tetrahydro[1]benzothieno[2,3-d]pyrimidine-7-carboxamide

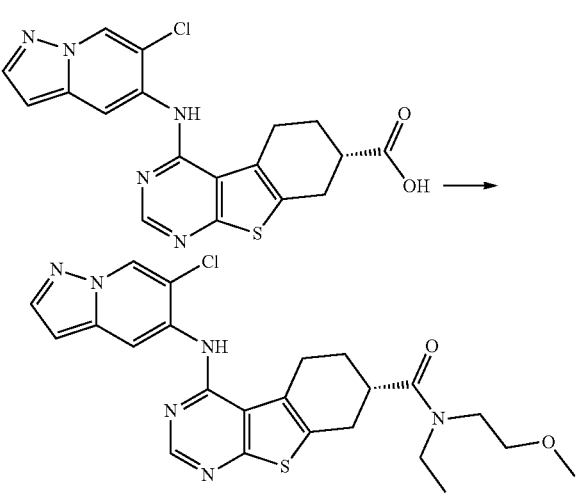

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using N-ethyl-2-methoxyethanamine to give after working up and purification 72.7 mg (76%) of the title compound.

¹H NMR (DMSO-d6): δ=1.04+1.16 (2H), 1.84 (1H), 2.09 (1H), 2.88-3.04 (2H), 3.06-3.64 (10H), 3.27+3.28 (3H), 6.66 (1H), 8.03 (1H), 8.33 (1H), 8.47-8.53 (2H), 9.15 (1H) ppm.

Example 71

(7S)-4-[(6-Chloropyrazolo[1,5-a]pyridin-5-yl)amino]-N,N-bis(2-methoxyethyl)-5,6,7,8-tetrahydro[1]benzothieno[2,3-d]pyrimidine-7-carboxamide

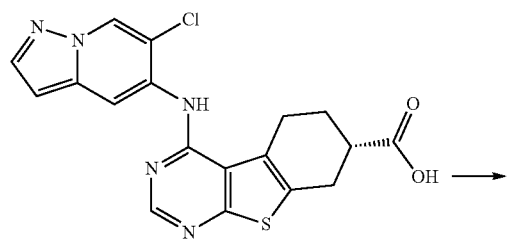

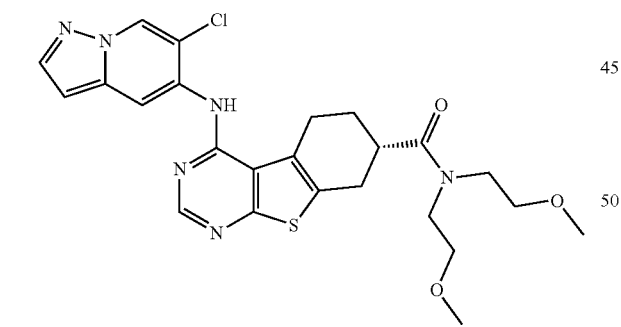

75 mg (188 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using 2-methoxy-N-(2-methoxyethyl)ethanamine to give after working up and purification 81.4 mg (80%) of the title compound.

¹H NMR (DMSO-d6): δ=1.83 (1H), 2.09 (1H), 2.87-3.03 (2H), 3.17-3.51 (8H), 3.27 (3H), 3.28 (3H), 3.53-3.72 (3H), 6.66 (1H), 8.03 (1H), 8.33 (1H), 8.50 (2H), 9.15 (1H) ppm.

Example 72

(7S)-4-[(6-Chloropyrazolo[1,5-a]pyridin-5-yl)amino]-5,6,7,8-tetrahydro[1]benzothieno[2,3-d]pyrimidin-7-yl[(1S,4S)-5-methyl-2,5-diazabicyclo[2.2.1]hept-2-yl]methanone

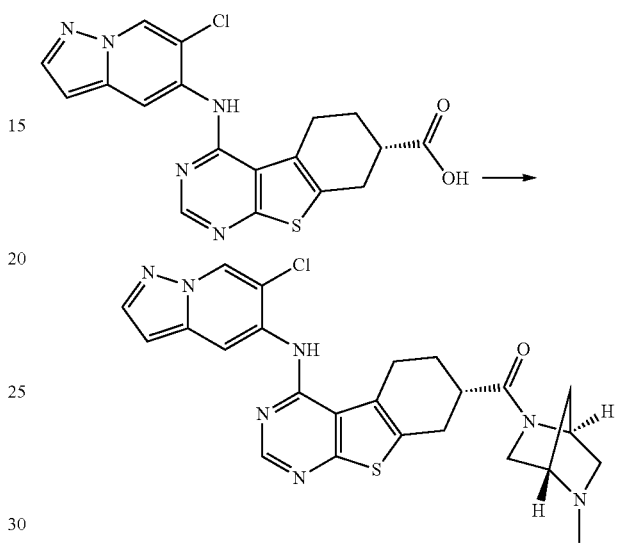

40 mg (100 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (1S,4S)-2-methyl-2,5-diazoniabicyclo[2.2.1]heptane dibromide to give after working up and purification 33.7 mg (65%) of the title compound.

¹H NMR (DMSO-d6): δ=1.65 (1H), 1.75-1.91 (2H), 2.10 (1H), 2.32+2.33 (3H), 2.44+2.53 (1H), 2.75+2.83 (1H), 2.85-3.71 (8H), 4.53+4.61 (1H), 6.66 (1H), 8.03 (1H), 8.34 (1H), 8.43-8.54 (2H), 9.14 (1H) ppm.

Example 73

(7S)-4-[(6-Chloropyrazolo[1,5-a]pyridin-5-yl)amino]-5,6,7,8-tetrahydro[1]benzothieno[2,3-d]pyrimidin-7-yl[(1R,4R)-5-methyl-2,5-diazabicyclo[2.2.1]hept-2-yl]methanone

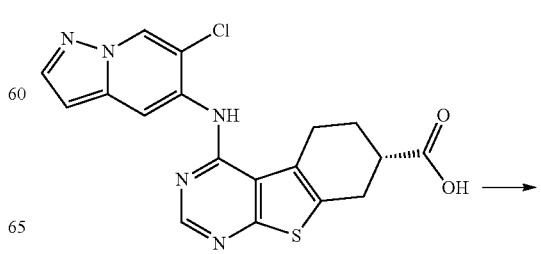

-continued

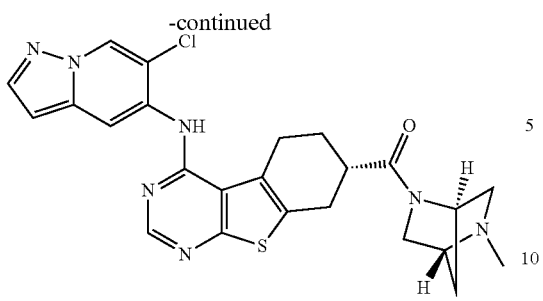

40 mg (100 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (1R,4R)-2-methyl-2,5-diazoniabicyclo[2.2.1]heptane dibromide to give after working up and purification 38.6 mg (74%) of the title compound.

$^1$H NMR (DMSO-d6): δ=1.61+1.70 (1H), 1.76-1.89 (2H), 2.13 (1H), 2.31+2.34 (3H), 2.44+2.54 (1H), 2.73-3.66 (9H), 4.55+4.59 (1H), 6.66 (1H), 8.03 (1H), 8.32 (1H), 8.46-8.57 (2H), 9.15 (1H) ppm.

Example 74

(7S)-4-[(6-Chloropyrazolo[1,5-a]pyridin-5-yl)amino]-5,6,7,8-tetrahydro[1]benzothieno[2,3-d]pyrimidin-7-yl[(1S,4S)-2-oxa-5-azabicyclo[2.2.1]hept-5-yl]methanone

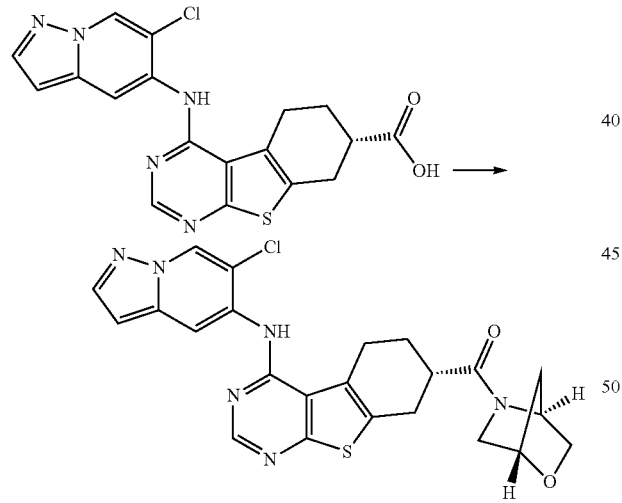

40 mg (100 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (1S,4S)-2-oxa-5-azoniabicyclo[2.2.1]heptane chloride to give after working up and purification 35.3 mg (70%) of the title compound.

$^1$H NMR (DMSO-d6): δ=1.77-1.90 (3H), 2.12 (1H), 2.82-3.26 (5H), 3.31 (1H), 3.55+3.66 (1H), 3.59+3.73 (1H), 3.77 (1H), 4.62+4.67 (1H), 4.77+4.89 (1H), 6.66 (1H), 8.03 (1H), 8.34 (1H), 8.41-8.55 (2H), 9.15 (1H) ppm.

Example 75

(7S)-4-[(6-Chloropyrazolo[1,5-a]pyridin-5-yl)amino]-5,6,7,8-tetrahydro[1]benzothieno[2,3-d]pyrimidin-7-yl[(1R,4R)-2-oxa-5-azabicyclo[2.2.1]hept-5-yl]methanone

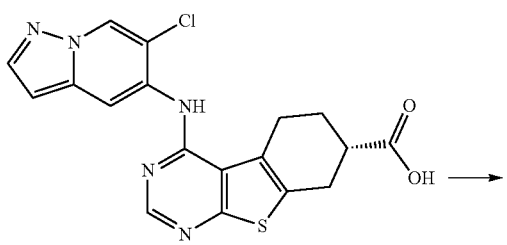

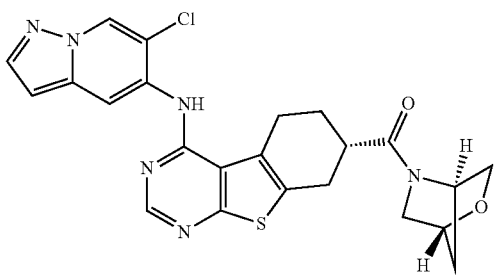

40 mg (100 μmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (1R,4R)-2-oxa-5-azoniabicyclo[2.2.1]heptane chloride to give after working up and purification 38.2 mg (75%) of the title compound.

$^1$H NMR (DMSO-d6): δ=1.77-1.92 (3H), 2.16 (1H), 2.78-3.40 (6H), 3.50-3.78 (3H), 4.62+4.68 (1H), 4.79+4.87 (1H), 6.66 (1H), 8.03 (1H), 8.33 (1H), 8.54 (1H), 8.50 (1H), 9.15 (1H) ppm.

Example 76

(7S)-4-[(6-Chloropyrazolo[1,5-a]pyridin-5-yl)amino]-5,6,7,8-tetrahydro[1]benzothieno[2,3-d]pyrimidin-7-yl[(3S)-3-methylmorpholin-4-yl]methanone

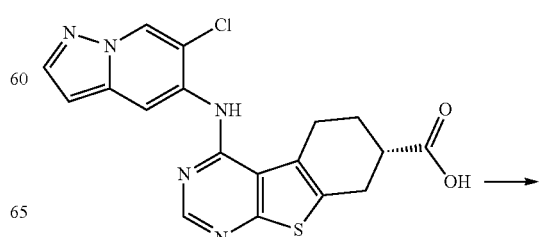

-continued

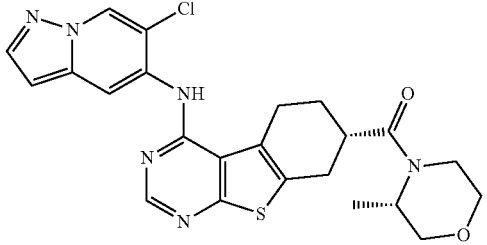

40 mg (100 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (3S)-3-methylmorpholine to give after working up and purification 37.4 mg (74%) of the title compound.

$^1$H NMR (DMSO-d6): δ=1.17+1.30 (3H), 1.79 (1H), 2.11 (1H), 2.86-4.48 (12H), 6.66 (1H), 8.03 (1H), 8.32 (1H), 8.51 (2H), 9.15 (1H) ppm.

Example 77

(7S)-4-[(6-Chloropyrazolo[1,5-a]pyridin-5-yl)amino]-5,6,7,8-tetrahydro[1]benzothieno[2,3-d]pyrimidin-7-yl][(3R)-3-methylmorpholin-4-yl]methanone

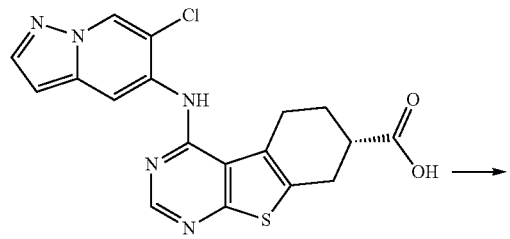

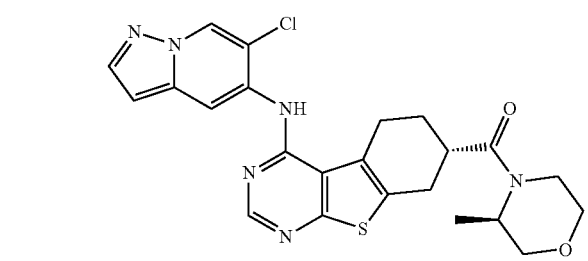

40 mg (100 µmol) (7S)-4-[(6-chloropyrazolo[1,5-a]pyridin-5-yl)amino]-5,6,7,8-tetrahydro[1]benzothieno[2,3-d]pyrimidine-7-carboxylic acid (prepared according to example 43a) were transformed in analogy to example 43 using (3R)-3-methylmorpholine to give after working up and purification 35.7 mg (70%) of the title compound.

$^1$H NMR (DMSO-d6): δ=1.16+1.32 (3H), 1.90 (1H), 2.10 (1H), 2.89-4.48 (12H), 6.67 (1H), 8.03 (1H), 8.34 (1H), 8.49 (2H), 9.15 (1H) ppm.

Example 78

(7S)-4-[(6-Methoxypyrazolo[1,5-a]pyridin-5-yl)amino]-N-methyl-5,6,7,8-tetrahydro[1]benzothieno[2,3-d]pyrimidine-7-carboxamide

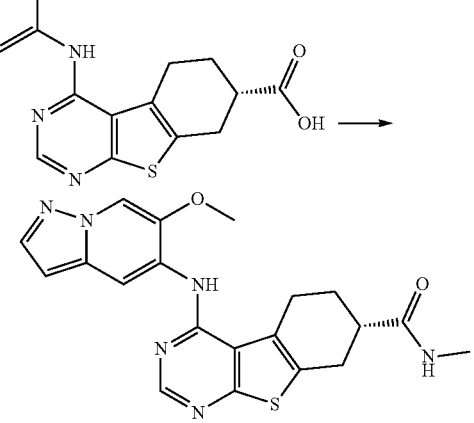

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using methanamine to give after working up and purification 39.0 mg (72%) of the title compound.

$^1$H NMR (DMSO-d6): δ=1.88 (1H), 2.20 (1H), 2.64 (3H), 2.68 (1H), 2.96 (2H), 3.11 (1H), 3.23 (1H), 4.00 (3H), 6.51 (1H), 7.84 (1H), 7.97 (1H), 8.33 (1H), 8.52 (1H), 8.61 (1H), 8.83 (1H) ppm.

Example 78a (7S)-4-[(6-Methoxypyrazolo[1,5-a]pyridin-5-yl)amino]-5,6,7,8-tetrahydro[1]benzothieno[2,3-d]pyrimidine-7-carboxylic acid

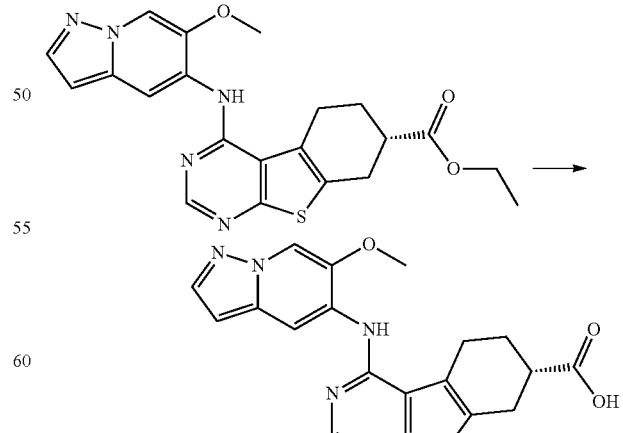

1.98 g (4.68 mmol) ethyl (7S)-4-[(6-methoxypyrazolo[1,5-a]pyridin-5-yl)amino]-5,6,7,8-tetrahydro[1]benzothieno

[2,3-d]pyrimidine-7-carboxylate (prepared according to intermediate example 78b) were transformed in analogy to example 2 to give after working up 1.85 g (99%) of the title compound.

Example 78b

Ethyl (7S)-4-[(6-methoxypyrazolo[1,5-a]pyridin-5-yl)amino]-5,6,7,8-tetrahydro[1]benzothieno[2,3-d]pyrimidine-7-carboxylate

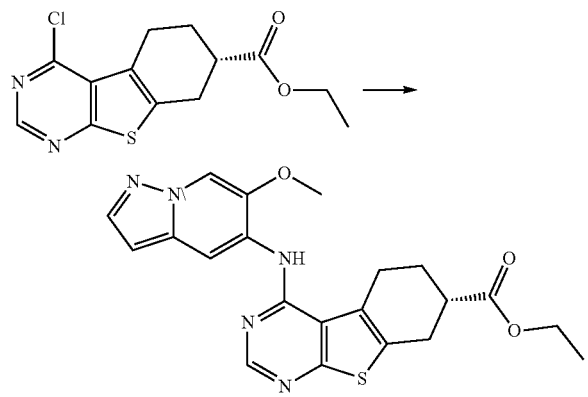

2.20 g (7.41 mmol) ethyl (7S)-4-chloro-5,6,7,8-tetrahydro[1]benzothieno[2,3-d]pyrimidine-7-carboxylate (prepared according to intermediate example 2b) were transformed in analogy to example 43b using 6-methoxypyrazolo[1,5-a]pyridin-5-amine (prepared according to intermediate example 78c) to give after working up 1.98 g (63%) of the title compound.

Example 78c

6-Methoxypyrazolo[1,5-a]pyridin-5-amine

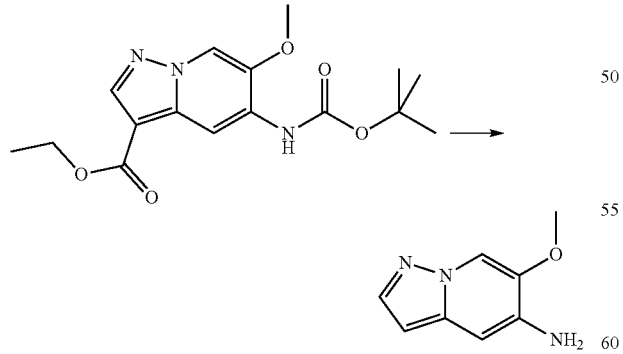

2.10 g (6.26 mmol) ethyl 5-[(tert-butoxycarbonyl)amino]-6-methoxypyrazolo[1,5-a]pyridine-3-carboxylate (prepared according to intermediate example 78d) were transformed in analogy to intermediate example 43c to give after working up 220 mg (17%) of the title compound isolated as HCl salt.

Example 78d

Ethyl 5-[(tert-butoxycarbonyl)amino]-6-methoxypyrazolo[1,5-a]pyridine-3-carboxylate

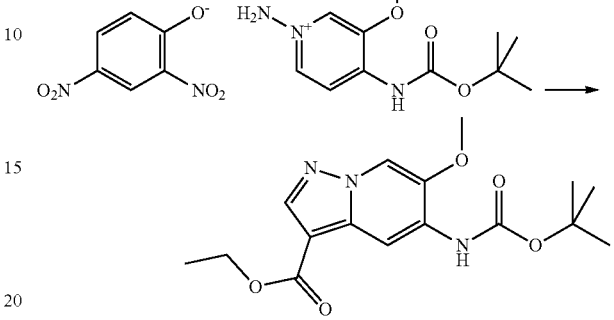

28 g crude 1-amino-4-[(tert-butoxycarbonyl)amino]-3-methoxypyridinium 2,4-dinitrophenolate (prepared according to intermediate example 78e) were transformed in analogy to intermediate example 43e to give after working up 2.10 g of the title compound.

Example 78e

1-Amino-4-[(tert-butoxycarbonyl)amino]-3-methoxypyridinium 2,4-dinitrophenolate

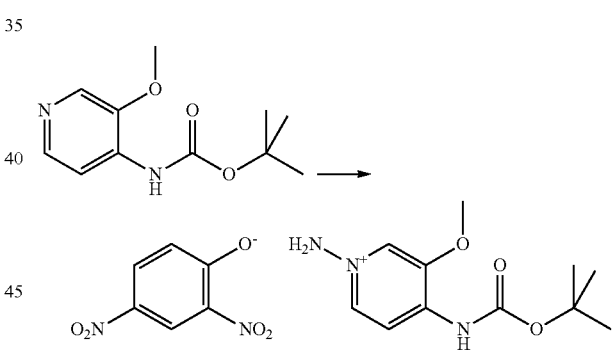

10.0 g (44.6 mmol) tert-butyl (3-methoxypyridin-4-yl)carbamate (prepared according to intermediate example 78f) were transformed in analogy to intermediate example 43f to give after working up 56 g crude title compound.

Example 78f tert-Butyl (3-methoxypyridin-4-yl)carbamate

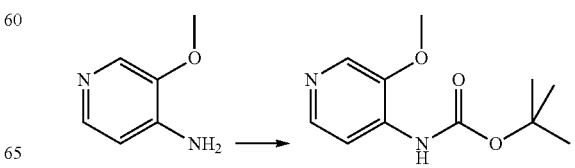

To a suspension of 25.0 g 3-methoxypyridin-4-amine (201.39 mmol) in 100 mL THF was added 402.8 mL lithium-bis(trimethylsilyl)amide (1 M in tetrahydrofurane) at 0° C. After stirring for 1 h, 48.4 g di-tert-butyl dicarbonate was added to the reaction mixture. The reaction mixture was stirred at 0° C. for 3 h, poured into saturated ammonium-chloride and extracted with ethyl acetate. The combined organic layer was dried over magnesium sulfate, filtered and concentrated under reduced pressure. The residue was purified by column chromatography to give 37 g of crude product, which was triturated with petroleum ether to give 20 g of the title compound.

Example 79

(7S)—N-(2,2-Difluoroethyl)-4-[(6-methoxypyrazolo[1,5-a]pyridin-5-yl)amino]-5,6,7,8-tetrahydro[1]benzothieno[2,3-d]pyrimidine-7-carboxamide

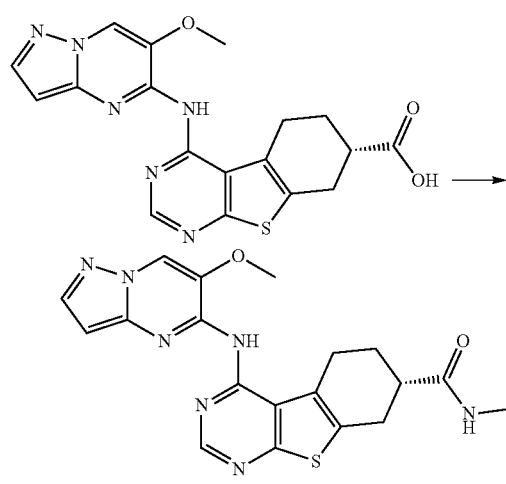

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2,2-difluoroethanamine to give after working up and purification 46.3 mg (76%) of the title compound.

$^1$H NMR (DMSO-d6): δ=1.91 (1H), 2.23 (1H), 2.78 (1H), 2.98 (2H), 3.11 (1H), 3.24 (1H), 3.41-3.65 (2H), 4.00 (3H), 6.06 (1H), 6.52 (1H), 7.84 (1H), 8.34 (1H), 8.47 (1H), 8.53 (1H), 8.62 (1H), 8.85 (1H) ppm.

Example 80

(7S)-4-[(6-Methoxypyrazolo[1,5-a]pyridin-5-yl)amino]-N-(3,3,3-trifluoropropyl)-5,6,7,8-tetrahydro[1]benzothieno[2,3-d]pyrimidine-7-carboxamide

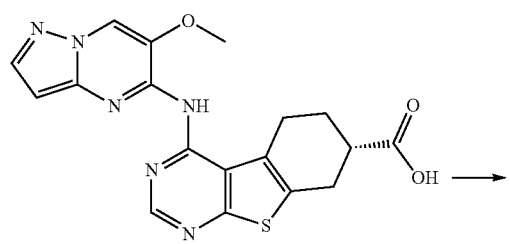

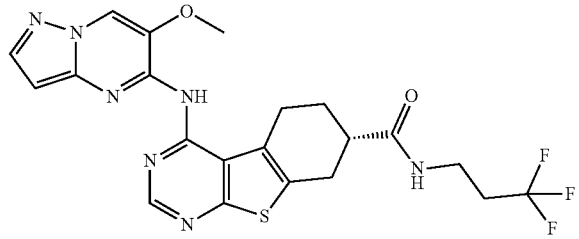

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3,3,3-trifluoropropan-1-aminium chloride to give after working up and purification 47.5 mg (49%) of the title compound.

$^1$H NMR (DMSO-d6): δ=1.89 (1H), 2.20 (1H), 2.40-2.49 (2H), 2.69 (1H), 2.96 (2H), 3.12 (1H), 3.23 (1H), 3.28-3.43 (2H), 4.00 (3H), 6.51 (1H), 7.84 (1H), 8.28 (1H), 8.33 (1H), 8.53 (1H), 8.62 (1H), 8.85 (1H) ppm.

Example 81

(7S)—N-(2-Hydroxy-2-methylpropyl)-4-[(6-methoxypyrazolo[1,5-a]pyridin-5-yl)amino]-5,6,7,8-tetrahydro[1]benzothieno[2,3-d]pyrimidine-7-carboxamide

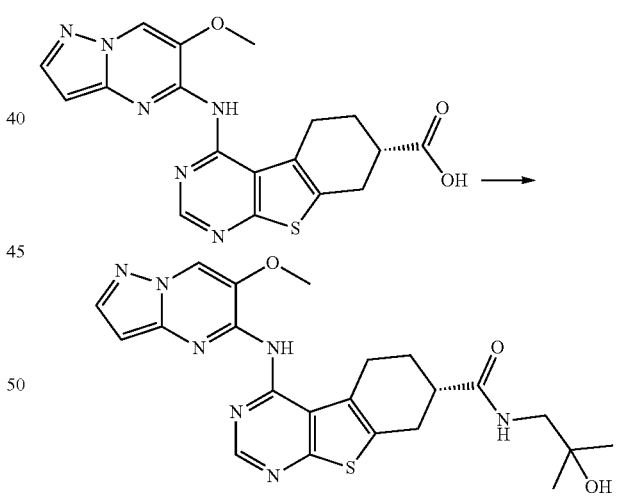

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 1-amino-2-methylpropan-2-ol to give after working up and purification 39.4 mg (63%) of the title compound.

$^1$H NMR (DMSO-d6): δ=1.09 (6H), 1.90 (1H), 2.22 (1H), 2.80 (1H), 2.96 (2H), 3.04 (1H), 3.13 (2H), 3.23 (1H), 4.00 (3H), 4.49 (1H), 6.51 (1H), 7.84 (1H), 7.91 (1H), 8.33 (1H), 8.53 (1H), 8.62 (1H), 8.85 (1H) ppm.

Example 82

(7S)—N-[2-(Dimethylamino)ethyl]-4-[(6-methoxypyrazolo[1,5-a]pyridin-5-yl)amino]-5,6,7,8-tetrahydro[1]benzothieno[2,3-d]pyrimidine-7-carboxamide

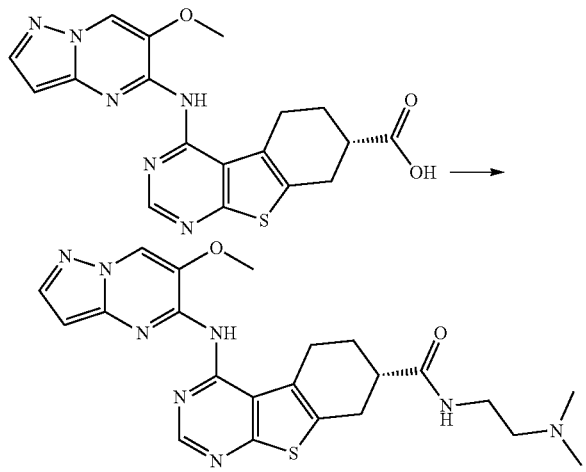

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N,N-dimethylethane-1,2-diamine to give after working up and purification 44.8 mg (72%) of the title compound.

$^1$H NMR (DMSO-d6): δ=1.88 (1H), 2.16 (6H), 2.19 (1H), 2.31 (2H), 2.70 (1H), 2.95 (2H), 3.07-3.27 (4H), 4.00 (3H), 6.51 (1H), 7.84 (1H), 7.96 (1H), 8.33 (1H), 8.53 (1H), 8.61 (1H), 8.85 (1H) ppm.

Example 83

(7S)—N-(2-Hydroxyethyl)-4-[(6-methoxypyrazolo[1,5-a]pyridin-5-yl)amino]-5,6,7,8-tetrahydro[1]benzothieno[2,3-d]pyrimidine-7-carboxamide

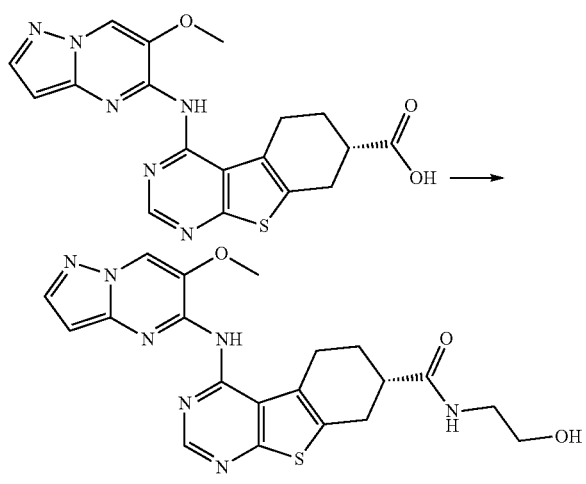

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2-aminoethanol to give after working up and purification 15.8 mg (27%) of the title compound.

$^1$H NMR (DMSO-d6): δ=1.88 (1H), 2.21 (1H), 2.70 (1H), 2.96 (2H), 3.09-3.28 (4H), 3.44 (2H), 4.01 (3H), 4.72 (1H), 6.52 (1H), 7.84 (1H), 8.04 (1H), 8.36 (1H), 8.54 (1H), 8.62 (1H), 8.85 (1H) ppm.

Example 84

(7S)—N-(2-Methoxyethyl)-4-[(6-methoxypyrazolo[1,5-a]pyridin-5-yl)amino]-5,6,7,8-tetrahydro[1]benzothieno[2,3-d]pyrimidine-7-carboxamide

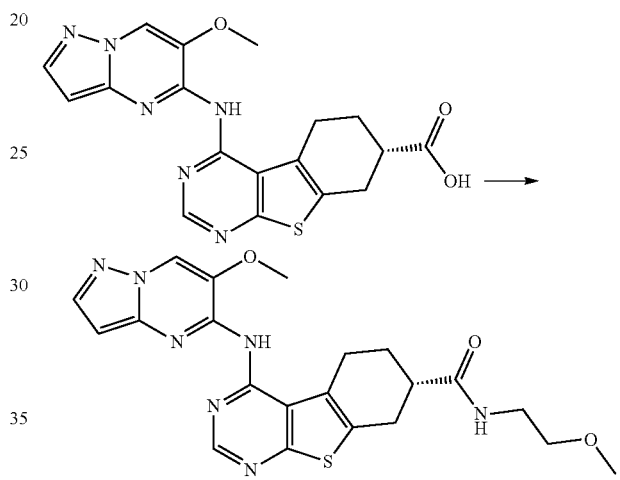

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2-methoxyethanamine to give after working up and purification 40.2 mg (67%) of the title compound.

$^1$H NMR (DMSO-d6): δ=1.88 (1H), 2.20 (1H), 2.71 (1H), 2.95 (2H), 3.11 (1H), 3.20-3.32 (3H), 3.27 (3H), 3.39 (2H), 4.00 (3H), 6.51 (1H), 7.84 (1H), 8.12 (1H), 8.34 (1H), 8.53 (1H), 8.62 (1H), 8.85 (1H) ppm.

Example 85

(7S)-4-[(6-Methoxypyrazolo[1,5-a]pyridin-5-yl)amino]-N-(propan-2-yl)-5,6,7,8-tetrahydro[1]benzothieno[2,3-d]pyrimidine-7-carboxamide

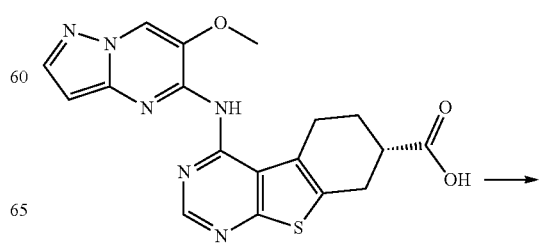

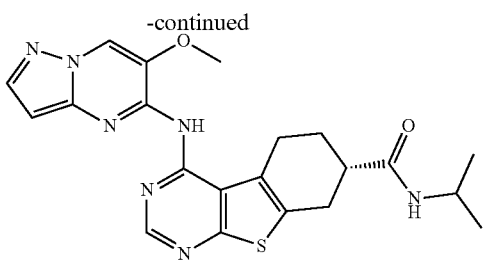

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using propan-2-amine to give after working up and purification 58.6 mg (67%) of the title compound.

$^1$H NMR (DMSO-d6): δ=1.09 (6H), 1.86 (1H), 2.19 (1H), 2.63 (1H), 2.94 (2H), 3.11 (1H), 3.23 (1H), 3.89 (1H), 4.00 (3H), 6.51 (1H), 7.84 (1H), 7.89 (1H), 8.34 (1H), 8.53 (1H), 8.61 (1H), 8.85 (1H) ppm.

Example 86

(7S)—N-tert-Butyl-4-[(6-methoxypyrazolo[1,5-a]pyridin-5-yl)amino]-5,6,7,8-tetrahydro[1]benzothieno[2,3-d]pyrimidine-7-carboxamide

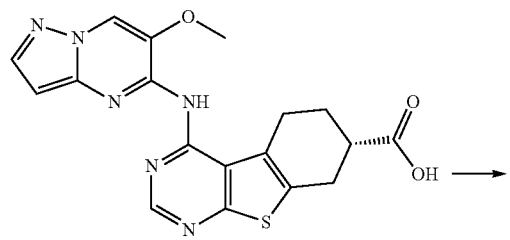

50 mg (126 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2-methylpropan-2-amine to give after working up and purification 19.8 mg (33%) of the title compound.

$^1$H NMR (DMSO-d6): δ=1.30 (9H), 1.83 (1H), 2.18 (1H), 2.65 (1H), 2.92 (2H), 3.09 (1H), 3.23 (1H), 4.01 (3H), 6.51 (1H), 7.62 (1H), 7.84 (1H), 8.35 (1H), 8.53 (1H), 8.62 (1H), 8.86 (1H) ppm.

Example 87

(7S)-4-[(6-Methoxypyrazolo[1,5-a]pyridin-5-yl)amino]-N-(1-methylcyclobutyl)-5,6,7,8-tetrahydro[1]benzothieno[2,3-d]pyrimidine-7-carboxamide

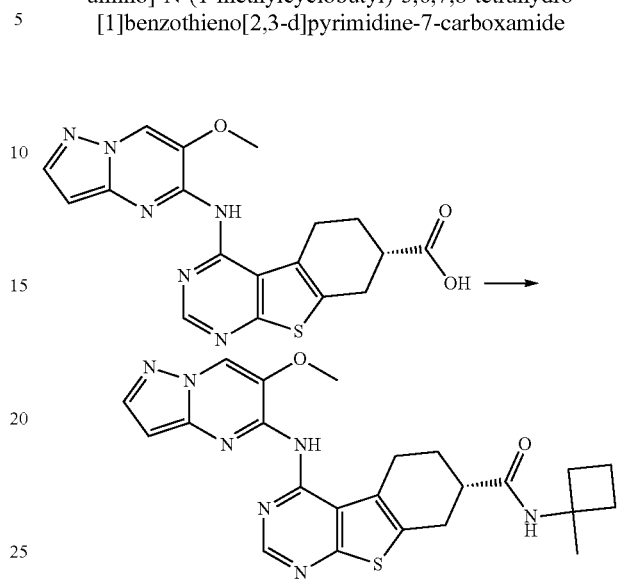

50 mg (126 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 1-methylcyclobutanamine to give after working up and purification 41.9 mg (68%) of the title compound.

$^1$H NMR (DMSO-d6): δ=1.40 (3H), 1.75-1.95 (5H), 2.17-2.31 (3H), 2.63 (1H), 2.94 (2H), 3.11 (1H), 3.24 (1H), 4.01 (3H), 6.52 (1H), 7.84 (1H), 8.04 (1H), 8.35 (1H), 8.53 (1H), 8.62 (1H), 8.85 (1H) ppm.

Example 88

(7S)—N-(4-Fluorophenyl)-4-[(6-methoxypyrazolo[1,5-a]pyridin-5-yl)amino]-5,6,7,8-tetrahydro[1]benzothieno[2,3-d]pyrimidine-7-carboxamide

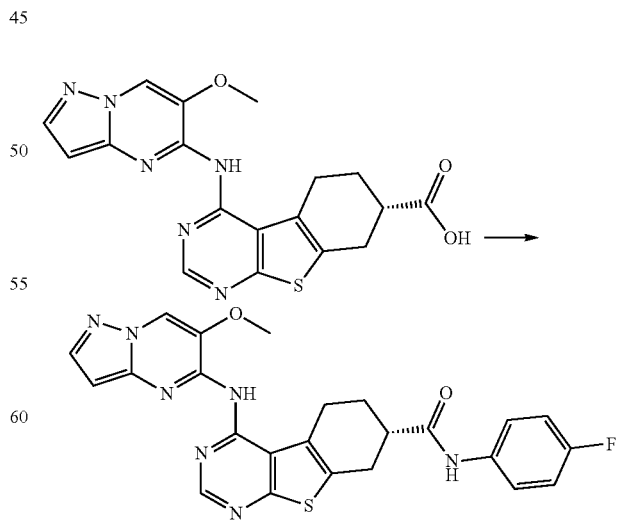

40 mg (101 μmol) (7S)-4-[(6-methoxypyrazolo[1,5-a]pyridin-5-yl)amino]-5,6,7,8-tetrahydro[1]benzothieno[2,3- d]pyrimidine-7-carboxylic acid (prepared according to example 78a) were transformed in analogy to example 43 using 4-fluoroaniline to give after working up and purification 39.2 mg (75%) of the title compound.

¹H NMR (DMSO-d6): δ=1.97 (1H), 2.35 (1H), 2.91 (1H), 3.01-3.15 (2H), 3.19 (1H), 3.30 (1H), 4.01 (3H), 6.52 (1H), 7.17 (2H), 7.67 (2H), 7.85 (1H), 8.37 (1H), 8.54 (1H), 8.63 (1H), 8.86 (1H), 10.19 (1H) ppm.

Example 89

(7S)—N-(3-Chlorophenyl)-4-[(6-methoxypyrazolo[1,5-a]pyridin-5-yl)amino]-5,6,7,8-tetrahydro[1]benzothieno[2,3-d]pyrimidine-7-carboxamide

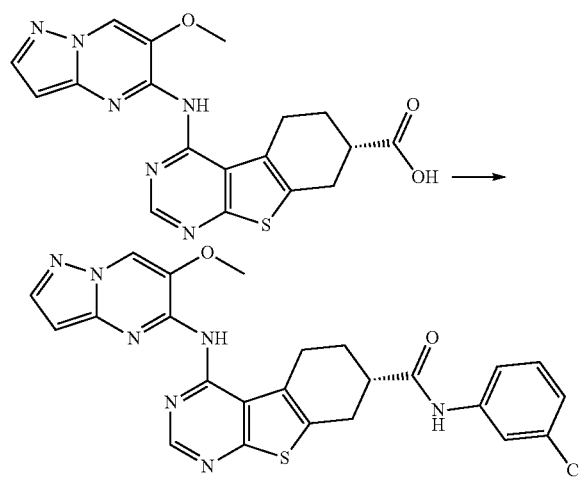

40 mg (101 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3-chloroaniline to give after working up and purification 29.9 mg (56%) of the title compound.

¹H NMR (DMSO-d6): δ=1.97 (1H), 2.36 (1H), 2.93 (1H), 3.01-3.25 (3H), 3.30 (1H), 4.01 (3H), 6.52 (1H), 7.13 (1H), 7.36 (1H), 7.51 (1H), 7.85 (1H), 7.89 (1H), 8.37 (1H), 8.54 (1H), 8.64 (1H), 8.86 (1H), 10.33 (1H) ppm.

Example 90

(7S)—N-(3,4-Dichlorophenyl)-4-[(6-methoxypyrazolo[1,5-a]pyridin-5-yl)amino]-5,6,7,8-tetrahydro[1]benzothieno[2,3-d]pyrimidine-7-carboxamide

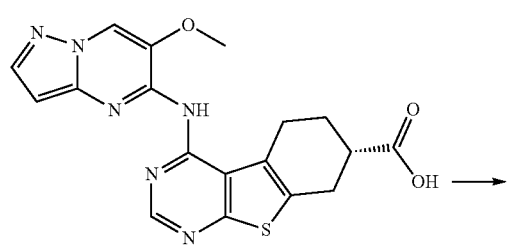

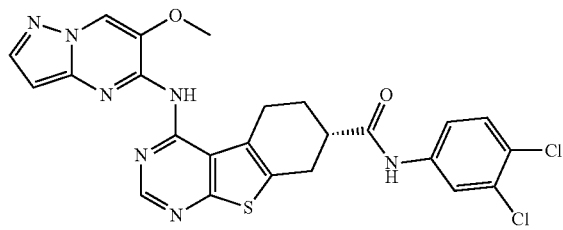

40 mg (101 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3,4-dichloroaniline to give after working up and purification 22.7 mg (40%) of the title compound.

¹H NMR (DMSO-d6): δ=1.97 (1H), 2.36 (1H), 2.92 (1H), 3.01-3.25 (3H), 3.30 (1H), 4.01 (3H), 6.52 (1H), 7.55 (1H), 7.60 (1H), 7.85 (1H), 8.07 (1H), 8.37 (1H), 8.54 (1H), 8.64 (1H), 8.86 (1H), 10.44 (1H) ppm.

Example 91

(7S)—N-(3-Chloro-4-fluorophenyl)-4-[(6-methoxypyrazolo[1,5-a]pyridin-5-yl)amino]-5,6,7,8-tetrahydro[1]benzothieno[2,3-d]pyrimidine-7-carboxamide

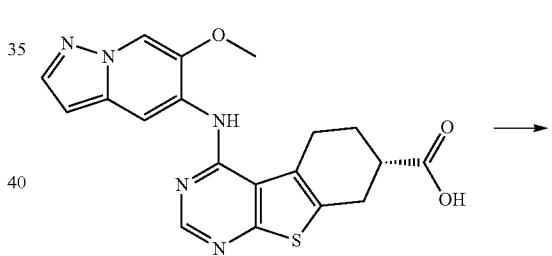

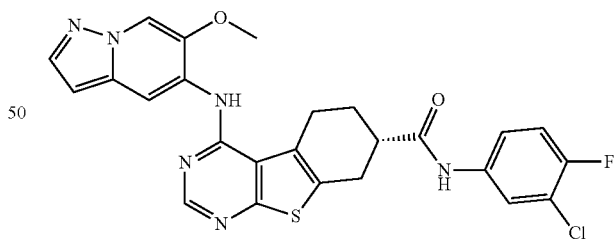

40 mg (101 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3-chloro-4-fluoroaniline to give after working up and purification 24.9 mg (45%) of the title compound.

¹H NMR (DMSO-d6): δ=1.97 (1H), 2.36 (1H), 2.91 (1H), 3.01-3.24 (3H), 3.30 (1H), 4.01 (3H), 6.52 (1H), 7.40 (1H), 7.53 (1H), 7.85 (1H), 8.00 (1H), 8.37 (1H), 8.54 (1H), 8.64 (1H), 8.86 (1H), 10.36 (1H) ppm.

Example 92

(7S)—N-(3-Fluorophenyl)-4-[(6-methoxypyrazolo[1,5-a]pyridin-5-yl)amino]-5,6,7,8-tetrahydro[1]benzothieno[2,3-d]pyrimidine-7-carboxamide

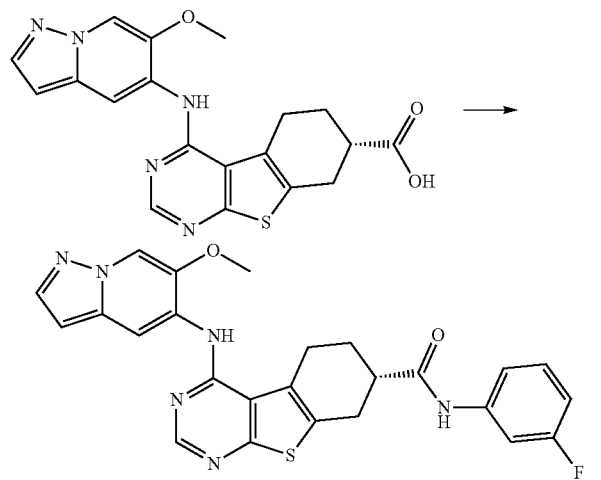

40 mg (101 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3-fluoroaniline to give after working up and purification 37.6 mg (72%) of the title compound.

¹H NMR (DMSO-d6): δ=1.97 (1H), 2.36 (1H), 2.93 (1H), 3.01-3.24 (3H), 3.30 (1H), 4.01 (3H), 6.52 (1H), 6.90 (1H), 7.33-7.41 (2H), 7.67 (1H), 7.85 (1H), 8.37 (1H), 8.54 (1H), 8.64 (1H), 8.86 (1H), 10.36 (1H) ppm.

Example 93

(7S)—N-(1H-Indol-5-yl)-4-[(6-methoxypyrazolo[1,5-a]pyridin-5-yl)amino]-5,6,7,8-tetrahydro[1]benzothieno[2,3-d]pyrimidine-7-carboxamide

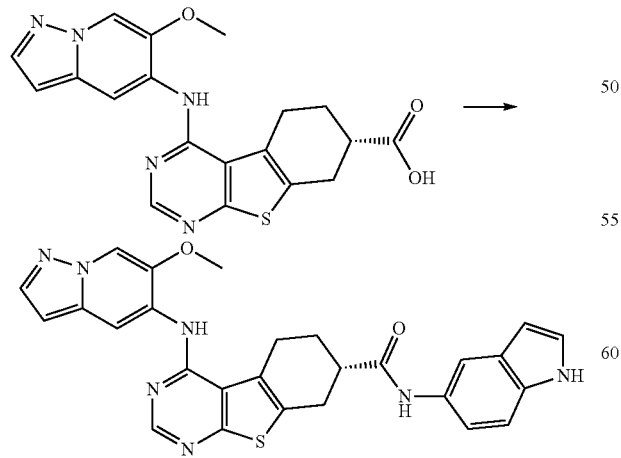

40 mg (101 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 1H-indol-5-amine to give after working up and purification 19.6 mg (35%) of the title compound.

¹H NMR (DMSO-d6): δ=2.00 (1H), 2.36 (1H), 2.93 (1H), 3.04-3.15 (2H), 3.21 (1H), 3.31 (1H), 4.02 (3H), 6.38 (1H), 6.53 (1H), 7.25 (1H), 7.30-7.35 (2H), 7.85 (1H), 7.93 (1H), 8.40 (1H), 8.55 (1H), 8.64 (1H), 8.87 (1H), 9.92 (1H), 11.02 (1H) ppm.

Example 94

(7S)—N-Ethyl-4-[(6-methoxypyrazolo[1,5-a]pyridin-5-yl)amino]-N-methyl-5,6,7,8-tetrahydro[1]benzothieno[2,3-d]pyrimidine-7-carboxamide

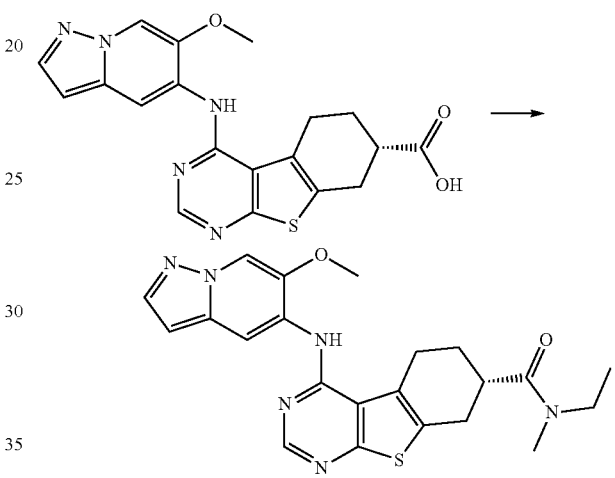

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N-methylethanamine to give after working up and purification 66.4 mg (76%) of the title compound.

¹H NMR (DMSO-d6): δ=1.04+1.17 (3H), 1.85 (1H), 2.15 (1H), 2.85+3.09 (3H), 2.89-3.04 (2H), 3.11-3.57 (5H), 4.01 (3H), 6.51 (1H), 7.84 (1H), 8.34 (1H), 8.53 (1H), 8.62 (1H), 8.84 (1H) ppm.

Example 95

(7S)—N-(2,2-Difluoroethyl)-4-[(6-methoxypyrazolo[1,5-a]pyridin-5-yl)amino]-N-methyl-5,6,7,8-tetrahydro[1]benzothieno[2,3-d]pyrimidine-7-carboxamide

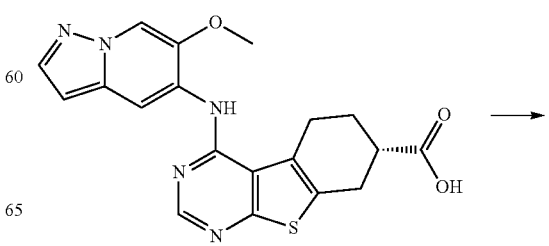

-continued

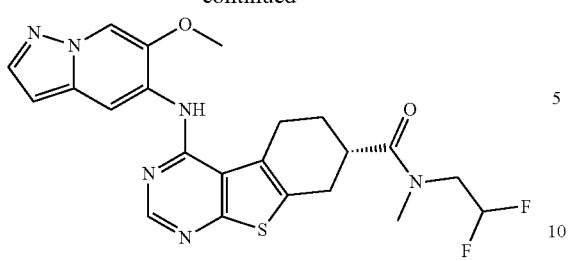

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2,2-difluoro-N-methylethanamine to give after working up and purification 77.7 mg (82%) of the title compound.

$^1$H NMR (DMSO-d6): δ=1.86 (1H), 2.14+2.21 (1H), 2.89-3.05 (3H), 3.16-3.31 (2H), 3.22 (3H), 3.65-4.10 (2H), 4.01+4.02 (3H), 6.15 (1H), 6.51 (1H), 7.84 (1H), 8.34 (1H), 8.53 (1H), 8.62 (1H), 8.85 (1H) ppm.

Example 96

(7S)-4-[(6-Methoxypyrazolo[1,5-a]pyridin-5-yl)amino]-N-methyl-N-(3,3,3-trifluoropropyl)-5,6,7,8-tetrahydro[1]benzothieno[2,3-d]pyrimidine-7-carboxamide

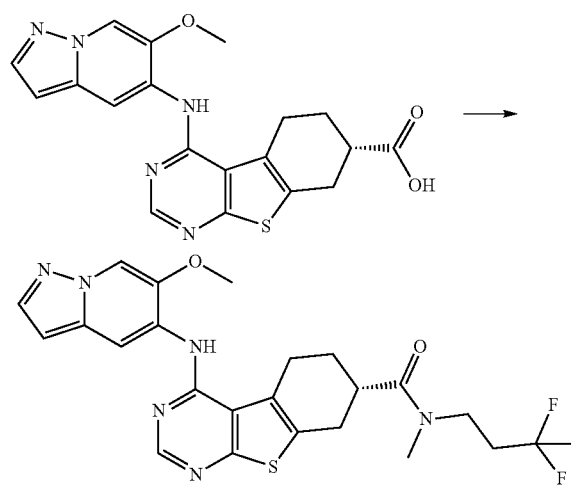

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3,3,3-trifluoro-N-methylpropan-1-aminium chloride to give after working up and purification 81.4 mg (81%) of the title compound.

$^1$H NMR (DMSO-d6): δ=1.84 (1H), 2.16 (1H), 2.46-2.77 (2H), 2.89+3.15 (3H), 2.90-3.01 (2H), 3.09-3.27 (3H), 3.47-3.77 (2H), 4.01 (3H), 6.51 (1H), 7.84 (1H), 8.33 (1H), 8.53 (1H), 8.62 (1H), 8.84 (1H) ppm.

Example 97

(7S)—N-Butyl-4-[(6-methoxypyrazolo[1,5-a]pyridin-5-yl)amino]-N-methyl-5,6,7,8-tetrahydro[1]benzothieno[2,3-d]pyrimidine-7-carboxamide

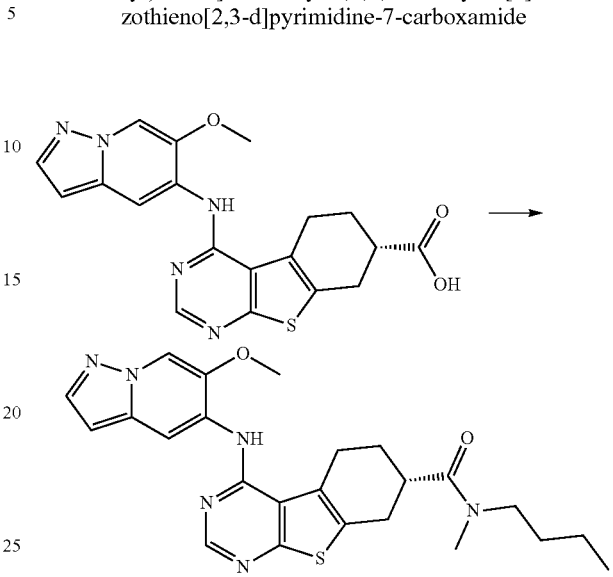

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N-methylbutan-1-amine to give after working up and purification 76.0 mg (82%) of the title compound.

$^1$H NMR (DMSO-d6): δ=0.89-0.95 (3H), 1.22-1.36 (2H), 1.47+1.55 (2H), 1.84 (1H), 2.15 (1H), 2.87+3.09 (3H), 2.89-3.04 (2H), 3.11-3.48 (5H), 4.01 (3H), 6.51 (1H), 7.84 (1H), 8.34 (1H), 8.53 (1H), 8.61 (1H), 8.84+8.85 (1H) ppm.

Example 98

1-((7S)-4-[(6-Methoxypyrazolo[1,5-a]pyridin-5-yl)amino]-5,6,7,8-tetrahydro[1]benzothieno[2,3-d]pyrimidin-7-ylcarbonyl)azetidine-3-carbonitrile

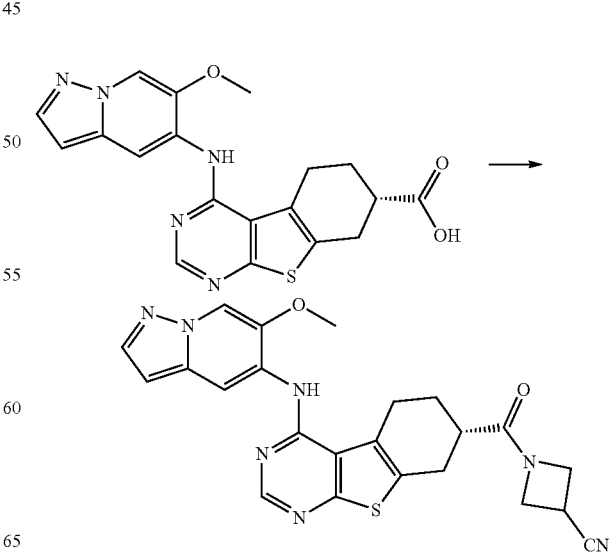

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3-cyanoazetidinium chloride to give after working up and purification 79.4 mg (87%) of the title compound.

$^1$H NMR (DMSO-d6): δ=1.81 (1H), 2.15+2.22 (1H), 2.77 (1H), 2.84-3.04 (2H), 3.14 (1H), 3.24 (1H), 3.83 (1H), 4.01+4.02 (3H), 4.06 (1H), 4.20 (1H), 4.48-4.60 (2H), 6.52 (1H), 7.84 (1H), 8.34 (1H), 8.53 (1H), 8.62 (1H), 8.84 (1H) ppm.

Example 99

(7S)—N-[3-(Dimethylamino)propyl]-4-[(6-methoxy-pyrazolo[1,5-a]pyridin-5-yl)amino]-N-methyl-5,6,7,8-tetrahydro[1]benzothieno[2,3-d]pyrimidine-7-carboxamide

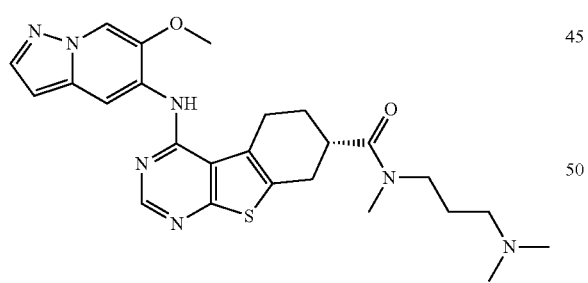

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N,N,N'-trimethylpropane-1,3-diamine to give after working up and purification 75.5 mg (77%) of the title compound.

$^1$H NMR (DMSO-d6): δ=1.61+1.70 (2H), 1.86 (1H), 2.12+2.13 (6H), 2.14-2.24 (3H), 2.87+3.11 (3H), 2.89-3.01 (2H), 3.12-3.51 (5H), 4.01 (3H), 6.51 (1H), 7.84 (1H), 8.33 (1H), 8.52 (1H), 8.61 (1H), 8.84 (1H) ppm.

Example 100

(3-Hydroxy-3-methylazetidin-1-yl)(7S)-4-[(6-methoxypyrazolo[1,5-a]pyridin-5-yl)amino]-5,6,7,8-tetrahydro[1]benzothieno[2,3-d]pyrimidin-7-yl-methanone

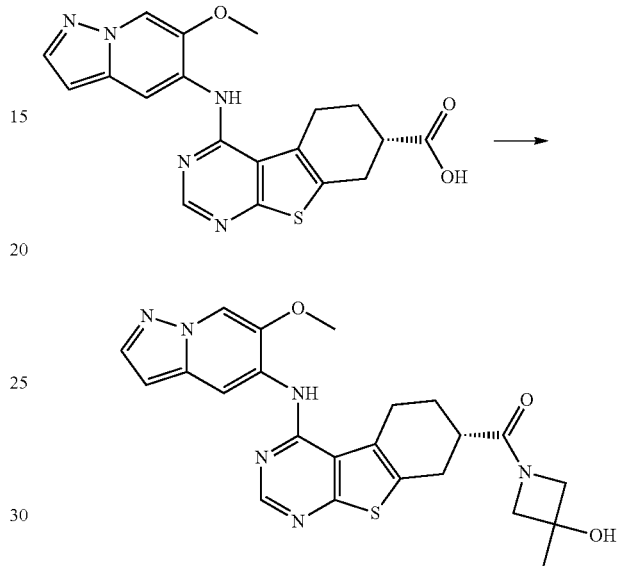

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3-hydroxy-3-methylazetidinium chloride to give after working up and purification 81.5 mg (88%) of the title compound.

$^1$H NMR (DMSO-d6): δ=1.40+1.42 (3H), 1.82 (1H), 2.16 (1H), 2.78 (1H), 2.93 (2H), 3.15 (1H), 3.24 (1H), 3.74 (2H), 4.01 (3H), 4.09 (2H), 5.69 (1H), 6.51 (1H), 7.84 (1H), 8.33 (1H), 8.53 (1H), 8.62 (1H), 8.84 (1H) ppm.

Example 101

(7S)—N-[2-(Dimethylamino)ethyl]-4-[(6-methoxy-pyrazolo[1,5-a]pyridin-5-yl)amino]-N-methyl-5,6,7,8-tetrahydro[1]benzothieno[2,3-d]pyrimidine-7-carboxamide

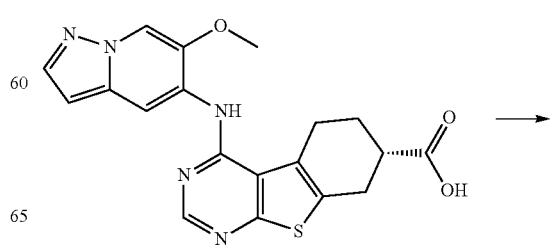

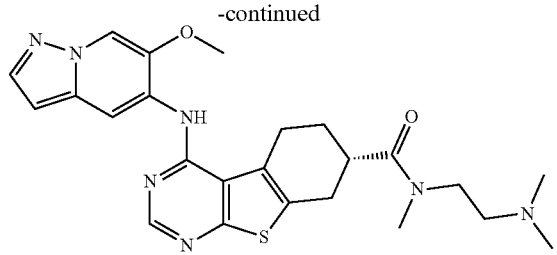

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N,N,N'-trimethylethane-1,2-diamine to give after working up and purification 64.4 mg (67%) of the title compound.

$^1$H NMR (DMSO-d6): δ=1.85 (1H), 2.15 (1H), 2.17+2.20 (6H), 2.36+2.44 (2H), 2.89+3.12 (3H), 2.92-3.04 (2H), 3.14-3.27 (3H), 3.31-3.54 (2H), 4.01 (3H), 6.51 (1H), 7.84 (1H), 8.33 (1H), 8.52 (1H), 8.61 (1H), 8.84 (1H) ppm.

Example 102

[3-(Dimethylamino)azetidin-1-yl](7S)-4-[(6-methoxypyrazolo[1,5-a]pyridin-5-yl)amino]-5,6,7,8-tetrahydro[1]benzothieno[2,3-d]pyrimidin-7-yl-methanone

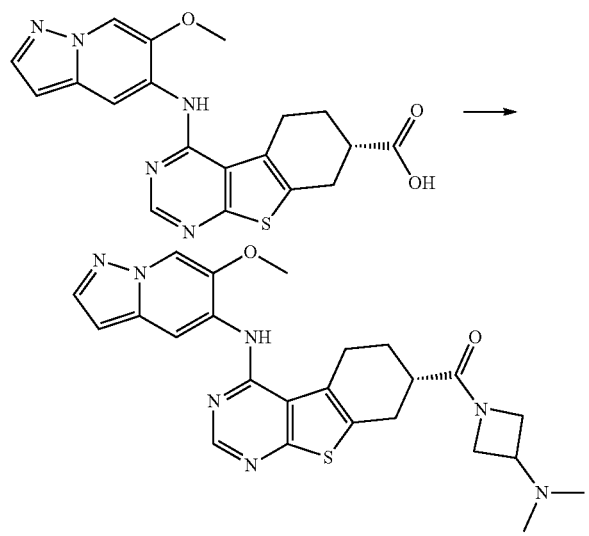

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 3-(dimethylammonio)azetidinium dichloride to give after working up and purification 44.0 mg (69%) of the title compound.

$^1$H NMR (DMSO-d6): δ=1.82 (1H), 2.10 (3H), 2.11 (3H), 2.17 (1H), 2.79 (1H), 2.86-2.99 (2H), 3.06 (1H), 3.14 (1H), 3.24 (1H), 3.68 (1H), 3.90 (1H), 4.01+4.02 (3H), 4.06 (1H), 4.27 (1H), 6.51 (1H), 7.84 (1H), 8.34 (1H), 8.53 (1H), 8.62 (1H), 8.84 (1H) ppm.

Example 103

(7S)—N-(2-Hydroxyethyl)-4-[(6-methoxypyrazolo[1,5-a]pyridin-5-yl)amino]-N-methyl-5,6,7,8-tetrahydro[1]benzothieno[2,3-d]pyrimidine-7-carboxamide

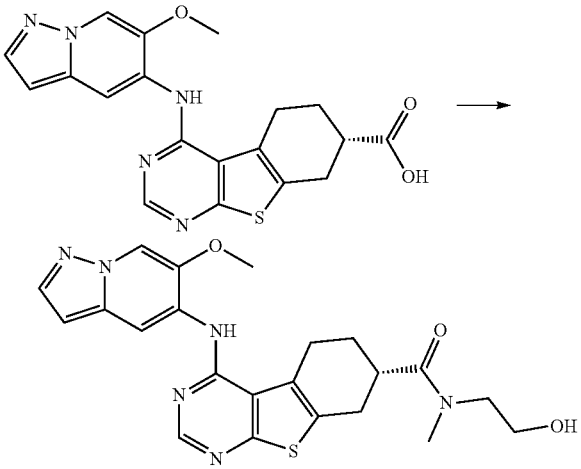

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2-(methylamino)ethanol to give after working up and purification 47.1 mg (52%) of the title compound.

$^1$H NMR (DMSO-d6): δ=1.85 (1H), 2.18 (1H), 2.89+3.16 (3H), 2.91-3.03 (2H), 3.13-3.62 (7H), 4.01 (3H), 4.70+4.88 (1H), 6.51 (1H), 7.84 (1H), 8.34 (1H), 8.53 (1H), 8.62 (1H), 8.85 (1H) ppm.

Example 104

(7S)—N-(2-Methoxyethyl)-4-[(6-methoxypyrazolo[1,5-a]pyridin-5-yl)amino]-N-methyl-5,6,7,8-tetrahydro[1]benzothieno[2,3-d]pyrimidine-7-carboxamide

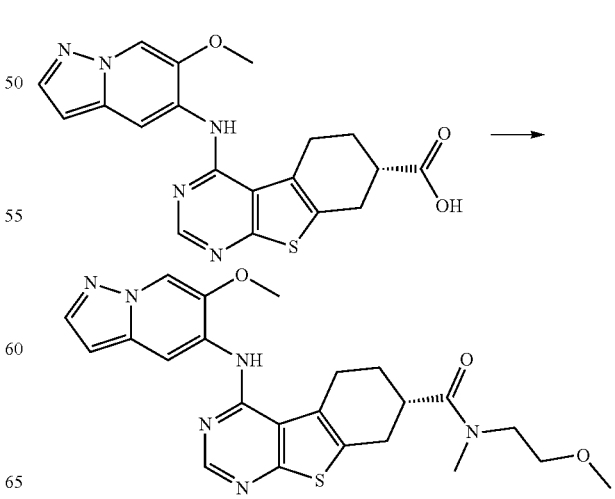

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2-methoxy-N-methylethanamine to give after working up and purification 73.1 mg (78%) of the title compound.

$^1$H NMR (DMSO-d6): δ=1.85 (1H), 2.16 (1H), 2.87-3.02 (2H), 2.90+3.15 (3H), 3.16-3.25 (3H), 3.27+3.29 (3H), 3.40-3.73 (4H), 4.00+4.01 (3H), 6.51 (1H), 7.84 (1H), 8.33 (1H), 8.52 (1H), 8.61 (1H), 8.84 (1H) ppm.

Example 105

(7S)-4-[(6-Methoxypyrazolo[1,5-a]pyridin-5-yl)amino]-N-methyl-N-(propan-2-yl)-5,6,7,8-tetrahydro[1]benzothieno[2,3-d]pyrimidine-7-carboxamide

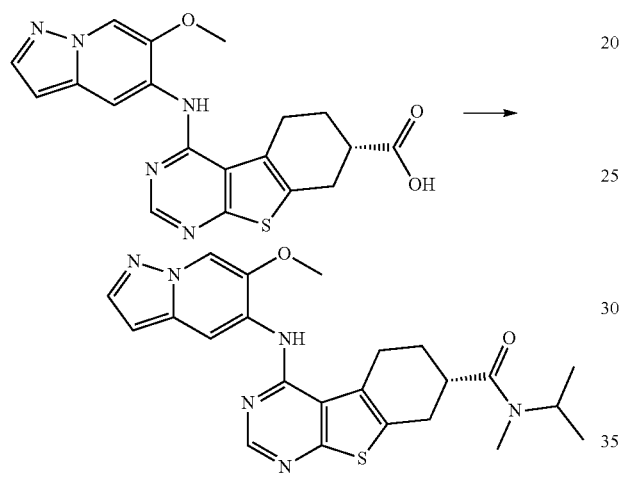

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N-methylpropan-2-amine to give after working up and purification 61.6 mg (68%) of the title compound.

$^1$H NMR (DMSO-d6): δ=1.07+1.20 (6H), 1.85 (1H), 2.12+2.16 (1H), 2.73+2.93 (3H), 2.88-3.04 (2H), 3.08-3.27 (3H), 4.01 (3H), 4.30+4.74 (1H), 6.51 (1H), 7.84 (1H), 8.33 (1H), 8.52 (1H), 8.61 (1H), 8.84+8.85 (1H) ppm.

Example 106

[(3R)-3-(Dimethylamino)pyrrolidin-1-yl](7S)-4-[(6-methoxypyrazolo[1,5-a]pyridin-5-yl)amino]-5,6,7,8-tetrahydro[1]benzothieno[2,3-d]pyrimidin-7-yl-methanone

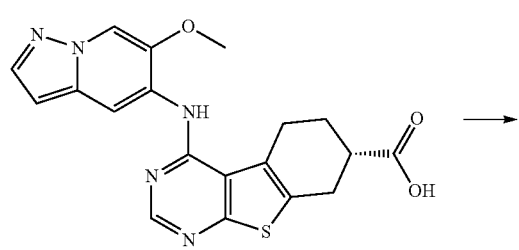

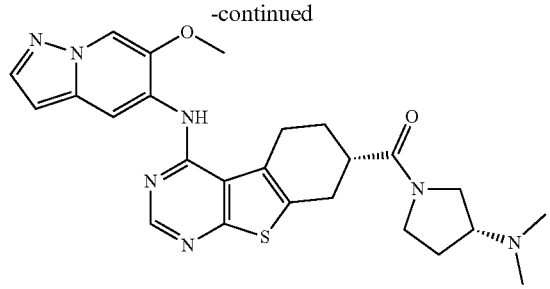

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (3R)—N,N-dimethylpyrrolidin-3-amine to give after working up and purification 79.6 mg (81%) of the title compound.

$^1$H NMR (DMSO-d6): δ=1.60-1.89 (2H), 2.01-2.22 (2H), 2.18+2.19 (6H), 2.67 (1H), 2.93-3.86 (8H), 3.79+3.89 (1H), 4.01 (3H), 6.51 (1H), 7.84 (1H), 8.35 (1H), 8.53 (1H), 8.62 (1H), 8.84 (1H) ppm.

Example 107

[(3S)-3-(Dimethylamino)pyrrolidin-1-yl](7S)-4-[(6-methoxypyrazolo[1,5-a]pyridin-5-yl)amino]-5,6,7,8-tetrahydro[1]benzothieno[2,3-d]pyrimidin-7-yl-methanone

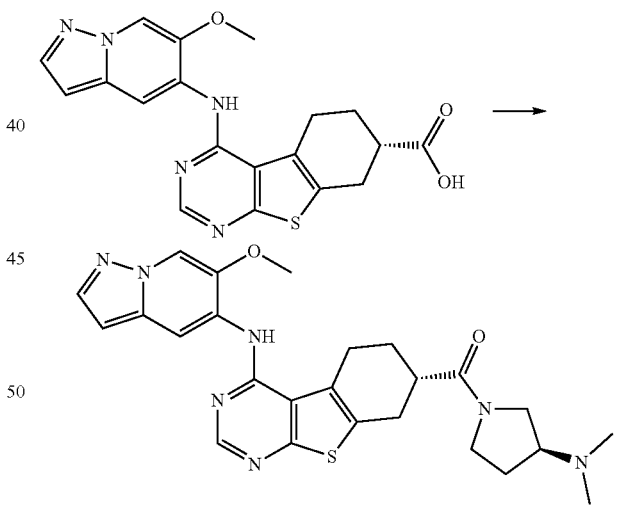

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (3S)—N,N-dimethylpyrrolidin-3-amine to give after working up and purification 81.0 mg (83%) of the title compound.

$^1$H NMR (DMSO-d6): δ=1.59-1.88 (2H), 2.00-2.23 (2H), 2.18+2.19 (6H), 2.62+2.75 (1H), 2.89-3.68 (8H), 3.77+3.95 (1H), 4.01 (3H), 6.51 (1H), 7.84 (1H), 8.34 (1H), 8.53 (1H), 8.62 (1H), 8.84 (1H) ppm.

Example 108

[(3S,4S)-3,4-Dihydroxypyrrolidin-1-yl][(7S)-4-[(6-methoxypyrazolo[1,5-a]pyridin-5-yl)amino]-5,6,7,8-tetrahydro[1]benzothieno[2,3-d]pyrimidin-7-yl-methanone

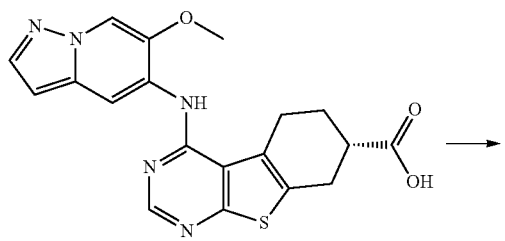

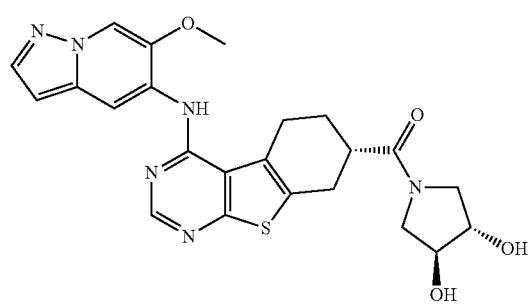

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (3S,4S)-pyrrolidine-3,4-diol to give after working up and purification 27.5 mg (43%) of the title compound.

$^1$H NMR (DMSO-d6): δ=1.84 (1H), 2.19 (1H), 2.91-3.03 (3H), 3.12-3.30 (2H), 3.32 (1H), 3.42-3.51 (2H), 3.75 (1H), 3.94 (1H), 4.01 (4H), 5.16 (1H), 5.25 (1H), 6.52 (1H), 7.84 (1H), 8.34 (1H), 8.53 (1H), 8.62 (1H), 8.85 (1H) ppm.

Example 109

[4-(Dimethylamino)piperidin-1-yl][(7S)-4-[(6-methoxypyrazolo[1,5-a]pyridin-5-yl)amino]-5,6,7,8-tetrahydro[1]benzothieno[2,3-d]pyrimidin-7-yl-methanone

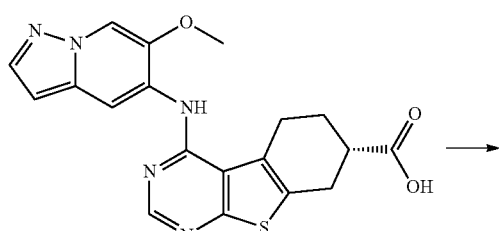

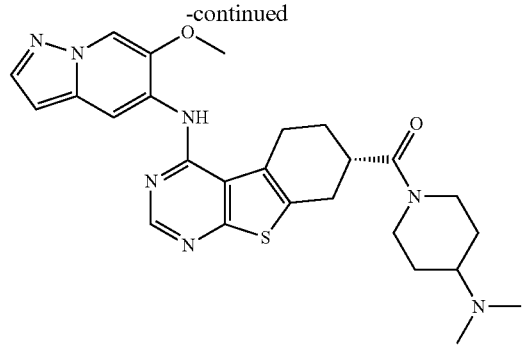

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N,N-dimethylpiperidin-4-amine to give after working up and purification 45.3 mg (67%) of the title compound.

$^1$H NMR (DMSO-d6): δ=1.21 (1H), 1.36 (1H), 1.71-1.94 (3H), 2.14 (1H), 2.18 (3H), 2.19 (3H), 2.33 (1H), 2.63 (1H), 2.89-3.02 (2H), 3.09 (1H), 3.16-3.27 (3H), 4.01 (3H), 4.06 (1H), 4.42 (1H), 6.52 (1H), 7.84 (1H), 8.34 (1H), 8.53 (1H), 8.62 (1H), 8.84 (1H) ppm.

Example 110

(4-[2-Dimethylamino)ethyl]methyl)aminopiperidin-1-yl)(7S)-4-[(6-methoxypyrazolo[1,5-a]pyridin-5-yl)amino]-5,6,7,8-tetrahydro[1]benzothieno[2,3-d]pyrimidin-7-ylmethanone

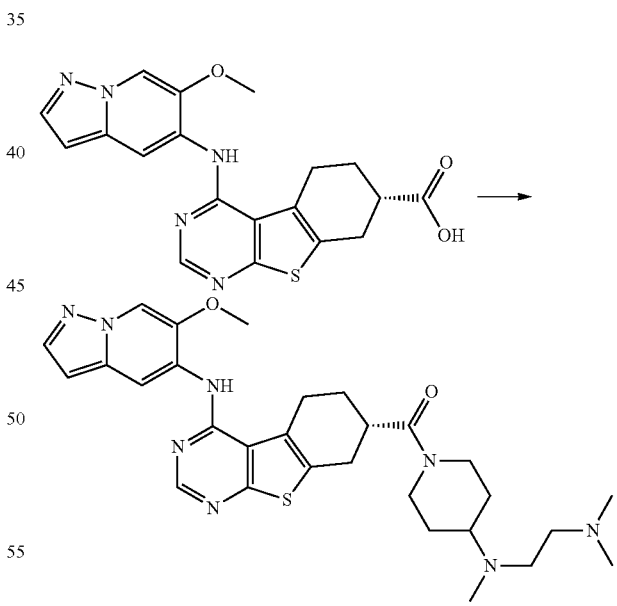

40 mg (101 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 4-{[2-(dimethylammonio)ethyl](methyl)ammonio}piperidinium trichloride to give after working up and purification 39.2 mg (65%) of the title compound.

$^1$H NMR (DMSO-d6): δ=1.25 (1H), 1.40 (1H), 1.68-1.93 (3H), 2.14 (7H), 2.18+2.20 (3H), 2.29 (2H), 2.43-2.64 (4H), 2.88-3.12 (3H), 3.16-3.26 (3H), 4.01 (3H), 4.09 (1H), 4.48 (1H), 6.51 (1H), 7.84 (1H), 8.34 (1H), 8.53 (1H), 8.62 (1H), 8.84 (1H) ppm.

Example 111

(7S)—N-[3-(Dimethylamino)propyl]-N-(2-hydroxyethyl)-4-[(6-methoxypyrazolo[1,5-a]pyridin-5-yl)amino]-5,6,7,8-tetrahydro[1]benzothieno[2,3-d]pyrimidine-7-carboxamide

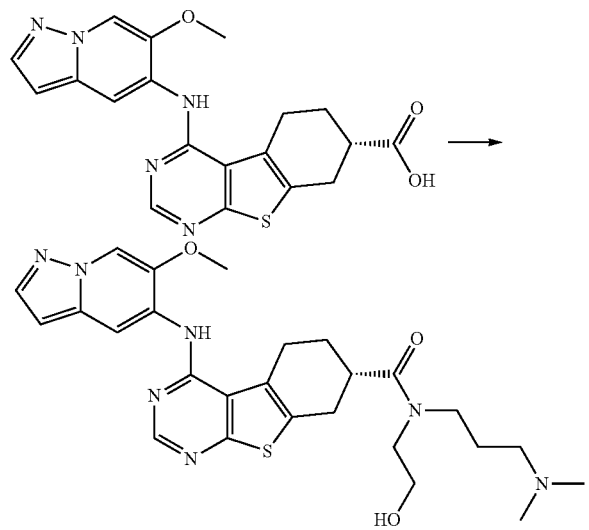

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2-{[3-(dimethylamino)propyl]amino}ethanol to give after working up and purification 54.4 mg (78%) of the title compound.

$^1$H NMR (DMSO-d6): δ=1.57-1.74 (2H), 1.87 (1H), 2.11+2.13 (6H), 2.12-2.24 (3H), 2.89-3.04 (2H), 3.12-3.58 (9H), 4.01 (3H), 4.71+4.89 (1H), 6.52 (1H), 7.84 (1H), 8.35 (1H), 8.54 (1H), 8.62 (1H), 8.85 (1H) ppm.

Example 112

[(2R,6S)-2,6-Dimethylmorpholin-4-yl](7S)-4-[(6-methoxypyrazolo[1,5-a]pyridin-5-yl)amino]-5,6,7,8-tetrahydro[1]benzothieno[2,3-d]pyrimidin-7-yl-methanone

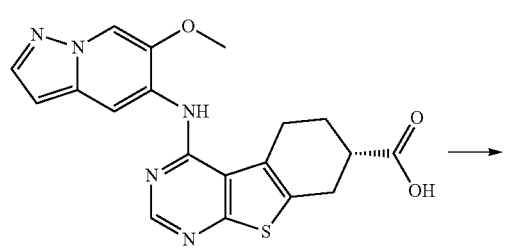

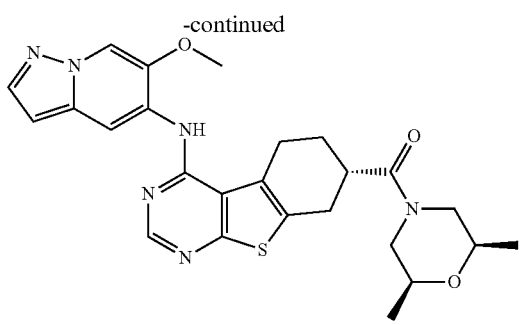

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (2R,6S)-2,6-dimethylmorpholine to give after working up and purification 60.1 mg (61%) of the title compound.

$^1$H NMR (DMSO-d6): δ=1.09-1.16 (6H), 1.86 (1H), 2.14 (1H), 2.28 (1H), 2.78 (1H), 2.89-3.06 (2H), 3.15-3.28 (3H), 3.45 (1H), 3.55 (1H), 4.01 (4H), 4.33 (1H), 6.51 (1H), 7.84 (1H), 8.33 (1H), 8.53 (1H), 8.61 (1H), 8.83 (1H) ppm.

Example 113

(7S)-4-[(6-Methoxypyrazolo[1,5-a]pyridin-5-yl)amino]-5,6,7,8-tetrahydro[1]benzothieno[2,3-d]pyrimidin-7-yl(4-methylpiperazin-1-yl)methanone

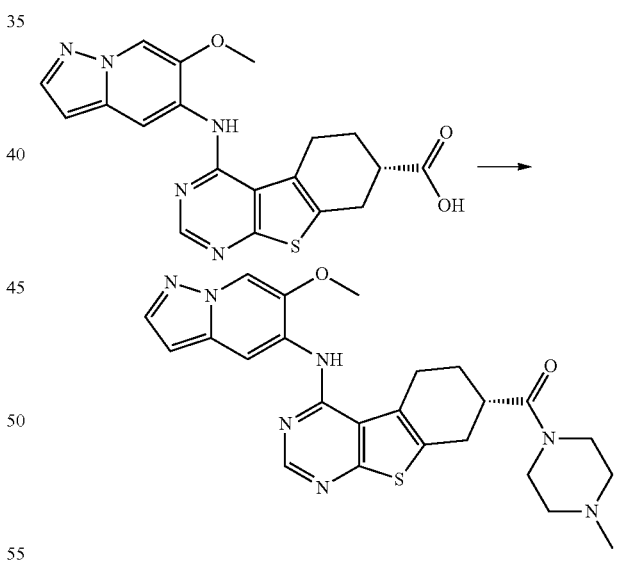

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 1-methylpiperazine to give after working up and purification 31.4 mg (49%) of the title compound.

$^1$H NMR (DMSO-d6): δ=1.85 (1H), 2.15 (1H), 2.21 (3H), 2.29 (2H), 2.36 (2H), 2.88-3.04 (2H), 3.14-3.26 (3H), 3.52 (2H), 3.60 (2H), 4.01 (3H), 6.51 (1H), 7.84 (1H), 8.33 (1H), 8.53 (1H), 8.62 (1H), 8.84 (1H) ppm.

Example 114

4-[2-(Dimethylamino)ethyl]piperazin-1-yl(7S)-4-[(6-methoxypyrazolo[1,5-a]pyridin-5-yl)amino]-5,6,7,8-tetrahydro[1]benzothieno[2,3-d]pyrimidin-7-yl-methanone

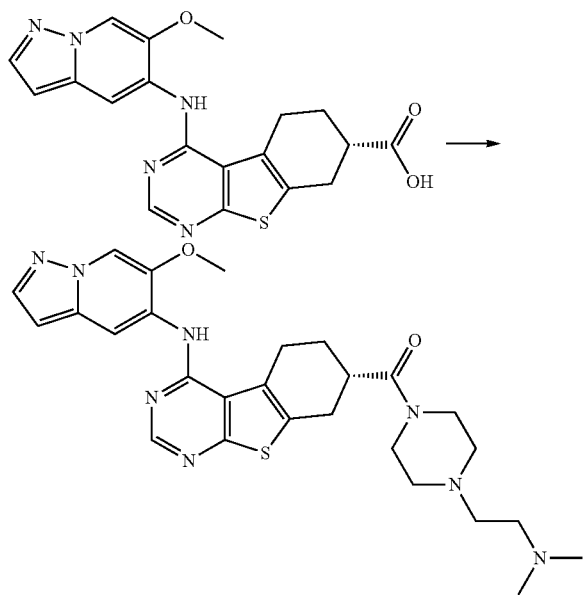

40 mg (101 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N,N-dimethyl-2-(piperazin-1-yl)ethanamine to give after working up and purification 38.4 mg (67%) of the title compound.

$^1$H NMR (DMSO-d6): δ=1.86 (1H), 2.14 (7H), 2.33-2.54 (8H), 2.88-3.04 (2H), 3.15-3.26 (3H), 3.50 (2H), 3.58 (2H), 4.02 (3H), 6.52 (1H), 7.84 (1H), 8.34 (1H), 8.53 (1H), 8.62 (1H), 8.84 (1H) ppm.

Example 115

(7S)—N-[2-(Dimethylamino)ethyl]-N-ethyl-4-[(6-methoxypyrazolo[1,5-a]pyridin-5-yl)amino]-5,6,7,8-tetrahydro[1]benzothieno[2,3-d]pyrimidine-7-carboxamide

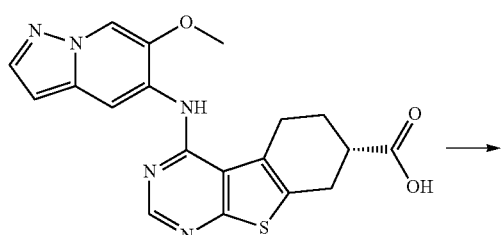

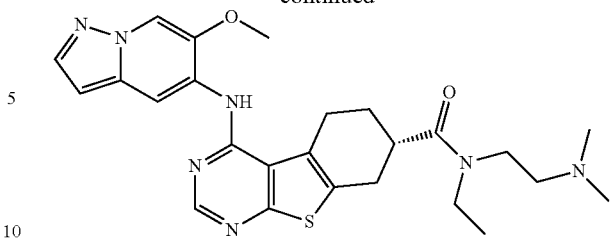

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N'-ethyl-N,N-dimethylethane-1,2-diamine to give after working up and purification 75.2 mg (76%) of the title compound.

$^1$H NMR (DMSO-d6): δ=1.06+1.17 (3H), 1.87 (1H), 2.12 (1H), 2.18+2.19 (6H), 2.35+2.43 (2H), 2.88-3.12 (3H), 3.17-3.54 (6H), 4.01 (3H), 6.51 (1H), 7.84 (1H), 8.34 (1H), 8.53 (1H), 8.62 (1H), 8.85 (1H) ppm.

Example 116

(7S)-4-[(6-Methoxypyrazolo[1,5-a]pyridin-5-yl)amino]-5,6,7,8-tetrahydro[1]benzothieno[2,3-d]pyrimidin-7-yl(morpholin-4-yl)methanone

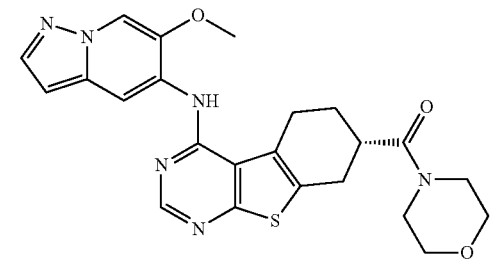

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using morpholine to give after working up and purification 76.2 mg (82%) of the title compound.

$^1$H NMR (DMSO-d6): δ=1.86 (1H), 2.16 (1H), 2.90-3.04 (2H), 3.14-3.27 (3H), 3.46-3.67 (8H), 4.01 (3H), 6.51 (1H), 7.84 (1H), 8.32 (1H), 8.52 (1H), 8.61 (1H), 8.83 (1H) ppm.

Example 117

(7S)—N-Ethyl-N-(2-hydroxyethyl)-4-[(6-methoxy-pyrazolo[1,5-a]pyridin-5-yl)amino]-5,6,7,8-tetrahydro[1]benzothieno[2,3-d]pyrimidine-7-carboxamide

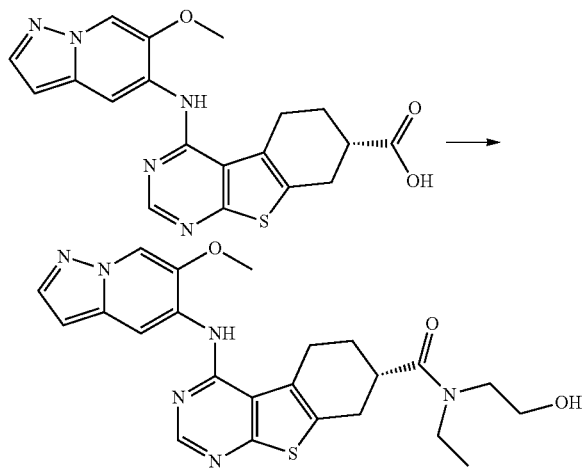

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2-(ethylamino)ethanol to give after working up and purification 67.6 mg (73%) of the title compound.

$^1$H NMR (DMSO-d6): δ=1.05+1.16 (3H), 1.87 (1H), 2.15 (1H), 2.89-3.59 (11H), 4.01 (3H), 4.71+4.88 (1H), 6.51 (1H), 7.84 (1H), 8.35 (1H), 8.53 (1H), 8.62 (1H), 8.85 (1H) ppm.

Example 118

(7S)—N-Ethyl-N-(2-methoxyethyl)-4-[(6-methoxy-pyrazolo[1,5-a]pyridin-5-yl)amino]-5,6,7,8-tetrahydro[1]benzothieno[2,3-d]pyrimidine-7-carboxamide

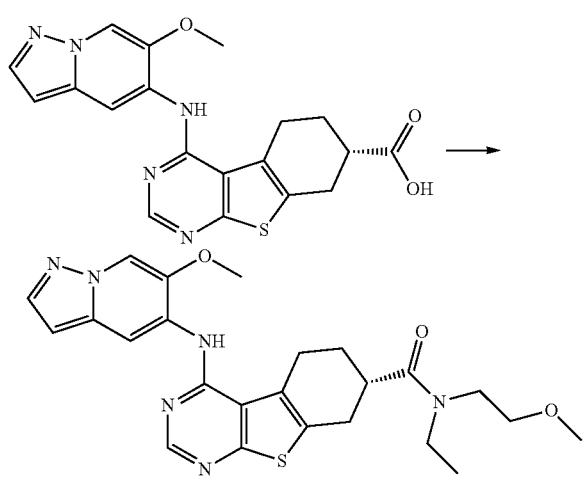

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N-ethyl-2-methoxyethanamine to give after working up and purification 76.2 mg (79%) of the title compound.

$^1$H NMR (DMSO-d6): δ=1.05+1.16 (3H), 1.86 (1H), 2.13 (1H), 2.87-3.04 (2H), 3.07-3.69 (9H), 3.27+3.29 (3H), 4.01+4.02 (3H), 6.51 (1H), 7.84 (1H), 8.34 (1H), 8.53 (1H), 8.61 (1H), 8.85 (1H) ppm.

Example 119

(7S)—N,N-Bis(2-methoxyethyl)-4-[(6-methoxy-pyrazolo[1,5-a]pyridin-5-yl)amino]-5,6,7,8-tetrahydro[1]benzothieno[2,3-d]pyrimidine-7-carboxamide

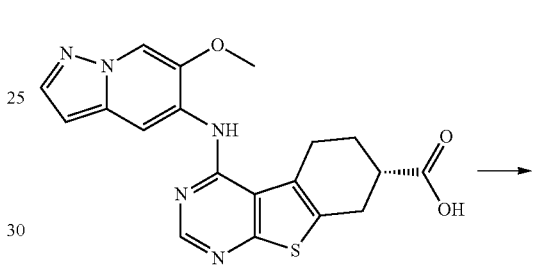

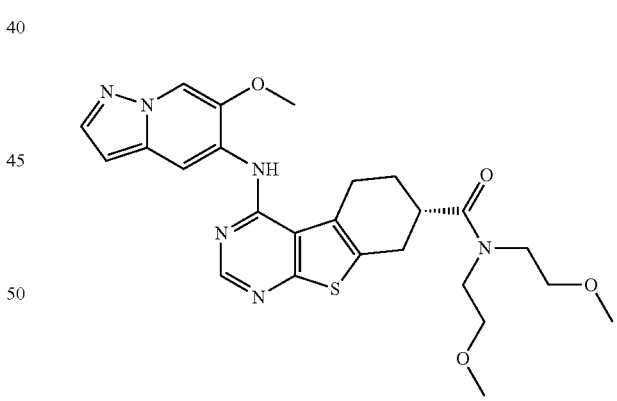

75 mg (190 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using 2-methoxy-N-(2-methoxyethyl)ethanamine to give after working up and purification 74.1 mg (73%) of the title compound.

$^1$H NMR (DMSO-d6): δ=1.85 (1H), 2.14 (1H), 2.87-3.02 (2H), 3.13-3.24 (3H), 3.27 (3H), 3.28 (3H), 3.37-3.52 (5H), 3.54-3.65 (2H), 3.72 (1H), 4.01 (3H), 6.51 (1H), 7.84 (1H), 8.34 (1H), 8.53 (1H), 8.61 (1H), 8.85 (1H) ppm.

Example 120

(7S)—N-tert-Butyl-4-[(6-methoxypyrazolo[1,5-a]pyridin-5-yl)amino]-N-methyl-5,6,7,8-tetrahydro[1]benzothieno[2,3-d]pyrimidine-7-carboxamide

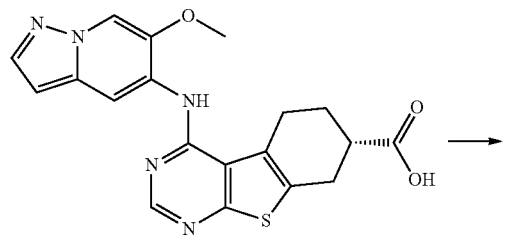

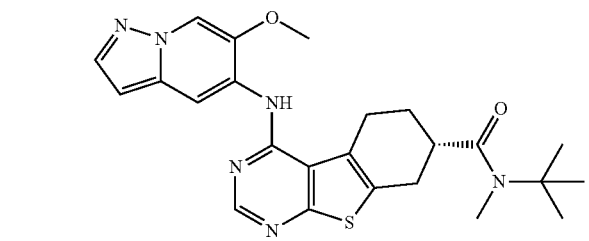

75 mg (190 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using N,2-dimethylpropan-2-amine to give after working up and purification 51.7 mg (56%) of the title compound.

$^1$H NMR (DMSO-d6): δ=1.39 (9H), 1.82 (1H), 2.15 (1H), 2.94 (2H), 3.01 (3H), 3.10-3.26 (3H), 4.01 (3H), 6.51 (1H), 7.84 (1H), 8.34 (1H), 8.53 (1H), 8.61 (1H), 8.85 (1H) ppm.

Example 121

(7S)-4-[(6-Methoxypyrazolo[1,5-a]pyridin-5-yl)amino]-5,6,7,8-tetrahydro[1]benzothieno[2,3-d]pyrimidin-7-yl[(1S,4S)-5-methyl-2,5-diazabicyclo[2.2.1]hept-2-yl]methanone

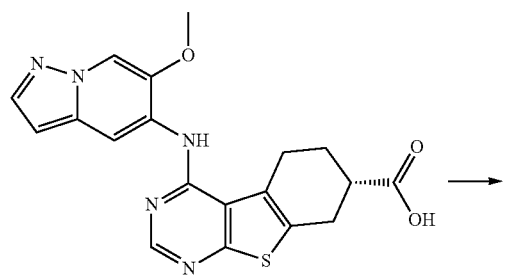

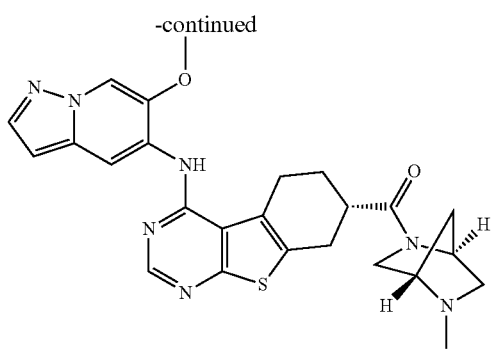

40 mg (101 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (1S,4S)-2-methyl-2,5-diazoniabicyclo[2.2.1]heptane dibromide to give after working up and purification 40.4 mg (78%) of the title compound.

$^1$H NMR (DMSO-d6): δ=1.63+1.68 (1H), 1.78-1.95 (2H), 2.14 (1H), 2.33 (3H), 2.44+2.55 (1H), 2.74-3.70 (9H), 4.00+4.01 (3H), 4.54+4.61 (1H), 6.51 (1H), 7.84 (1H), 8.34 (1H), 8.52 (1H), 8.61 (1H), 8.83+8.84 (1H) ppm.

Example 122

(7S)-4-[(6-Methoxypyrazolo[1,5-a]pyridin-5-yl)amino]-5,6,7,8-tetrahydro[1]benzothieno[2,3-d]pyrimidin-7-yl[(1R,4R)-5-methyl-2,5-diazabicyclo[2.2.1]hept-2-yl]methanone

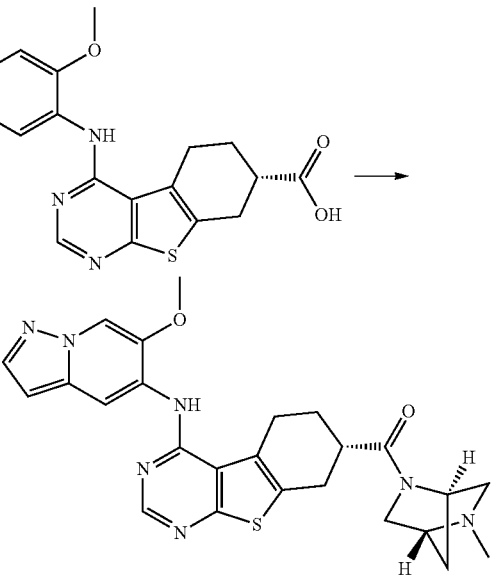

40 mg (101 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (1R,4R)-2-methyl-2,5-diazoniabicyclo[2.2.1]heptane dibromide to give after working up and purification 40.6 mg (78%) of the title compound.

$^1$H NMR (DMSO-d6): δ=1.60+1.71 (1H), 1.77-1.90 (2H), 2.17 (1H), 2.31+2.35 (3H), 2.47+2.57 (1H), 2.71-3.67 (9H), 4.02 (3H), 4.55+4.61 (1H), 6.51 (1H), 7.84 (1H), 8.34 (1H), 8.53 (1H), 8.62 (1H), 8.85 (1H) ppm.

Example 123

(7S)-4-[(6-Methoxypyrazolo[1,5-a]pyridin-5-yl)amino]-5,6,7,8-tetrahydro[1]benzothieno[2,3-d]pyrimidin-7-yl[(1S,4S)-2-oxa-5-azabicyclo[2.2.1]hept-5-yl]methanone

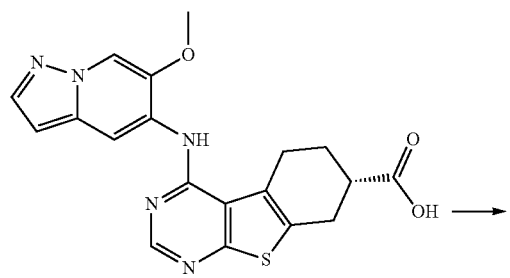

40 mg (101 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (1S,4S)-2-oxa-5-azoniabicyclo[2.2.1]heptane chloride to give after working up and purification 37.6 mg (74%) of the title compound.

$^1$H NMR (DMSO-d6): δ=1.78-1.93 (3H), 2.17 (1H), 2.81-3.38 (6H), 3.55+3.66 (1H), 3.61+3.74 (1H), 3.79 (1H), 4.00+4.01 (3H), 4.63+4.68 (1H), 4.78+4.89 (1H), 6.51 (1H), 7.84 (1H), 8.33+8.34 (1H), 8.53 (1H), 8.62 (1H), 8.84 (1H) ppm.

Example 124

(7S)-4-[(6-Methoxypyrazolo[1,5-a]pyridin-5-yl)amino]-5,6,7,8-tetrahydro[1]benzothieno[2,3-d]pyrimidin-7-yl[(1R,4R)-2-oxa-5-azabicyclo[2.2.1]hept-5-yl]methanone

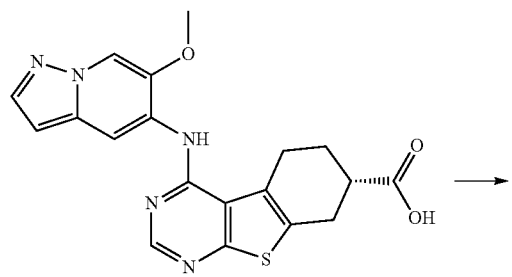

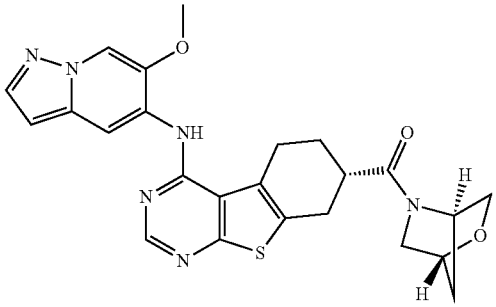

40 mg (101 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (1R,4R)-2-oxa-5-azoniabicyclo[2.2.1]heptane chloride to give after working up and purification 40.5 mg (80%) of the title compound.

$^1$H NMR (DMSO-d6): δ=1.78-1.92 (3H), 2.21 (1H), 2.77-3.31 (6H), 3.53-3.79 (3H), 4.02 (3H), 4.63+4.69 (1H), 4.79+4.89 (1H), 6.51 (1H), 7.84 (1H), 8.34 (1H), 8.53 (1H), 8.62 (1H), 8.86 (1H) ppm.

Example 125

(7S)-4-[(6-Methoxypyrazolo[1,5-a]pyridin-5-yl)amino]-5,6,7,8-tetrahydro[1]benzothieno[2,3-d]pyrimidin-7-yl[(3S)-3-methylmorpholin-4-yl]methanone

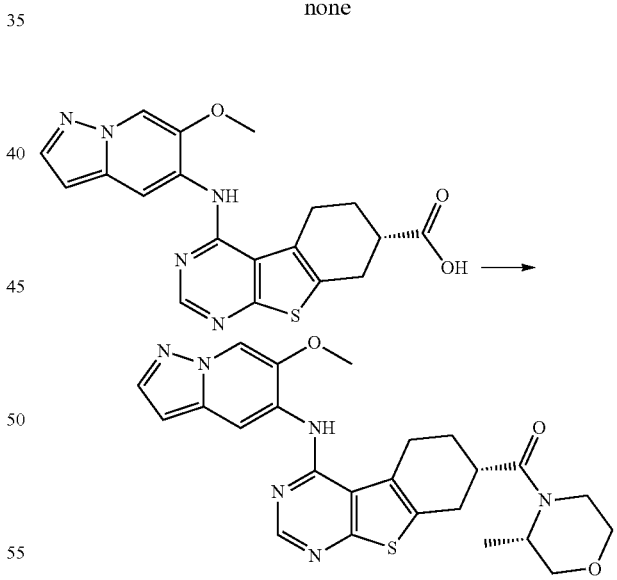

50 mg (126 μmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (3S)-3-methylmorpholine to give after working up and purification 52.7 mg (83%) of the title compound.

$^1$H NMR (DMSO-d6): δ=1.17+1.30 (3H), 1.84 (1H), 2.13+2.18 (1H), 2.87-4.49 (12H), 4.02 (3H), 6.51 (1H), 7.84 (1H), 8.34 (1H), 8.53 (1H), 8.62 (1H), 8.85 (1H) ppm.

Example 126

(7S)-4-[(6-Methoxypyrazolo[1,5-a]pyridin-5-yl)amino]-5,6,7,8-tetrahydro[1]benzothieno[2,3-d]pyrimidin-7-yl][(3R)-3-methylmorpholin-4-yl]methanone

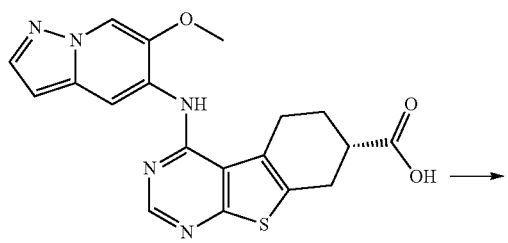

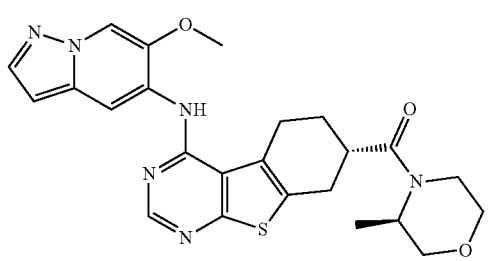

50 mg (126 µmol) (7S)-4-[(6-methoxypyrazolo[1,5-a]pyridin-5-yl)amino]-5,6,7,8-tetrahydro[1]benzothieno[2,3-d]pyrimidine-7-carboxylic acid (prepared according to example 78a) were transformed in analogy to example 43 using (3R)-3-methylmorpholine to give after working up and purification 50.0 mg (79%) of the title compound.

$^{1}$H NMR (DMSO-d6): δ=1.16+1.33 (3H), 1.92 (1H), 2.14 (1H), 2.87-4.47 (12H), 4.01 (3H), 6.51 (1H), 7.84 (1H), 8.33 (1H), 8.53 (1H), 8.62 (1H), 8.84 (1H) ppm.

The following example compounds are prepared analogously to the methods described above:

Example 127

(7S)—N-Methyl-4-(pyrazolo[1,5-a]pyridin-5-ylamino)-N-(3,3,3-trifluoropropyl)-5,6,7,8-tetrahydro[1]benzothieno[2,3-d]pyrimidine-7-carboxamide

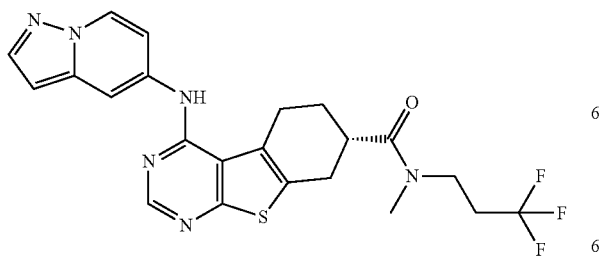

Example 128

(2,2-Dimethylpyrrolidin-1-yl)[(7S)-4-(pyrazolo[1,5-a]pyridin-5-ylamino)-5,6,7,8-tetrahydro[1]benzothieno[2,3-d]pyrimidin-7-yl]methanone

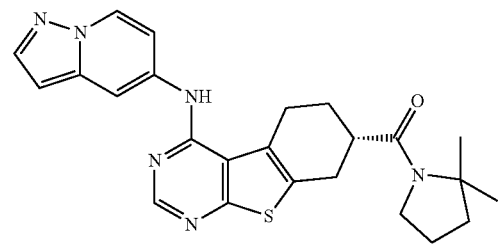 [SMILES: CC1(C)CCCN1C(=O)[C@H]1CCc2c(sc3ncnc(Nc4ccn5nccc5c4)c23)C1]

Example 129

(7S)—N-[(2S)-1-Methoxypropan-2-yl]-N-methyl-4-(pyrazolo[1,5-a]pyridin-5-ylamino)-5,6,7,8-tetrahydro[1]benzothieno[2,3-d]pyrimidine-7-carboxamide

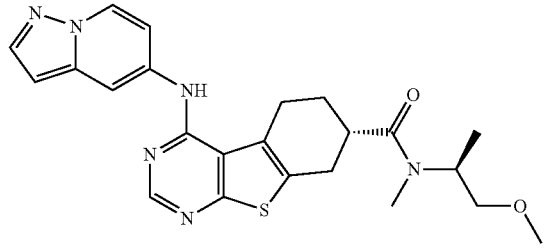 [SMILES: COC[C@H](C)N(C)C(=O)[C@H]1CCc2c(sc3ncnc(Nc4ccn5nccc5c4)c23)C1]

Example 130

(7S)—N-[(2R)-1-Methoxypropan-2-yl]-N-methyl-4-(pyrazolo[1,5-a]pyridin-5-ylamino)-5,6,7,8-tetrahydro[1]benzothieno[2,3-d]pyrimidine-7-carboxamide

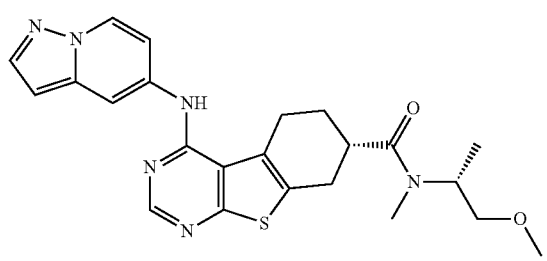 [SMILES: COC[C@@H](C)N(C)C(=O)[C@H]1CCc2c(sc3ncnc(Nc4ccn5nccc5c4)c23)C1]

Example 131

(7S)—N-[(2S)-2-Methoxypropyl]-N-methyl-4-(pyrazolo[1,5-a]pyridin-5-ylamino)-5,6,7,8-tetrahydro[1]benzothieno[2,3-d]pyrimidine-7-carboxamide

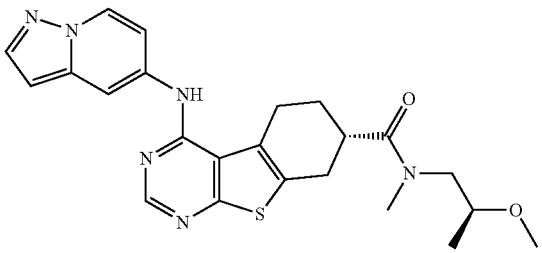 [SMILES: CO[C@@H](C)CN(C)C(=O)[C@H]1CCc2c(sc3ncnc(Nc4ccn5nccc5c4)c23)C1]

Example 132

(7S)—N-[(2R)-2-Methoxypropyl]-N-methyl-4-(pyrazolo[1,5-a]pyridin-5-ylamino)-5,6,7,8-tetrahydro[1]benzothieno[2,3-d]pyrimidine-7-carboxamide

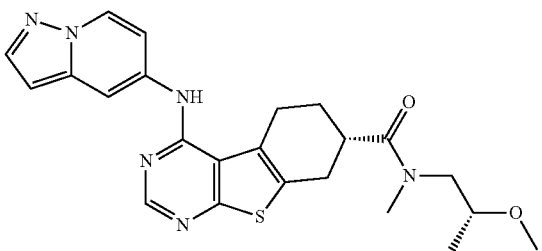 [SMILES: CO[C@H](C)CN(C)C(=O)[C@H]1CCc2c(sc3ncnc(Nc4ccn5nccc5c4)c23)C1]

Example 133

(7S)—N-(1-Methoxy-2-methylpropan-2-yl)-N-methyl-4-(pyrazolo[1,5-a]pyridin-5-ylamino)-5,6,7,8-tetrahydro[1]benzothieno[2,3-d]pyrimidine-7-carboxamide

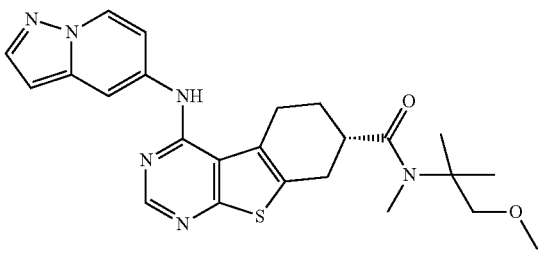 [SMILES: COCC(C)(C)N(C)C(=O)[C@H]1CCc2c(sc3ncnc(Nc4ccn5nccc5c4)c23)C1]

Example 134

(7S)—N-(2-Hydroxy-2-methylpropyl)-4-[(6-methoxypyrazolo[1,5-a]pyridin-5-yl)amino]-N-methyl-5,6,7,8-tetrahydro[1]benzothieno[2,3-d]pyrimidine-7-carboxamide

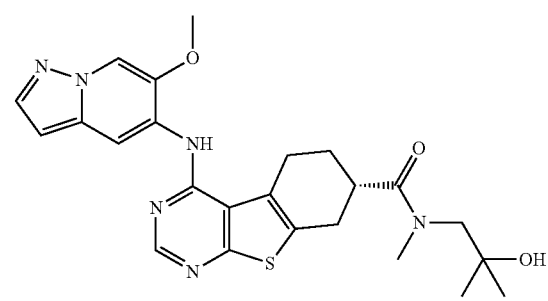 [SMILES: COc1cn2nccc2cc1Nc1ncnc2sc3c(c12)CC[C@H](C(=O)N(C)CC(C)(C)O)C3]

Example 135

(7S)—N-(2-Aminoethyl)-4-[(6-methoxypyrazolo[1,5-a]pyridin-5-yl)amino]-N-methyl-5,6,7,8-tetrahydro[1]benzothieno[2,3-d]pyrimidine-7-carboxamide

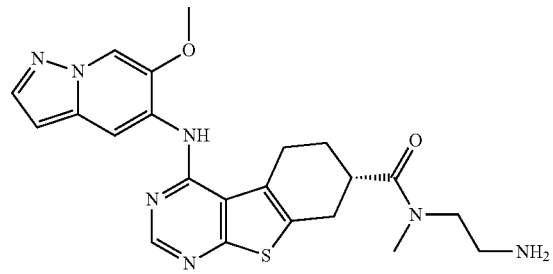 [SMILES: COc1cn2nccc2cc1Nc1ncnc2sc3c(c12)CC[C@H](C(=O)N(C)CCN)C3]

Example 136

(7S)—N-[2-(Dimethylamino)-2-oxoethyl]-4-[(6-methoxypyrazolo[1,5-a]pyridin-5-yl)amino]-N-methyl-5,6,7,8-tetrahydro[1]benzothieno[2,3-d]pyrimidine-7-carboxamide

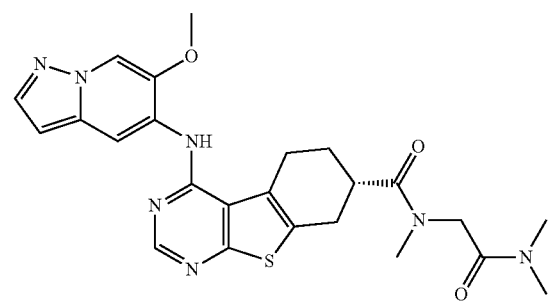 [SMILES: COc1cn2nccc2cc1Nc1ncnc2sc3c(c12)CC[C@H](C(=O)N(C)CC(=O)N(C)C)C3]

Example 137

Azetidin-1-yl{(7S)-4-[(6-methoxypyrazolo[1,5-a]pyridin-5-yl)amino]-5,6,7,8-tetrahydro[1]benzothieno[2,3-d]pyrimidin-7-yl}methanone

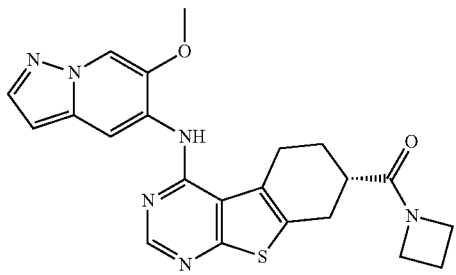 [SMILES: COc1cn2nccc2cc1Nc1ncnc2sc3c(c12)CC[C@H](C(=O)N1CCC1)C3]

Example 138

(3,3-Difluoroazetidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone

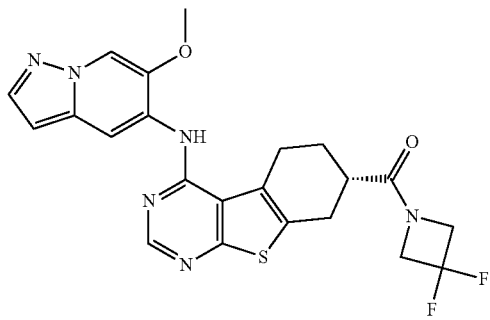 [SMILES: COc1cn2nccc2cc1Nc1ncnc2sc3c(c12)CC[C@H](C(=O)N1CC(F)(F)C1)C3]

Example 139

(3-Hydroxyazetidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone

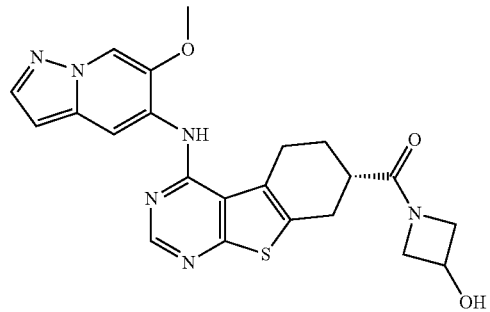 [SMILES: COc1cn2nccc2cc1Nc1ncnc2sc3c(c12)CC[C@H](C(=O)N1CC(O)C1)C3]

Example 140

1-({(7S)-4-[(6-Methoxypyrazolo[1,5-a]pyridin-5-yl)amino]-5,6,7,8-tetrahydro[1]benzothieno[2,3-d]pyrimidin-7-yl}carbonyl)piperidin-4-one

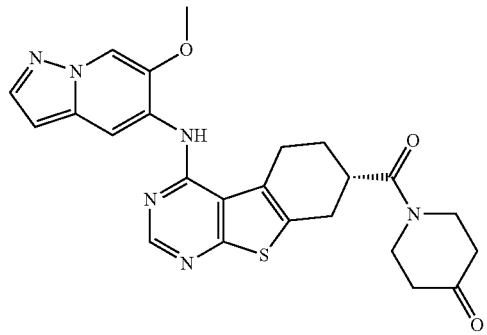 [SMILES: COc1cn2nccc2cc1Nc1ncnc2sc3c(c12)CC[C@H](C(=O)N1CCC(=O)CC1)C3]

Example 141

(3,3-Difluoropyrrolidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone

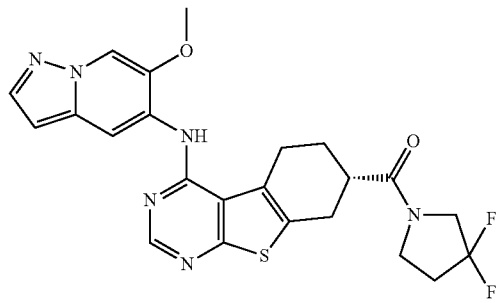 [SMILES: COc1cn2nccc2cc1Nc1ncnc2sc3c(c12)CC[C@H](C(=O)N1CCC(F)(F)C1)C3]

Example 142

(2,2-Dimethylpyrrolidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone

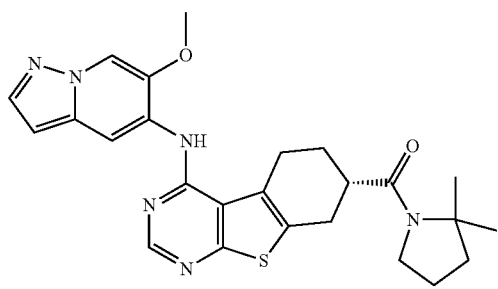 [SMILES: COc1cn2nccc2cc1Nc1ncnc2sc3c(c12)CC[C@H](C(=O)N1CCCC1(C)C)C3]

Example 143

{(7S)-4-[(6-Methoxypyrazolo[1,5-a]pyridin-5-yl)amino]-5,6,7,8-tetrahydro[1]benzothieno[2,3-d]pyrimidin-7-yl}(2-oxa-6-azaspiro[3.3]hept-6-yl)methanone

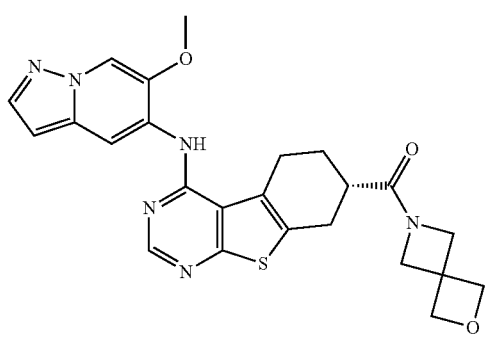 [SMILES: COc1cn2nccc2cc1Nc1ncnc2sc3c(c12)CC[C@H](C(=O)N1CC2(COC2)C1)C3]

Example 144

[(2R,6R)-2,6-Dimethylmorpholin-4-yl]{(7S)-4-[(6-methoxypyrazolo[1,5-a]pyridin-5-yl)amino]-5,6,7,8-tetrahydro[1]benzothieno[2,3-d]pyrimidin-7-yl}methanone

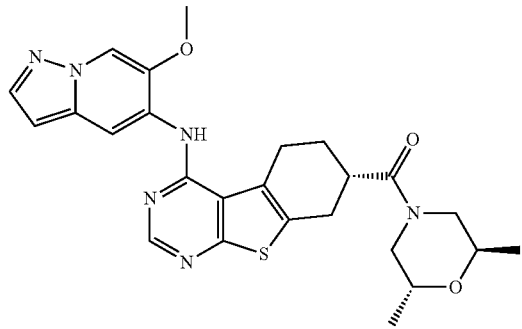 [SMILES: COc1cn2nccc2cc1Nc1ncnc2sc3c(c12)CC[C@H](C(=O)N1C[C@@H](C)O[C@H](C)C1)C3]

Example 145

[(2S,6S)-2,6-Dimethylmorpholin-4-yl]{(7S)-4-[(6-methoxypyrazolo[1,5-a]pyridin-5-yl)amino]-N-methyl-5,6,7,8-tetrahydro[1]benzothieno[2,3-d]pyrimidin-7-yl}methanone

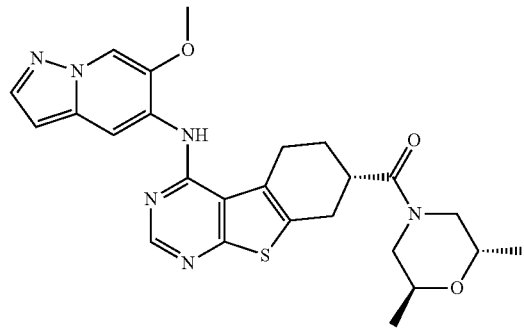 [SMILES: COc1cn2nccc2cc1Nc1ncnc2sc3c(c12)CC[C@H](C(=O)N1C[C@H](C)O[C@@H](C)C1)C3]

Example 146

(7S)—N-[(2S)-1-Methoxypropan-2-yl]-4-[(6-methoxypyrazolo[1,5-a]pyridin-5-yl)amino]-N-methyl-5,6,7,8-tetrahydro[1]benzothieno[2,3-d]pyrimidine-7-carboxamide

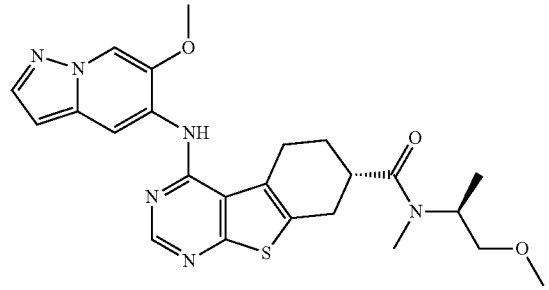 [SMILES: COC[C@H](C)N(C)C(=O)[C@H]1CCc2c(sc3ncnc(Nc4cc5ccnn5cc4OC)c23)C1]

Example 147

(7S)—N-[(2R)-1-Methoxypropan-2-yl]-4-[(6-methoxypyrazolo[1,5-a]pyridin-5-yl)amino]-N-methyl-5,6,7,8-tetrahydro[1]benzothieno[2,3-d]pyrimidine-7-carboxamide

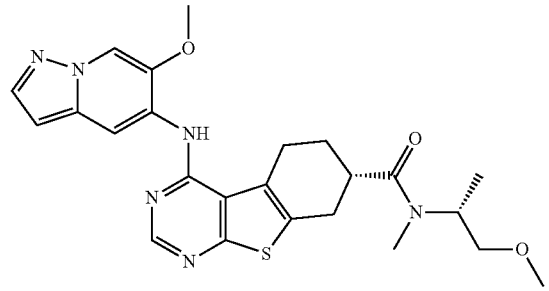 [SMILES: COC[C@@H](C)N(C)C(=O)[C@H]1CCc2c(sc3ncnc(Nc4cc5ccnn5cc4OC)c23)C1]

Example 148

(7S)—N-[(2S)-2-Methoxypropyl]-4-[(6-methoxypyrazolo[1,5-a]pyridin-5-yl)amino]-N-methyl-5,6,7,8-tetrahydro[1]benzothieno[2,3-d]pyrimidine-7-carboxamide

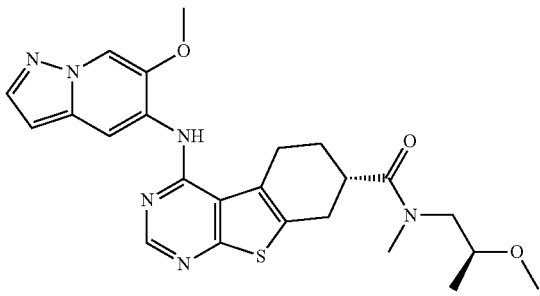 [SMILES: COc1cn2nccc2cc1Nc1ncnc2sc3c(c12)CC[C@H](C(=O)N(C)C[C@H](C)OC)C3]

Example 149

(7S)—N-[(2R)-2-Methoxypropyl]-4-[(6-methoxypyrazolo[1,5-a]pyridin-5-yl)amino]-N-methyl-5,6,7,8-tetrahydro[1]benzothieno[2,3-d]pyrimidine-7-carboxamide

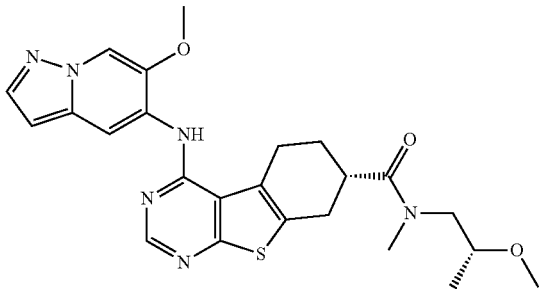 [SMILES: COc1cn2nccc2cc1Nc1ncnc2sc3c(c12)CC[C@H](C(=O)N(C)C[C@@H](C)OC)C3]

Example 150

(7S)—N-(1-Methoxy-2-methylpropan-2-yl)-4-[(6-methoxypyrazolo[1,5-a]pyridin-5-yl)amino]-N-methyl-5,6,7,8-tetrahydro[1]benzothieno[2,3-d]pyrimidine-7-carboxamide

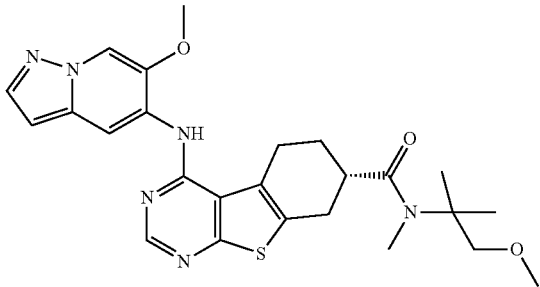 [SMILES: COCC(C)(C)N(C)C(=O)[C@H]1CCc2c(sc3ncnc(Nc4cc5ccnn5cc4OC)c23)C1]

Example 151

(7S)-4-[(6-Chloropyrazolo[1,5-a]pyridin-5-yl)amino]-N-(2-hydroxy-2-methylpropyl)-N-methyl-5,6,7,8-tetrahydro[1]benzothieno[2,3-d]pyrimidine-7-carboxamide

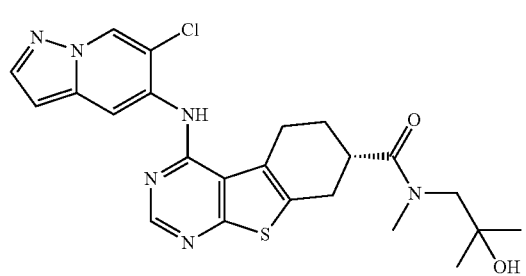 [SMILES: CN(CC(C)(C)O)C(=O)[C@H]1CCc2c(sc3ncnc(Nc4cc5ccnn5cc4Cl)c23)C1]

Example 152

(7S)—N-(2-Aminoethyl)-4-[(6-chloropyrazolo[1,5-a]pyridin-5-yl)amino]-N-methyl-5,6,7,8-tetrahydro[1]benzothieno[2,3-d]pyrimidine-7-carboxamide

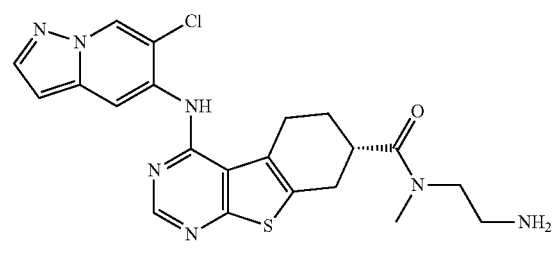 [SMILES: CN(CCN)C(=O)[C@H]1CCc2c(sc3ncnc(Nc4cc5ccnn5cc4Cl)c23)C1]

Example 153

(7S)-4-[(6-Chloropyrazolo[1,5-a]pyridin-5-yl)amino]-N-[2-(dimethylamino)-2-oxoethyl]-N-methyl-5,6,7,8-tetrahydro[1]benzothieno[2,3-d]pyrimidine-7-carboxamide

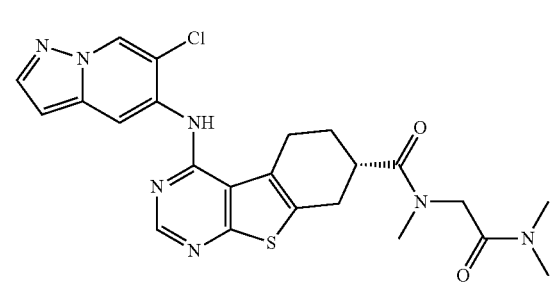 [SMILES: CN(C)C(=O)CN(C)C(=O)[C@H]1CCc2c(sc3ncnc(Nc4cc5ccnn5cc4Cl)c23)C1]

Example 154

Azetidin-1-yl{(7S)-4-[(6-chloropyrazolo[1,5-a]pyridin-5-yl)amino]-5,6,7,8-tetrahydro[1]benzothieno[2,3-d]pyrimidin-7-yl}methanone

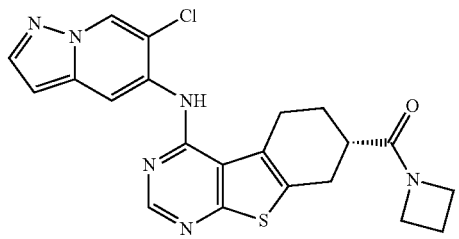 [SMILES: O=C([C@H]1CCc2c(sc3ncnc(Nc4cc5ccnn5cc4Cl)c23)C1)N1CCC1]

Example 155

{(7S)-4-[(6-Chloropyrazolo[1,5-a]pyridin-5-yl)amino]-5,6,7,8-tetrahydro[1]benzothieno[2,3-d]pyrimidin-7-yl}(3,3-difluoroazetidin-1-yl)methanone

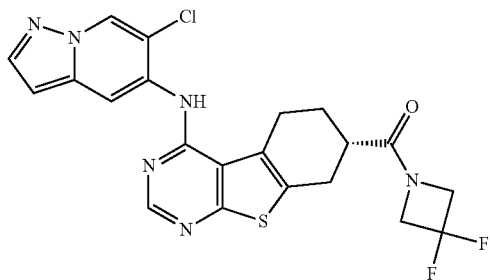 [SMILES: O=C([C@H]1CCc2c(sc3ncnc(Nc4cc5ccnn5cc4Cl)c23)C1)N1CC(F)(F)C1]

Example 156

{(7S)-4-[(6-Chloropyrazolo[1,5-a]pyridin-5-yl)amino]-5,6,7,8-tetrahydro[1]benzothieno[2,3-d]pyrimidin-7-yl}(3-hydroxyazetidin-1-yl)methanone

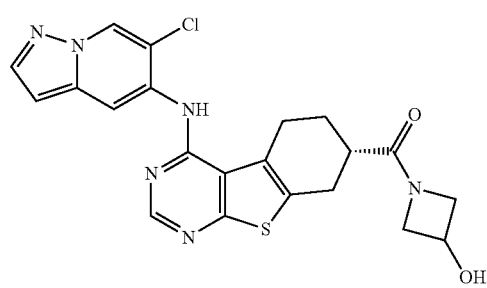 [SMILES: O=C([C@H]1CCc2c(sc3ncnc(Nc4cc5ccnn5cc4Cl)c23)C1)N1CC(O)C1]

Example 157

1-({(7S)-4-[(6-Chloropyrazolo[1,5-a]pyridin-5-yl)amino]-5,6,7,8-tetrahydro[1]benzothieno[2,3-d]pyrimidin-7-yl}carbonyl)piperidin-4-one

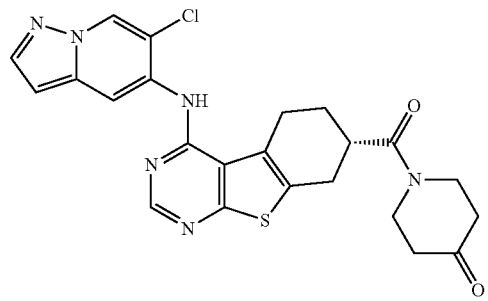 [SMILES: O=C1CCN(C(=O)[C@H]2CCc3c(sc4ncnc(Nc5cc6ccnn6cc5Cl)c34)C2)CC1]

Example 158

{(7S)-4-[(6-Chloropyrazolo[1,5-a]pyridin-5-yl)amino]-5,6,7,8-tetrahydro[1]benzothieno[2,3-d]pyrimidin-7-yl}(3,3-difluoropyrrolidin-1-yl)methanone

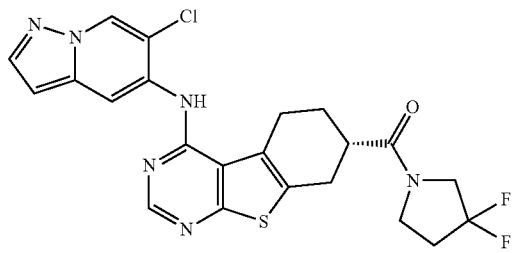 [SMILES: O=C([C@H]1CCc2c(sc3ncnc(Nc4cc5ccnn5cc4Cl)c23)C1)N1CCC(F)(F)C1]

Example 159

{(7S)-4-[(6-Chloropyrazolo[1,5-a]pyridin-5-yl)amino]-5,6,7,8-tetrahydro[1]benzothieno[2,3-d]pyrimidin-7-yl}(2,2-dimethylpyrrolidin-1-yl)methanone

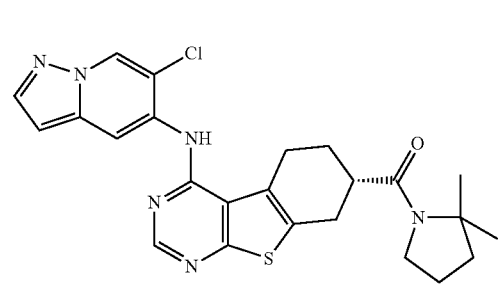 [SMILES: CC1(C)CCCN1C(=O)[C@H]1CCc2c(sc3ncnc(Nc4cc5ccnn5cc4Cl)c23)C1]

Example 160

{(7S)-4-[(6-Chloropyrazolo[1,5-a]pyridin-5-yl)amino]-5,6,7,8-tetrahydro[1]benzothieno[2,3-d]pyrimidin-7-yl}(2-oxa-6-azaspiro[3.3]hept-6-yl)methanone

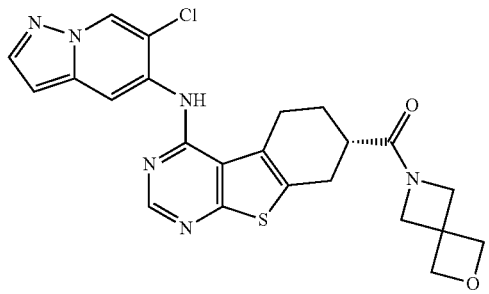 [SMILES: O=C([C@H]1CCc2c(sc3ncnc(Nc4cc5ccnn5cc4Cl)c23)C1)N1CC2(COC2)C1]

Example 161

{(7S)-4-[(6-Chloropyrazolo[1,5-a]pyridin-5-yl)amino]-5,6,7,8-tetrahydro[1]benzothieno[2,3-d]pyrimidin-7-yl}[(2R,6R)-2,6-dimethylmorpholin-4-yl]methanone

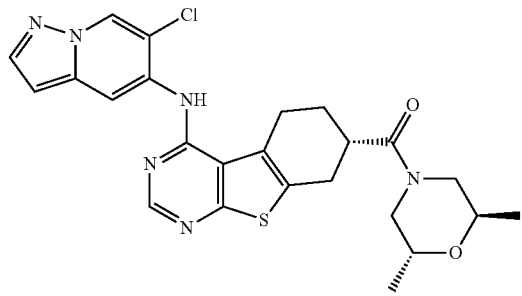 [SMILES: C[C@@H]1CN(C(=O)[C@H]2CCc3c(sc4ncnc(Nc5cc6ccnn6cc5Cl)c34)C2)C[C@@H](C)O1]

Example 162

{(7S)-4-[(6-Chloropyrazolo[1,5-a]pyridin-5-yl)amino]-5,6,7,8-tetrahydro[1]benzothieno[2,3-d]pyrimidin-7-yl}[(2S,6S)-2,6-dimethylmorpholin-4-yl]methanone

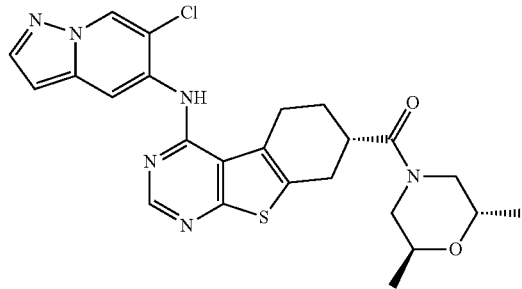 [SMILES: C[C@H]1CN(C(=O)[C@H]2CCc3c(sc4ncnc(Nc5cc6ccnn6cc5Cl)c34)C2)C[C@H](C)O1]

Example 163

(7S)-4-[(6-Chloropyrazolo[1,5-a]pyridin-5-yl)amino]-N-[(2S)-1-methoxypropan-2-yl]-N-methyl-5,6,7,8-tetrahydro[1]benzothieno[2,3-d]pyrimidine-7-carboxamide

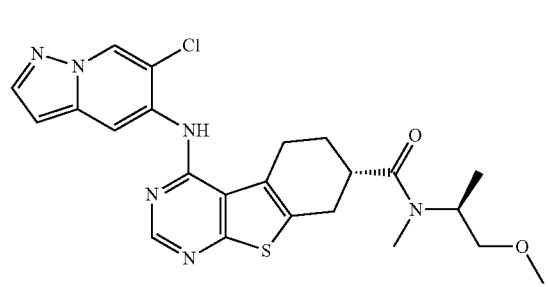 [SMILES: COC[C@H](C)N(C)C(=O)[C@H]1CCc2c(sc3ncnc(Nc4cc5ccnn5cc4Cl)c23)C1]

Example 164

(7S)-4-[(6-Chloropyrazolo[1,5-a]pyridin-5-yl)amino]-N-[(2R)-1-methoxypropan-2-yl]-N-methyl-5,6,7,8-tetrahydro[1]benzothieno[2,3-d]pyrimidine-7-carboxamide

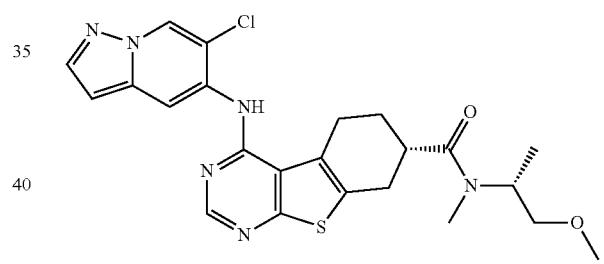

Example 165

(7S)-4-[(6-Chloropyrazolo[1,5-a]pyridin-5-yl)amino]-N-[(2S)-2-methoxypropyl]-N-methyl-5,6,7,8-tetrahydro[1]benzothieno[2,3-d]pyrimidine-7-carboxamide

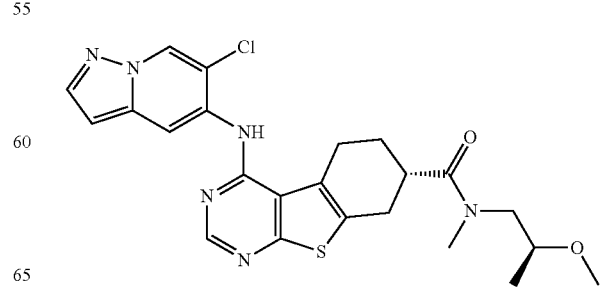

Example 166

(7S)-4-[(6-Chloropyrazolo[1,5-a]pyridin-5-yl)amino]-N-[(2R)-2-methoxypropyl]-N-methyl-5,6,7,8-tetrahydro[1]benzothieno[2,3-d]pyrimidine-7-carboxamide

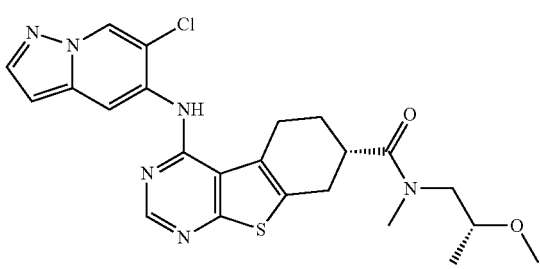 [SMILES: CO[C@H](C)CN(C)C(=O)[C@H]1CCc2c(sc3ncnc(Nc4cc5ccnn5cc4Cl)c23)C1]

Example 167

(7S)-4-[(6-Chloropyrazolo[1,5-a]pyridin-5-yl)amino]-N-[1-methoxy-2-methylpropan-2-yl]-N-methyl-5,6,7,8-tetrahydro[1]benzothieno[2,3-d]pyrimidine-7-carboxamide

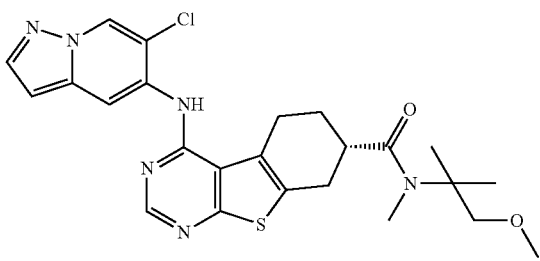 [SMILES: COCC(C)(C)N(C)C(=O)[C@H]1CCc2c(sc3ncnc(Nc4cc5ccnn5cc4Cl)c23)C1]

Example 168

(7S)-4-[(6-(Dimethylamino)pyrazolo[1,5-a]pyridin-5-yl)amino]-N,N-dimethyl-5,6,7,8-tetrahydro[1]benzothieno[2,3-d]pyrimidine-7-carboxamide

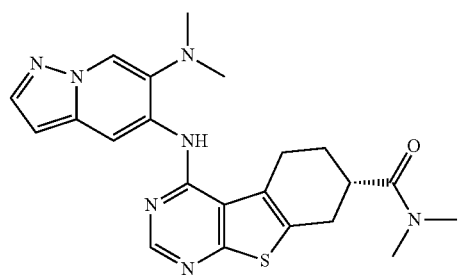 [SMILES: CN(C)C(=O)[C@H]1CCc2c(sc3ncnc(Nc4cc5ccnn5cc4N(C)C)c23)C1]

Example 169

(7S)-4-[(6-(Dimethylamino)pyrazolo[1,5-a]pyridin-5-yl)amino]-N-methyl-N-(3,3,3-trifluoropropyl)-5,6,7,8-tetrahydro[1]benzothieno[2,3-d]pyrimidine-7-carboxamide

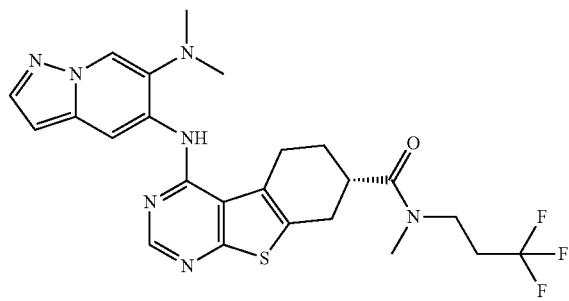 [SMILES: CN(CCC(F)(F)F)C(=O)[C@H]1CCc2c(sc3ncnc(Nc4cc5ccnn5cc4N(C)C)c23)C1]

Example 170

(7S)—N-(2-Hydroxy-2-methylpropyl)-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide

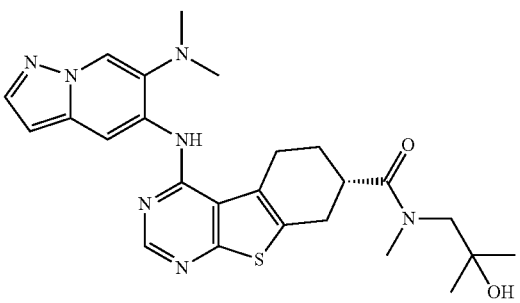 [SMILES: CN(CC(C)(C)O)C(=O)[C@H]1CCc2c(sc3ncnc(Nc4cc5ccnn5cc4N(C)C)c23)C1]

Example 171

(7S)—N-(2,2-Difluoroethyl)-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide

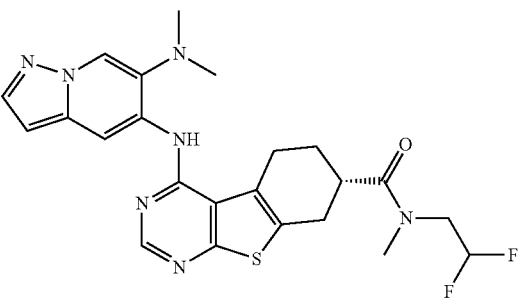 [SMILES: CN(CC(F)F)C(=O)[C@H]1CCc2c(sc3ncnc(Nc4cc5ccnn5cc4N(C)C)c23)C1]

Example 172

(7S)-4-[(6-(Dimethylamino)pyrazolo[1,5-a]pyridin-5-yl)amino]-N-isopropyl-N-methyl-5,6,7,8-tetrahydro[1]benzothieno[2,3-d]pyrimidine-7-carboxamide

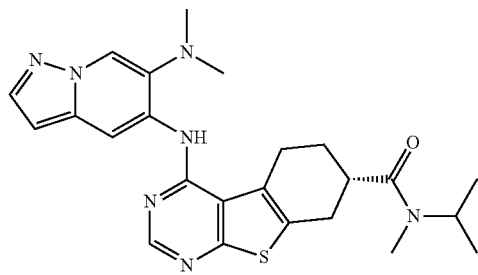 [SMILES: CC(C)N(C)C(=O)[C@H]1CCc2c(sc3ncnc(Nc4cc5ccnn5cc4N(C)C)c23)C1]

Example 173

(7S)-4-[(6-(Dimethylamino)pyrazolo[1,5-a]pyridin-5-yl)amino]-N-ethyl-N-(2-hydroxyethyl)-5,6,7,8-tetrahydro[1]benzothieno[2,3-d]pyrimidine-7-carboxamide

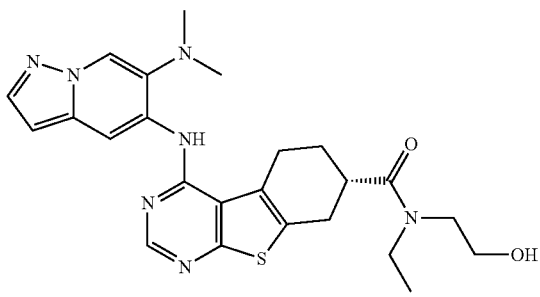 [SMILES: CCN(CCO)C(=O)[C@H]1CCc2c(sc3ncnc(Nc4cc5ccnn5cc4N(C)C)c23)C1]

Example 174

(7S)-4-[(6-(Dimethylamino)pyrazolo[1,5-a]pyridin-5-yl)amino]-N-(2-methoxyethyl)-N-methyl-5,6,7,8-tetrahydro[1]benzothieno[2,3-d]pyrimidine-7-carboxamide

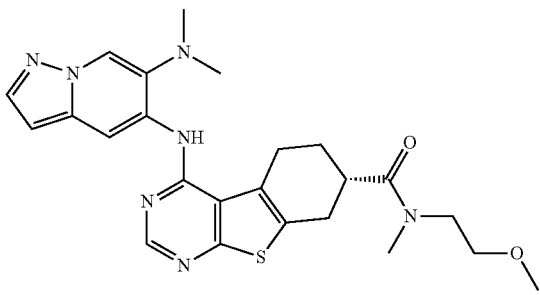

Example 175

(7S)—N-(2-Aminoethyl)-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide

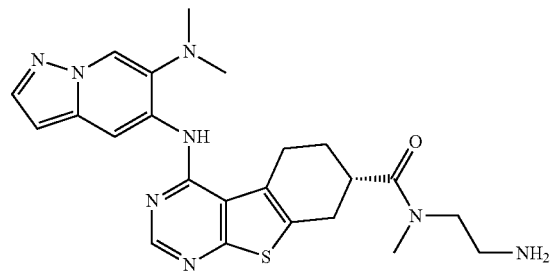 [SMILES: CN(CCN)C(=O)[C@H]1CCc2c(sc3ncnc(Nc4cc5ccnn5cc4N(C)C)c23)C1]

Example 176

(7S)—N-[2-(Dimethylamino)ethyl]-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide

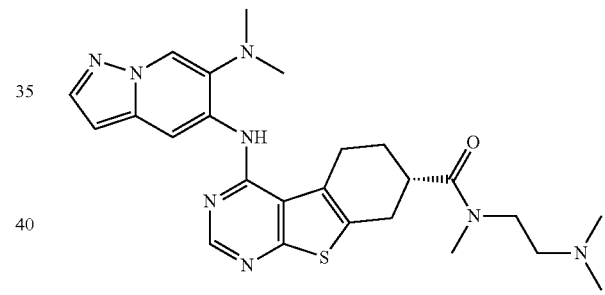

Example 177

(7S)—N-[2-(Dimethylamino)-2-oxoethyl]-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide

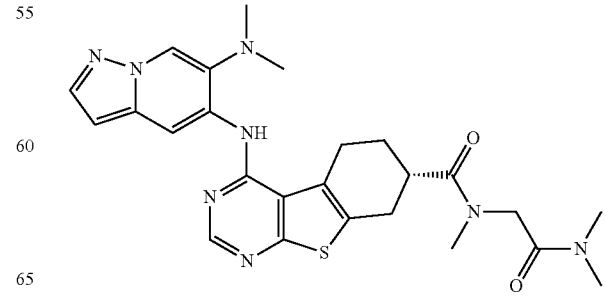

Example 178

(7S)—N-[3-(Dimethylamino)propyl]-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide

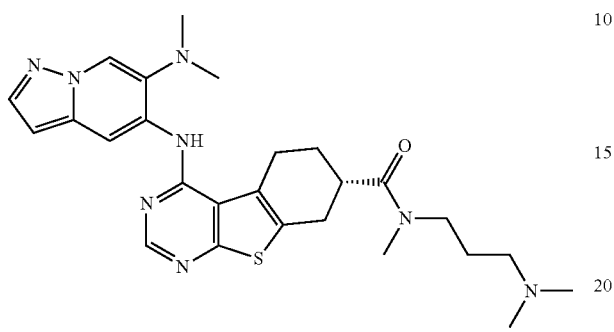

Example 179

Azetidin-1-yl{(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone

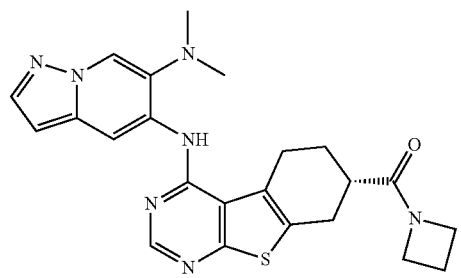 [SMILES: CN(C)c1cn2nccc2cc1Nc1ncnc2sc3c(c12)CC[C@H](C(=O)N1CCC1)C3]

Example 180

(3,3-Difluoroazetidin-1-yl){(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone

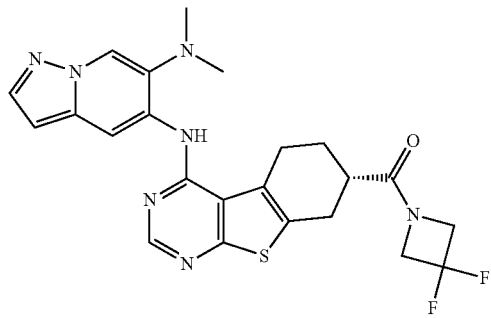 [SMILES: CN(C)c1cn2nccc2cc1Nc1ncnc2sc3c(c12)CC[C@H](C(=O)N1CC(F)(F)C1)C3]

Example 181

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}(3-hydroxyazetidin-1-yl)methanone

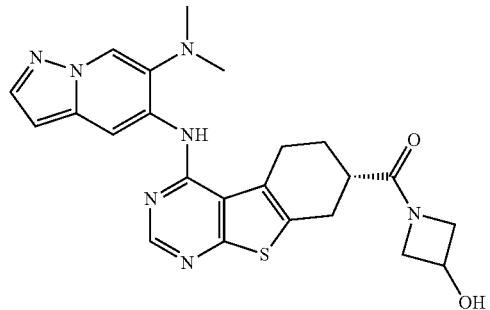 [SMILES: CN(C)c1cn2nccc2cc1Nc1ncnc2sc3c(c12)CC[C@H](C(=O)N1CC(O)C1)C3]

Example 182

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}(3-hydroxy-3-methylazetidin-1-yl)methanone

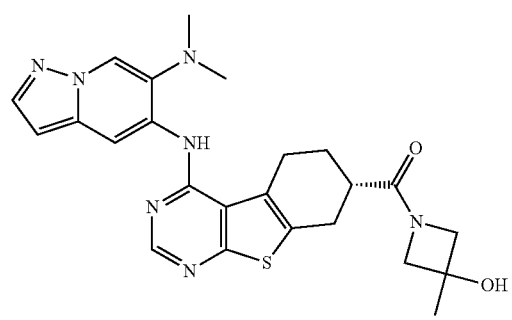 [SMILES: CN(C)c1cn2nccc2cc1Nc1ncnc2sc3c(c12)CC[C@H](C(=O)N1CC(C)(O)C1)C3]

Example 183

1-({(7S)-4-[(6-(Dimethylamino)pyrazolo[1,5-a]pyridin-5-yl)amino]-5,6,7,8-tetrahydro[1]benzothieno[2,3-d]pyrimidin-7-yl}carbonyl)azetidine-3-carbonitrile

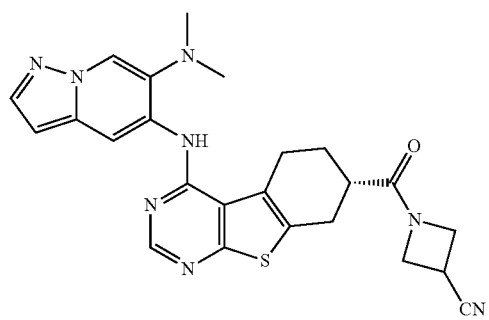

151
Example 184

[3-(Dimethylamino)azetidin-1-yl]{(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone

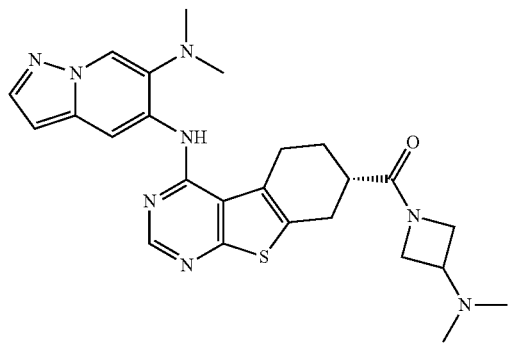 [SMILES: CN(C)c1cn2nccc2cc1Nc1ncnc2sc3c(c12)CC[C@H](C(=O)N1CC(N(C)C)C1)C3]

Example 185

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}(4-methylpiperazin-1-yl)methanone

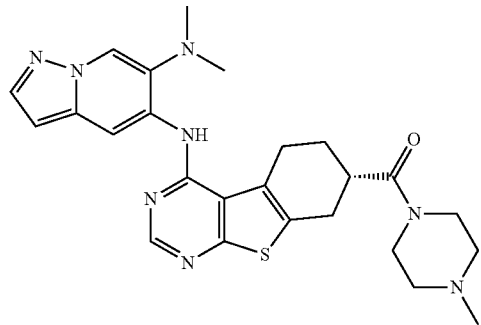 [SMILES: CN1CCN(C(=O)[C@H]2CCc3c(sc4ncnc(Nc5cc6ccnn6cc5N(C)C)c34)C2)CC1]

152
Example 186

{4-[2-(Dimethylamino)ethyl]piperazin-1-yl}{(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone

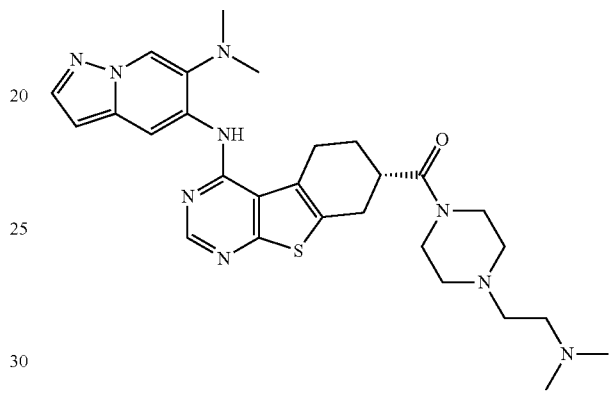

Example 187

(4-{[2-(Dimethylamino)ethyl](methyl)amino}piperidin-1-yl){(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone

Example 188

[4-(Dimethylamino)piperidin-1-yl]{(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone

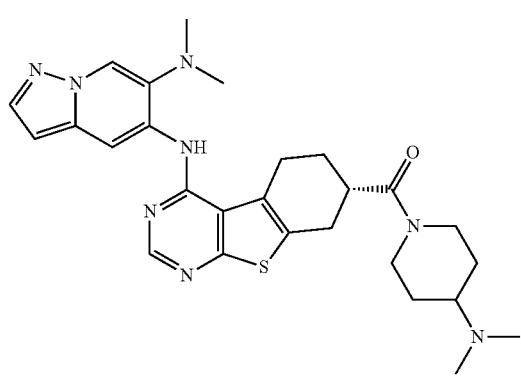 [SMILES: CN(C)c1cn2nccc2cc1Nc1ncnc2sc3c(c12)CC[C@H](C(=O)N1CCC(N(C)C)CC1)C3]

Example 189

1-({(7S)-4-[(6-(Dimethylamino)pyrazolo[1,5-a]pyridin-5-yl)amino]-5,6,7,8-tetrahydro[1]benzothieno[2,3-d]pyrimidin-7-yl}carbonyl)piperidin-4-one

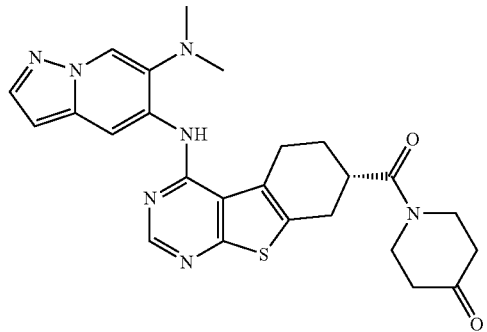 [SMILES: CN(C)c1cn2nccc2cc1Nc1ncnc2sc3c(c12)CC[C@H](C(=O)N1CCC(=O)CC1)C3]

Example 190

(3,3-Difluoropyrrolidin-1-yl){(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone

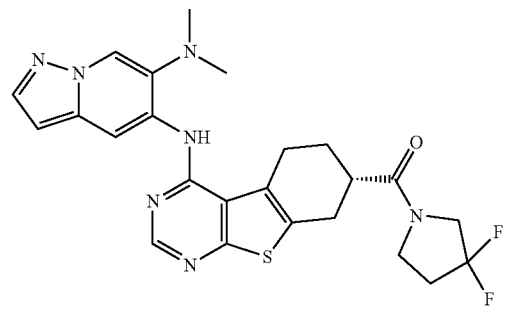 [SMILES: CN(C)c1cn2nccc2cc1Nc1ncnc2sc3c(c12)CC[C@H](C(=O)N1CCC(F)(F)C1)C3]

Example 191

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}(2,2-dimethylpyrrolidin-1-yl)methanone

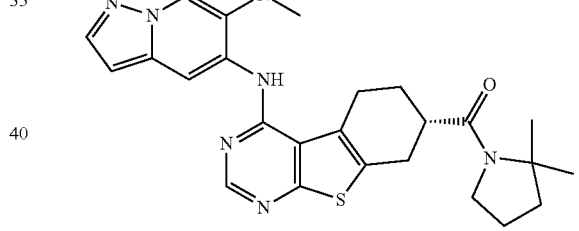

Example 192

{(7S)-4-[(6-(dimethylamino)pyrazolo[1,5-a]pyridin-5-yl)amino]-5,6,7,8-tetrahydro[1]benzothieno[2,3-d]pyrimidin-7-yl}morpholin-4-yl)methanone

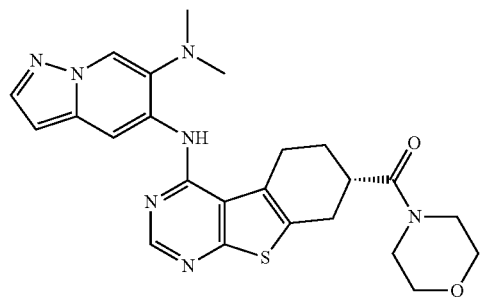 [SMILES: CN(C)c1cn2nccc2cc1Nc1ncnc2sc3c(c12)CC[C@H](C(=O)N1CCOCC1)C3]

155
Example 193

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}(2-oxa-6-azaspiro[3.3]hept-6-yl)methanone

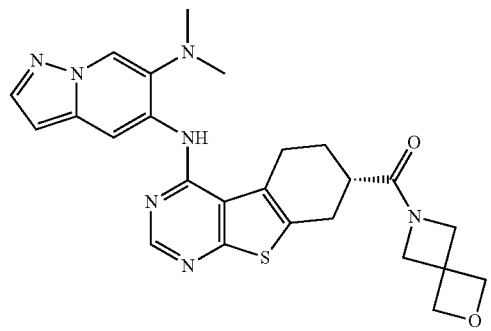

Example 194

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(2R,6S)-2,6-dimethylmorpholin-4-yl]methanone

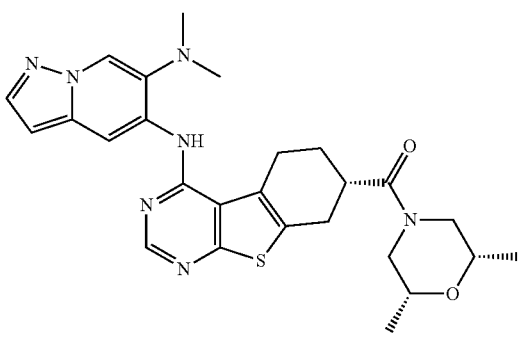 [SMILES: C[C@@H]1CN(C(=O)[C@H]2CCc3c(sc4ncnc(Nc5cc6ccnn6cc5N(C)C)c34)C2)C[C@H](C)O1]

156
Example 195

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(2R,6R)-2,6-dimethylmorpholin-4-yl]methanone

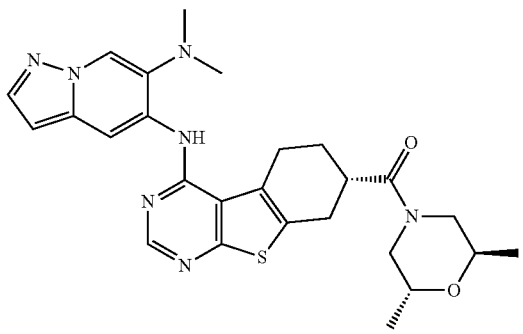 [SMILES: C[C@@H]1CN(C(=O)[C@H]2CCc3c(sc4ncnc(Nc5cc6ccnn6cc5N(C)C)c34)C2)C[C@@H](C)O1]

Example 196

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(2S,6S)-2,6-dimethylmorpholin-4-yl]methanone

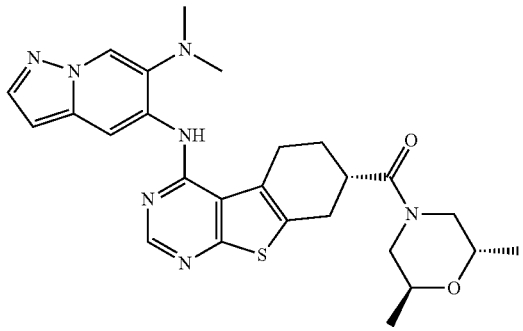 [SMILES: C[C@H]1CN(C(=O)[C@H]2CCc3c(sc4ncnc(Nc5cc6ccnn6cc5N(C)C)c34)C2)C[C@H](C)O1]

Example 197

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(3S)-3-methylmorpholin-4-yl]methanone

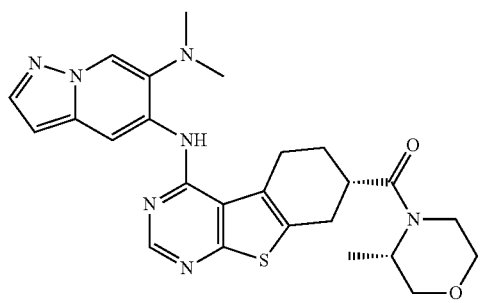 [SMILES: C[C@H]1COCCN1C(=O)[C@H]1CCc2c(sc3ncnc(Nc4cc5ccnn5cc4N(C)C)c23)C1]

Example 198

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(3R)-3-methylmorpholin-4-yl]methanone

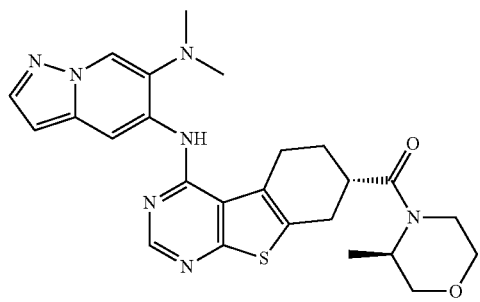 [SMILES: C[C@@H]1COCCN1C(=O)[C@H]1CCc2c(sc3ncnc(Nc4cc5ccnn5cc4N(C)C)c23)C1]

Example 199

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(1S,4S)-2-oxa-5-azabicyclo[2.2.1]hept-5-yl]methanone

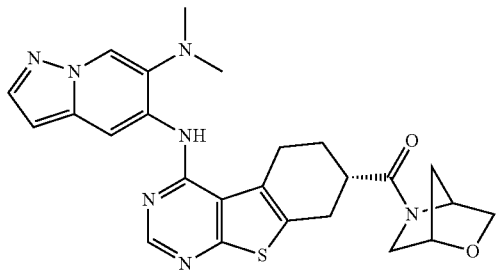 [SMILES: CN(C)c1cn2nccc2cc1Nc1ncnc2sc3c(c12)CC[C@H](C(=O)N1CC2CC1CO2)C3]

Example 200

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(1R,4R)-2-oxa-5-azabicyclo[2.2.1]hept-5-yl]methanone

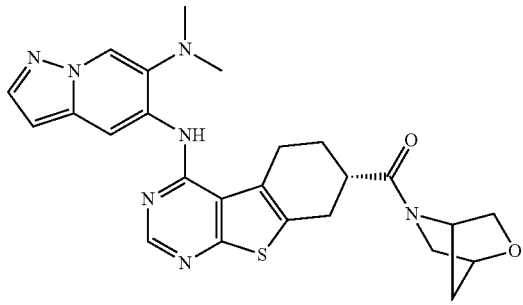 [SMILES: CN(C)c1cn2nccc2cc1Nc1ncnc2sc3c(c12)CC[C@H](C(=O)N1CC2CC1CO2)C3]

Example 201

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(1S,4S)-5-methyl-2,5-diazabicyclo[2.2.1]hept-2-yl]methanone

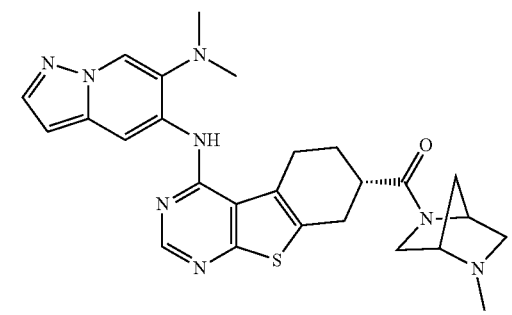 [SMILES: CN(C)c1cn2nccc2cc1Nc1ncnc2sc3c(c12)CC[C@H](C(=O)N1CC2CC1CN2C)C3]

Example 202

{(7S)-4-[(6-(Dimethylamino)pyrazolo[1,5-a]pyridin-5-yl)amino]-5,6,7,8-tetrahydro[1]benzothieno[2,3-d]pyrimidin-7-yl}[(1R,4R)-5-methyl-2,5-diazabicyclo[2.2.1]hept-2-yl]methanone

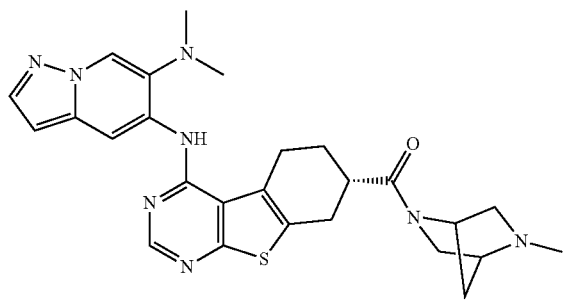 [SMILES: CN(C)c1cn2nccc2cc1Nc1ncnc2sc3c(c12)CC[C@H](C(=O)N1CC2CC1CN2C)C3]

Example 203

(7S)-4-[(6-(Dimethylamino)pyrazolo[1,5-a]pyridin-5-yl)amino]-N-[(2S)-1-methoxypropan-2-yl]-N-methyl-5,6,7,8-tetrahydro[1]benzothieno[2,3-d]pyrimidine-7-carboxamide

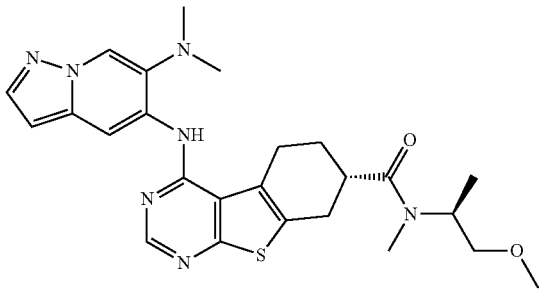 [SMILES: COC[C@H](C)N(C)C(=O)[C@H]1CCc2c(sc3ncnc(Nc4cc5ccnn5cc4N(C)C)c23)C1]

Example 204

(7S)-4-[(6-(Dimethylamino)pyrazolo[1,5-a]pyridin-5-yl)amino]-N-[(2R)-1-methoxypropan-2-yl]-N-methyl-5,6,7,8-tetrahydro[1]benzothieno[2,3-d]pyrimidine-7-carboxamide

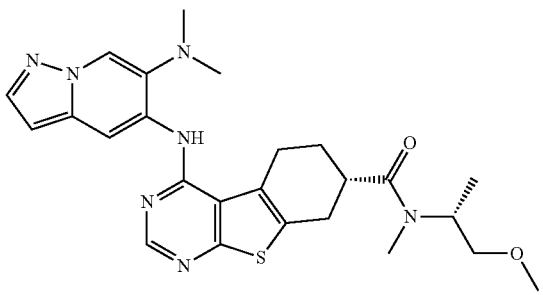 [SMILES: COC[C@@H](C)N(C)C(=O)[C@H]1CCc2c(sc3ncnc(Nc4cc5ccnn5cc4N(C)C)c23)C1]

Example 205

(7S)-4-[(6-(Dimethylamino)pyrazolo[1,5-a]pyridin-5-yl)amino]-N-[(2S)-2-methoxypropyl]-N-methyl-5,6,7,8-tetrahydro[1]benzothieno[2,3-d]pyrimidine-7-carboxamide

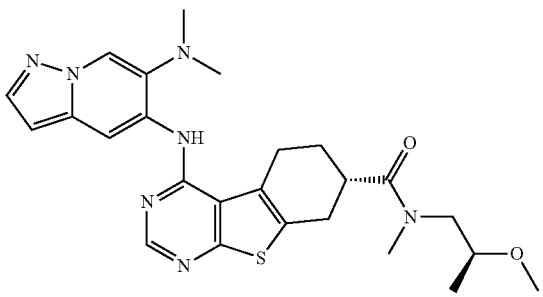

Example 206

(7S)-4-[(6-(Dimethylamino)pyrazolo[1,5-a]pyridin-5-yl)amino]-N-[(2R)-2-methoxypropyl]-N-methyl-5,6,7,8-tetrahydro[1]benzothieno[2,3-d]pyrimidine-7-carboxamide

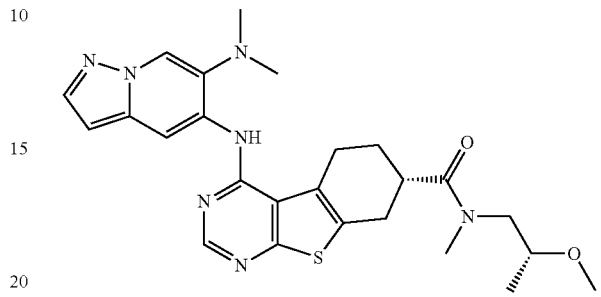

Example 207

(7S)-4-[(6-(Dimethylamino)pyrazolo[1,5-a]pyridin-5-yl)amino]-N-(1-methoxy-2-methylpropan-2-yl)-N-methyl-5,6,7,8-tetrahydro[1]benzothieno[2,3-d]pyrimidine-7-carboxamide

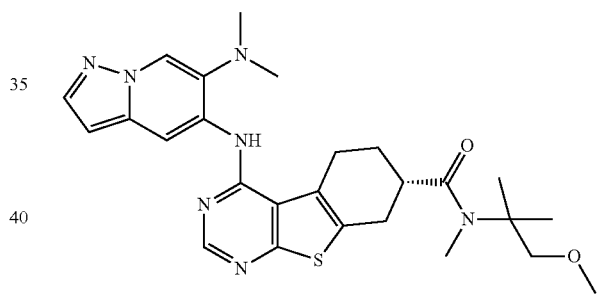

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For or al administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate: one or more colouring agents: one or more flavouring agents: and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates: anionic detergents, for example, alkyl, aryl, and olefin sulfonates, alkyl, olefin, ether, and monoglyceride sulfates, and sulfosuccinates: non-ionic detergents, for example, fatty amine oxides, fatty acid alkanolamides, and poly(oxyethylene-oxypropylene)s or ethylene oxide or propylene oxide copolymers: and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia: dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311: Strickley, R. G "Parenteral Formulations of Small Molecule Therapeutics Marketed in the United States (1999)-Part-1" PDA Journal of Pharmaceutical Science & Technology 1999, 53(6), 324-349: and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide); tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth): and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes.

These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, topoisomerase inhibitors, proteasome inhibitors, biological response modifiers, anti-hormones or agents used for the treatment of inflammatory diseases or pain disorders.

The terms "chemotherapeutic agent" and anti-cancer agent", include but are not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, deforolimus, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, enzastaurin, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, larotaxel, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methylaminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, novolimus, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, perifosine, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, rapamycin, razoxane, regorafenib, risedronic acid, rituximab, romidepsin, romiplostim, sagopilone, sargramostim, selumetinib, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trametinib, trastuzumab, treosulfan, tretinoin, triciribine, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin, zotarolimus, ARRY-162, ARRY-300, ARRY-704, AS-703026, AZD-5363, AZD-8055, BEZ-235, BGT-226, BKM-120, BYL-719, CAL-101, CC-223, CH-5132799, E-6201, GDC-0032, GDC-0068, GDC-0623, GDC-0941, GDC-0973, GDC-0980, GSK-2110183, GSK-2126458, GSK-2141795, INK128, MK-2206, OSI-027, PF-04691502, PF-05212384, PX-866, RG-7167, RO-4987655, RO-5126766, TAK-733, UCN-01, WX-554, XL-147, XL-765, ZSTK-474.

The terms "chemotherapeutic agent" and anti-cancer agent", also include protein therapeutics such as an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-(linked lintuzumab, EM-1421, HyperAcute vaccine, tucotuzumab celmoleukin, galiximab, HPV-16-E7, Javelin-prostate cancer, Javelin-melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B.

The terms "chemotherapeutic agent" and "anti-cancer agent", also include monoclonal antibodies useful as the protein therapeutic such as muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemo-therapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Beyond the "chemotherapeutic agent" and "anti cancer agent" the invention can be combined with further "anti-inflammatory" and "anti-pain agents" which include but are not limited to abatacept, or anti-bacterial agents (e.g. penicilline, vancomycin, ciprofloxacin), anti-viral agents (e.g. aciclovir, oseltamivir), anti-mycotic agents (e.g. naftifine, nystatin), azathioprine, belimumab, corticosteroids (e.g. prednisone, prednisolone, methylprednisolone, hydrocortisone, betamethasone), cyclophosphamide, IgE antibody, immunoglobulin and gammaglobuline, IL-1 inhibitors (e.g. anakinra, canakinumab, rilonacept), "immunomodulatory and immunosuppressive agents" like cyclosporine, mercaptopurine, Methotrexat®; interferon including beta-interferon (IFN beta-1a: Avonex® and IFN beta-1b: Betaferon®), Jak/STAT inhibitors (e.g. tofacitinib, baricitinib, GLPG0634), leflunomide, mycophenolic acid, nonsteroidal anti-inflammatory drugs (NSAIDS) (e.g. ibuprofen, naproxen, etodolac, celecoxib, colchicine), paracetamol, phosphodiesterase-inhibitor (e.g. apremilast, roflumilast), rapamycin, rituximab, sulfasalazine, tacrolimus and TNF-antagonist (e.g. Humira®, etanercept, infliximab).

In addition, combination also includes ACE (angiotensin-converting-enzyme) inhibitors (e.g. benazepril), acetylsalicylic acid, acetylcholinesterase inhibitors (e.g. donepezil, rivastigmine, galantamine, tacrine), anticholinergic agents (e.g. trihexyphenidyle, glycopyrronium bromid), anticonvulsant agents (e.g. gabapentin), anti-diarrhoeal drug (e.g. loperamide or laxatives), antileukotriene agents (e.g. montelukast), beta blocker (e.g. metoprolol), beta2-adrenergic agonists (e.g. salbutamol), calcium channel blockers (e.g. nifedipine), chloroquine, COMT (Catechol-O-Methyltransferase)-inhibitors (e.g. entacapone), diuretics (e.g. hydrochlorothiazide), dopamine agonists (e.g. ropinrole, pramipexole, bromocriptine), efalizumab, fingolimod, glatiramer acetate, glibenclamide, insulin therapy, L-DOPA/Carbidopa (L-3,4-Dihydroxyphenylalanin), MAO-B (monoamine oxidase B) inhibitors (e.g. selegiline), mesalazine, metformin, methylxanthine drugs (e.g. theophylline), mitoxantrone, natalizumab, NMDA (N-Methyl-D-Aspartat) receptor antagonists (e.g. amantadine, memantine), probiotics (e.g. mutaflor, VSL#3®, *Lactobacillus* GG, *Lactobacillus plantarum, L. acidophilus, L. casei, Bifidobacterium infantis* 35624, *Enterococcus fecium* SF68, *Bifidobacterium longum*), statin (e.g. simvastatin), sulfonylureas (e.g. tolnutamide, glimepiride), urea and vitamin-D analoga (e.g. calcipotriol, calcitriol, tacalcitol).

Mention should also be made of medicaments comprising at least one of the inventive compounds and one or more further active ingredients, especially EP4 inhibitors (prostaglandin E2 receptor 4 inhibitors), P2X3 inhibitors (P2X purinoceptor 3), PTGES inhibitors (prostaglandin E synthase inhibitors) or AKR1C$_3$ inhibitors (aldo-keto reductase family 1 member C$_3$ inhibitors), for treatment and/or prevention of the aforementioned disorders.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage.

Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit MKNK1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, or pancreatitis.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof: etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant serin threonin kinase activity," includes any abnormal expression or activity of the gene encoding the kinase or of the polypeptide it encodes. Examples of such aberrant activity, include, but are not limited to, over-expression of the gene or polypeptide: gene amplification: mutations which produce constitutively-active or hyperactive kinase activity: gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Pain-Associated Diseases and Gynaecological Disorders.

The present invention also provides methods for the treatment or prophylaxis of inflammation and pain-associated diseases.

In particular aspect of the invention as reported above a compound of formula (I), (Ia) or (Ib) is for the treatment of pain syndromes including acute, chronic, inflammatory and neuropathic pain, preferably inflammatory pain, surgical pain, visceral pain, dental pain, premenstrual pain, gynaecological disease, preferably dysmenorrhea, dyspareunia or endometriosis, adenomyosis, endometriosis-associated pain, or other endometriosis-associated symptoms, wherein said symptoms are in particular endometriosis-associated dysmenorrhea, dyspareunia, dysuria, or dyschezia, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, chronic lower back pain, phantom limb pain, pelvic pain syndrome, chronic pelvic pain, neuroma pain, complex regional pain syndrome, pain associated with gastrointestinal distension, chronic arthritic pain and related neuralgias, and pain associated with cancer, pain associated with chemotherapy, HIV and HIV treatment-induced neuropathy; and pain associated with diseases or disorders selected from the group consisting of hyperalgesia, allodynia, irritable bowel syndrome.

In addition, the present invention is for the use of the treatment and prevention of inflammatory diseases including inflammatory bowel disease (ulcerative colitis and Crohn's disease), hyperaemia, sepsis, metabolic disorders, e.g. obesity, insulin resistance, diabetes; atherosclerosis, reperfusion injury, inflammatory bone resorption, pulmonary fibrosis, acute respiratory distress syndrome, and intestinal polyposis, inflammatory skin diseases like psoriasis, pemphigus vulgaris, fibrotic diseases like idiopathic pulmonary fibrosis, skin fibrosis, systemic sclerosis, autism disorders, liver diseases like nonalcoholic fatty liver disease, hepatic fibrosis; lung diseases like chronic obstructive pulmonary disease, asthma, pneumonia; neurodegenerative diseases like Parkinson's disease, Alzheimer's disease; stroke, postischemic brain injury, brain ischemia, alopecia, acute coronary syndrome, myocardial infarction, autoimmune diseases like autoimmune encephalomyelitis, multiple sclerosis; arthritis (such as osteoarthritis and rheumatoid arthritis); interstitial cystitis, hypertrophy, ischemia/reperfusion injury, allergic rhinitis, burn wound, osteoporosis.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays

Examples were tested in selected biological assays one or more times. When tested more than once, data are reported as either average values or as median values, wherein
 the average value, also referred to as the arithmetic mean value, represents the sum of the values obtained divided by the number of times tested, and
 the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

MKNK1 Kinase Assay

MKNK1-inhibitory activity of compounds of the present invention was quantified employing the MKNK1 TR-FRET assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (SEQ ID NO: 1, C-terminus in amide form) was used, which can be purchased e.g. from the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (0.1 µM=>final conc. in the 5 µL assay volume is 0.06 µM) in assay buffer and the resulting mixture was incubated for a reaction time of 45 min at 22° C. The concentration of MKNK1 was adjusted depending of the activity of the enzyme lot and was chosen appropriate to have the assay in the linear range, typical concentrations were in the range of 0.05 µg/ml. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

MKNK1 Kinase High ATP Assay

MKNK1-inhibitory activity at high ATP of compounds of the present invention after their preincubation with MKNK1 was quantified employing the TR-FRET-based MKNK1 high ATP assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (SEQ ID NO: 1, C-terminus in amide form) was used, which can be purchased e.g. from the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 μL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 μL of a solution of adenosine-tri-phosphate (ATP, 3.3 mM=>final conc. in the 5 μL assay volume is 2 mM) and substrate (0.1 μM=>final conc. in the 5 μL assay volume is 0.06 μM) in assay buffer and the resulting mixture was incubated for a reaction time of 30 min at 22° C. The concentration of MKNK1 was adjusted depending of the activity of the enzyme lot and was chosen appropriate to have the assay in the linear range, typical concentrations were in the range of 0.003 μg/mL. The reaction was stopped by the addition of 5 μL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated. Data are presented in Table 1.

TABLE 1

| Example | MKNK1 $IC_{50}$ [nM] |
|---|---|
| 1 | 64 |
| 2 | 707 |
| 3 | 80 |
| 4 | 21 |
| 5 | 21 |
| 6 | 12 |
| 7 | 65 |
| 8 | 42 |
| 9 | 49 |
| 10 | 33 |
| 11 | 62 |
| 12 | 24 |
| 13 | 17 |
| 14 | 7 |
| 15 | 4 |
| 16 | 19 |
| 17 | 33 |
| 18 | 19 |
| 19 | 21 |
| 20 | 26 |
| 21 | 19 |
| 22 | 21 |
| 23 | 23 |
| 24 | 20 |
| 25 | 13 |
| 26 | 14 |
| 27 | 13 |
| 28 | 19 |
| 29 | 20 |
| 30 | 16 |
| 31 | 26 |
| 32 | 25 |
| 33 | 96 |
| 34 | 71 |
| 35 | 75 |
| 36 | 91 |
| 37 | 56 |
| 38 | 25 |
| 39 | 41 |
| 40 | 6 |
| 41 | 11 |
| 42 | 11 |
| 43 | 35 |
| 44 | 54 |
| 45 | 12 |
| 46 | 11 |
| 47 | 18 |
| 48 | 35 |
| 49 | 15 |
| 50 | 7 |
| 51 | 5 |
| 52 | 8 |
| 53 | 9 |
| 54 | 11 |
| 55 | 18 |
| 56 | 41 |
| 57 | 12 |
| 58 | 2 |
| 59 | 1 |
| 60 | 18 |
| 61 | 13 |
| 62 | 6 |
| 63 | 15 |
| 64 | 10 |
| 65 | 5 |
| 66 | 6 |
| 67 | 30 |
| 68 | 4 |
| 69 | 6 |
| 70 | 7 |
| 71 | 12 |
| 72 | 14 |
| 73 | 4 |
| 74 | 22 |
| 75 | 56 |
| 76 | 7 |
| 77 | 21 |

TABLE 1-continued

| Example | MKNK1 IC$_{50}$ [nM] |
|---|---|
| 78 | 5 |
| 79 | 3 |
| 80 | 3 |
| 81 | 2 |
| 82 | 3 |
| 83 | 3 |
| 84 | 3 |
| 85 | 4 |
| 86 | 4 |
| 87 | 4 |
| 88 | 8 |
| 89 | 24 |
| 90 | 235 |
| 91 | 48 |
| 92 | 7 |
| 93 | 3 |
| 94 | 1 |
| 95 | 2 |
| 96 | 7 |
| 97 | 1 |
| 98 | 1 |
| 99 | 1 |
| 100 | <1 |
| 101 | 2 |
| 102 | 2 |
| 103 | 3 |
| 104 | 1 |
| 105 | 2 |
| 106 | <1 |
| 107 | <1 |
| 108 | 1 |
| 109 | 1 |
| 110 | <1 |
| 111 | 3 |
| 112 | 2 |
| 113 | 1 |
| 114 | <1 |
| 115 | 1 |
| 116 | 1 |
| 117 | 1 |
| 118 | 1 |
| 119 | <1 |
| 120 | 5 |
| 121 | 1 |
| 122 | <1 |
| 123 | 2 |
| 124 | 1 |
| 125 | 1 |
| 126 | 1 | nd: not yet determined

MKNK 2 Kinase High ATP Assay

MKNK 2-inhibitory activity at high ATP of compounds of the present invention after their preincubation with MKNK 2 was quantified employing the TR-FRET-based MKNK 2 high ATP assay as described in the following paragraphs.

A recombinant fusion protein of Glutathione-S-Transferase (GST, N-terminally) and human full-length MKNK 2 (Genbank accession number NP_060042.2), expressed in insect cells using baculovirus expression system, purified via glutathione sepharose affinity chromatography, and activated in vitro with MAPK12, was purchased from Invitrogen (product no PV5608) and used as enzyme. As substrate for the kinase reaction the biotinylated peptide biotin-Ahx-IKKRKLTRRKSLKG (SEQ ID NO: 1, C-terminus in amide form) was used which can be purchased e.g. form the company Biosyntan (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of MKNK 2 in aqueous assay buffer [50 mM HEPES pH 7.5, 5 mM MgCl$_2$, 1.0 mM dithiothreitol, 0.005% (v/v) Nonidet-P40 (G-Biosciences, St. Louis, USA)] was added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (0.1 µM=>final conc. in the 5 µl assay volume is 0.06 µM) in assay buffer and the resulting mixture was incubated for a reaction time of 30 min at 22° C. The concentration of MKNK 2 was adjusted depending of the activity of the enzyme lot and was chosen appropriate to have the assay in the linear range, typical concentrations were in the range of 0.0045 µg/ml. The reaction was stopped by the addition of 5 µl of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL665. Therefore, the fluorescence emissions at 620 nm and 665 nm after excitation at 350 nm were measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and IC$_{50}$ values were calculated.

EGFR Kinase Assay

EGFR inhibitory activity of compounds of the present invention was quantified employing the TR-FRET based EGFR assay as described in the following paragraphs.

Epidermal Growth Factor Receptor (EGFR) affinity purified from human carcinoma A431 cells (Sigma-Aldrich, # E3641) was used as kinase. As substrate for the kinase reaction the biotinylated peptide biotin-Ahx-AEEEEYFEL-VAKKK (SEQ ID NO: 2, C-terminus in amid form) was used which can be purchased e.g. form the company Biosynthan GmbH (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of EGFR in aqueous assay [50 mM Hepes/HCl pH 7.0, 1 mM MgCl$_2$, 5 mM MnCl$_2$, 0.5 mM activated sodium ortho-vanadate, 0.005% (v/v) Tween-20] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 μM=>final conc. in the 5 μL assay volume is 10 μM) and substrate (1.67 μM=>final conc. in the 5 μL assay volume is 1 μM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration were in the range of 3 U/ml. The reaction was stopped by the addition of 5 μl of a solution of HTRF detection reagents (0.1 μM streptavidine-XL665 [Cis Biointernational] and 1 nM PT66-Tb-Chelate, an terbium-chelate labelled anti-phospho-tyrosine antibody from Cis Biointernational [instead of the PT66-Tb-chelate PT66-Eu-Cryptate from Perkin Elmer can also be used]) in an aqueous EDTA-solution (80 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Eu-Chelate. Subsequently the amount of phosphorylated substrate was evaluated by measurement of the resonance energy transfer from the PT66-Eu-Chelate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated.

CDK2/CycE Kinase Assay

CDK2/CycE inhibitory activity of compounds of the present invention can be quantified employing the CDK2/CycE TR-FRET assay as described in the following paragraphs.

Recombinant fusion proteins of GST and human CDK2 and of GST and human CycE, expressed in insect cells (Sf9) and purified by Glutathion-Sepharose affinity chromatography, can be purchased from ProQinase GmbH (Freiburg, Germany). As substrate for the kinase reaction biotinylated peptide biotin-Ttds-YISPLKSPYKISEG (SEQ ID NO: 3, C-terminus in amid form) can be used which can be purchased e.g. from the company JERINI peptide technologies (Berlin, Germany).

For the assay 50 nL of a 100 fold concentrated solution of the test compound in DMSO is pipetted into a black low volume 384 well microtiter plate (Greiner Bio-One, Frickenhausen, Germany), 2 μL of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (1.25 μM=>final conc. in the 5 μL assay volume is 0.75 μM) in assay buffer and the resulting mixture is incubated for a reaction time of 25 min at 22° C. The concentration of CDK2/CycE is adjusted depending of the activity of the enzyme lot and is chosen appropriate to have the assay in the linear range, typical concentrations are in the range of 130 ng/ml. The reaction is stopped by the addition of 5 μL of a solution of TR-FRET detection reagents (0.2 μM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture is incubated 1 h at 22° C. to allow the formation of complex between the phosphorylated biotinylated peptide and the detection reagents. Subsequently the amount of phosphorylated substrate is evaluated by measurement of the resonance energy transfer from the Eu-chelate to the streptavidine-XL. Therefore, the fluorescence emissions at 620 nm and 665 nm after excitation at 350 nm is measured in a TR-FRET reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Usually the test compounds are tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values are calculated.

PDGFRß Kinase Assay

PDGFRß inhibitory activity of compounds of the present invention can be quantified employing the PDGFRß HTRF assay as described in the following paragraphs.

As kinase, a GST-His fusion protein containing a C-terminal fragment of human PDGFRß (amino acids 561-1106, expressed in insect cells [SF9] and purified by affinity chromatography, purchased from Proqinase [Freiburg i.Brsg., Germany] is used. As substrate for the kinase reaction the biotinylated poly-Glu, Tyr (4:1) copolymer (#61GTOBLA) from Cis Biointernational (Marcoule, France) is used.

For the assay 50 nL of a 100 fold concentrated solution of the test compound in DMSO is pipetted into a black low volume 384 well microtiter plate (Greiner Bio-One, Frickenhausen, Germany), 2 μL of a solution of PDGFRß in aqueous assay buffer [50 mM HEPES/NaOH pH 7.5, 10 mM $MgCl_2$, 2.5 mM dithiothreitol, 0.01% (v/v) Triton-X100 (Sigma)] are added and the mixture was incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (2.27 μg/ml=>final conc. in the 5 μL assay volume is 1.36 μg/ml [~30 nM]) in assay buffer and the resulting mixture is incubated for a reaction time of 25 min at 22° C. The concentration of PDGFRß in the assay is adjusted depending of the activity of the enzyme lot and is chosen appropriate to have the assay in the linear range, typical enzyme concentrations are in the range of about 125 μg/μL (final conc. in the 5 μL assay volume). The reaction is stopped by the addition of 5 µL of a solution of HTRF detection reagents (200 nM streptavidine-XLent [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture is incubated 1 h at 22° C. to allow the binding of the biotinylated phosphorylated peptide to the streptavidine-XLent and the PT66-Eu-Chelate. Subsequently the amount of phosphorylated substrate is evaluated by measurement of the resonance energy transfer from the PT66-Eu-Chelate to the streptavidine-XLent. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated.

Fyn Kinase Assay

C-terminally His6-tagged human recombinant kinase domain of the human T-Fyn expressed in baculovirus infected insect cells (purchased from Invitrogen, P3042) is used as kinase. As substrate for the kinase reaction the biotinylated peptide biotin-KVEKIGEGTYGVV (SEQ ID NO: 4, C-terminus in amid form) is used which can be purchased e.g. form the company Biosynthan GmbH (Berlin-Buch, Germany).

For the assay 50 nL of a 100 fold concentrated solution of the test compound in DMSO is pipetted into a black low volume 384 well microtiter plate (Greiner Bio-One, Frickenhausen, Germany), 2 µL of a solution of T-Fyn in aqueous assay buffer [25 mM Tris/HCl pH 7.2, 25 mM $MgCl_2$, 2 mM dithiothreitol, 0.1% (w/v) bovine serum albumin, 0.03% (v/v) Nonidet-P40 (Sigma)]. are added and the mixture is incubated for 15 min at 22° C. to allow pre-binding of the test compounds to the enzyme before the start of the kinase reaction. Then the kinase reaction is started by the addition of 3 µL of a solution of adenosine-tri-phosphate (ATP, 16.7 µM=>final conc. in the 5 µL assay volume is 10 µM) and substrate (2 µM=>final conc. in the 5 µL assay volume is 1.2 µM) in assay buffer and the resulting mixture is incubated for a reaction time of 60 min at 22° C. The concentration of Fyn is adjusted depending on the activity of the enzyme lot and is chosen appropriate to have the assay in the linear range, typical concentration was 0.13 nM. The reaction is stopped by the addition of 5 µL of a solution of HTRF detection reagents (0.2 µM streptavidine-XL [Cisbio Bioassays, Codolet, France) and 0.66 nM PT66-Eu-Chelate, an europium-chelate labelled anti-phospho-tyrosine antibody from Perkin Elmer [instead of the PT66-Tb-Cryptate from Cisbio Bioassays can also be used]) in an aqueous EDTA-solution (125 mM EDTA, 0.2% (w/v) bovine serum albumin in 50 mM HEPES/NaOH pH 7.0).

The resulting mixture is incubated 1 h at 22° C. to allow the binding of the biotinylated phosphorylated peptide to the streptavidine-XL and the PT66-Eu-Chelate. Subsequently the amount of phosphorylated substrate is evaluated by measurement of the resonance energy transfer from the PT66-Eu-Chelate to the streptavidine-XL. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compounds are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and 1050 values are calculated.

Flt4 Kinase Assay

Flt4 inhibitory activity of compounds of the present invention can be quantified employing the Flt4 TR-FRET assay as described in the following paragraphs.

As kinase, a GST-His fusion protein containing a C-terminal fragment of human Flt4 (amino acids 799-1298, expressed in insect cells [SF9] and purified by affinity chromatography, purchased from Proqinase [Freiburg i.Brsg., Germany] is used. As substrate for the kinase reaction the biotinylated peptide Biotin-Ahx-GGEEEEY-FELVKKKK (SEQ ID NO: 5, C-terminus in amide form, purchased from Biosyntan, Berlin-Buch, Germany) is used.

For the assay 50 nL of a 100 fold concentrated solution of the test compound in DMSO was pipetted into a black low volume 384 well microtiter plate (Greiner Bio-One, Frickenhausen, Germany), 2 µL of a solution of Flt4 in aqueous assay buffer [25 mM HEPES pH 7.5, 10 mM $MgCl_2$, 2 mM dithiothreitol, 0.01% (v/v) Triton-X100 (Sigma), 0.5 mM EGTA, and 5 mM ß-phospho-glycerol] are added and the mixture is incubated for 15 min at 22° C. to allow pre-binding of the test compounds to the enzyme before the start of the kinase reaction. Then the kinase reaction is started by the addition of 3 µL of a solution of adenosine-tri-phosphate (ATP, 16.7 µM=>final conc. in the 5 µL assay volume is 10 µM) and substrate (1.67 µM=>final conc. in the 5 µL assay volume is 1 µM) in assay buffer and the resulting mixture is incubated for a reaction time of 45 min at 22° C. The concentration of Flt4 in the assay is adjusted depending of the activity of the enzyme lot and was chosen appropriate to have the assay in the linear range, typical enzyme concentrations are in the range of about 120 pg/µL (final conc. in the 5 µL assay volume). The reaction is stopped by the addition of 5 µL of a solution of HTRF detection reagents (200 nM streptavidine-XL665 [Cis Biointernational] and 1 nM PT66-Tb-Cryptate, an terbium-cryptate labelled anti-phospho-tyrosine antibody from Cisbio Bioassays (Codolet, France) in an aqueous EDTA-solution (50 mM EDTA, 0.2% (w/v) bovine serum albumin in 50 mM HEPES pH 7.5).

The resulting mixture is incubated 1 h at 22° C. to allow the binding of the biotinylated phosphorylated peptide to the streptavidine-XL665 and the PT66-Tb-Cryptate. Subsequently the amount of phosphorylated substrate is evaluated by measurement of the resonance energy transfer from the PT66-Tb-Cryptate to the streptavidine-XL665. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated.

TrkA Kinase Assay

TrkA inhibitory activity of compounds of the present invention can be quantified employing the TrkA HTRF assay as described in the following paragraphs.

As kinase, a GST-His fusion protein containing a C-terminal fragment of human TrkA (amino acids 443-796, expressed in insect cells [SF9] and purified by affinity chromatography, purchased from Proqinase [Freiburg i.Brsg., Germany] is used. As substrate for the kinase reaction the biotinylated poly-Glu, Tyr (4:1) copolymer (#61GTOBLA) from Cis Biointernational (Marcoule, France) is used.

For the assay 50 nL of a 100 fold concentrated solution of the test compound in DMSO is pipetted into a black low volume 384 well microtiter plate (Greiner Bio-One, Frickenhausen, Germany), 2 µL of a solution of TrkA in aqueous assay buffer [8 mM MOPS/HCl pH 7.0, 10 mM $MgCl_2$, 1 mM dithiothreitol, 0.01% (v/v) NP-40 (Sigma), 0.2 mM EDTA] are added and the mixture was incubated for 15 min at 22° C. to allow pre-binding of the test compounds to the enzyme before the start of the kinase reaction. Then the kinase reaction is started by the addition of 3 µL of a solution of adenosine-tri-phosphate (ATP, 16.7 µM=>final conc. in the 5 µL assay volume is 10 µM) and substrate (2.27 µg/ml=>final conc. in the 5 µL assay volume is 1.36 µg/ml [~30 nM]) in assay buffer and the resulting mixture is incubated for a reaction time of 60 min at 22° C. The concentration of TrkA in the assay is adjusted depending of the activity of the enzyme lot and is chosen appropriate to have the assay in the linear range, typical enzyme concentrations are in the range of about 20 pg/µL (final conc. in the 5 µL assay volume). The reaction is stopped by the addition of 5 µL of a solution of HTRF detection reagents (30 nM streptavidine-XL665 [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture is incubated 1 h at 22° C. to allow the binding of the biotinylated phosphorylated peptide to the streptavidine-XL665 and the PT66-Eu-Chelate. Subsequently the amount of phosphorylated substrate is evaluated by measurement of the resonance energy transfer from the PT66-Eu-Chelate to the streptavidine-XL665. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated.

AlphaScreen SureFire eIF4E Ser209 Phosphorylation Assay

The AlphaScreen SureFire eIF4E Ser209 phosorylation assay can be used to measure the phosphorylation of endogenous eIF4E in cellular lysates. The AlphaScreen SureFire technology allows the detection of phosphorylated proteins in cellular lysates. In this assay, sandwich antibody complexes, which are only formed in the presence of the analyte (p-eIF4E Ser209), are captured by AlphaScreen donor and acceptor beads, bringing them into close proximity. The excitation of the donor bead provokes the release of singlet oxygen molecules that triggers a cascade of energy transfer in the Acceptor beads, resulting in the emission of light at 520-620 nm.

Surefire EIF4e AlphaScreen in A549 Cells with 20% FCS Stimulation

For the assay the AlphaScreen SureFire p-eIF4E Ser209 10K Assay Kit and the AlphaScreen ProteinA Kit (for 10K Assay Points) Both from Perkin Elmer are Used.

On day one 50.000 A549 cells are plated in a 96-well plate in 100 µL per well in growth medium (DMEM/Hams' F12 with stable Glutamin, 10% FCS) and incubated at 37° C. After attachment of the cells, medium is changed to starving medium (DMEM, 0.1% FCS, without Glucose, with Glutamin, supplemented with 5 g/L Maltose). On day two, test compounds are serially diluted in 50 µL starving medium with a final DMSO concentration of 1% and are added to A549 cells in test plates at a final concentration range from as high 10 µM to as low 10 nM depending on the activities of the tested compounds. Treated cells are incubated at 37° C. for 2 h. 37 ul FCS is added to the wells (=final FCS concentration 20%) for 20 min. Then medium is removed and cells are lysed by adding 50 µL lysis buffer. Plates are then agitated on a plate shaker for 10 min. After 10 min lysis time, 4 µL of the lysate is transferred to a 384 well plate (Proxiplate from Perkin Elmer) and 5 µL Reaction Buffer plus Activation Buffer mix containing AlphaScreen Acceptor beads is added. Plates are sealed with TopSeal-A adhesive film, gently agitated on a plate shaker for 2 hours at room temperature. Afterwards 2 µL Dilution buffer with AlphaScreen Donor beads are added under subdued light and plates are sealed again with TopSeal-A adhesive film and covered with foil. Incubation takes place for further 2 h gently agitation at room temperature. Plates are then measured in an EnVision reader (Perkin Elmer) with the AlphaScreen program. Each data point (compound dilution) is measured as triplicate.

Proliferation Assays

The tumor cell proliferation assay which can be used to test the compounds of the present invention involves a readout called Cell Titer-Glow® Luminescent Cell Viability Assay developed by Promega® (B. A. Cunningham, "A Growing Issue: Cell Proliferation Assays, Modern kits ease quantification of cell growth", *The Scientist* 2001, 15(13), 26; S. P. Crouch et al., "The use of ATP bioluminescence as a measure of cell proliferation and cytotoxicity", *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

In Vitro Tumor Cell Proliferation Assay:

Cultivated tumour cells (MOLM-13 (human acute myeloid leukemia cells obtained from DSMZ # ACC 554), JJN-3 (human plasma cell leukemia cells obtained from DSMZ # ACC 541), Ramos (RA1) (human Burkitt's lymphoma cells obtained from ATCC # CRL-159)) are plated at a density of 2,500 cells/well (JJN-3), 3,000 cells/well (MOLM-13), 4,000 cells/well (Ramos (RA1)), in a 96-well multititer plate (Costar 3603 black/clear bottom) in 100 μL of their respective growth medium supplemented with 10% fetal calf serum. After 24 hours, the cells of one plate (zero-point plate) are measured for viability. Therefore, 70 μL/well CTG solution (Promega Cell Titer Glo solution (catalog # G755B and G756B)) is added to zero-point plate. The plates are mixed for two minutes on orbital shaker to ensure cell lysis and incubated for ten minutes at room temperature in the dark to stabilize luminescence signal. The samples are read on a VICTOR 3 plate reader. In parallel, serially test compounds are diluted in growth medium, and 50 μL of 3× dilutions/well are pipetted into the test plates (final concentrations: 0 μM, as well as in the range of 0.001-30 μM). The final concentration of the solvent dimethyl sulfoxide is 0.3-0.4%. The cells are incubated for 3 days in the presence of test substances. 105 μL/well CTG solution (Promega Cell Titer Glo solution (catalog # G755B and G756B)) is added to the test wells. The plates are mixed for 2 minutes on an orbital shaker to ensure cell lysis and incubated for 10 min at room temperature in the dark to stabilize luminescence signal. The samples are read on a VICTOR 3 plate reader. The change of cell number, in percent, is calculated by normalization of the measured values to the extinction values of the zero-point plate (=0%) and the extinction of the untreated (0 μm) cells (=100%).

tumours, endocrine tumours, mammary and other gynaecological tumours, urological tumours including renal, bladder and prostate tumours, skin tumours, and sarcomas, and/or metastases thereof.

In Vitro IL-1β (Interleukin-1 beta, IL-1b)-Induced Cytokine Secretion of Human PBMCs (Peripheral Blood Mononuclear Cells)

The effect of the chemical compounds on the induced cytokine secretion of human PBMCs has been investigated. Here, the cytokine secretion has been induced by IL-1β which binding to its receptors leads to the activation of the MKNK signaling pathway.

Human PBMCs have been isolated from anti-coagulated human whole blood donated from healthy volunteers by pre-filling Leucosep tubes with ficoll-paque (15 ml, Biochrom, order ID: L6115) and adding 20 ml whole blood. After centrifugation of the blood at 800 g for 15 min at room temperature (RT) plasma including thrombocytes has been discarded. PBMCs were transferred to a new falcon tube, washed with PBS (phosphate-buffered saline) at 250 g for 10 min at RT and resuspended in complete medium [RPMI 1640, without L-glutamine (PAA, order ID: E15-039), 10% FCS; 50 U/ml Penicillin, 50 μg/ml Streptomycin (PAA, order ID: P11-010) and 1% L-glutamine (Sigma, order ID: G7513)]. The assay was performed in a 96-well plate at a cell density of $2.5 \times 10^5$ cells/well as triplicates. The compounds were serially diluted in DMSO and added to the PBMCs at a range of $3 \times 10^{-9}$ M to $1 \times 10^{-5}$ M with a final concentration of 0.4% DMSO, respectively. Treatment of PBMCs with 0.4% DMSO was used as control. After 30 min of incubation, PBMCs were stimulated with 20 ng/ml IL-1β (R&D, order ID: 201-LB CF) for 24 hours. Cell viability was measured using the CellTiter-Glo Luminescent Assay

| Overview cell lines for proliferation assays | | | |
|---|---|---|---|
| Cell line | Origin | Cell number/well | Culture Medium |
| MOLM-13 (obtained from DSMZ # ACC 554) | human acute myeloid leukemia | 3000 | RPMI 1640 with stable Glutamin with 10% Fetal Bovine Serum |
| JJN-3 (obtained from DSMZ # ACC 541) | human plasma cell leukemia | 2500 | 45% Dulbecco's Modified Eagle Medium with stable Glutamin, 45% Iscove's Modified Dulbecco's Media with stable Glutamin and 10% Fetal Bovine Serum |
| Ramos (RA1) (obtained from ATCC # CRL-159) | human Burkitt's lymphoma | 4000 | RPMI 1640 media with stable Glutamin with 10% Fetal Bovine Serum |

Thus the compounds of the present invention effectively inhibit one or more kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal (Promega, order ID: G7571) following the manufacturers protocol. The amount of secreted TNF-α (tumor necrosis factor-alpha) in the supernatant was determined using the Human ProInflammatory 9-Plex (MSD, order ID: K15007B) according to manufacturer's instruction. The inhibitory activity was determined as the relation to the control in percent. $IC_{50}$ values were calculated using the 4-parameter logistic model.

Figure 1B:
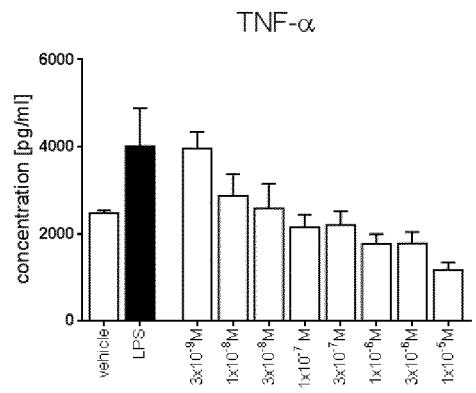
FIG. 1b depicts the inhibition of TNF-α secretion by the compound of example 41 in human peripheral blood mononuclear cells in vitro.

As an illustration, compound from example 41 with no effect on cell viability but inhibition of the secretion of TNF-α is shown in FIGS. 1a and 1b. $IC_{50}$ values are presented in Table 3.

FIG. 1a-b: Compound of example 41 has no effect on cell viability (FIG. 1a) but inhibits the secretion of TNF-α in a dose dependent manner (FIG. 1b).

TABLE 2

| Example | TNF-α IC$_{50}$ |
|---|---|
| 15 | ++ |
| 27 | + |
| 32 | ++ |
| 39 | + |
| 41 | ++ |
| 51 | ++ |
| 53 | + |
| 54 | ++ |
| 65 | ++ |
| 85 | +++ |
| 95 | ++ |
| 98 | + |
| 100 | +++ |
| 102 | ++ |
| 103 | +++ |
| 104 | +++ |
| 106 | +++ |
| 113 | ++ |
| 116 | ++ |
| 125 | + |

Compounds with an IC$_{50}$ ≥ 0.1 µM: +
Compounds with an IC$_{50}$ 0.1-0.01 µM: ++
Compounds with an IC$_{50}$ 0.01-0.001 µM: +++

In Vivo CFA (Complete Freund's Adjuvant)-Induced Inflammatory Pain in Rats

The complete Freund's adjuvant (CFA)-induced inflammatory pain model can be used to evaluate the effect of the chemical compounds on pain.

On day 0, rats (Sprague-Dawley, 10 animals/group) receive either vehicle or the chemical compound before injection of CFA followed by daily treatment until day 7. To inject 100 µl of 100% CFA (Sigma, order ID: F5881) subcutaneously into the plantar surface of the left hind paw rats are anesthetized with 2.5-5% isoflurane in oxygen. Mechanical allodynia is assessed using von Frey filaments according to the "up-down" method described by Chaplan et al (1994) on day 7. Here, calibrated monofilaments (von Frey filaments) are applied to the plantar surface of the rat hind paw for a period of 4-6 seconds, or until a nocifensive paw withdrawal occurres.

In Vivo Pharmacokinetics in Rats

For in vivo pharmacokinetic experiments test compounds were are administered to male Wistar rats intravenously at doses of 0.3 to 1 mg/kg and intragastral at doses of 0.5 to 10 mg/kg formulated as solutions using solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g. 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparintubes (Monovettee, Sarstedt) and centrifuged for 15 min at 3000 rpm. An aliquot of 100 µL from the supernatant (plasma) was taken and precipitated by addition of 400 µL cold acetonitril and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0–tlast)norm: Area under the concentration-time curve from t=0 h to the last time point for which plasma concentrations could be measured divided by the administered dose (in kg*h/L); t½: terminal half-life (in h); F: oral bioavailability: AUCnorm after intragastral administration divided by AUCnorm after intravenous administration (in %).

The invention claimed is:

1. A compound of formula (I):

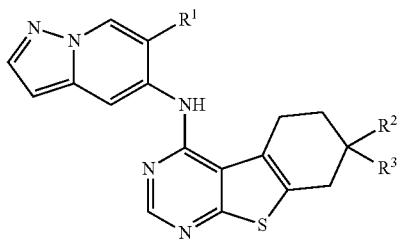

(I)

in which:

R$^1$ represents a hydrogen atom or a halogen atom or a group selected from the group consisting of: hydroxy-, cyano-, $C_1$-$C_6$-alkyl-, $C_2$-$C_6$-alkenyl-, $C_2$-$C_6$-alkynyl-, $C_1$-$C_6$-alkoxy-, halo-$C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, (5- to 10-membered heterocycloalkenyl)-O—, —N(R$^{5a}$)R$^{5b}$, —SR$^{5a}$, and —SF$_5$ groups;

wherein said $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkyl-, $C_4$-$C_8$-cycloalkenyl-, $C_3$-$C_6$-cycloalkyloxy-, (3- to 10-membered heterocycloalkyl)-, (3- to 10-membered heterocycloalkyl)-O—, $C_5$-$C_8$-cycloalkenyloxy-, (5- to 10-membered heterocycloalkenyl)-, and (5- to 10-membered heterocycloalkenyl)-O— groups are optionally substituted, identically or differently, with 1, 2, 3, 4 or 5 R$^4$ groups;

R$^2$ represents a hydrogen atom or a group selected from the group consisting of: $C_1$-$C_6$-alkyl-, $C_2$-$C_6$-alkenyl-, $C_1$-$C_6$-alkoxy-, halo-$C_1$-$C_6$-alkyl-, and halo-$C_1$-$C_6$-alkoxy-groups;

wherein said $C_1$-$C_6$-alkyl-, $C_2$-$C_6$-alkenyl-, and $C_1$-$C_6$-alkoxy-groups are optionally substituted, identically or differently, with 1, 2, or 3 R$^7$ groups;

R$^3$ represents a hydrogen atom or a group selected from the group consisting of: $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, heteroaryl-, cyano-, and —(CH$_2$)$_q$—X—(CH$_2$)$_p$—R$^5$ groups;

wherein said $C_1$-$C_6$-alkyl-, $C_3$-$C_6$-cycloalkyl-, $C_4$-$C_6$-cycloalkenyl-, $C_2$-$C_6$-alkenyl-, $C_2$-$C_6$-alkynyl-, 3- to 10-membered heterocycloalkyl-, 4- to 10-membered heterocycloalkenyl-, aryl-, and heteroaryl-groups are optionally substituted, identically or differently, with 1, 2, 3, 4 or 5 R$^4$ groups;

X represents a bond or a bivalent group selected from the group consisting of: —O—, —S—, —S(=O)—, —S(=O)$_2$—, —S(=O)—N(R$^{5a}$)—, —N(R$^{5a}$)—S(=O)—, —S(=O)$_2$—N(R$^{5a}$)—, —N(R$^{5a}$)—S (=O)₂—, —S(=O)(=NR⁵ᵃ)—, —C(=O)—, —N(R⁵ᵃ)—, —C(=O)—O—, —O—C(=O)—, —C(=S)—, —O—C(=S)—, —C(=O)—N(R⁵ᵃ)—, —N(R⁵ᵃ)—C(=O)—, —N(R⁵ᵃ)—C(=O)—N(R⁵ᵇ)—, —O—C(=O)—N(R⁵ᵃ)—, and —N(R⁵ᵃ)—C(=O)—O— bivalent groups;

R⁴ represents halo-, hydroxy-, oxo-(O=), cyano-, nitro-, C₁-C₆-alkyl-, C₂-C₆-alkenyl-, C₂-C₆-alkynyl-, halo-C₁-C₆-alkyl-, C₁-C₆-alkoxy-, halo-C₁-C₆-alkoxy-, hydroxy-C₁-C₆-alkyl-, C₁-C₆-alkoxy-C₁-C₆-alkyl-, halo-C₁-C₆-alkoxy-C₁-C₆-alkyl-, R⁶—O—, —C(=O)—R⁶, —C(=O)—O—R⁶, —O—C(=O)—R⁶, —N(R⁶ᵃ)—C(=O)—R⁶ᵇ, —N(R⁶ᵃ)—C(=O)—O—R⁶ᵇ, —N(R⁶ᵃ)—C(=O)—N(R⁶ᵇ)R⁶ᶜ, —N(R⁶ᵃ)R⁶ᵇ, —N(R⁶ᵃ)R⁶ᵈ, —C(=O)—N(R⁶ᵃ)R⁶ᵇ, R⁶—S—, R⁶—S(=O)—, R⁶—S(=O)₂—, —N(R⁶ᵃ)—S(=O)—R⁶ᵇ, —S(=O)—N(R⁶ᵃ)R⁶ᵇ, —N(R⁶ᵃ)—S(=O)₂—R⁶ᵇ, —S(=O)₂—N(R⁶ᵃ)R⁶ᵇ, —S(=O)=N(R⁶ᵃ)R⁶ᵇ, —N=S(=O)(R⁶ᵃ)R⁶ᵇ, or —(C₁-C₆-alkyl)-N(R⁶ᵃ)R⁶ᵇ;

R⁵ᵃ, R⁵ᵇ are the same or different and are independently selected from R⁵;

R⁵ represents a hydrogen atom or a group selected from the group consisting of: C₁-C₆-alkyl-, C₃-C₆-cycloalkyl-, 3- to 10-membered heterocycloalkyl-, aryl-, and heteroaryl-groups;

wherein said C₁-C₆-alkyl-, C₃-C₆-cycloalkyl-, 3- to 10-membered heterocycloalkyl-, aryl-, and heteroaryl-groups are optionally substituted, identically or differently, with 1, 2, 3, 4 or 5 R⁴ groups;

or N(R⁵ᵃ)R⁵ together represent a 3- to 10-membered heterocycloalkyl-group, said group being optionally substituted, identically or differently, with 1, 2, 3, 4 or 5 R⁴ groups;

R⁶ᵃ, R⁶ᵇ, R⁶ᶜ are the same or different and are independently selected from R⁶;

R⁶ represents a hydrogen atom, a C₁-C₆-alkyl-group, or a C₃-C₆-cycloalkyl-group;

or R⁶ᵃ and R⁶ᵇ, or R⁶ᵃ and R⁶ᶜ, or R⁶ᵇ and R⁶ᶜ together may form a C₂-C₆-alkylene group, in which optionally one methylene can be replaced by —O—, —C(=O)—, —NH—, or —N(C₁-C₄-alkyl)-;

R⁶ᵈ represents —(C₁-C₆-alkyl)-N(R⁶ᵃ)R⁶ᵇ;

R⁷ represents halo-, hydroxy-, oxo-(O=), cyano-, or nitro-;

p represents an integer of 0, 1, 2 or 3; and q represents an integer of 0, 1, 2 or 3;

or a pharmaceutical acceptable salt thereof, or a mixture of same.

2. The compound according to claim 1,
wherein
R¹ represents a hydrogen atom or a halogen atom or a group selected from the group consisting of: C₁-C₃-alkyl-, C₁-C₃-alkoxy-, halo-C₁-C₃-alkyl-, —N(CH₃)₂, and —S—(C₁-C₃-alkyl) groups.

3. The compound according to claim 1,
wherein
R¹ represents a hydrogen atom or a —O—CH₃ group.

4. The compound according to claim 1,
wherein
R² represents a hydrogen atom.

5. The compound according to claim 1,
wherein
R³ represents C₁-C₆-alkyl- or —(CH₂)q—X—(CH₂)p—R⁵ group;
wherein said C₁-C₆-alkyl-group is optionally substituted, identically or differently, with 1, 2, 3, 4 or 5 R⁴ groups.

6. The compound according to claim 1,
wherein
X represents a bivalent group selected from the group consisting of: —C(=O)—, —C(=O)—O—, and —C(=O)—N(R⁵ᵃ)— groups.

7. The compound according to claim 1,
wherein
X represents a bivalent —C(=O)—N(R⁵ᵃ)— group.

8. The compound according to claim 1,
wherein
R⁴ represents halo-, hydroxy-, cyano-, C₁-C₃-alkyl-, C₁-C₃-alkoxy-, —N(R⁶ᵃ)—C(=O)—O—R⁶ᵇ, —N(R⁶ᵃ)R⁶ᵇ, —N(R⁶ᵃ)R⁶ᵈ, —C(=O)—N(R⁶ᵃ)R⁶ᵇ, or —(C₁-C₃-alkyl)-N(R⁶ᵃ)R⁶ᵇ.

9. The compound according to claim 1,
wherein
R⁵ᵃ, R⁵ᵇ are the same or different and are independently selected from R⁵;
R⁵ represents a hydrogen atom or a C₁-C₃-alkyl-group;
wherein said C₁-C₃-alkyl-group is optionally substituted, identically or differently, with 1, 2 or 3 R⁴ groups.

10. The compound according to claim 1,
wherein
N(R⁵ᵃ)R⁵ together represent a 3- to 10-membered heterocycloalkyl-group,
wherein said 3- to 10-membered heterocycloalkyl-group is optionally substituted, identically or differently, with 1 or 2 R⁴ groups.

11. The compound according to claim 1,
wherein
R⁶ᵃ, R⁶ᵇ, R⁶ᶜ are the same or different and are independently selected from R⁶;
R⁶ represents a hydrogen atom or a C₁-C₃-alkyl-group; and
R⁶ᵈ represents a —(C₁-C₃-alkyl)-N(R⁶ᵃ)R⁶ᵇ group.

12. The compound according to claim 1, wherein
p represents 0; and
q represents 0.

13. A compound selected from the group consisting of:
(RS) N,N-dimethyl-4-(pyrazolo[1,5-a]pyridin-5-ylamino)-5,6,7,8-tetrahydro[1]benzothieno[2,3-d]pyrimidine-7-carboxamide,
(7S)-4-(pyrazolo[1,5-a]pyridin-5-ylamino)-5,6,7,8-tetrahydro[1]benzothieno[2,3-d]pyrimidine-7-carboxylic acid,
[(3R)-3-methylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone,
(7S)—N-[2-(dimethylamino)ethyl]-N-methyl-4-(pyrazolo[1,5-a]pyridin-5-ylamino)-5,6,7,8-tetrahydro[1]benzothieno[2,3-d]pyrimidine-7-carboxamide,
[(2R,6S)-2,6-dimethylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone,
[(3R)-3-(dimethylamino)pyrrolidin-1-yl][(7S)-4-(pyrazolo[1,5-a]pyridin-5-ylamino)-5,6,7,8-tetrahydro[1]benzothieno[2,3-d]pyrimidin-7-yl]methanone,
[(3S)-3-methylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone,
(7S)—N-(2-methoxyethyl)-N-methyl-4-(pyrazolo[1,5-a]pyridin-5-ylamino)-5,6,7,8-tetrahydro[1]benzothieno[2,3-d]pyrimidine-7-carboxamide,
[(2S,6S)-2,6-dimethylmorpholin-4-yl][(7S)-4-(pyrazolo[1,5-a]pyridin-5-ylamino)-5,6,7,8-tetrahydro[1]benzothieno[2,3-d]pyrimidin-7-yl]methanone,

[(2R,6R)-2,6-dimethylmorpholin-4-yl][(7S)-4-(pyrazolo [1,5-a]pyridin-5-ylamino)-5,6,7,8-tetrahydro[1]benzothieno[2,3-d]pyrimidin-7-yl]methanone,
morpholin-4-yl[(7S)-4-(pyrazolo[1,5-a]pyridin-5-ylamino)-5,6,7,8-tetrahydro[1]benzothieno[2,3-d]pyrimidin-7-yl]methanone,
3-Azabicyclo[3.1.0]hex-3-yl[(7S)-4-(pyrazolo[1,5-a]pyridin-5-ylamino)-5,6,7,8-tetrahydro[1]benzothieno[2,3-d]pyrimidin-7-yl]methanone,
[(3R,5S)-3,5-dimethylmorpholin-4-yl][(7S)-4-(pyrazolo [1,5-a]pyridin-5-ylamino)-5,6,7,8-tetrahydro[1]benzothieno[2,3-d]pyrimidin-7-yl]methanone,
[(3R,5R)-3,5-dimethylmorpholin-4-yl][(7S)-4-(pyrazolo [1,5-a]pyridin-5-ylamino)-5,6,7,8-tetrahydro[1]benzothieno[2,3-d]pyrimidin-7-yl]methanone,
(7S)-4-[(6-methoxypyrazolo[1,5-a]pyridin-5-yl)amino]-N,N-dimethyl-5,6,7,8-tetrahydro[1]benzothieno[2,3-d]pyrimidine-7-carboxamide,
(7S)—N-isopropyl-N-methyl-4-(pyrazolo[1,5-a]pyridin-5-ylamino)-5,6,7,8-tetrahydro[1]benzothieno[2,3-d]pyrimidine-7-carboxamide,
(7S)—N,N-dimethyl-4-(pyrazolo[1,5-a]pyridin-5-ylamino)-5,6,7,8-tetrahydro[1]benzothieno[2,3-d]pyrimidine-7-carboxamide,
(7S)—N-(2,2-difluoroethyl)-N-methyl-4-(pyrazolo[1,5-a]pyridin-5-ylamino)-5,6,7,8-tetrahydro[1]benzothieno[2,3-d]pyrimidine-7-carboxamide,
(7S)—N-(2-hydroxy-2-methylpropyl)-N-methyl-4-(pyrazolo[1,5-a]pyridin-5-ylamino)-5,6,7,8-tetrahydro[1]benzothieno[2,3-d]pyrimidine-7-carboxamide,
azetidin-1-yl[(7S)-4-(pyrazolo[1,5-a]pyridin-5-ylamino)-5,6,7,8-tetrahydro[1]benzothieno[2,3-d]pyrimidin-7-yl]methanone,
(7S)—N-ethyl-N-(2-hydroxyethyl)-4-(pyrazolo[1,5-a]pyridin-5-ylamino)-5,6,7,8-tetrahydro[1]benzothieno[2,3-d]pyrimidine-7-carboxamide,
1-{[(7S)-4-(pyrazolo[1,5-a]pyridin-5-ylamino)-5,6,7,8-tetrahydro[1]benzothieno[2,3-d]pyrimidin-7-yl]carbonyl}azetidine-3-carbonitrile,
(3,3-difluoroazetidin-1-yl)[(7S)-4-(pyrazolo[1,5-a]pyridin-5-ylamino)-5,6,7,8-tetrahydro[1]benzothieno[2,3-d]pyrimidin-7-yl]methanone,
(3-hydroxyazetidin-1-yl)[(7S)-4-(pyrazolo[1,5-a]pyridin-5-ylamino)-5,6,7,8-tetrahydro[1]benzothieno[2,3-d]pyrimidin-7-yl]methanone,
tert-butyl [2-(methyl{[(7S)-4-(pyrazolo[1,5-a]pyridin-5-ylamino)-5,6,7,8-tetrahydro[1]benzothieno[2,3-d]pyrimidin-7-yl]carbonyl}amino)ethyl]carbamate,
(7S)—N-[2-(dimethylamino)-2-oxoethyl]-N-methyl-4-(pyrazolo[1,5-a]pyridin-5-ylamino)-5,6,7,8-tetrahydro[1]benzothieno[2,3-d]pyrimidine-7-carboxamide,
(7S)—N-[3-(dimethylamino)propyl]-N-methyl-4-(pyrazolo[1,5-a]pyridin-5-ylamino)-5,6,7,8-tetrahydro[1]benzothieno[2,3-d]pyrimidine-7-carboxamide,
[3-(dimethylamino)azetidin-1-yl][(7S)-4-(pyrazolo[1,5-a]pyridin-5-ylamino)-5,6,7,8-tetrahydro[1]benzothieno[2,3-d]pyrimidin-7-yl]methanone,
(4-methylpiperazin-1-yl)[(7S)-4-(pyrazolo[1,5-a]pyridin-5-ylamino)-5,6,7,8-tetrahydro[1]benzothieno[2,3-d]pyrimidin-7-yl]methanone,
(3-hydroxy-3-methylazetidin-1-yl)[(7S)-4-(pyrazolo[1,5-a]pyridin-5-ylamino)-5,6,7,8-tetrahydro[1]benzothieno[2,3-d]pyrimidin-7-yl]methanone,
{4-[2-(dimethylamino)ethyl]piperazin-1-yl}[(7S)-4-(pyrazolo[1,5-a]pyridin-5-ylamino)-5,6,7,8-tetrahydro[1]benzothieno[2,3-d]pyrimidin-7-yl]methanone,
[4-(dimethylamino)piperidin-1-yl][(7S)-4-(pyrazolo[1,5-a]pyridin-5-ylamino)-5,6,7,8-tetrahydro[1]benzothieno[2,3-d]pyrimidin-7-yl]methanone,
1-{[(7S)-4-(pyrazolo[1,5-a]pyridin-5-ylamino)-5,6,7,8-tetrahydro[1]benzothieno[2,3-d]pyrimidin-7-yl]carbonyl}piperidin-4-one,
(3,3-difluoropyrrolidin-1-yl)[(7S)-4-(pyrazolo[1,5-a]pyridin-5-ylamino)-5,6,7,8-tetrahydro[1]benzothieno[2,3-d]pyrimidin-7-yl]methanone,
2-oxa-6-azaspiro[3.3]hept-6-yl[(7S)-4-(pyrazolo[1,5-a]pyridin-5-ylamino)-5,6,7,8-tetrahydro[1]benzothieno[2,3-d]pyrimidin-7-yl]methanone,
(1S,4S)-2-oxa-5-azabicyclo[2.2.1]hept-5-yl[(7S)-4-(pyrazolo[1,5-a]pyridin-5-ylamino)-5,6,7,8-tetrahydro[1]benzothieno[2,3-d]pyrimidin-7-yl]methanone,
(1R,4R)-2-oxa-5-azabicyclo[2.2.1]hept-5-yl[(7S)-4-(pyrazolo[1,5-a]pyridin-5-ylamino)-5,6,7,8-tetrahydro[1]benzothieno[2,3-d]pyrimidin-7-yl]methanone
[(1S,4S)-5-methyl-2,5-diazabicyclo[2.2.1]hept-2-yl][(7S)-4-(pyrazolo[1,5-a]pyridin-5-ylamino)-5,6,7,8-tetrahydro[1]benzothieno[2,3-d]pyrimidin-7-yl]methanone,
(7S)—N-(2-aminoethyl)-N-methyl-4-(pyrazolo[1,5-a]pyridin-5-ylamino)-5,6,7,8-tetrahydro[1]benzothieno[2,3-d]pyrimidine-7-carboxamide,
(4-{[2-(dimethylamino)ethyl](methyl)amino}piperidin-1-yl)[(7S)-4-(pyrazolo[1,5-a]pyridin-5-ylamino)-5,6,7,8-tetrahydro[1]benzothieno[2,3-d]pyrimidin-7-yl]methanone,
[(3S)-3-(dimethylamino)pyrrolidin-1-yl][(7S)-4-(pyrazolo[1,5-a]pyridin-5-ylamino)-5,6,7,8-tetrahydro[1]benzothieno[2,3-d]pyrimidin-7-yl]methanone,
[(1R,4R)-5-methyl-2,5-diazabicyclo[2.2.1]hept-2-yl][(7S)-4-(pyrazolo[1,5-a]pyridin-5-ylamino)-5,6,7,8-tetrahydro[1]benzothieno[2,3-d]pyrimidin-7-yl]methanone,
(7S)—N-methyl-4-(pyrazolo[1,5-a]pyridin-5-ylamino)-N-(3,3,3-trifluoropropyl)-5,6,7,8-tetrahydro[1]benzothieno[2,3-d]pyrimidine-7-carboxamide,
(2,2-dimethylpyrrolidin-1-yl)[(7S)-4-(pyrazolo[1,5-a]pyridin-5-ylamino)-5,6,7,8-tetrahydro[1]benzothieno[2,3-d]pyrimidin-7-yl]methanone,
(7S)—N-[(2S)-1-methoxypropan-2-yl]-N-methyl-4-(pyrazolo[1,5-a]pyridin-5-ylamino)-5,6,7,8-tetrahydro[1]benzothieno[2,3-d]pyrimidine-7-carboxamide,
(7S)—N-[(2R)-1-methoxypropan-2-yl]-N-methyl-4-(pyrazolo[1,5-a]pyridin-5-ylamino)-5,6,7,8-tetrahydro[1]benzothieno[2,3-d]pyrimidine-7-carboxamide,
(7S)—N-[(2S)-2-methoxypropyl]-N-methyl-4-(pyrazolo[1,5-a]pyridin-5-ylamino)-5,6,7,8-tetrahydro[1]benzothieno[2,3-d]pyrimidine-7-carboxamide,
(7S)—N-[(2R)-2-methoxypropyl]-N-methyl-4-(pyrazolo[1,5-a]pyridin-5-ylamino)-5,6,7,8-tetrahydro[1]benzothieno[2,3-d]pyrimidine-7-carboxamide,
(7S)—N-(1-methoxy-2-methylpropan-2-yl)-N-methyl-4-(pyrazolo[1,5-a]pyridin-5-ylamino)-5,6,7,8-tetrahydro[1]benzothieno[2,3-d]pyrimidine-7-carboxamide,
(7S)-4-[(6-methoxypyrazolo[1,5-a]pyridin-5-yl)amino]-N-methyl-N-(3,3,3-trifluoropropyl)-5,6,7,8-tetrahydro[1]benzothieno[2,3-d]pyrimidine-7-carboxamide,
(7S)—N-(2-hydroxy-2-methylpropyl)-4-[(6-methoxypyrazolo[1,5-a]pyridin-5-yl)amino]-N-methyl-5,6,7,8-tetrahydro[1]benzothieno[2,3-d]pyrimidine-7-carboxamide,
(7S)—N-(2,2-difluoroethyl)-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-isopropyl-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-ethyl-N-(2-hydroxyethyl)-4-[(6-methoxypyrazolo [1,5-a]pyridin-5-yl)amino]-5,6,7,8-tetrahydro[1]benzothieno[2,3-d]pyrimidine-7-carboxamide, (7S)—N-(2-methoxyethyl)-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-(2-aminoethyl)-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-[2-(dimethylamino)ethyl]-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-[2-(dimethylamino)-2-oxoethyl]-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-[3-(dimethylamino)propyl]-4-[(6-methoxypyrazolo[1,5-a]pyridin-5-yl)amino]-N-methyl-5,6,7,8-tetrahydro[1]benzothieno[2,3-d]pyrimidine-7-carboxamide, azetidin-1-yl{(7S)-4-[(6-methoxypyrazolo[1,5-a]pyridin-5-yl)amino]-5,6,7,8-tetrahydro[1]benzothieno[2,3-d]pyrimidin-7-yl}methanone, (3,3-difluoroazetidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone, (3-hydroxyazetidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone, (3-hydroxy-3-methylazetidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone, 1-({(7S)-4-[(6-methoxypyrazolo[1,5-a]pyridin-5-yl)amino]-5,6,7,8-tetrahydro[1]benzothieno[2,3-d]pyrimidin-7-yl}carbonyl)azetidine-3-carbonitrile,

[3-(dimethylamino)azetidin-1-yl]{(7S)-4-[(6-methoxypyrazolo[1,5-a]pyridin-5-yl)amino]-5,6,7,8-tetrahydro[1]benzothieno[2,3-d]pyrimidin-7-yl}methanone, {(7S)-4-[(6-methoxypyrazolo[1,5-a]pyridin-5-yl)amino]-5,6,7,8-tetrahydro[1]benzothieno[2,3-d]pyrimidin-7-yl}(4-methylpiperazin-1-yl)methanone, {4-[2-(dimethylamino)ethyl]piperazin-1-yl}{(7S)-4-[(6-methoxypyrazolo[1,5-a]pyridin-5-yl)amino]-5,6,7,8-tetrahydro[1]benzothieno[2,3-d]pyrimidin-7-yl}methanone, (4-{[2-(dimethylamino)ethyl](methyl)amino}piperidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone,

[4-(dimethylamino)piperidin-1-yl]{(7S)-4-[(6-methoxypyrazolo[1,5-a]pyridin-5-yl)amino]-5,6,7,8-tetrahydro[1]benzothieno[2,3-d]pyrimidin-7-yl}methanone, 1-({(7S)-4-[(6-methoxypyrazolo[1,5-a]pyridin-5-yl)amino]-5,6,7,8-tetrahydro[1]benzothieno[2,3-d]pyrimidin-7-yl}carbonyl)piperidin-4-one, (3,3-difluoropyrrolidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone, (2,2-dimethylpyrrolidin-1-yl){(7S)-4-[(6-methoxypyrazolo[1,5-a]pyridin-5-yl)amino]-5,6,7,8-tetrahydro[1]benzothieno[2,3-d]pyrimidin-7-yl}methanone, {(7S)-4-[(6-methoxypyrazolo[1,5-a]pyridin-5-yl)amino]-5,6,7,8-tetrahydro[1]benzothieno[2,3-d]pyrimidin-7-yl}(morpholin-4-yl)methanone, {(7S)-4-[(6-methoxypyrazolo[1,5-a]pyridin-5-yl)amino]-5,6,7,8-tetrahydro[1]benzothieno[2,3-d]pyrimidin-7-yl}(2-oxa-6-azaspiro[3.3]hept-6-yl)methanone,

[(2R,6S)-2,6-dimethylmorpholin-4-yl]{(7S)-4-[(6-methoxypyrazolo[1,5-a]pyridin-5-yl)amino]-5,6,7,8-tetrahydro[1]benzothieno[2,3-d]pyrimidin-7-yl}methanone,

[(2R,6R)-2,6-dimethylmorpholin-4-yl]{(7S)-4-[(6-methoxypyrazolo[1,5-a]pyridin-5-yl)amino]-5,6,7,8-tetrahydro[1]benzothieno[2,3-d]pyrimidin-7-yl}methanone,

[(2S,6S)-2,6-dimethylmorpholin-4-yl]{(7S)-4-[(6-methoxypyrazolo[1,5-a]pyridin-5-yl)amino]-5,6,7,8-tetrahydro[1]benzothieno[2,3-d]pyrimidin-7-yl}methanone, {(7S)-4-[(6-methoxypyrazolo[1,5-a]pyridin-5-yl)amino]-5,6,7,8-tetrahydro[1]benzothieno[2,3-d]pyrimidin-7-yl}[(3S)-3-methylmorpholin-4-yl]methanone, {(7S)-4-[(6-methoxypyrazolo[1,5-a]pyridin-5-yl)amino]-5,6,7,8-tetrahydro[1]benzothieno[2,3-d]pyrimidin-7-yl}[(3R)-3-methylmorpholin-4-yl]methanone, {(7S)-4-[(6-methoxypyrazolo[1,5-a]pyridin-5-yl)amino]-5,6,7,8-tetrahydro[1]benzothieno[2,3-d]pyrimidin-7-yl}[(1S,4S)-2-oxa-5-azabicyclo[2.2.1]hept-5-yl]methanone, {(7S)-4-[(6-methoxypyrazolo[1,5-a]pyridin-5-yl)amino]-5,6,7,8-tetrahydro[1]benzothieno[2,3-d]pyrimidin-7-yl}[(1R,4R)-2-oxa-5-azabicyclo[2.2.1]hept-5-yl]methanone, {(7S)-4-[(6-methoxypyrazolo[1,5-a]pyridin-5-yl)amino]-5,6,7,8-tetrahydro[1]benzothieno[2,3-d]pyrimidin-7-yl}[(1S,4S)-5-methyl-2,5-diazabicyclo[2.2.1]hept-2-yl]methanone, {(7S)-4-[(6-methoxypyrazolo[1,5-a]pyridin-5-yl)amino]-5,6,7,8-tetrahydro[1]benzothieno[2,3-d]pyrimidin-7-yl}[(1R,4R)-5-methyl-2,5-diazabicyclo[2.2.1]hept-2-yl]methanone, (7S)—N-[(2S)-1-methoxypropan-2-yl]-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-[(2R)-1-methoxypropan-2-yl]-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-[(2S)-2-methoxypropyl]-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-[(2R)-2-methoxypropyl]-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)—N-(1-methoxy-2-methylpropan-2-yl)-4-[(6-methoxypyrazolo[1,5-a]pyridin-5-yl)amino]-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N,N-dimethyl-5,6,7,8-tetrahydro[1]benzothieno[2,3-d]pyrimidine-7-carboxamide, (7S)-4-[(6-chloropyrazolo[1,5-a]pyridin-5-yl)amino]-N-methyl-N-(3,3,3-trifluoropropyl)-5,6,7,8-tetrahydro[1]benzothieno[2,3-d]pyrimidine-7-carboxamide, (7S)-4-[(6-chloropyrazolo[1,5-a]pyridin-5-yl)amino]-N-(2-hydroxy-2-methylpropyl)-N-methyl-5,6,7,8-tetrahydro[1]benzothieno[2,3-d]pyrimidine-7-carboxamide (7S)-4-[(6-chloropyrazolo[1,5-a]pyridin-5-yl)amino]-N-(2,2-difluoroethyl)-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-isopropyl-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-ethyl-N-(2-hydroxyethyl)-5,6,7,8-tetrahydro[1]benzothieno[2,3-d]pyrimidine-7-carboxamide, (7S)-4-[(6-chloropyrazolo[1,5-a]pyridin-5-yl)amino]-N-(2-methoxyethyl)-N-methyl-5,6,7,8-tetrahydro[1]benzothieno[2,3-d]pyrimidine-7-carboxamide, (7S)—N-(2-aminoethyl)-4-[(6-chloropyrazolo[1,5-a]pyridin-5-yl)amino]-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-[2-(dimethylamino)ethyl]-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-[2-(dimethylamino)-2-oxoethyl]-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-[3-(dimethylamino)propyl]-N-methyl-5,6,7,8-tetrahydro[1]benzothieno[2,3-d]pyrimidine-7-carboxamide, azetidin-1-yl{(7S)-4-[(6-chloropyrazolo[1,5-a]pyridin-5-yl)amino]-5,6,7,8-tetrahydro[1]benzothieno[2,3-d]pyrimidin-7-yl}methanone, {(7S)-4-[(6-chloropyrazolo[1,5-a]pyridin-5-yl)amino]-5,6,7,8-tetrahydro[1]benzothieno[2,3-d]pyrimidin-7-yl}(3,3-difluoroazetidin-1-yl)methanone, {(7S)-4-[(6-chloropyrazolo[1,5-a]pyridin-5-yl)amino]-5,6,7,8-tetrahydro[1]benzothieno[2,3-d]pyrimidin-7-yl}(3-hydroxyazetidin-1-yl)methanone, {(7S)-4-[(6-chloropyrazolo[1,5-a]pyridin-5-yl)amino]-5,6,7,8-tetrahydro[1]benzothieno[2,3-d]pyrimidin-7-yl}(3-hydroxy-3-methylazetidin-1-yl)methanone, 1-({(7S)-4-[(6-chloropyrazolo[1,5-a]pyridin-5-yl)amino]-5,6,7,8-tetrahydro[1]benzothieno[2,3-d]pyrimidin-7-yl}carbonyl)azetidine-3-carbonitrile, {(7S)-4-[(6-chloropyrazolo[1,5-a]pyridin-5-yl)amino]-5,6,7,8-tetrahydro[1]benzothieno[2,3-d]pyrimidin-7-yl}[3-(dimethylamino)azetidin-1-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}(4-methylpiperazin-1-yl)methanone, {(7S)-4-[(6-chloropyrazolo[1,5-a]pyridin-5-yl)amino]-5,6,7,8-tetrahydro[1]benzothieno[2,3-d]pyrimidin-7-yl}(4-{2-(dimethylamino)ethyl]piperazin-1-yl}methanone, {(7S)-4-[(6-chloropyrazolo[1,5-a]pyridin-5-yl)amino]-5,6,7,8-tetrahydro[1]benzothieno[2,3-d]pyrimidin-7-yl}(4-{[2-(dimethylamino)ethyl](methyl)amino}piperidin-1-yl)methanone, {(7S)-4-[(6-chloropyrazolo[1,5-a]pyridin-5-yl)amino]-5,6,7,8-tetrahydro[1]benzothieno[2,3-d]pyrimidin-7-yl}[4-(dimethylamino)piperidin-1-yl]methanone, 1-({(7S)-4-[(6-chloropyrazolo[1,5-a]pyridin-5-yl)amino]-5,6,7,8-tetrahydro[1]benzothieno[2,3-d]pyrimidin-7-yl}carbonyl)piperidin-4-one, {(7S)-4-[(6-chloropyrazolo[1,5-a]pyridin-5-yl)amino]-5,6,7,8-tetrahydro[1]benzothieno[2,3-d]pyrimidin-7-yl}(3,3-difluoropyrrolidin-1-yl)methanone, {(7S)-4-[(6-chloropyrazolo[1,5-a]pyridin-5-yl)amino]-5,6,7,8-tetrahydro[1]benzothieno[2,3-d]pyrimidin-7-yl}(2,2-dimethylpyrrolidin-1-yl)methanone, {(7S)-4-[(6-chloropyrazolo[1,5-a]pyridin-5-yl)amino]-5,6,7,8-tetrahydro[1]benzothieno[2,3-d]pyrimidin-7-yl}(morpholin-4-yl)methanone, {(7S)-4-[(6-chloropyrazolo[1,5-a]pyridin-5-yl)amino]-5,6,7,8-tetrahydro[1]benzothieno[2,3-d]pyrimidin-7-yl}(2-oxa-6-azaspiro[3.3]hept-6-yl)methanone, {(7S)-4-[(6-chloropyrazolo[1,5-a]pyridin-5-yl)amino]-5,6,7,8-tetrahydro[1]benzothieno[2,3-d]pyrimidin-7-yl}[(2R,6S)-2,6-dimethylmorpholin-4-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}[(2R,6R)-2,6-dimethylmorpholin-4-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}[(2S,6S)-2,6-dimethylmorpholin-4-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}[(3 S)-3-methylmorpholin-4-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}[(3R)-3-methylmorpholin-4-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}[(1S,4S)-2-oxa-5-azabicyclo[2.2.1]kept-5-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}[(1R,4R)-2-oxa-5-azabicyclo[2.2.1]kept-5-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}[(1S,4S)-5-methyl-2,5-diazabicyclo[2.2.1]hept-2-yl]methanone, {(7S)-4-[(6-chloropyrazolo[1,5-a]pyridin-5-yl)amino]-5,6,7,8-tetrahydro[1]benzothieno[2,3-d]pyrimidin-7-yl}[(1R,4R)-5-methyl-2,5-diazabicyclo[2.2.1]hept-2-yl]methanone, (7S)-4-[(6-chloropyrazolo[1,5-a]pyridin-5-yl)amino]-N-[(2S)-1-methoxypropan-2-yl]-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-[(2R)-1-methoxypropan-2-yl]-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-[(2S)-2-methoxypropyl]-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-[(2R)-2-methoxypropyl]-N-methyl-5,6,7,8-tetrahydro[1]benzothieno[2,3-d]pyrimidine-7-carboxamide, (7S)-4-[(6-chloropyrazolo[1,5-a]pyridin-5-yl)amino]-N-[1-methoxy-2-methylpropan-2-yl]-N-methyl-5,6,7,8-tetrahydro[1]benzothieno[2,3-d]pyrimidine-7-carboxamide, (7S)-4-[(6-(dimethylamino)pyrazolo[1,5-a]pyridin-5-yl)amino]-N,N-dimethyl-5,6,7,8-tetrahydro[1]benzothieno[2,3-d]pyrimidine-7-carboxamide, (7S)-4-[(6-(dimethylamino)pyrazolo[1,5-a]pyridin-5-yl)amino]-N-methyl-N-(3,3,3-trifluoropropyl)-5,6,7,8-tetrahydro[1]benzothieno[2,3-d]pyrimidine-7-carboxamide, (7S)—N-(2-hydroxy-2-methylpropyl)-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide, (7S)—N-(2,2-difluoroethyl)-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide, (7S)-4-[(6-(dimethylamino)pyrazolo[1,5-a]pyridin-5-yl)amino]-N-isopropyl-N-methyl-5,6,7,8-tetrahydro[1]benzothieno[2,3-d]pyrimidine-7-carboxamide, (7S)-4-[(6-(dimethylamino)pyrazolo[1,5-a]pyridin-5-yl)amino]-N-ethyl-N-(2-hydroxyethyl)-5,6,7,8-tetrahydro[1]benzothieno[2,3-d]pyrimidine-7-carboxamide, (7S)-4-[(6-(dimethylamino)pyrazolo[1,5-a]pyridin-5-yl)amino]-N-(2-methoxyethyl)-N-methyl-5,6,7,8-tetrahydro[1]benzothieno[2,3-d]pyrimidine-7-carboxamide, (7S)—N-(2-aminoethyl)-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide, (7S)—N-[2-(dimethylamino)ethyl]-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide, (7S)—N-[2-(dimethylamino)-2-oxoethyl]-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide, (7S)—N-[3-(dimethylamino)propyl]-4-[(6-(dimethylamino)pyrazolo[1,5-a]pyridin-5-yl)amino]-N-methyl-5,6,7,8-tetrahydro[1]benzothieno[2,3-d]pyrimidine-7-carboxamide, azetidin-1-yl{(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone, (3,3-difluoroazetidin-1-yl){(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}(3-hydroxyazetidin-1-yl)methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}(3-hydroxy-3-methylazetidin-1-yl)methanone, 1-({(7S)-4-[(6-(dimethylamino)pyrazolo[1,5-a]pyridin-5-yl)amino]-5,6,7,8-tetrahydro[1]benzothieno[2,3-d]pyrimidin-7-yl}carbonyl)azetidine-3-carbonitrile,

[3-(dimethylamino)azetidin-1-yl]{(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}(4-methylpiperazin-1-yl)methanone, {4-[2-(dimethylamino)ethyl]piperazin-1-yl}{(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone, (4-{[2-(dimethylamino)ethyl](methyl)amino}piperidin-1-yl){(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone,

[4-(dimethylamino)piperidin-1-yl]{(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone, 1-({(7S)-4-[(6-(dimethylamino)pyrazolo[1,5-a]pyridin-5-yl)amino]-5,6,7,8-tetrahydro[1]benzothieno[2,3-d]pyrimidin-7-yl}carbonyl)piperidin-4-one, (3,3-difluoropyrrolidin-1-yl){(7S)-4-[(6-(dimethylamino)pyrazolo[1,5-a]pyridin-5-yl)amino]-5,6,7,8-tetrahydro[1]benzothieno[2,3-d]pyrimidin-7-yl}methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}(2,2-dimethylpyrrolidin-1-yl)methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}(morpholin-4-yl)methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}(2-oxa-6-azaspiro[3.3]hept-6-yl)methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(2R,6S)-2,6-dimethylmorpholin-4-yl]methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(2R,6R)-2,6-dimethylmorpholin-4-yl]methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(2S,6S)-2,6-dimethylmorpholin-4-yl]methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(3S)-3-methylmorpholin-4-yl]methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(3R)-3-methylmorpholin-4-yl]methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(1S,4S)-2-oxa-5-azabicyclo[2.2.1]hept-5-yl]methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(1R,4R)-2-oxa-5-azabicyclo[2.2.1]hept-5-yl]methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(1S,4S)-5-methyl-2,5-diazabicyclo[2.2.1]hept-2-yl]methanone, {(7S)-4-[(6-(dimethylamino)pyrazolo[1,5-a]pyridin-5-yl)amino]-5,6,7,8-tetrahydro[1]benzothieno[2,3-d]pyrimidin-7-yl}[(1R,4R)-5-methyl-2,5-diazabicyclo[2.2.1]hept-2-yl]methanone, (7S)-4-[(6-(dimethylamino)pyrazolo[1,5-a]pyridin-5-yl)amino]-N-[(2S)-1-methoxypropan-2-yl]-N-methyl-5,6,7,8-tetrahydro[1]benzothieno[2,3-d]pyrimidine-7-carboxamide, (7S)-4-[(6-(dimethylamino)pyrazolo[1,5-a]pyridin-5-yl)amino]-N-[(2R)-1-methoxypropan-2-yl]-N-methyl-5,6,7,8-tetrahydro[1]benzothieno[2,3-d]pyrimidine-7-carboxamide, (7S)-4-[(6-(dimethylamino)pyrazolo[1,5-a]pyridin-5-yl)amino]-N-[(2 S)-2-methoxypropyl]-N-methyl-5,6,7,8-tetrahydro[1]benzothieno[2,3-d]pyrimidine-7-carboxamide, (7S)-4-[(6-(dimethylamino)pyrazolo[1,5-a]pyridin-5-yl)amino]-N-[(2R)-2-methoxypropyl]-N-methyl-5,6,7,8-tetrahydro[1]benzothieno[2,3-d]pyrimidine-7-carboxamide, and (7S)-4-[(6-(dimethylamino)pyrazolo[1,5-a]pyridin-5-yl)amino]-N-(1-methoxy-2-methylpropan-2-yl)-N-methyl-5,6,7,8-tetrahydro[1]benzothieno[2,3-d]pyrimidine-7-carboxamide, or a pharmaceutical acceptable salt thereof, or a mixture of same.

14. A method of preparing a compound of formula (I) according to claim 1, comprising:

reacting an intermediate compound of formula (II):

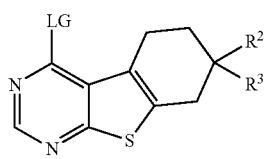

(II)

wherein $R^2$ and $R^3$ are as defined for formula (I), and LG represents a leaving group;

with an intermediate compound of formula (III):

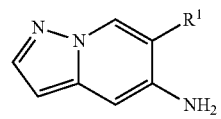

(III)

wherein $R^1$ is as defined for formula (I).

15. A pharmaceutical composition comprising a compound of formula (I), or a stereoisomer, or a pharmaceutical acceptable salt thereof, or a mixture of same, according to claim 1, and a pharmaceutically acceptable diluent or carrier.

16. A method for treating a disease in a human in need thereof, wherein the disease is acute pain, chronic pain, inflammatory pain, neuropathic pain, or pancreatitis, comprising administering an effective amount of a compound of formula (I), or stereoisomer, pharmaceutical acceptable salt thereof, or mixture of same, according to claim 1 to the human.

17. The method of claim 14, wherein LG represents a chlorine atom.

18. The method of claim 16, wherein the disease is acute pain.

19. The method of claim 16, wherein the disease is chronic pain.

20. The method of claim 16, wherein the disease is inflammatory pain.

21. The method of claim 16, wherein the disease is neuropathic pain.

22. The method of claim 16, wherein the disease is pancreatitis.

* * * * *